United States Patent
Lee et al.

(10) Patent No.: US 9,831,443 B2
(45) Date of Patent: Nov. 28, 2017

(54) CONDENSED CYCLIC COMPOUND AND ORGANIC LIGHT-EMITTING DEVICE COMPRISING THE SAME

(71) Applicant: Samsung Display Co., Ltd., Yongin, Gyeonggi-Do (KR)

(72) Inventors: Eun-Young Lee, Yongin (KR); Young-Kook Kim, Yongin (KR); Jun-Ha Park, Yongin (KR); Sung-Soo Bae, Yongin (KR); Eun-Jae Jeong, Yongin (KR); Seok-Hwan Hwang, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 314 days.

(21) Appl. No.: 14/558,491

(22) Filed: Dec. 2, 2014

(65) Prior Publication Data
US 2015/0270498 A1    Sep. 24, 2015

(30) Foreign Application Priority Data
Mar. 19, 2014  (KR) .......................... 10-2014-0032165

(51) Int. Cl.
| | | |
|---|---|---|
| H01L 51/00 | (2006.01) | |
| C09K 11/02 | (2006.01) | |
| C07D 405/14 | (2006.01) | |
| C07D 311/78 | (2006.01) | |
| C07D 405/10 | (2006.01) | |
| C09K 11/06 | (2006.01) | |
| H01L 51/50 | (2006.01) | |

(52) U.S. Cl.
CPC ........ *H01L 51/0073* (2013.01); *C07D 311/78* (2013.01); *C07D 405/10* (2013.01); *C07D 405/14* (2013.01); *C09K 11/06* (2013.01); *H01L 51/0052* (2013.01); *H01L 51/0054* (2013.01); *H01L 51/0058* (2013.01); *H01L 51/0067* (2013.01); *C09K 2211/1033* (2013.01); *C09K 2211/1048* (2013.01); *C09K 2211/1062* (2013.01); *C09K 2211/1088* (2013.01); *H01L 51/0072* (2013.01); *H01L 51/5072* (2013.01)

(58) Field of Classification Search
None
See application file for complete search history.

(56) References Cited

U.S. PATENT DOCUMENTS

| | | |
|---|---|---|
| 5,645,948 A | 7/1997 | Shi et al. |
| 2003/0165715 A1 | 9/2003 | Yoon et al. |
| | (Continued) | |

FOREIGN PATENT DOCUMENTS

| | | |
|---|---|---|
| JP | 10-017860 A | 1/1998 |
| JP | 11-087067 A | 3/1999 |
| | (Continued) | |

OTHER PUBLICATIONS

Machine English translation of Kamioka et al. (JP 2011-204844 A). May 3, 2017.*

(Continued)

*Primary Examiner* — J. L. Yang
(74) *Attorney, Agent, or Firm* — Knobbe Martens Olson & Bear LLP

(57) ABSTRACT

A condensed cyclic compound and an organic light-emitting device including the same are provided.

20 Claims, 1 Drawing Sheet

(56) References Cited

U.S. PATENT DOCUMENTS

| | | |
|---|---|---|
| 2004/0053069 A1 | 3/2004 | Sotoyama et al. |
| 2004/0137270 A1 | 7/2004 | Seo et al. |
| 2013/0306958 A1 | 11/2013 | Ito et al. |

FOREIGN PATENT DOCUMENTS

| | | |
|---|---|---|
| JP | 2007-123863 A | 5/2007 |
| JP | 4060669 | 12/2007 |
| JP | 2009-096771 A | 5/2009 |
| JP | 2010-195708 A | 9/2010 |
| JP | 2011-204844 A | 10/2011 |
| KR | 10-0525408 B1 | 11/2005 |
| KR | 10-0691543 B1 | 3/2007 |
| KR | 10-2012-0051598 A | 5/2012 |
| WO | WO 2012/070226 A1 | 5/2012 |
| WO | WO 2012/157474 A1 | 11/2012 |

OTHER PUBLICATIONS

Tang, C.W. et al. "Organic electroluminescent diodes", *Applied Physics Letters*, Sep. 21, 1987, 51(12):913-915.

Adachi, C. et al. "Confinement of charge carriers and molecular excitons within 5-nm-thick emitter layer in organic electroluminescent devices with a double heterostructure". *Applied Physics Letters*, Aug. 6, 1990, 57(6):531-533.

Johansson, N. et al. "Solid-State Amplified Spontaneous Emission in Some Spiro-Type Molecules: A New Concept for the Design of Solid-State Lasing Molecules", *Advanced Materials*, 1998, 10(14):1136-1141.

Tao, Y.T. et al. "Sharp green electroluminescence from 1H-pyrazolo[3,4-b]quinoline-based light-emitting diodes", *Applied Physics Letters*, Sep. 11, 2000, 77(11):1575-1577.

Sakamoto, Y. et al. "Synthesis, Characterization, and Electron-Transport Property of Perfluorinated Phenylene Dendrimers", *J. Am. Chem. Soc.*, 2000, 122(8):1832-1833.

Yamaguchi, S. et al. "Diphenylamino-Substituted 2,5-Diarylsiloles for Single-Layer Organic Electroluminescent Devices", *Chemistry Letters*, 2001, pp. 98-99.

* cited by examiner

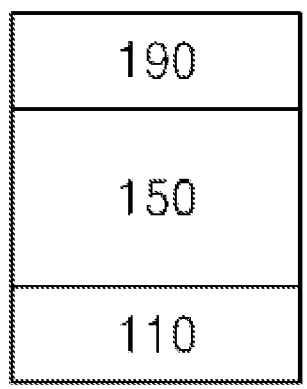

CONDENSED CYCLIC COMPOUND AND ORGANIC LIGHT-EMITTING DEVICE COMPRISING THE SAME

CROSS-REFERENCE TO RELATED APPLICATION

This application claims the benefit of Korean Patent Application No. 10-2014-0032165, filed on Mar. 19, 2014, in the Korean Intellectual Property Office, the disclosure of which is incorporated herein in its entirety by reference.

BACKGROUND

Field

One or more embodiments of the present disclosure relate to a condensed cyclic compound and an organic light-emitting device including the same.

Description of the Related Art

An organic light-emitting device may have a structure in which a first electrode, a hole transport region, an emission layer, an electron transport region, and a second electrode are sequentially disposed in this order on a substrate. Holes injected from the first electrode move to the emission layer via the hole transport region, while electrons injected from the second electrode move to the emission layer via the electron transport region. Carriers such as the holes and electrons recombine in the emission layer to generate exitons. When the exitons drop from an excited state to a ground state, light is emitted.

SUMMARY

One or more embodiments of the present disclosure include a novel condensed cyclic compound and an organic light-emitting device including the same.

Additional aspects will be set forth in part in the description which follows and, in part, will be apparent from the description, or may be learned by practice of the presented embodiments.

According to one or more embodiments of the present disclosure, there is provided a condensed cyclic compound represented by Formula 1A or 1B:

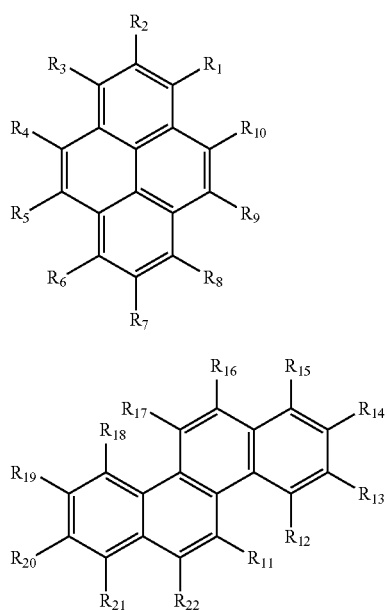

<Formula 1A>

<Formula 1B>

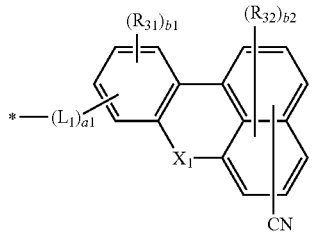

<Formula 2-1>

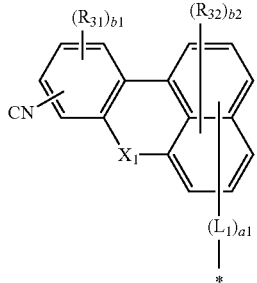

<Formula 2-2> wherein, in Formulae 1A, 1B, 2-1, and 2-2, $X_1$ is O or S;

$L_1$ is selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent nonaromatic condensed polycyclic group, and a substituted or unsubstituted divalent nonaromatic condensed heteropolycyclic group;

a1 is selected from 0, 1, 2, and 3;

$R_1$ to $R_{22}$ are each independently selected from a group represented by Formula 2-1, a group represented by Formula 2-2, a hydrogen, a deuterium, —F, —Cl, —Br, —I, a hydroxyl group, a cyano group, a nitro group, an amino group, an amidino group, a hydrazine group, a hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, a substituted or unsubstituted monovalent nonaromatic condensed heteropolycyclic group, —N($Q_1$)($Q_2$), —Si($Q_3$)($Q_4$)($Q_5$), and —B($Q_6$)($Q_7$);

at least one of $R_1$ to $R_{10}$ is a group represented by Formula 2-1 or 2-2, and at least one of $R_{11}$ to $R_{22}$ is a group represented by Formula 2-1 or 2-2;

b1 is an integer selected from 1 to 3;

b2 is an integer selected from 1 to 5; and

* in Formulae 2-1 and 2-2 is a binding site with a core represented by Formula 1A or Formula 1B;

wherein at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocyclolalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent nonaromatic condensed polycyclic group, and the substituted monovalent nonaromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, each substituted with at least one of a deuterium atom, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $R_{31}$, $R_{32}$, $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent nonaromatic condensed polycyclic group, and a monovalent aromatic condensed heteropolycyclic group.

According to one or more embodiments of the present disclosure, an organic light-emitting device includes: a first electrode; a second electrode disposed opposite to the first electrode; and an organic layer disposed between the first electrode and the second electrode and including an emission layer, wherein the organic layer includes at least one of the condensed cyclic compounds of Formula 1A or 1B described above.

BRIEF DESCRIPTION OF THE DRAWINGS

These and/or other aspects will become apparent and more readily appreciated from the following description of the embodiments, taken in conjunction with the accompanying drawing in which:

The FIGURE is a schematic view of a structure of an organic light-emitting device according to an embodiment of the present disclosure.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present disclosure, there is provided a condensed cyclic compound represented by Formula 1A or 1B, wherein at least one of $R_1$ to $R_{10}$ in Formula 1A is a group represented by Formula 2-1 or a group represented by Formula 2-2, and at least one of $R_{11}$ to $R_{22}$ in Formula 1B is a group represented by Formula 2-1 or a group represented by Formula 2-2:

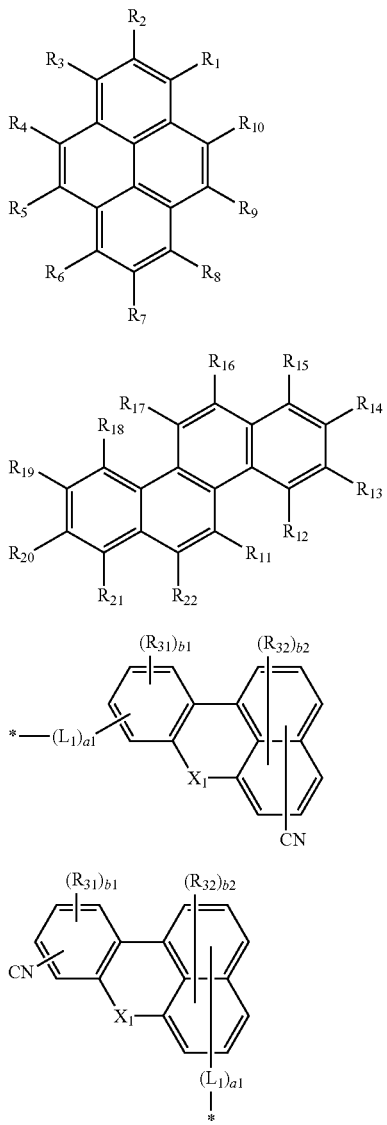

<Formula 1A>

<Formula 1B>

<Formula 2-1>

<Formula 2-2>

The condensed cyclic compounds of Formulae 1A and 1B may each independently include at least one of the group of Formula 2-1 and the group of Formula 2-2 as a substituent. In Formulae 2-1 and 2-2, * is a binding site with carbon in a pyrene backbone of a pyrene core of Formula 1A or with carbon in a chrysene backbone of a chrysene core of Formula 1B.

In Formulae 2-1 and 2-2, $X_1$ may be O or S. For example, in Formulae 2-1 and 2-2, $X_1$ may be O, but is not limited thereto.

In Formulae 2-1 and 2-2, $L_1$ may be selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent nonaromatic condensed polycyclic group, and a substituted or unsubstituted divalent nonaromatic condensed heteropolycyclic group.

In some embodiments, in Formulae 2-1 and 2-2, $L_1$ may be selected from
a phenylene group, a pentalenylene group, an indeylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolyene group, an imidazopyridinylene group, and an imidazopyrimidinylene group, a phenylene group, a pentalenylene group, an indeylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolyene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, an a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indeyl group, a naphthyl group, an azulenyl group, a heptalenyl group, an indacenyl group, an acenaphthyl group, a fluorenyl group, a spirofluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In some embodiments, in Formulae 2-1 and 2-2, $L_1$ may be represented by one of Formulae 3-1 to 3-32:

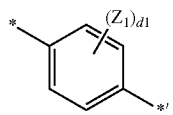

Formula 3-1

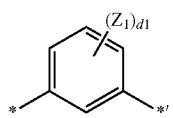

Formula 3-2

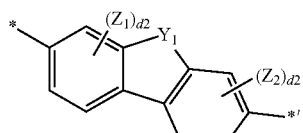

Formula 3-3

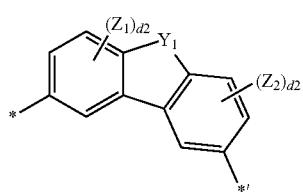

Formula 3-4

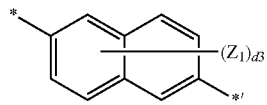

Formula 3-5

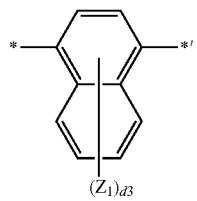

Formula 3-6

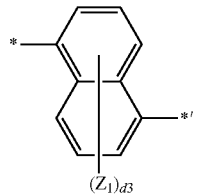

Formula 3-7

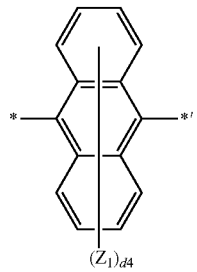

Formula 3-8

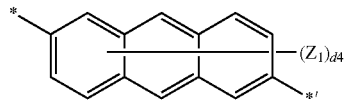

Formula 3-9

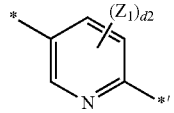

Formula 3-10

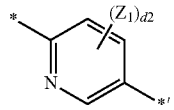

Formula 3-11

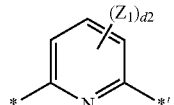

Formula 3-12

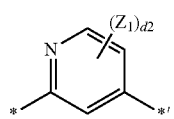

Formula 3-13

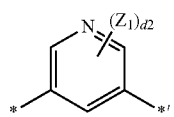

Formula 3-14

-continued

Formula 3-15
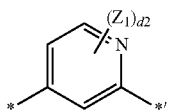

Formula 3-16
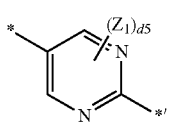

Formula 3-17
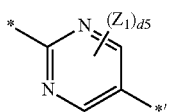

Formula 3-18
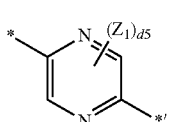

Formula 3-19
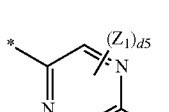

Formula 3-20
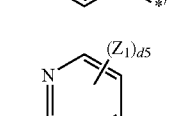

Formula 3-21
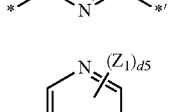

Formula 3-22
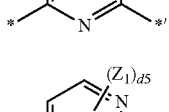

Formula 3-23
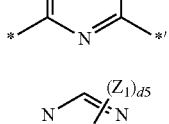

Formula 3-24
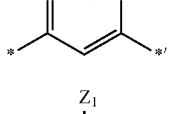

Formula 3-25
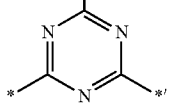

Formula 3-26
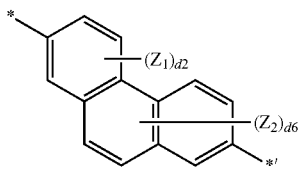

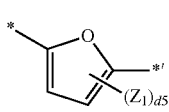

Formula 3-27
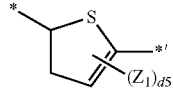

Formula 3-28
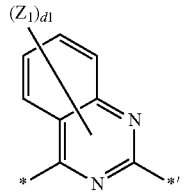

Formula 3-29
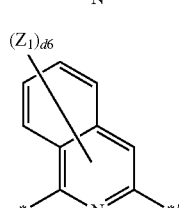

Formula 3-30
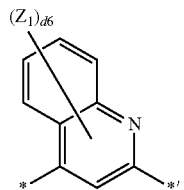

Formula 3-31
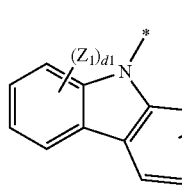

Formula 3-32

In Formulae 3-1 to 3-32, $Y_1$, may be O, S, $C(Z_3)(Z_4)$, $N(Z_5)$, or $Si(Z_6)(Z_7)$;

$Z_1$ to $Z_7$ may be each independently selected from a hydrogen, a deuterium, —F, —Cl, —Br, —I, a hydroxyl group, a cyano group, a nitro group, an amino group, an amidino groups, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzo-fluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 may be an integer selected from 1 to 4, d2 may be an integer selected from 1 to 3, d3 may be an integer selected from 1 to 6, d4 may be an integer selected from 1 to 8, d5 may be 1 or 2, d6 may be an integer selected from 1 to 5, and * and *' may be binding sites with adjacent atoms.

In some other embodiments, in Formulae 2-1 and 2-2, $L_1$ may be represented by one of Formulae 4-1 to 4-23. However, embodiments of the present disclosure are not limited thereto:
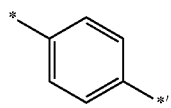
Formula 4-1
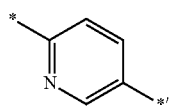
Formula 4-2
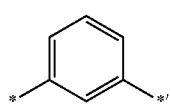
Formula 4-3
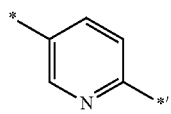
Formula 4-4
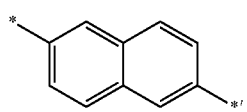
Formula 4-5
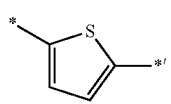
Formula 4-6
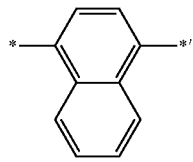
Formula 4-7
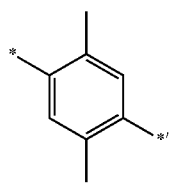
Formula 4-8
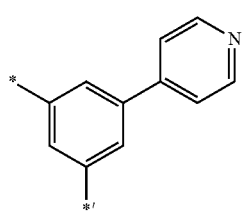
Formula 4-9
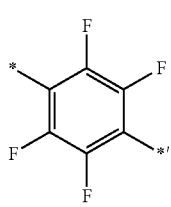
Formula 4-10
-continued
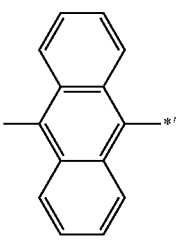
Formula 4-11
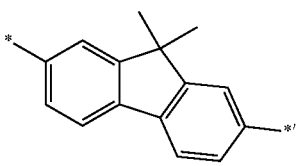
Formula 4-12
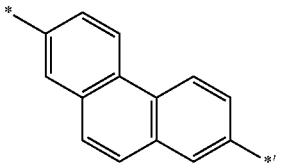
Formula 4-13
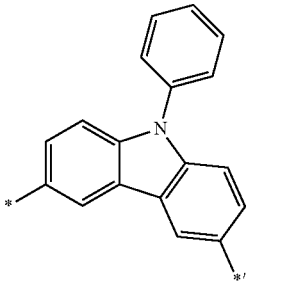
Formula 4-14
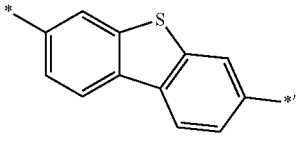
Formula 4-15
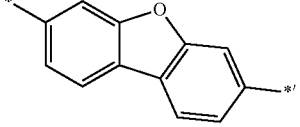
Formula 4-16
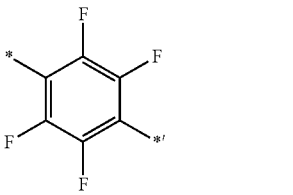
Formula 4-17
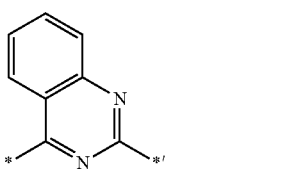
Formula 4-18

Formula 4-19

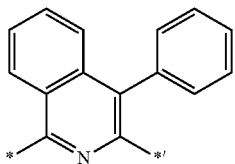

Formula 4-20

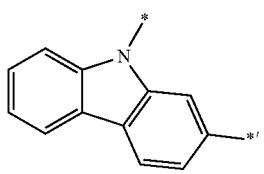

Formula 4-21

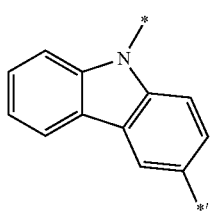

Formula 4-22

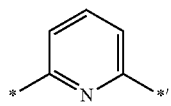

Formula 4-23

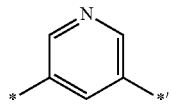

In Formulae 4-1 to 4-23, * and *' may be binding sites with adjacent atoms.

In Formulae 2-1 and 2-2, a1 may be selected from 0, 1, 2, and 3. For example, a1 in Formulae 2-1 and 2-2 may be 0 or 1. When a1 in Formulae 2-1 and 2-2 is 0, $(L_1)_{a1}$- may be a single bond. When a1 in Formulae 2-1 and 2-2 is 2 or greater, a plurality of $L_1$s may be identical to or different from each other.

In Formulae 1A and 1B, $R_1$ to $R_{22}$ may be each independently selected from a group represented by Formula 2-1, a group represented by Formula 2-2, a hydrogen, a deuterium, —F, —Cl, —Br, —I, a hydroxyl group, a cyano group, a nitro group, an amino group, an amidino group, a hydrazine group, a hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, a substituted or unsubstituted monovalent non-aromatic condensed heteropolycyclic group (wherein the substituted monovalent nonaromatic condensed heteropolycyclic group may exclude the group of Formula 2-1 and the group of Formula 2-2), —N($Q_1$)($Q_2$), —Si($Q_3$)($Q_4$)($Q_5$), and —B($Q_6$)($Q_7$); and at least one of $R_1$ to $R_{10}$ may be a group represented by Formula 2-1 or 2-2, and at least one of $R_1$ to $R_{22}$ may be a group represented by Formula 2-1 or 2-2.

In some embodiments, at least one substituent of $R_1$ to $R_{10}$ in Formula 1A, except for the groups represented by Formulae 2-1 and Formula 2-2, and at least one substituent of $R_{11}$ to $R_{22}$ in Formula 1B, except for the groups represented by Formulae 2-1 and Formula 2-2, may be each independently an electron transport moiety selected from a substituted or unsubstituted $C_2$-$C_{20}$ heteroaryl group, and a substituted or unsubstituted monovalent non-aromatic condensed heteropolycyclic group. For example, at least one substituent of $R_1$ to $R_{10}$ in Formula 1A, except for the groups represented by Formulae 2-1 and Formula 2-2, and at least one substituent of $R_{11}$ to $R_{22}$ in Formula 1B, except for the groups represented by Formulae 2-1 and Formula 2-2, may be each independently selected from a substituted or unsubstituted $C_2$-$C_{20}$ heteroaryl group including at least one N as a ring-forming element, and a substituted or unsubstituted monovalent non-aromatic condensed heteropolycyclic group including at least one N as a ring-forming element. However, embodiments of the present disclosure are not limited thereto.

For example, at least one substituent of $R_1$ to $R_{10}$ in Formula 1A, except for the groups represented by Formulae 2-1 and Formula 2-2, and at least one substituent of $R_{11}$ to $R_{22}$ in Formula 1B, except for the groups represented by Formulae 2-1 and Formula 2-2, may be each independently selected from a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, and a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group. However, embodiments of the present disclosure are not limited thereto.

In some embodiments, in Formulae 1A and 1B, $R_1$ to $R_{22}$ may be each independently selected from a group represented by Formula 2-1, a group represented by Formula 2-2, a hydrogen, a deuterium, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, and Si($Q_3$)($Q_4$)($Q_5$), wherein $Q_3$ to $Q_5$ may be each independently selected from a $C_1$-$C_{20}$ alkyl group, a $C_1$-$C_{20}$ alkoxy group, a phenyl group, and a nahthyl group; and at least one of $R_1$ to $R_{10}$ may be a group represented by Formula 2-1 or Formula 2-2, and at least one of $R_{11}$ to $R_{22}$ may be a group represented by Formula 2-1 or Formula 2-2.

In some other embodiments, in Formulae 1A and 1B, $R_1$ to $R_{22}$ may be each independently selected from a group represented by Formula 2-1, a group represented by Formulae 2-2, hydrogen, a deuterium, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and Si($Q_3$)($Q_4$)($Q_5$), wherein $Q_3$ to $Q_5$ may be each independently selected from a $C_1$-$C_{20}$ alkyl group, a $C_1$-$C_{20}$ alkoxy group, a phenyl group, and a nahthyl group; and at least one of $R_1$ to $R_{10}$ may be a group represented by Formula 2-1 or Formula 2-2, and at least one of $R_{11}$ to $R_{22}$ may be a group represented by Formula 2-1 or Formula 2-2.

In some embodiments, $R_1$ or $R_2$ in Formula 1A may be a group represented by Formula 2-1 or Formula 2-2.

In some embodiments, one of $R_1$ to $R_{10}$ in Formula 1A, and one of $R_{11}$ to $R_{22}$ in Formula 1B may be a group represented by Formula 2-1 or Formula 2-2. The pyrene backbone of the pyrene core represented by Formula 1A may include only one of the group of Formula 2-1 and the group of Formula 2-2 as a substituent, and the chrysene backbone of the chrysene core represented by Formula 1B may include only one of the group of Formula 2-1 and the group of Formula 2-2 as a substituent.

In some embodiments, $R_1$ to $R_{22}$ in Formulae 1A and 1B may be each independently selected from a group of Formula 2-1, a group of Formula 2-2, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, Si($Q_3$)($Q_4$)($Q_5$) (where $Q_3$ to $Q_5$ may be each independently selected from a $C_1$-$C_{20}$ alkyl group, a $C_1$-$C_{20}$ alkoxy group, a phenyl group, and a naphthyl group), and the groups of Formulae 5-1 to 5-35, wherein at least one of $R_1$ to $R_{10}$ may be a group of Formula 2-1 or a group of Formula 2-2, and at least one of $R_{11}$ to $R_{22}$ may be a group of Formula 2-1 or a group of Formula 2-2. However, embodiments of the present disclosure are not limited thereto:

Formula 5-1

Formula 5-2

Formula 5-3

Formula 5-4

Formula 5-5

Formula 5-6

Formula 5--7

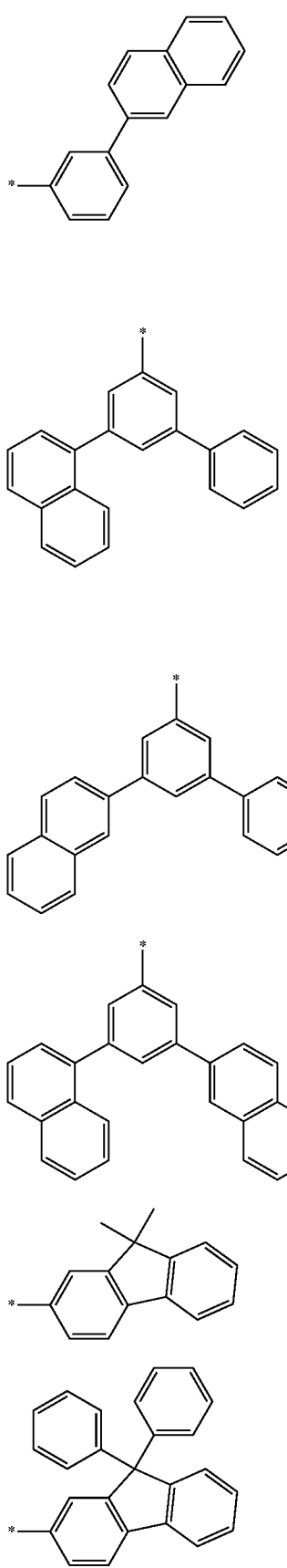
Formula 5-8
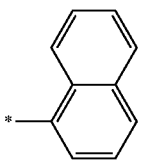
Formula 5-9
Formula 5-10
Formula 5-11
Formula 5-12
Formula 5-13
Formula 5-14
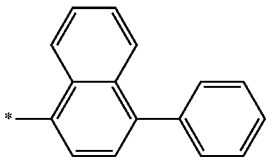
Formula 5-15
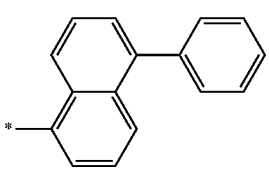
Formula 5-16
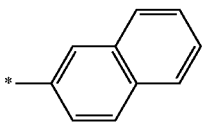
Formula 5-17
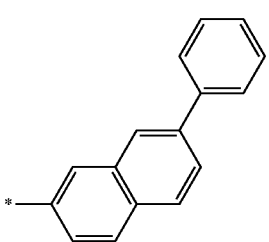
Formula 5-18
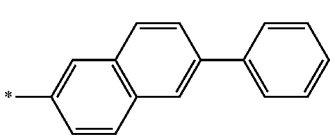
Formula 5-19
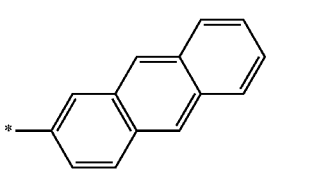
Formula -20
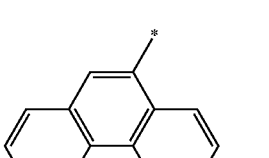
Formula 5-21
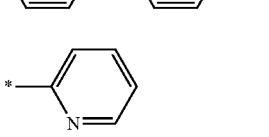
Formula 5-22
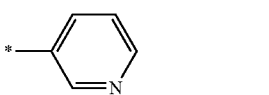
Formula 5-23

Formula 5-24
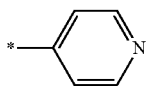

Formula 5-25
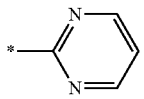

Formula 5-26
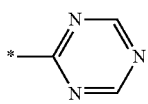

Formula 5-27
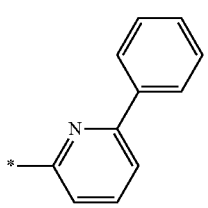

Formula 5-28
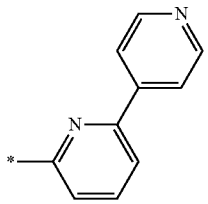

Formula 5-29
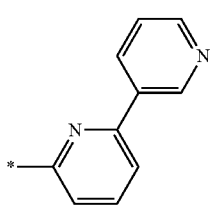

Formula 5-30
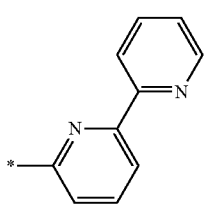

Formula 5-31
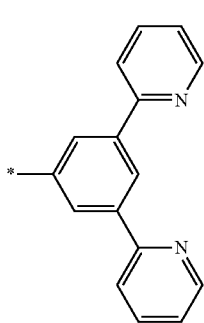

Formula 5-32
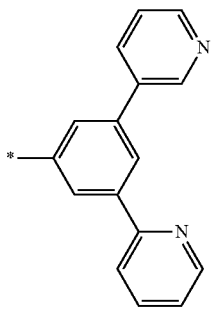

Formula 5-33
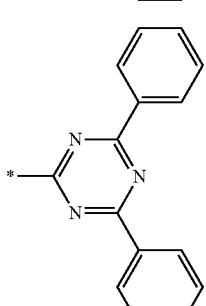

Formula 5-34
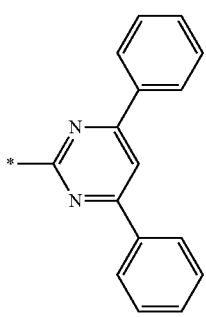

Formula 5-35
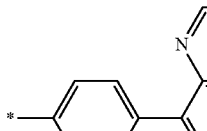

In some embodiments, $R_{31}$ and $R_{32}$ in Formulae 2-1 and 2-2 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

For example, $R_{31}$ and $R_{32}$ in Formulae 2-1 and 2-2 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a phosphoric acid group or a salt thereof, a $C_1$-$C_{20}$ alkyl group, a $C_1$-$C_{20}$ alkoxy group, a phenyl group, a naphthyl group, a fluorenyl group, spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but are not limited thereto.

In some embodiments, $R_{31}$ and $R_{32}$ in Formulae 2-1 and 2-2 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group.

In some other embodiments, $R_{31}$ and $R_{32}$ in Formulae 2-1 and 2-2 may be both hydrogens.

In Formulae 2-1 and 2-2, b1, which indicates the number of $R_{31}$s, may be an integer selected from 1 to 3. When b1 is 2 or greater, b1 number of $R_{31}$s may be identical to or different from each other.

In Formulae 2-1 and 2-2, b2, which indicates the number of $R_{32}$s, may be an integer selected from 1 to 5. When b2 is 2 or greater, b2 number of $R_{32}$s may be identical to or different from each other.

In some embodiments, the group of Formula 2-1 may be selected from groups represented by Formulae 2-1(1), 2-1(2), and 2-1(3), and the group of Formula 2-2 may be selected from groups represented by Formulae 2-2(1) and 2-2(2). However, embodiments of the present disclosure are not limited thereto:

<Formula 2-1(1)>

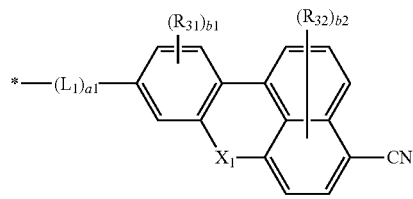

<Formula 2-1(2)>

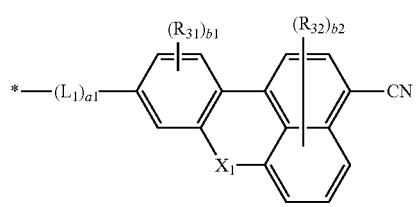

<Formula 2-1(3)>

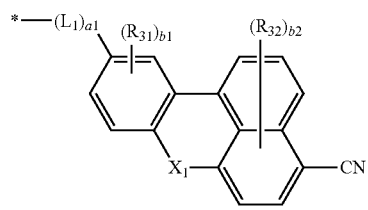

<Formula 2-2(1)>

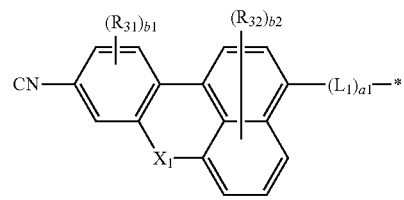

<Formula 2-2(2)>

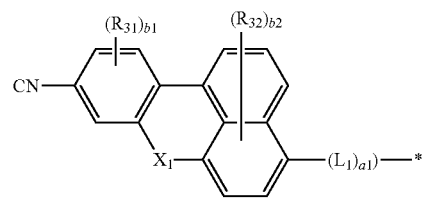

In Formulae 2-1(1), 2-1(2), 2-1(3), 2-2(1), and 2-2(2), $X_1$, $L_1$, $a_1$, $R_{31}$, $R_{32}$, b1, and b2 may be the same as those defined above, and thus detailed descriptions thereof will be omitted here.

With regard to the definition of $R_1$ to $R_{22}$ in Formulae 1A and 1B, the "substituted monovalent non-aromatic condensed heteropolycyclic group" for $R_1$ to $R_{22}$ may exclude the group of Formula 2-1 and the group of Formula 2-2.

In some embodiments, the condensed cyclic compound of Formula 1A may be represented by one of Formulae 1A-1 to 1A-4, and the condensed cyclic compound of Formula 1B may be represented by one of Formulae 1B-1 and 1B-2:

<Formula 1A-1>

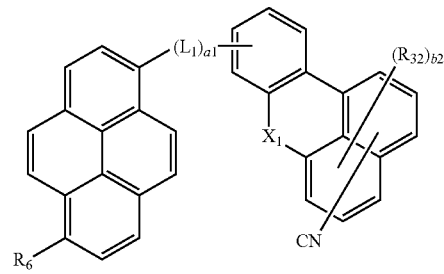

<Formula 1A-2>

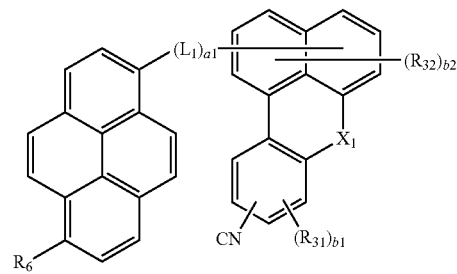

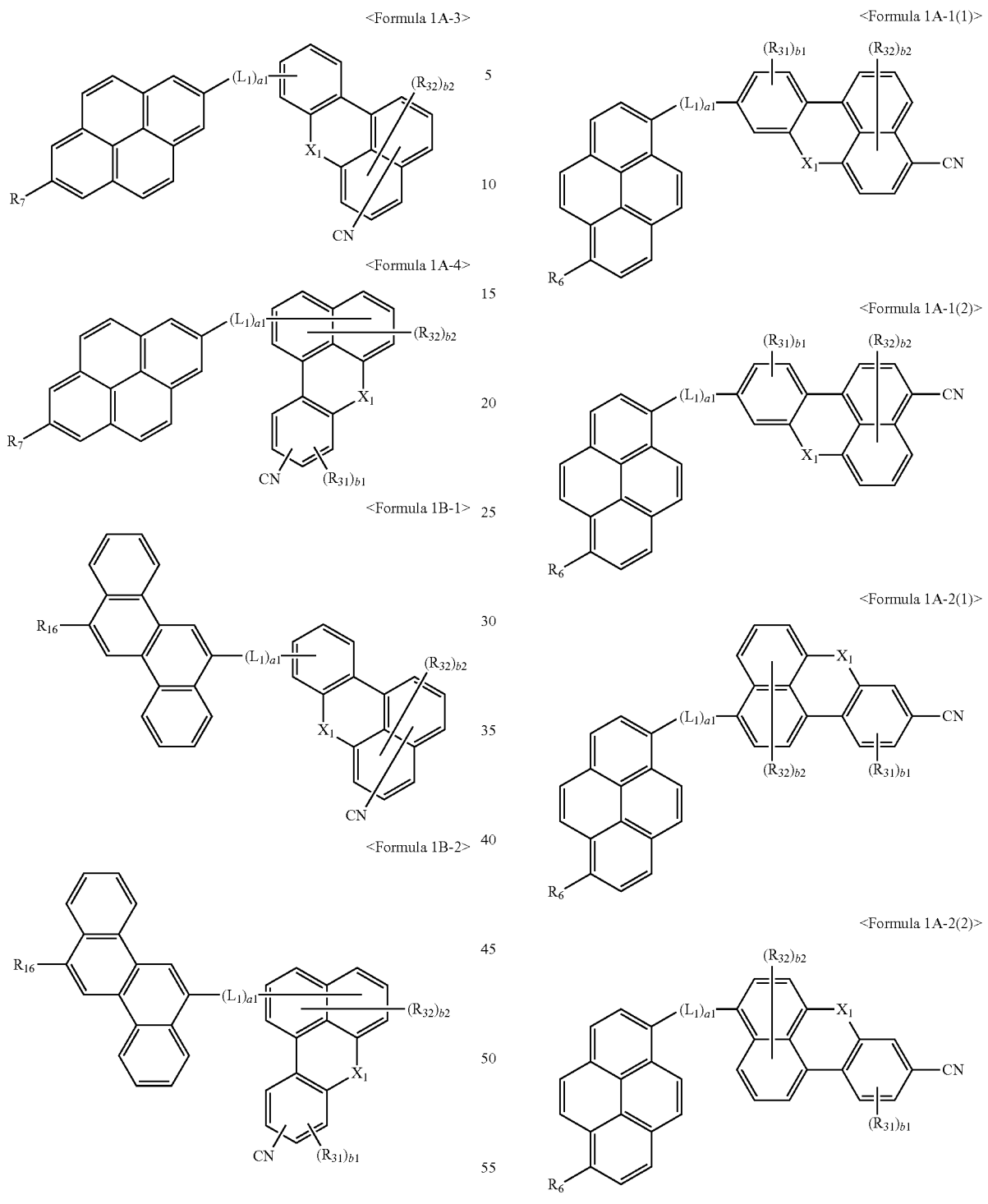
In Formulae 1A-1 to 1A-4, and Formulae 1B-1 and 1B-2, $X_1$, $L_1$, a1, $R_6$, $R_7$, $R_{31}$, $R_{32}$, b1, and b2 may be the same as those defined herein.
In some other embodiments, the condensed cyclic compound of Formula 1A may be represented by one of Formulae 1A-1(1), 1A-1(2), 1A-2(1), 1A-2(2), 1A-3(1), 1A-3(2), 1A-3(3), 1A-4(1), and 1A-4(2), and the condensed cyclic compound of Formula 1B may be represented by one of Formulae 1B-1(1), 1B-1(2), 1B-1(3), 1B-2(1), and 1B-2(2):

<Formula 1A-3(2)>

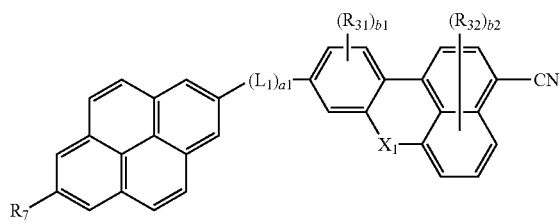

<Formula 1B-1(2)>

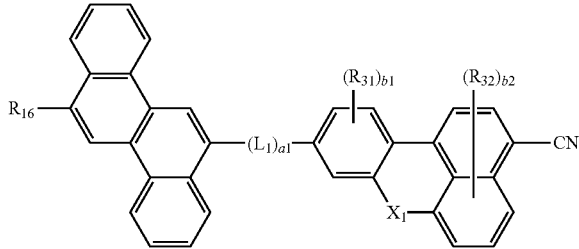

<Formula 1A-3(3)>

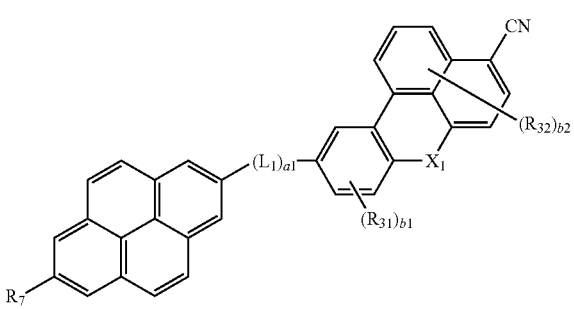

<Formula 1B-1(3)>

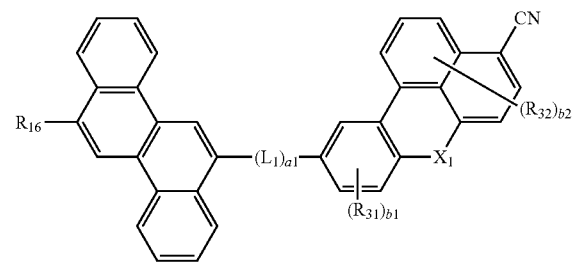

<Formula 1A-4(1)>

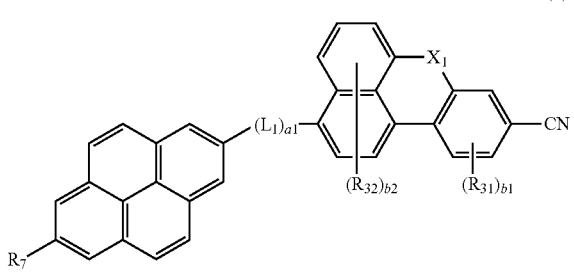

<Formula 1B-2(1)>

<Formula 1A-4(2)>

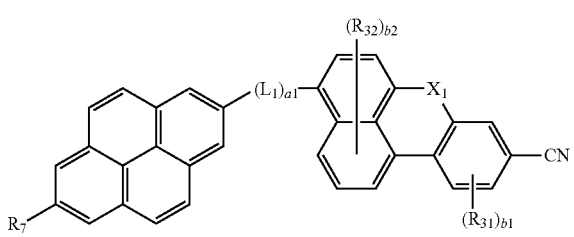

<Formula 1B-2(2)>

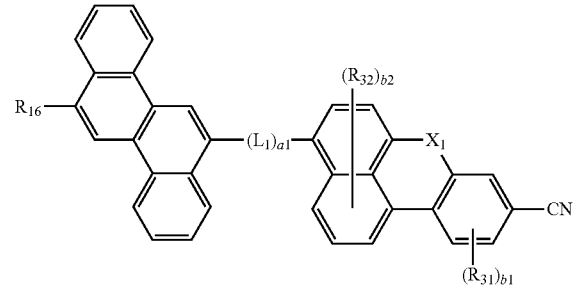

<Formula 1B-1(1)>

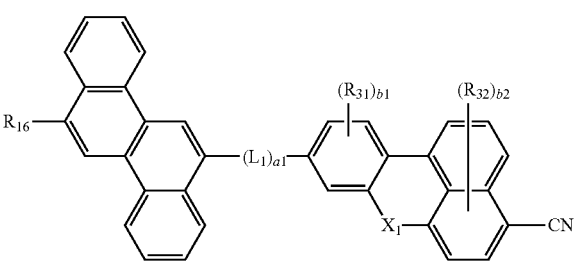

In Formulae 1A-1(1), 1A-1(2), 1A-2(1), 1A-2(2), 1A-3(1), 1A-3(2), 1A-3(3), 1A-4(1), 1A-4(2), 1B-1(1), 1B-1(2), 1B-1(3), 1B-2(1), and 1B(2), $X_1$, $L_1$, a1, $R_6$, $R_7$, $R_{16}$, $R_{31}$, $R_{32}$, b1, and b2 may be the same as those defined herein.

For example, the condensed cyclic compound of Formula 1A or Formula 1B may be represented by one of Formulae 1A-1(1), 1A-1(2), 1A-2(1), 1A-2(2), 1A-3(1), 1A-3(2), 1A-3(3), 1A-4(1), 1A-4(2), 1B-1(1), 1B-1(2), 1B-1(3), 1B-2(1), and 1B(2), wherein, in Formulae 1A-1(1), 1A-1(2), 1A-2(1), 1A-2(2), 1A-3(1), 1A-3(2), 1A-3(3), 1A-4(1), 1A-4(2), 1B-1(1), 1B-1(2), 1B-1(3), 1B-2(1), and 1B(2), $L_1$ may be selected from groups represented by Formulae 3-1 to 3-32 (for example, groups represented by Formulae 4-1 to 4-23);

a1 may be 0 or 1;

$R_6$, $R_7$, and $R_{16}$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, $Si(Q_3)(Q_4)(Q_5)$ (where $Q_3$ to $Q_5$ may be each independently selected from a $C_1$-$C_{20}$ alkyl group, a $C_1$-$C_{20}$ alkoxy group, a phenyl group, and a naphthyl group), and the groups represented by Formulae 5-1 to 5-35;

$R_{31}$ and $R_{32}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group; and b1 and b2 may be an integer selected from 1 to 3. However, embodiments of the present disclosure are not limited thereto.

In some embodiments, the condensed cyclic compound of Formula 1 may be one of Compounds 1A to 133A and Compounds 1B to 92B.

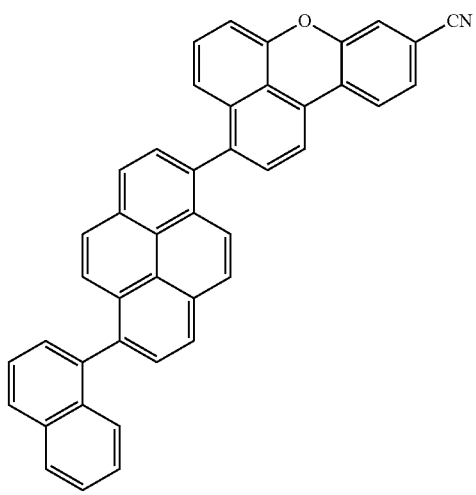

4A

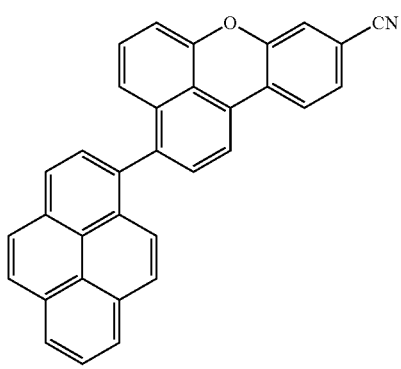

1A

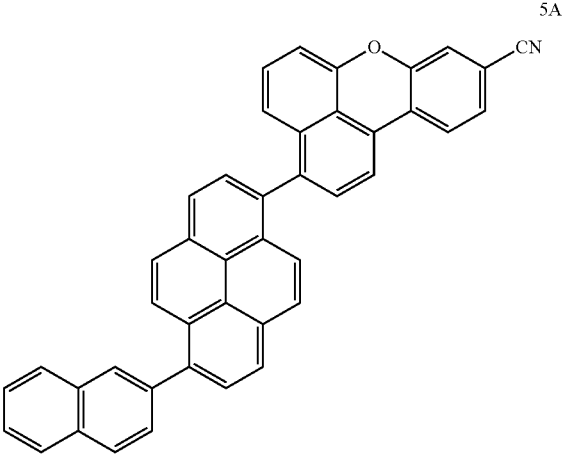

5A

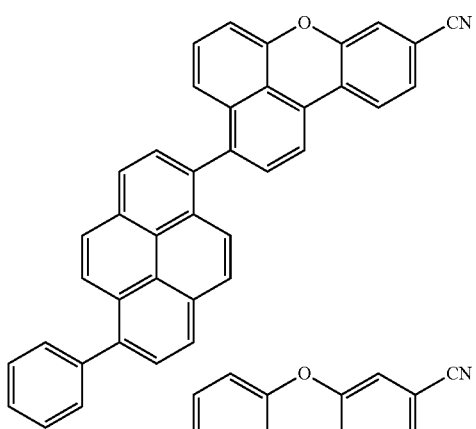

2A

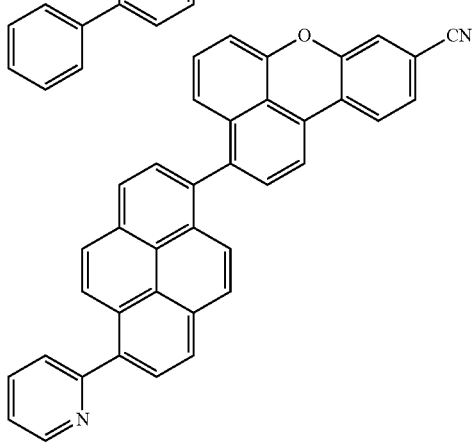

3A

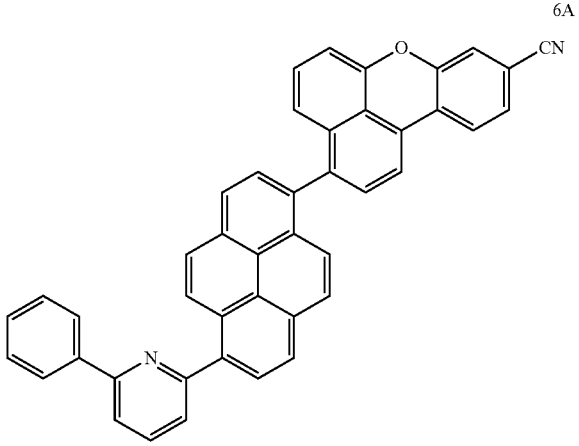

6A

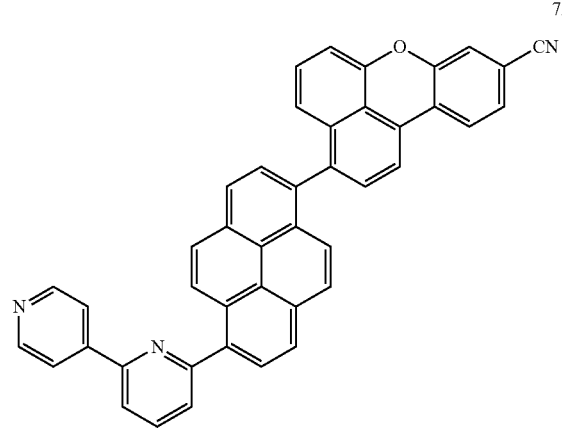
7A
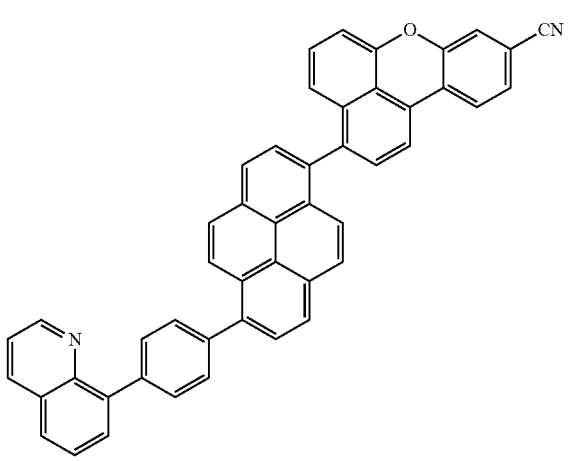
8A
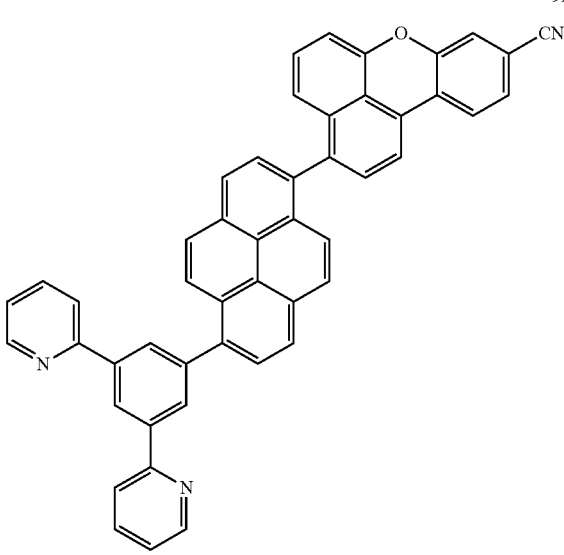
9A
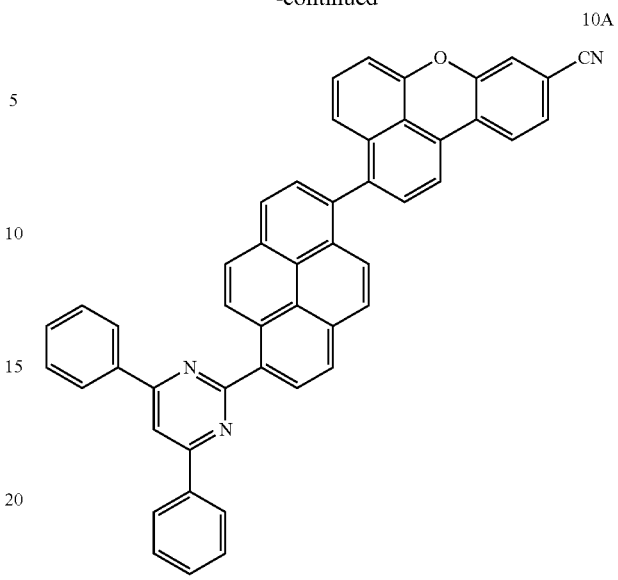
10A
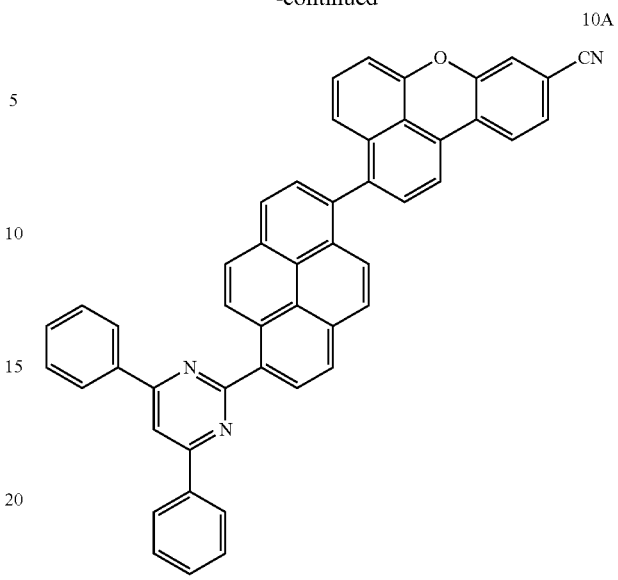
11A
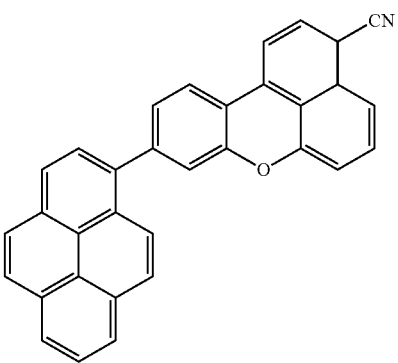
12A -continued
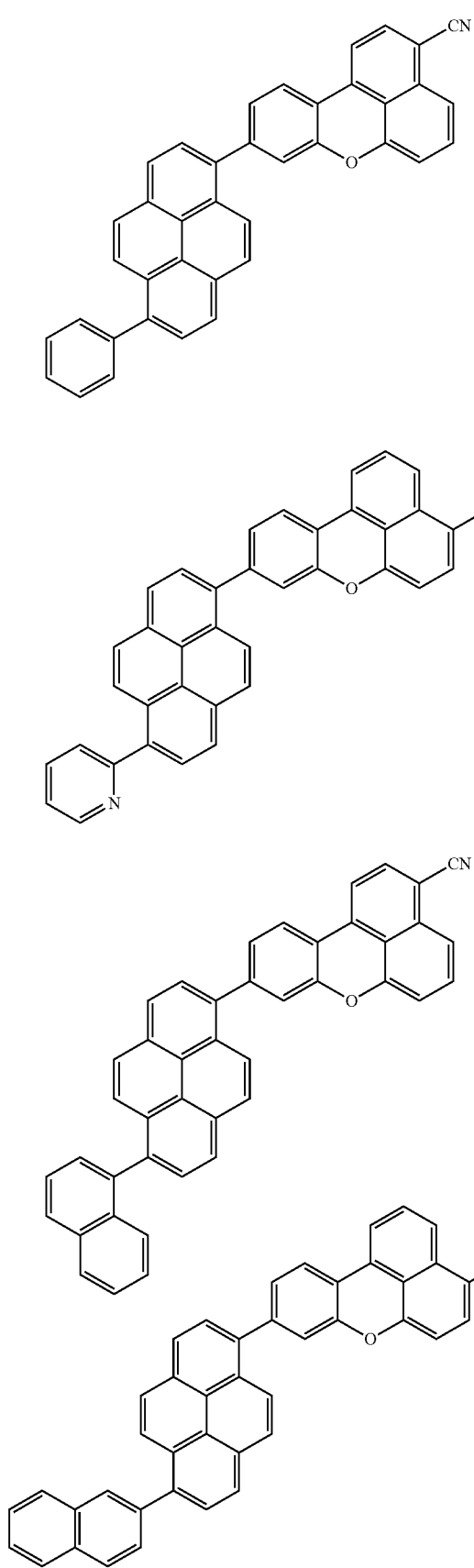
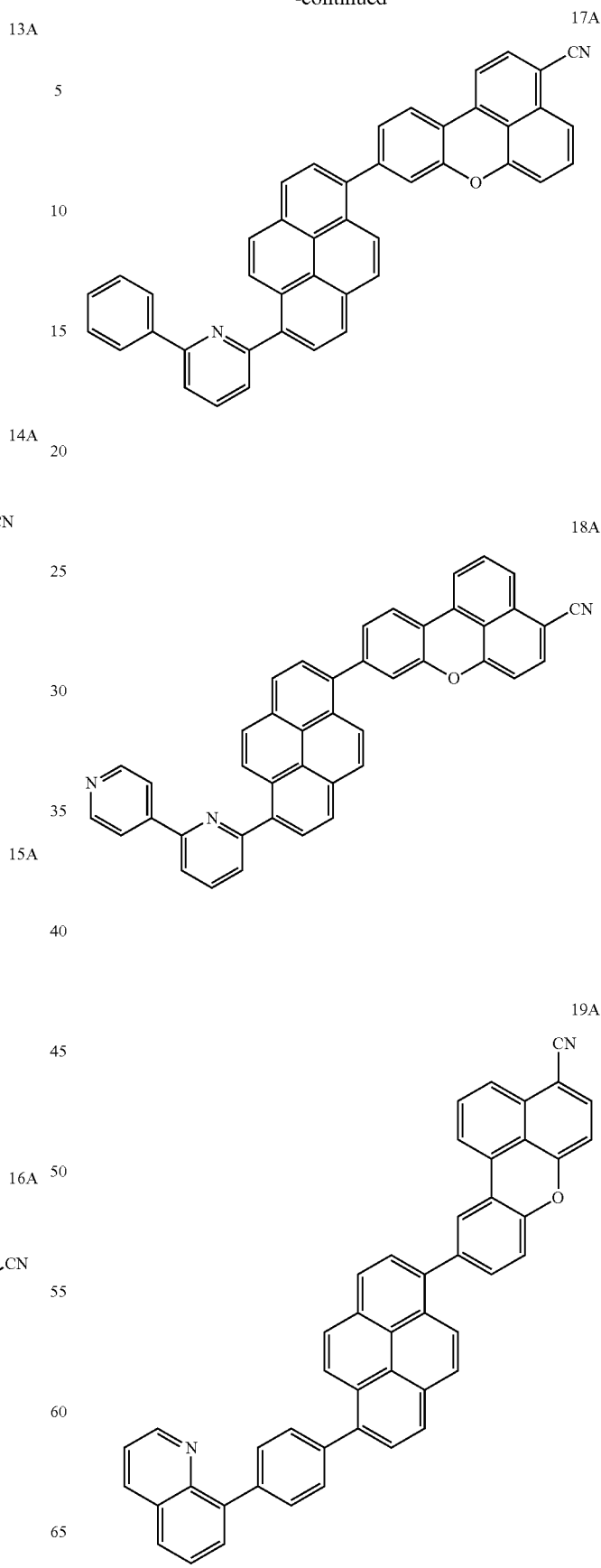

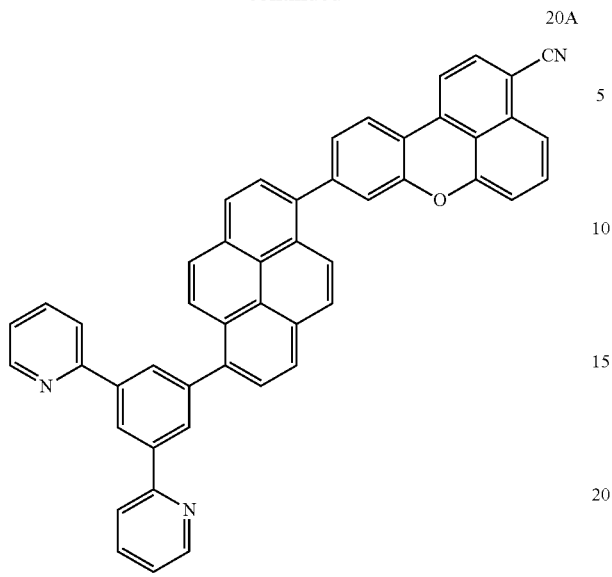
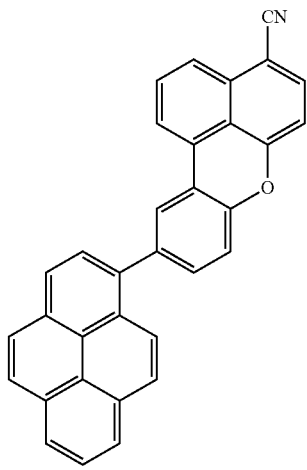
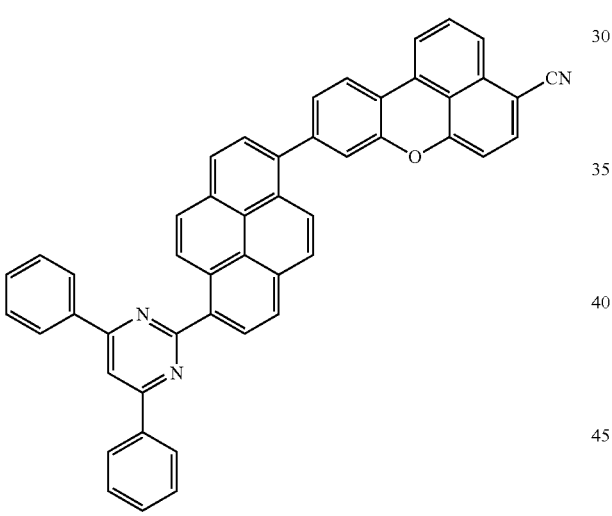
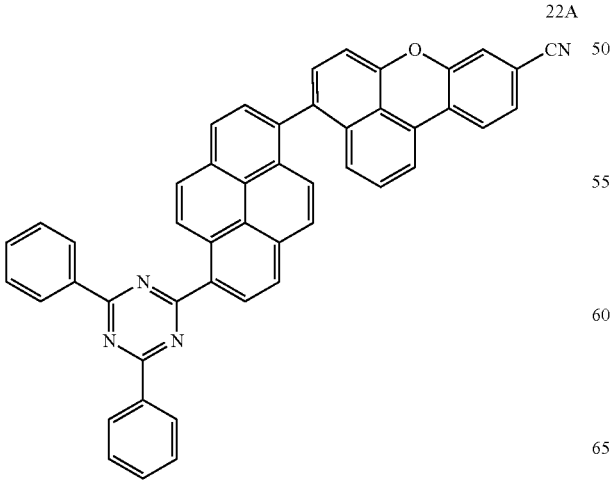
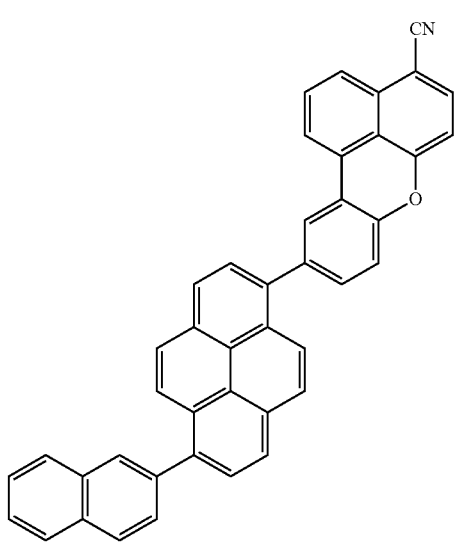

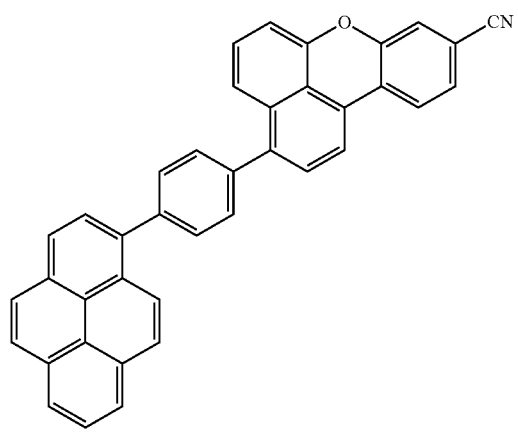
26A
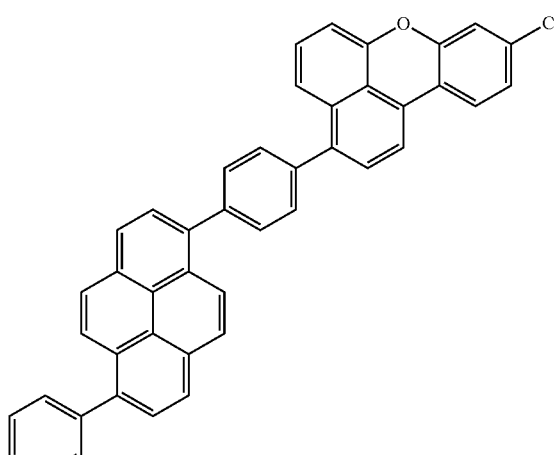
27A
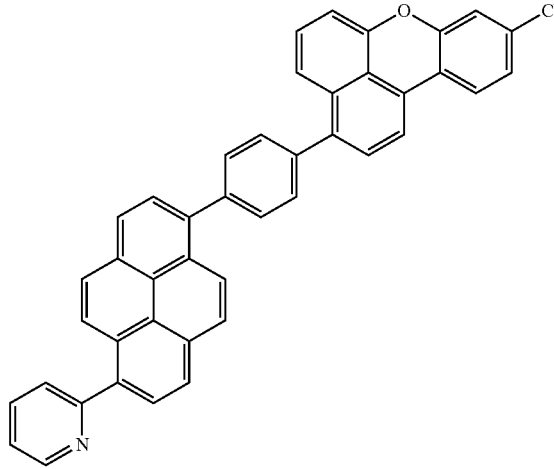
28A
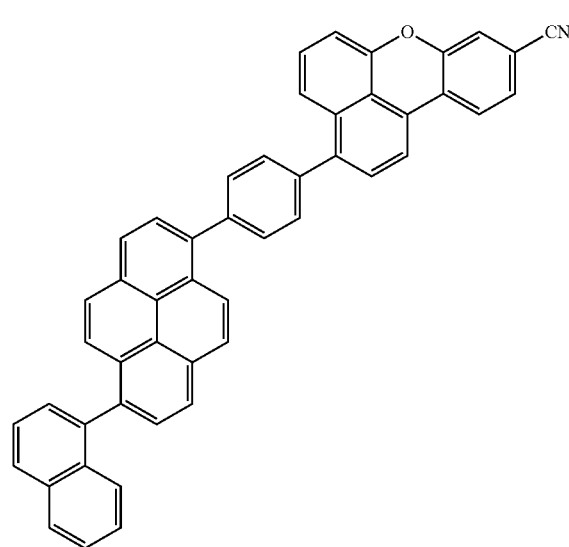
29A
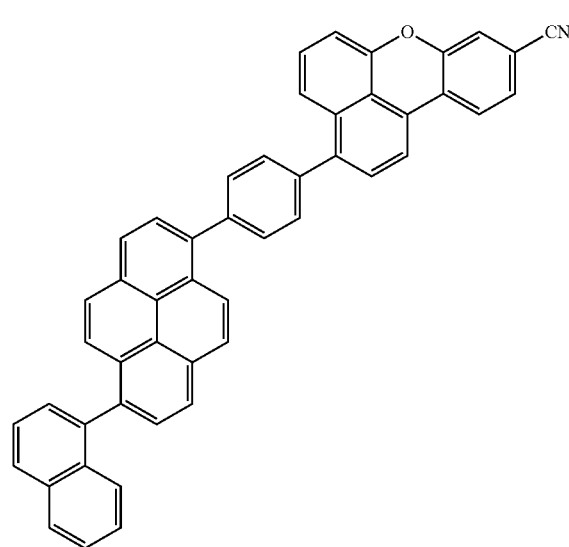
30A
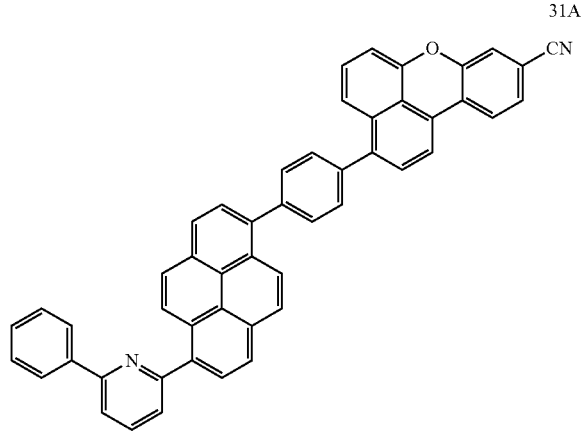
31A -continued
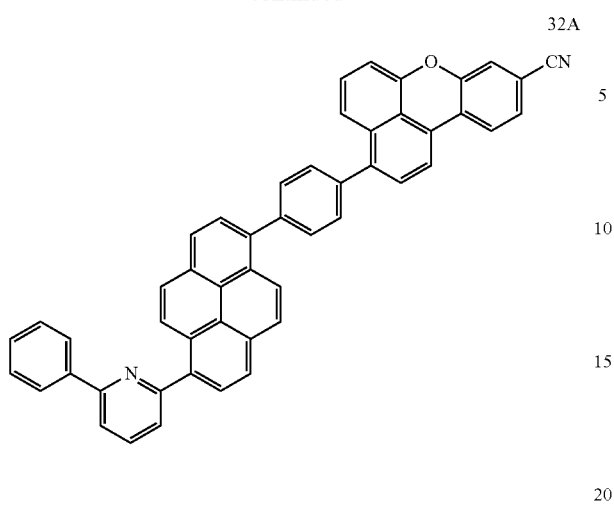
32A
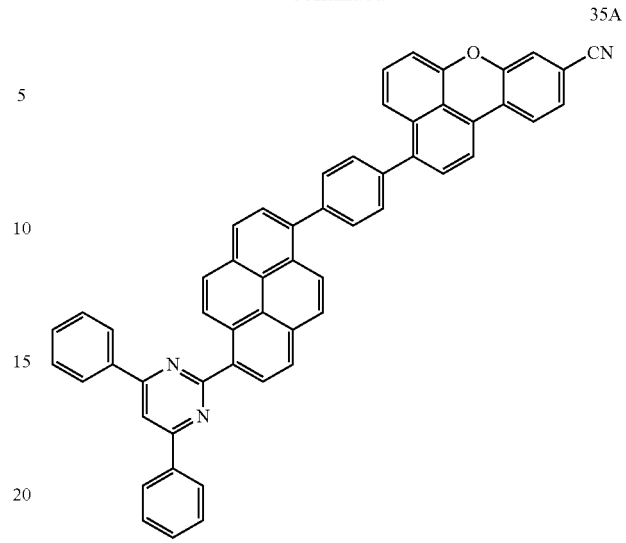
35A
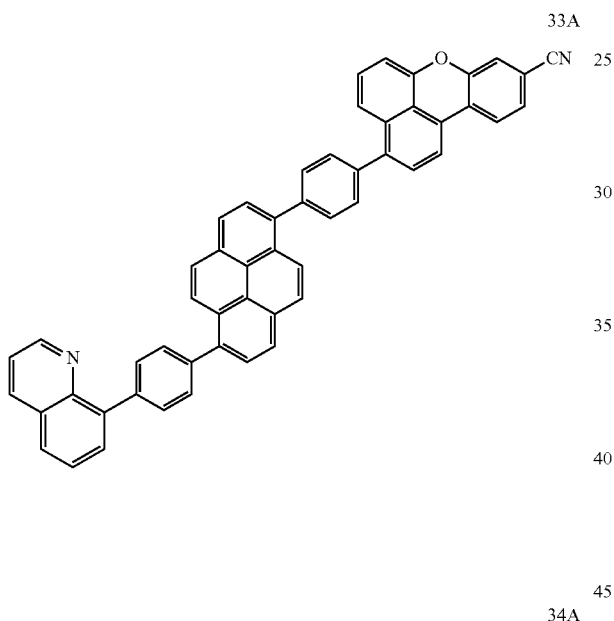
33A
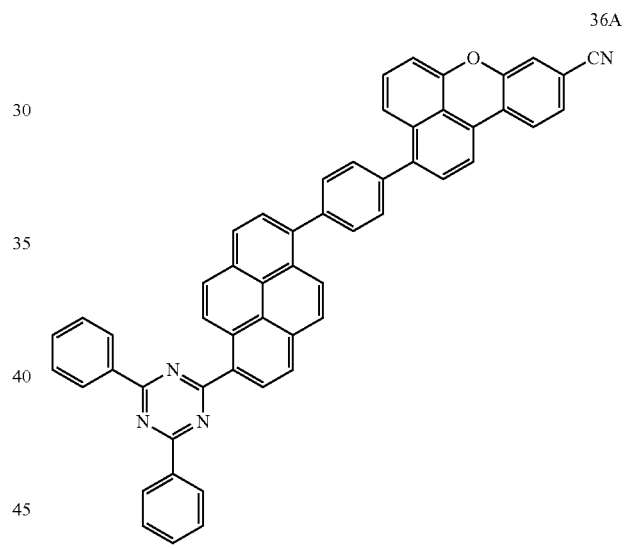
36A
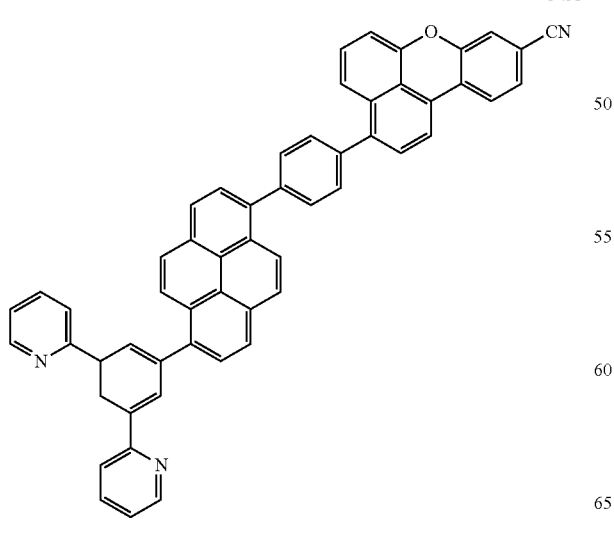
34A
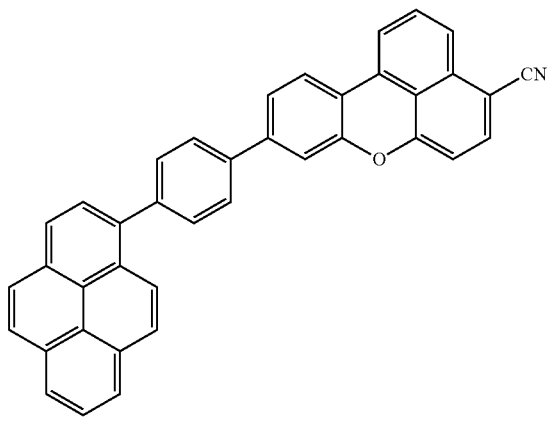
37A -continued

38A

39A

40A

41A

42A

43A

44A

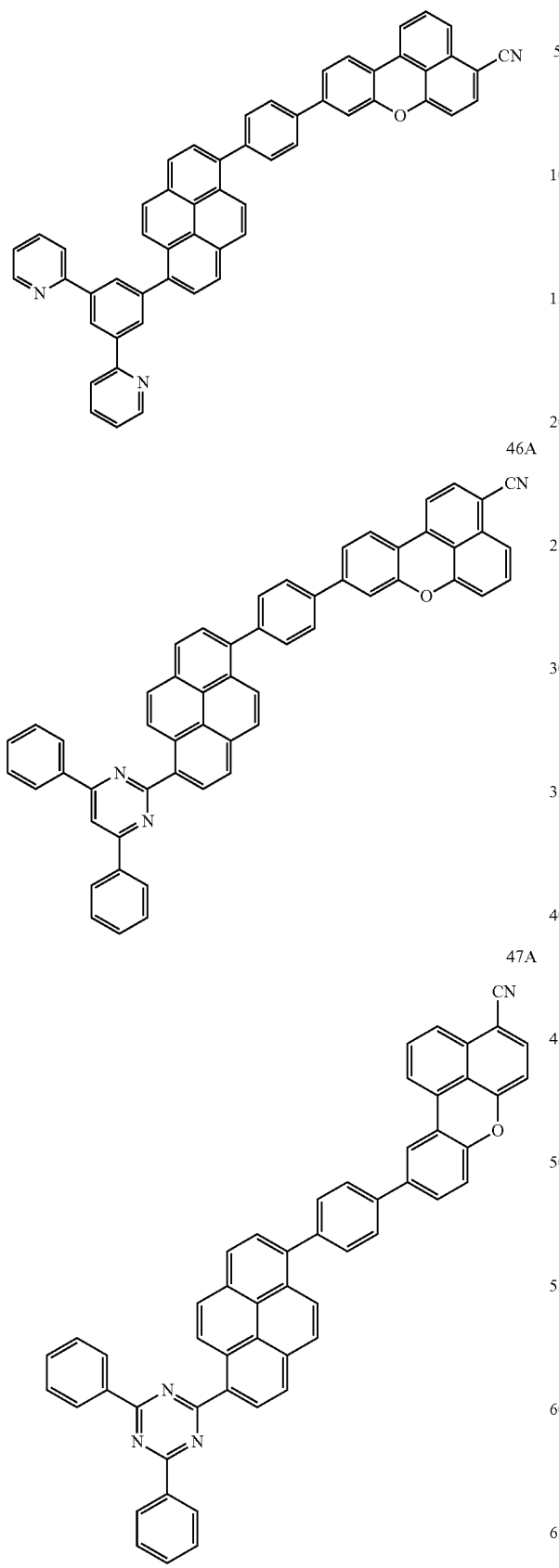
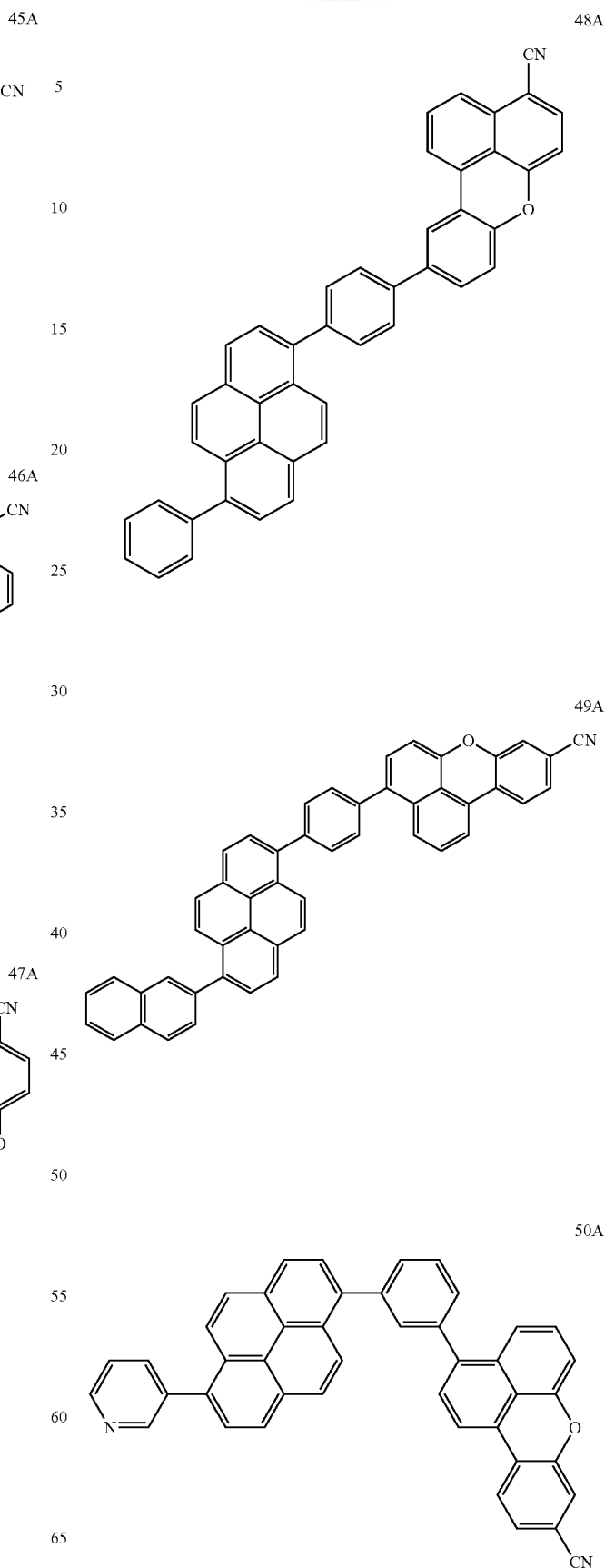

51A
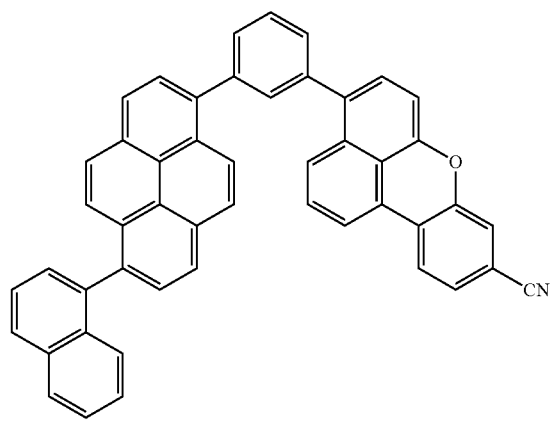
52A
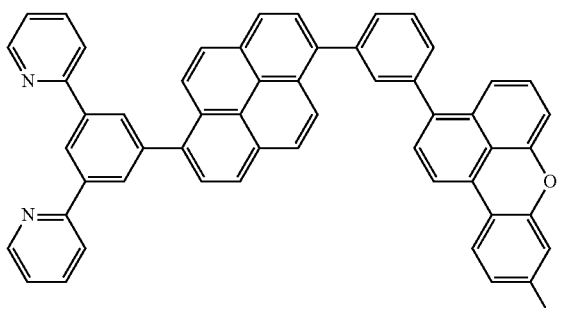
53A
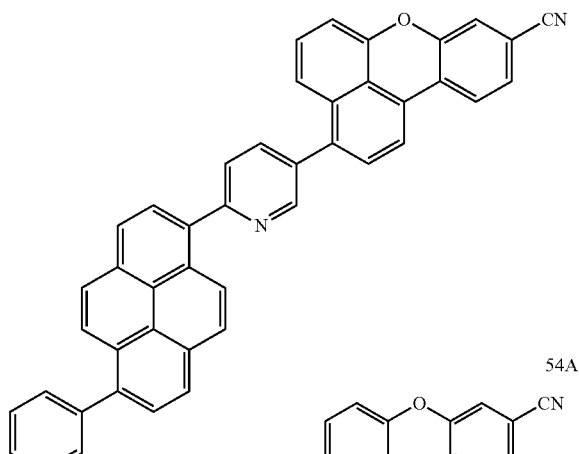
54A
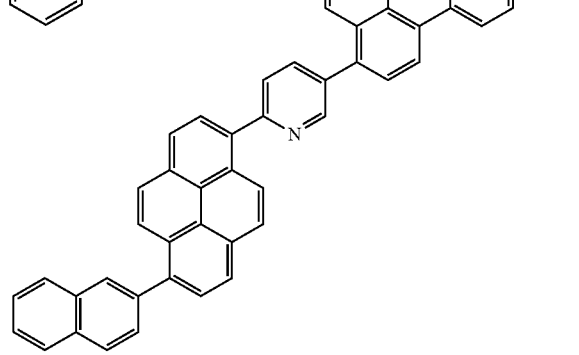
55A
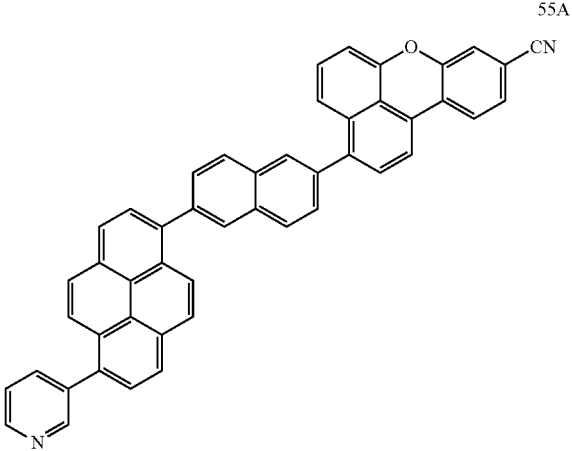
56A
57A
58A
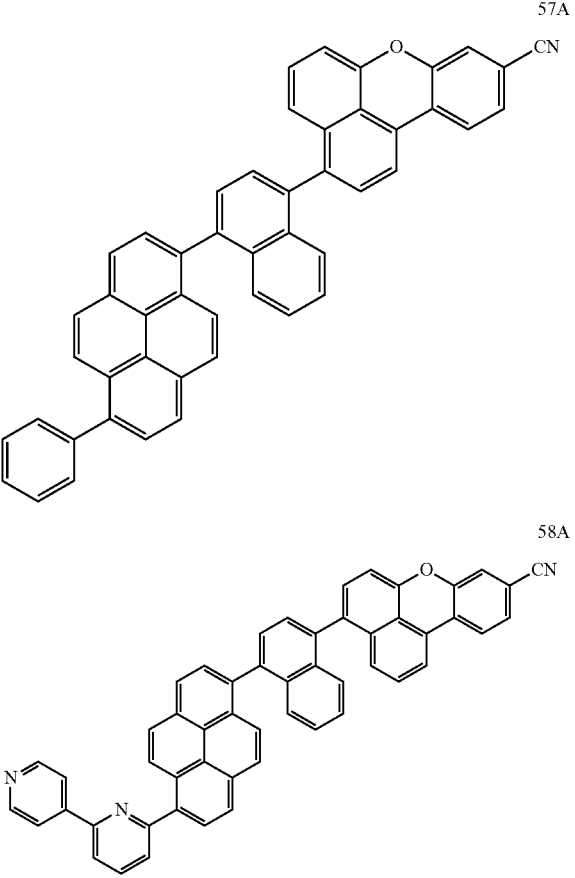

-continued
59A
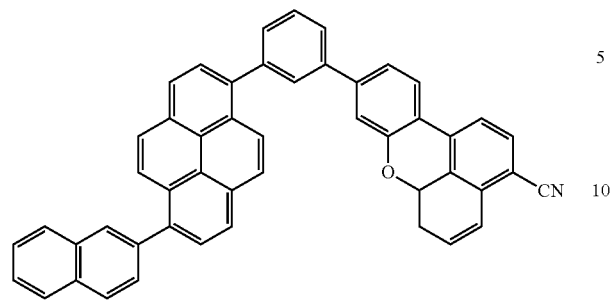
60A
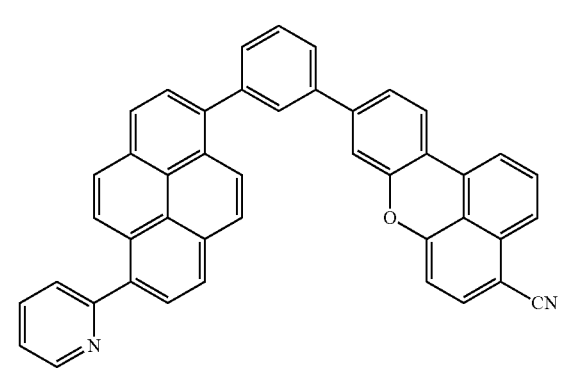
61A
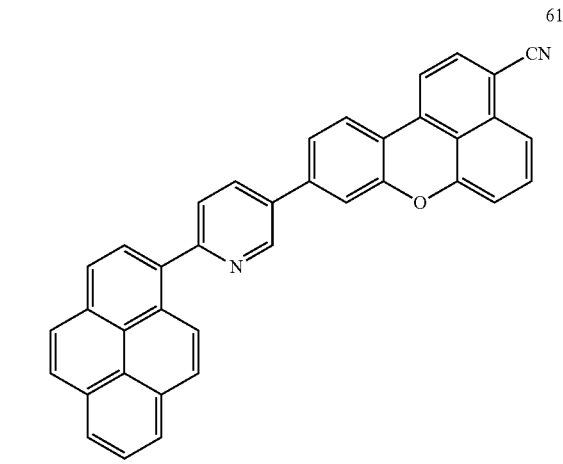
62A
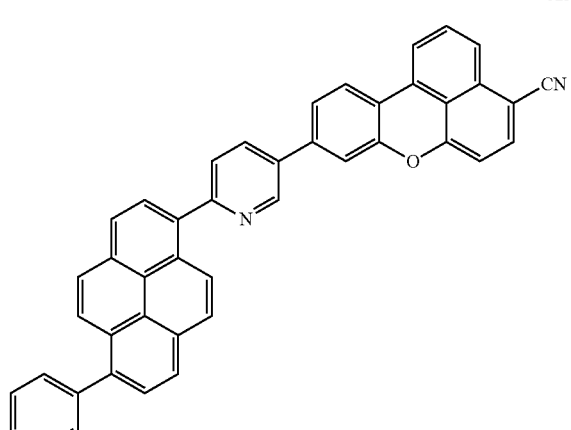
-continued
63A
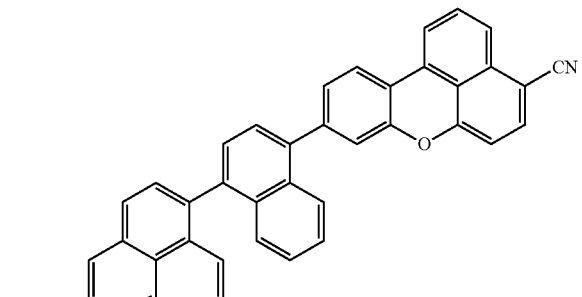
64A
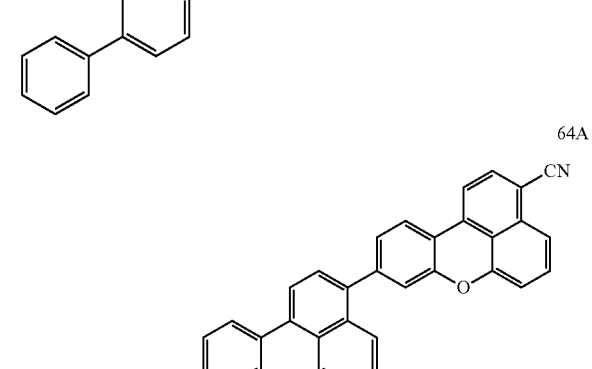
65A
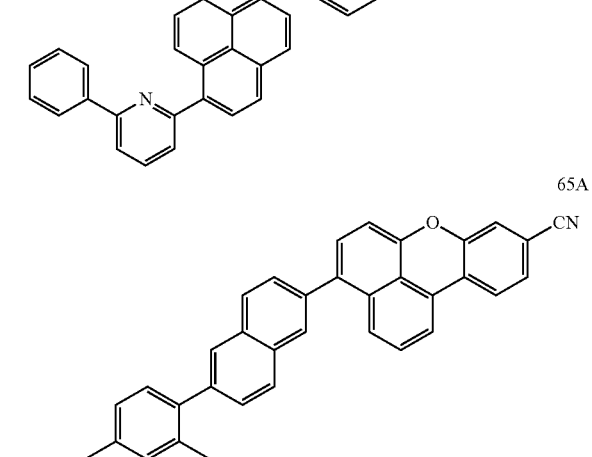
66A
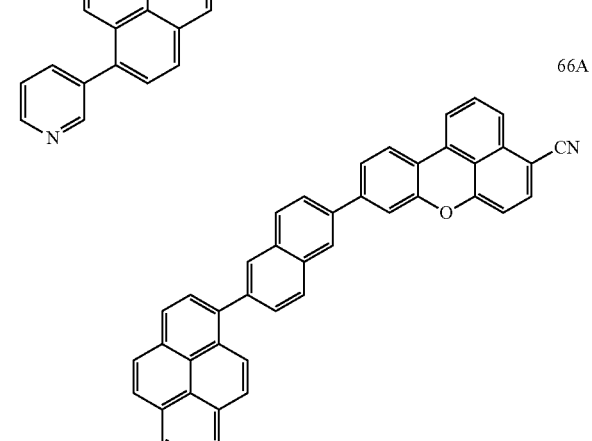
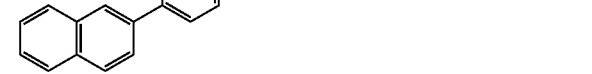

-continued
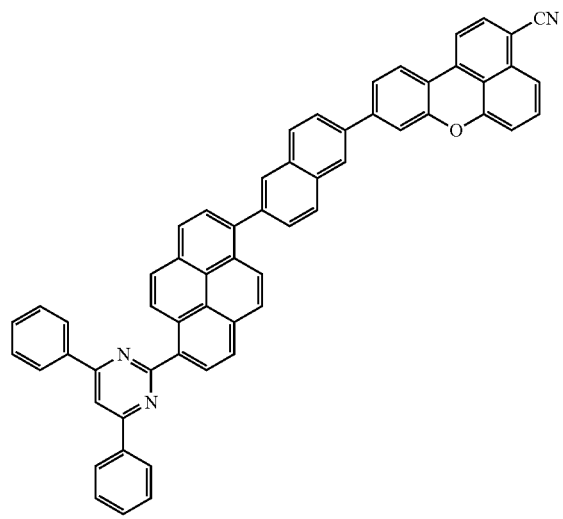
67A
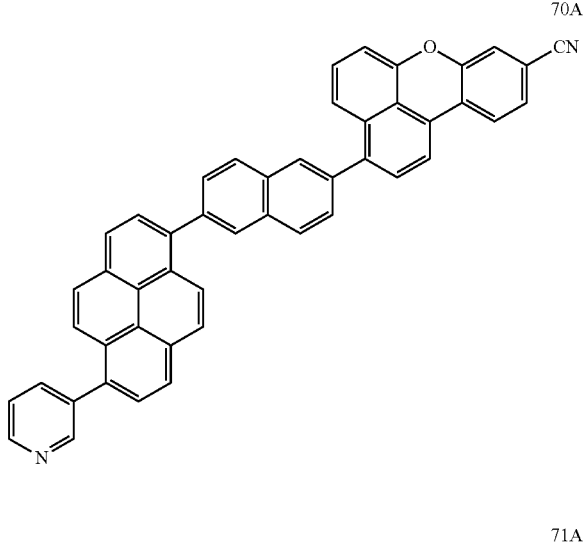
70A
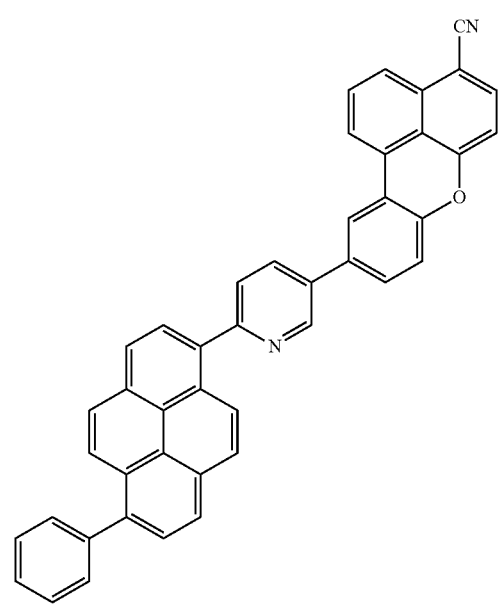
68A
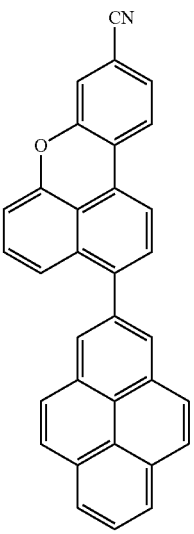
71A
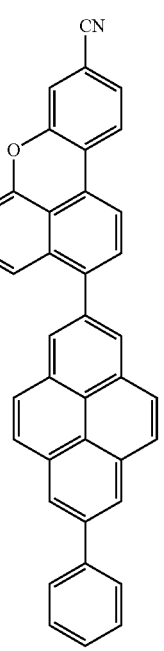
72A
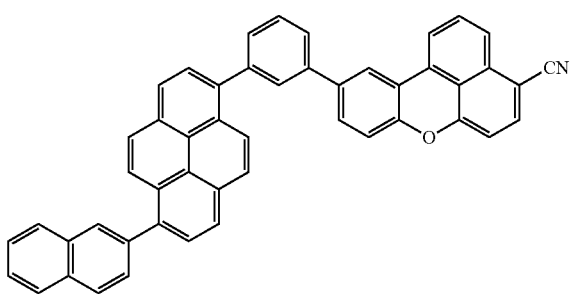
69A 73A
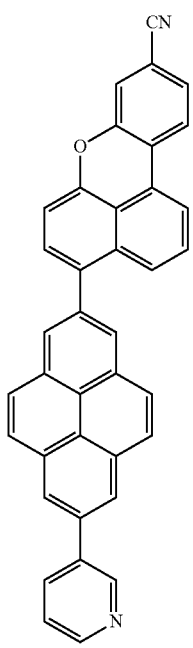
74A
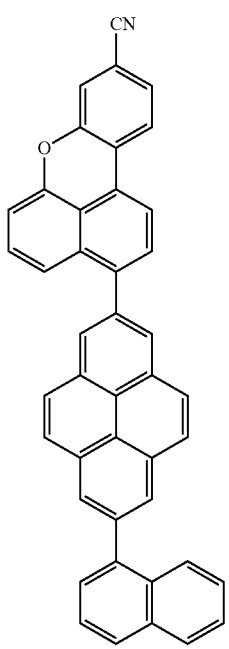
75A
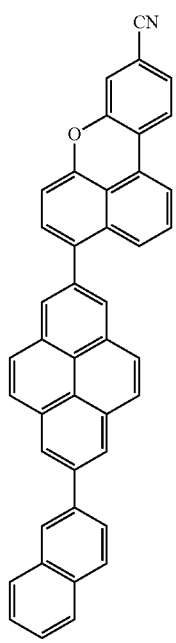
76A
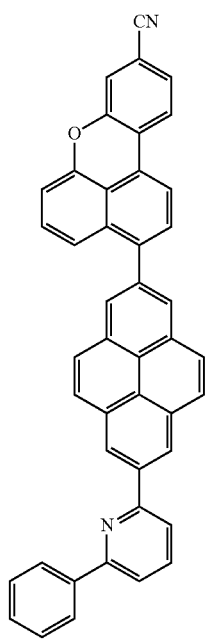

77A
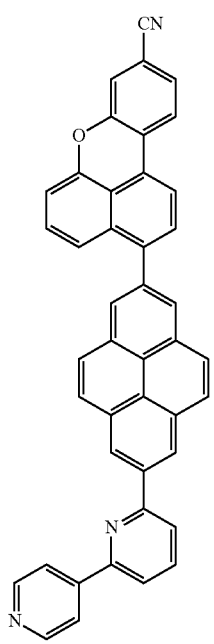
78A
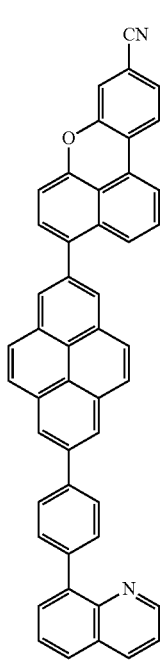
79A
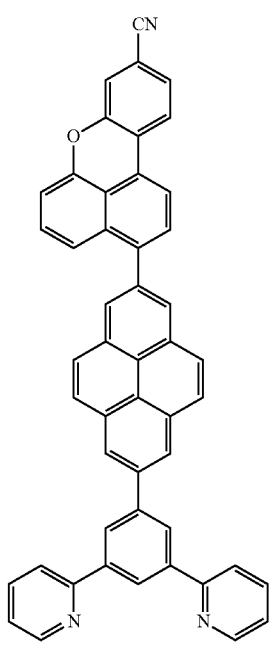
80A
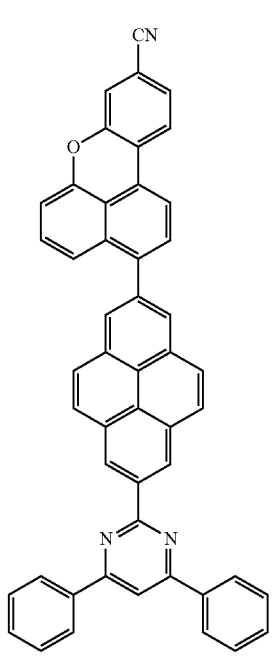

55
-continued
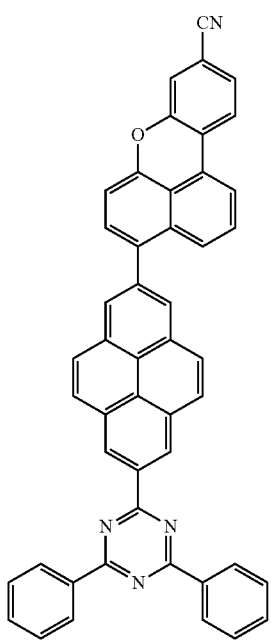
56
-continued
81A
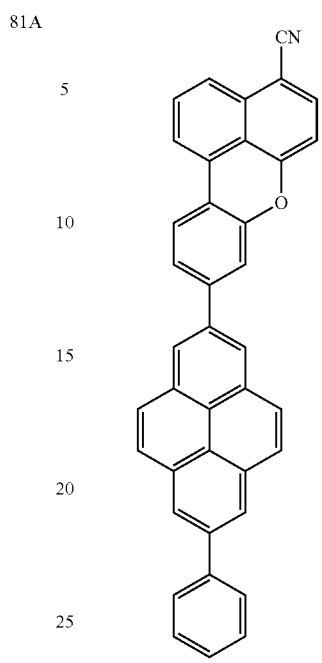
83A
82A
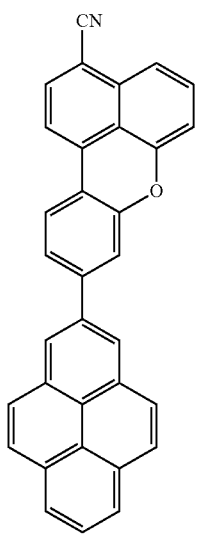
84A
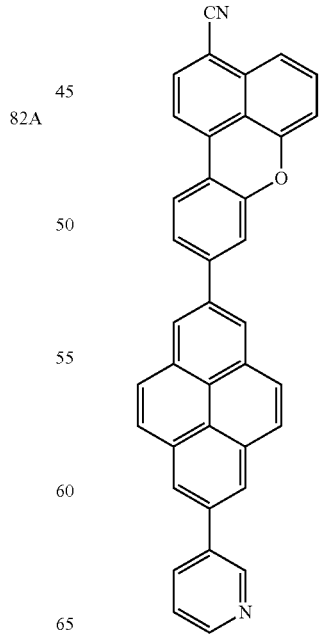

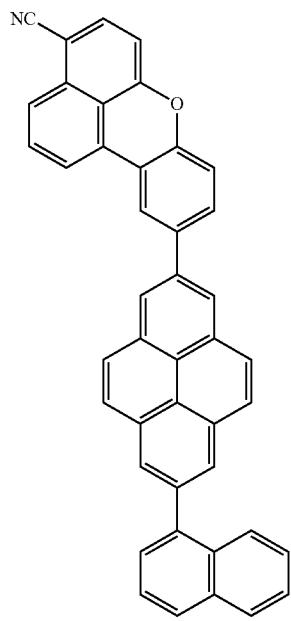
85A
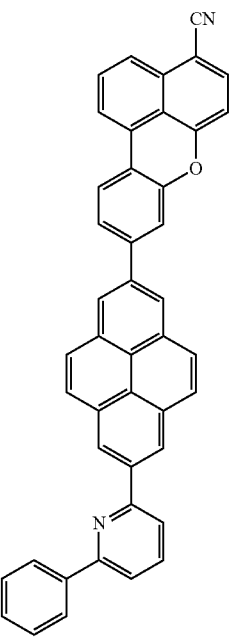
87A
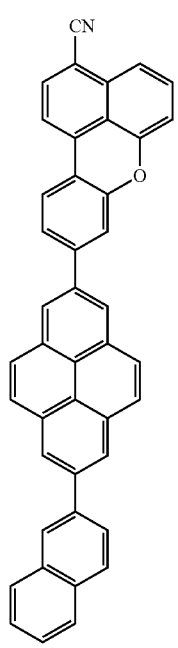
86A
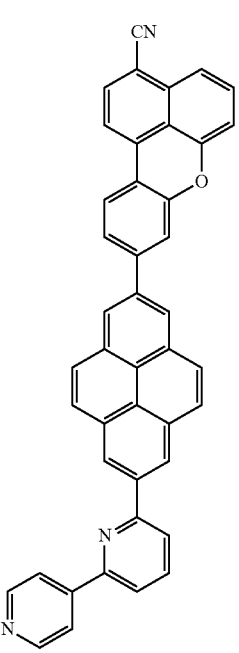
88A

89A
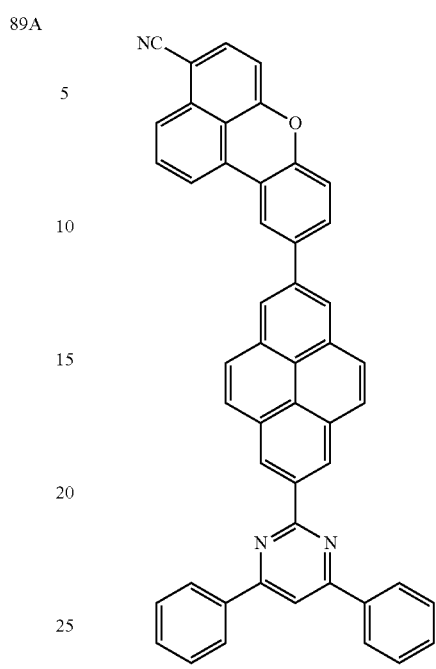
91A
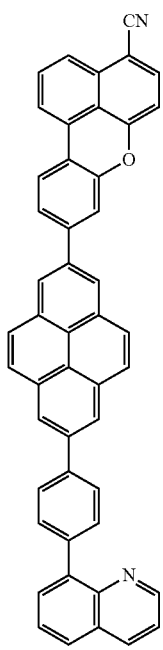
90A
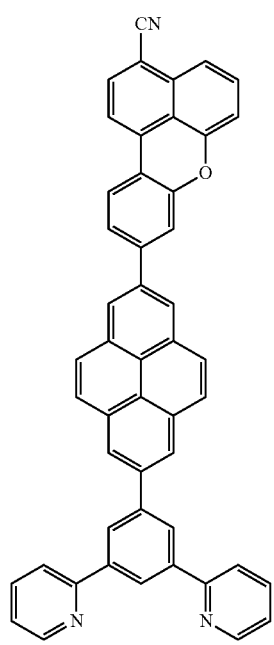
92A
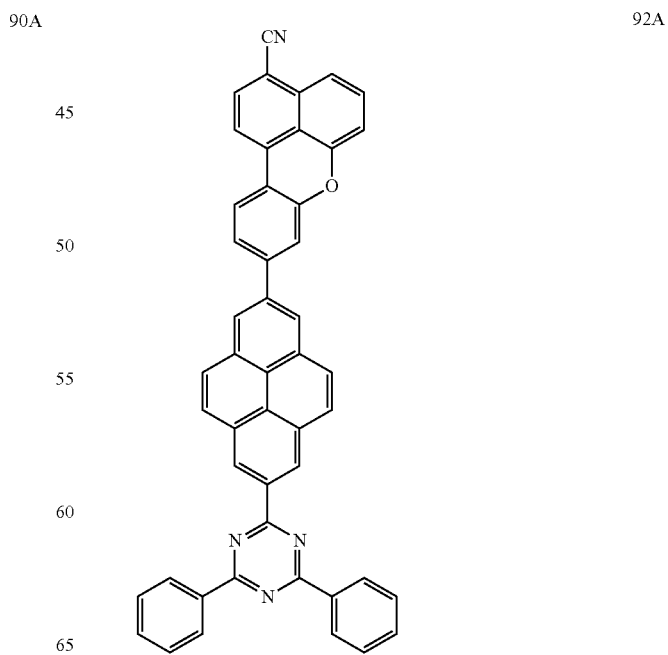

61
-continued
93A
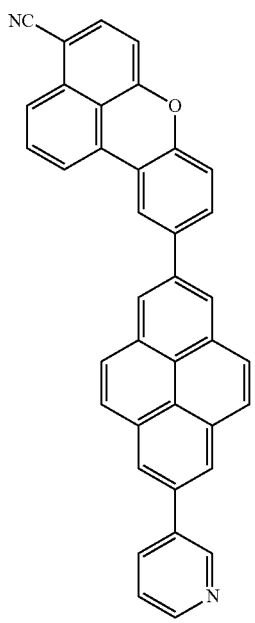
94A
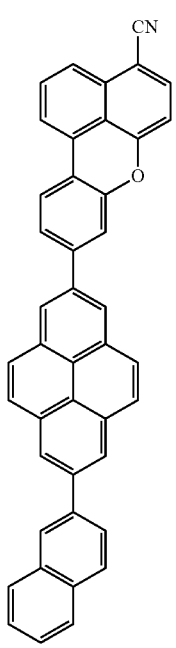
62
-continued
95A
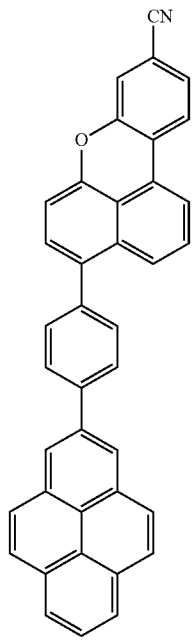
96A
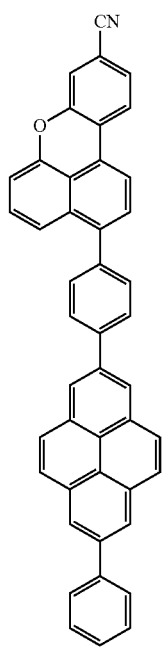

-continued
97A
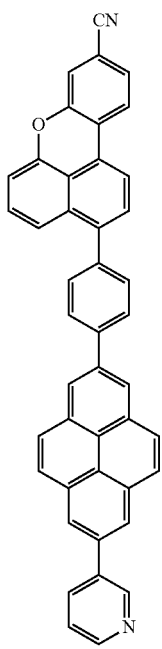
98A
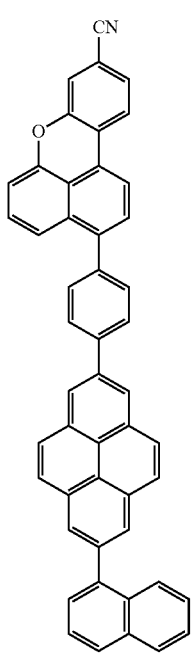
-continued
99A
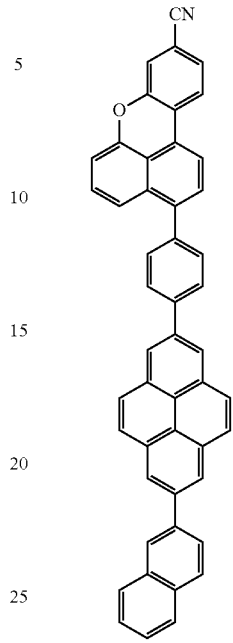
100A
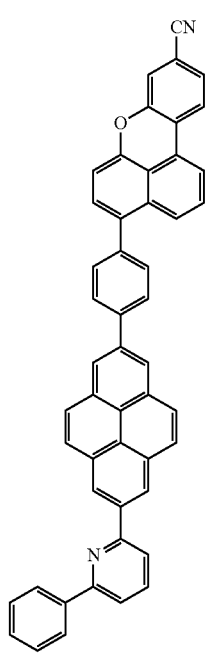

101A
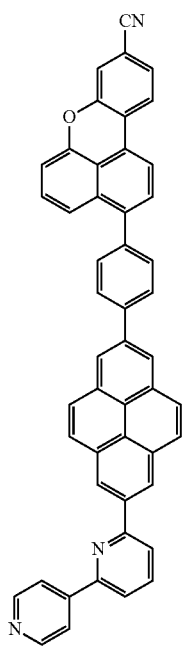
103A
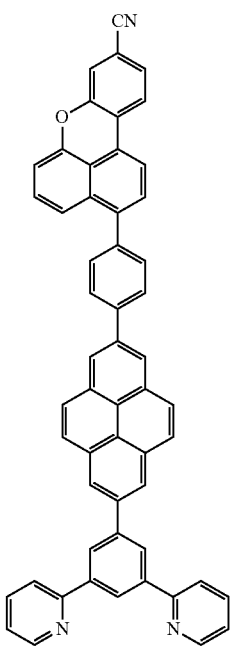
102A
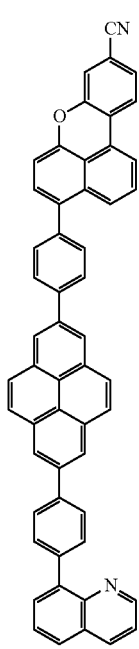
104A
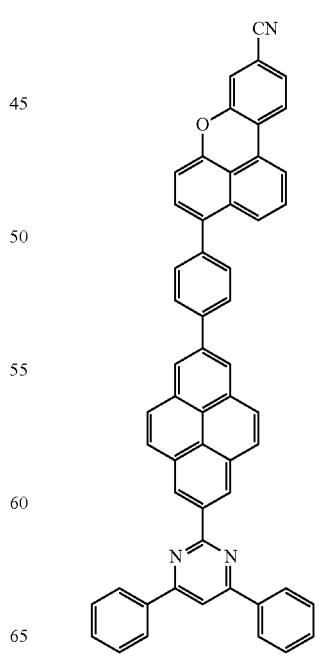

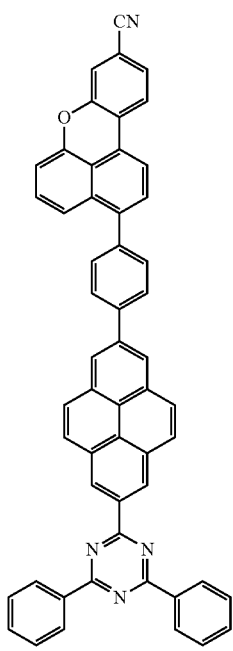 105A
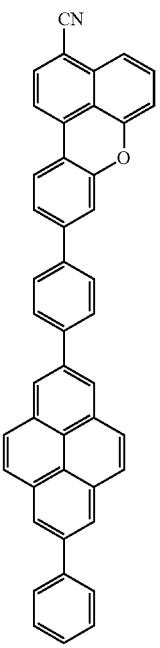 107A
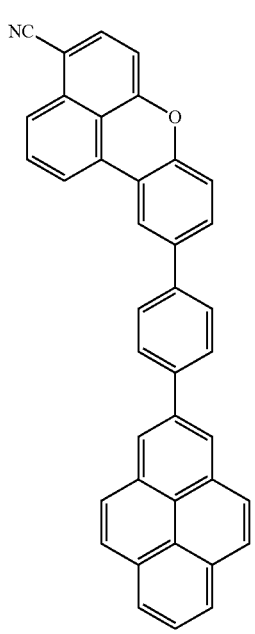 106A
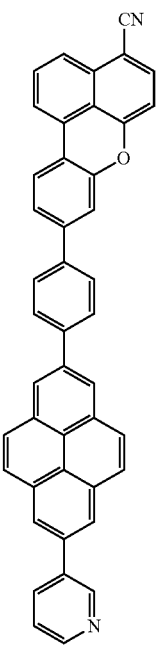 108A

-continued
109A
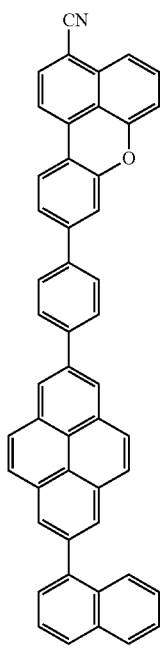
111A
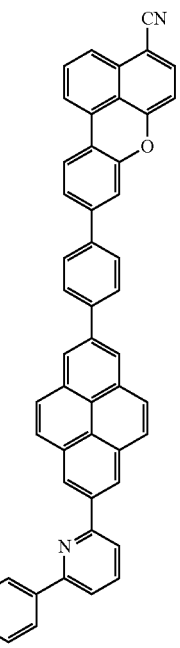
110A
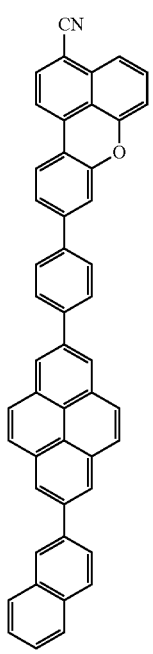
112A
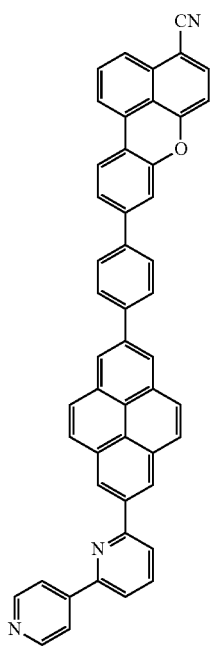

-continued
113A 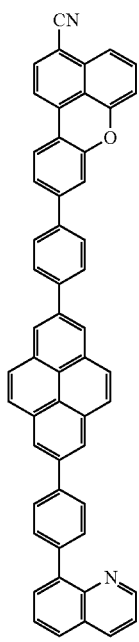
115A 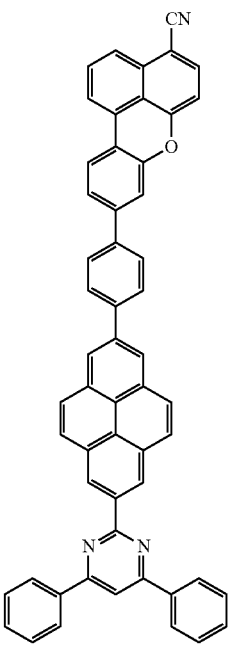
114A 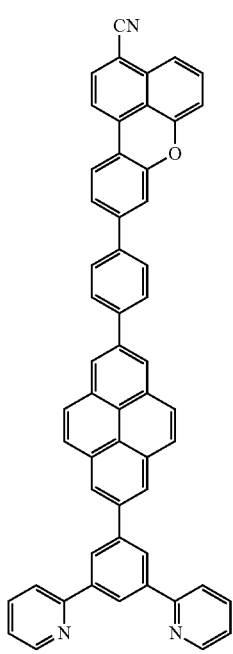
116A 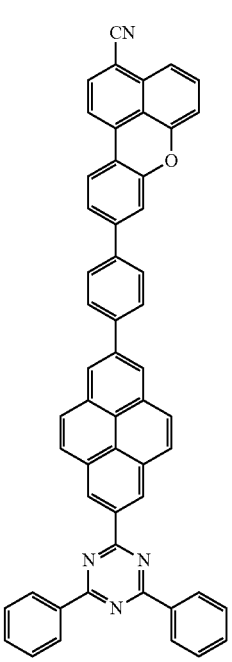

117A 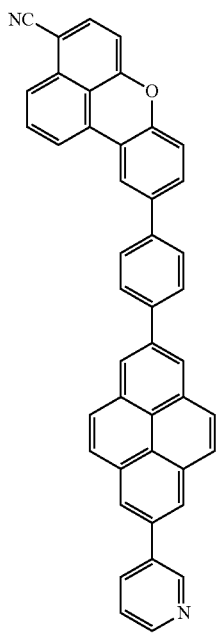
118A 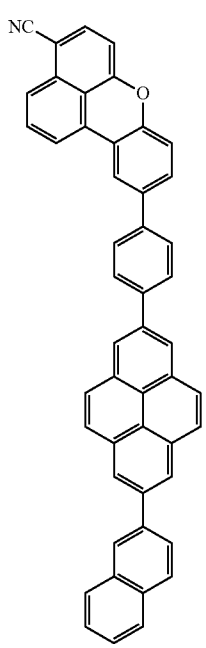
119A 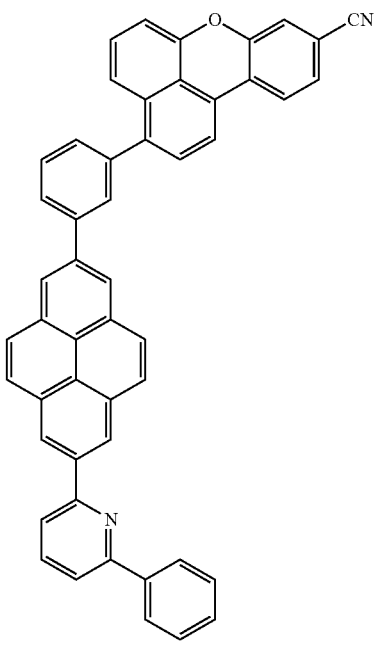
120A 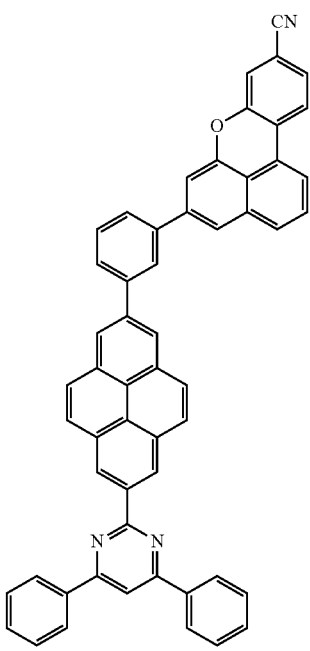

121A
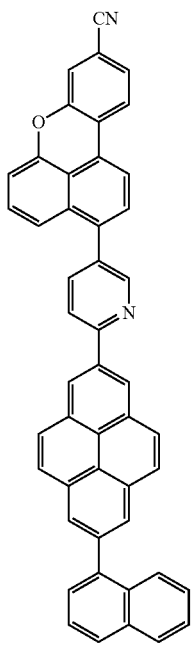
122A
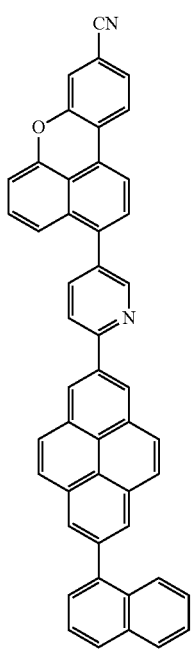
123A
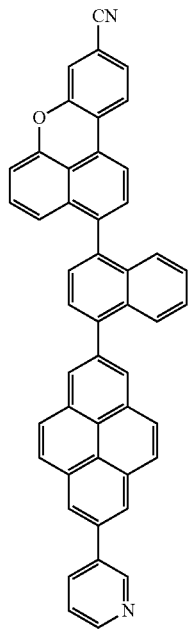
124A
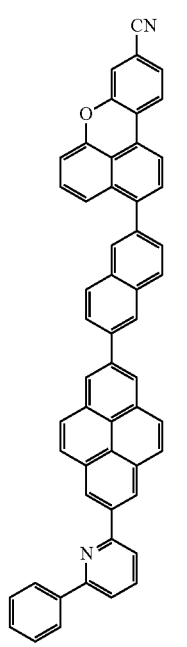

77 -continued
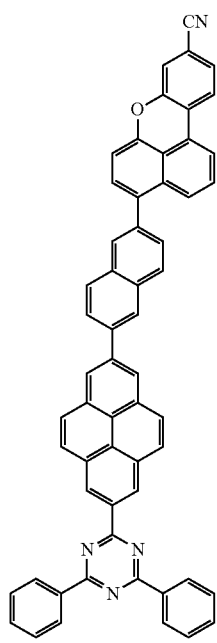
125A
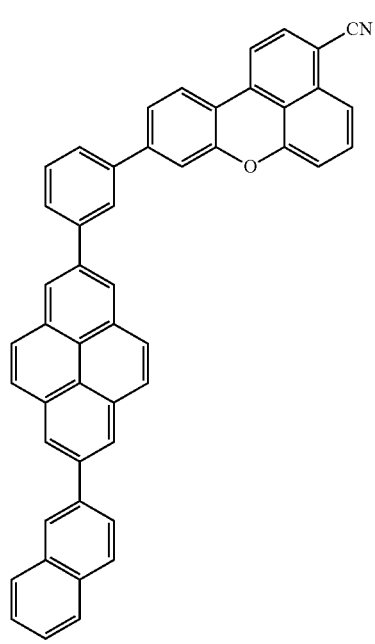
126A
78 -continued
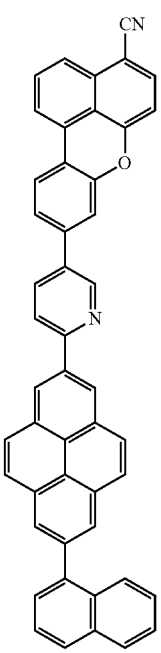
127A
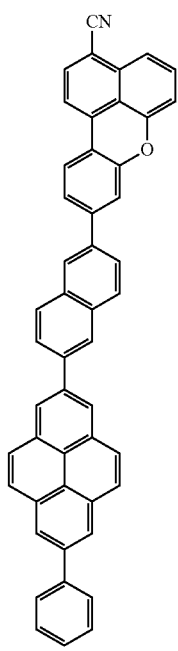
128A 129A
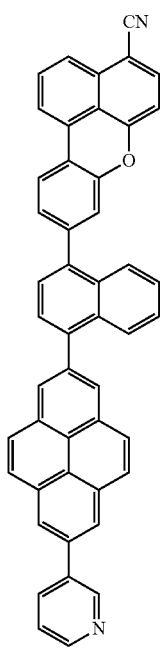
131A
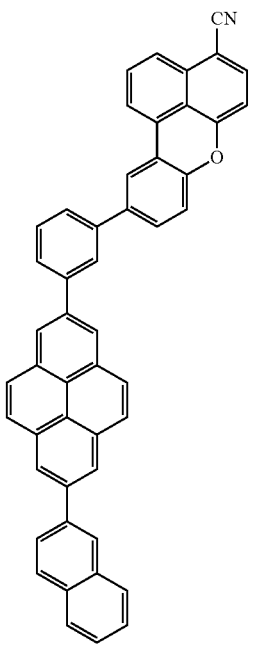
130A
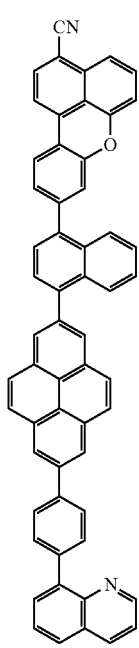
132A
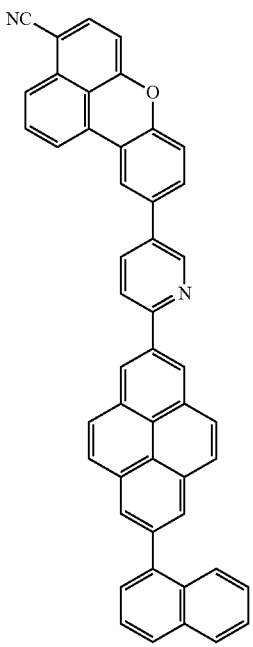

81
-continued
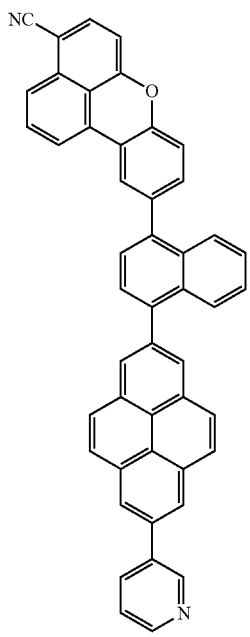
133A
1B
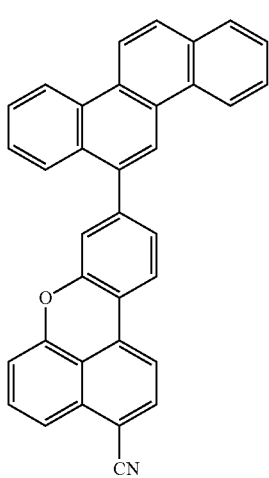
82
-continued
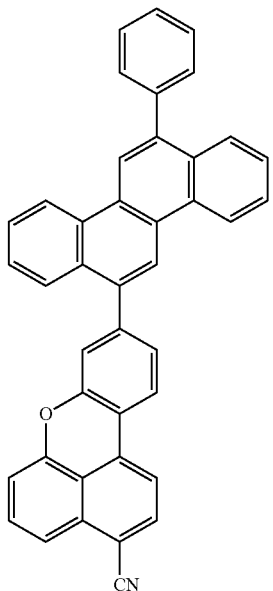
2B
3B
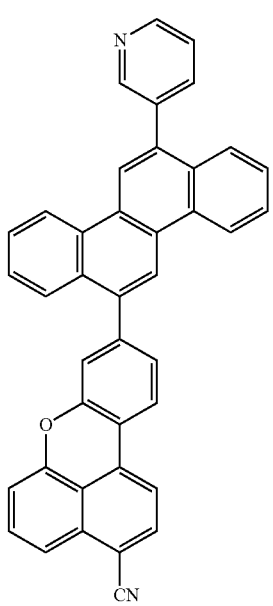

83
-continued
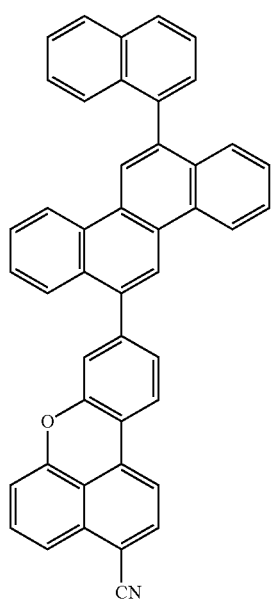
4B
84
-continued
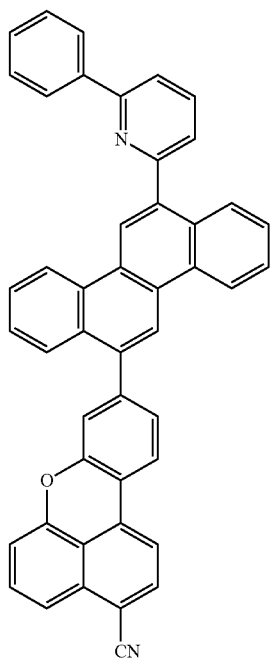
6B
5B
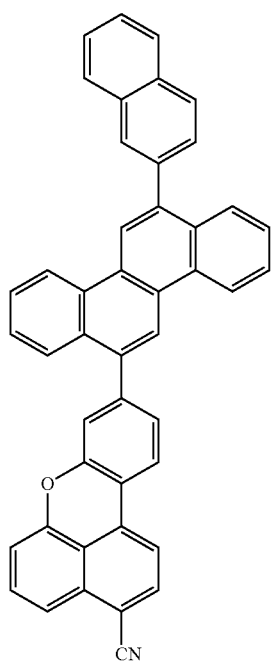
7B
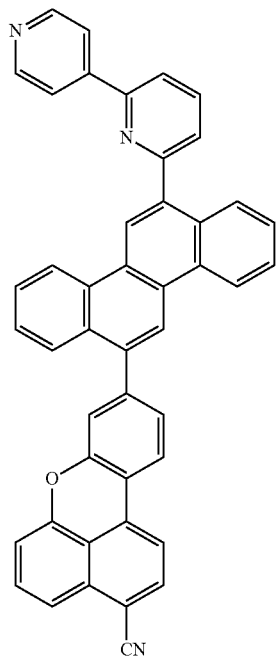

85
-continued
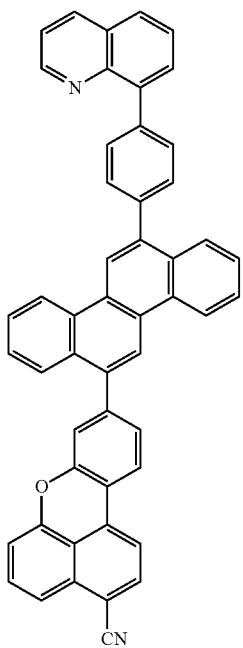
8B
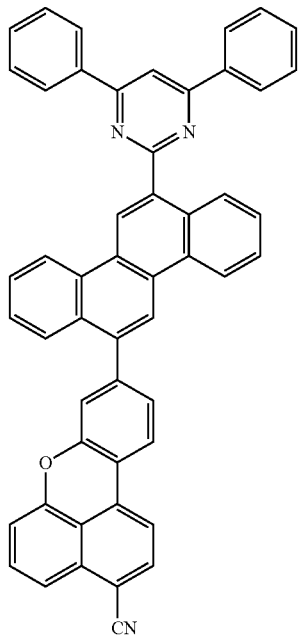
86
-continued
10B
9B
11B
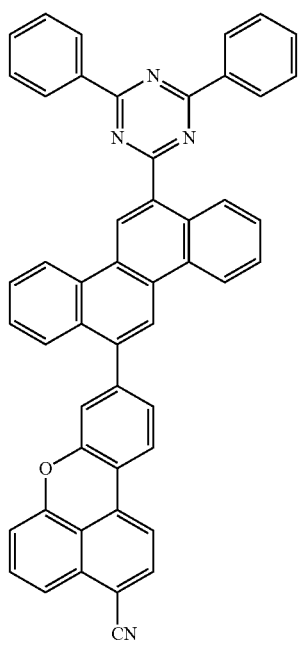

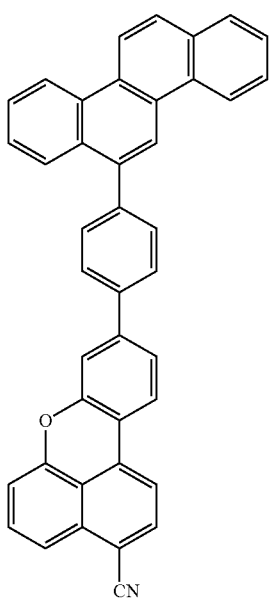
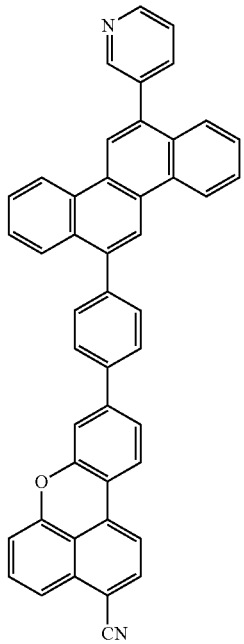
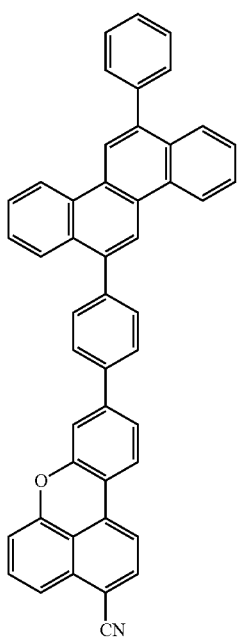
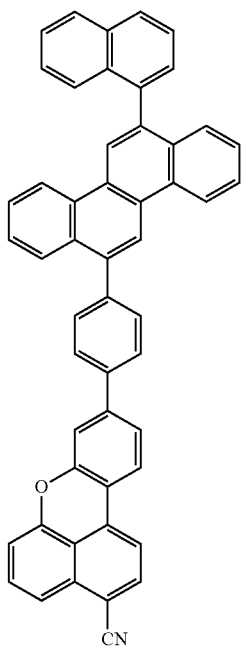

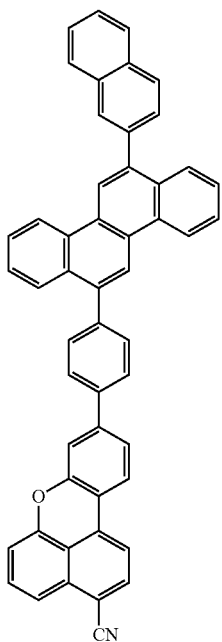
16B
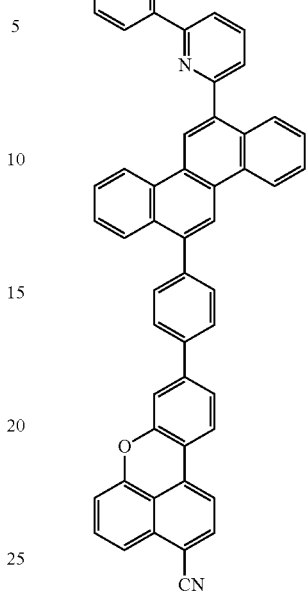
17B
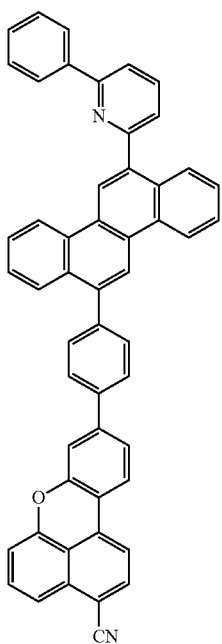
18B
19B

20B
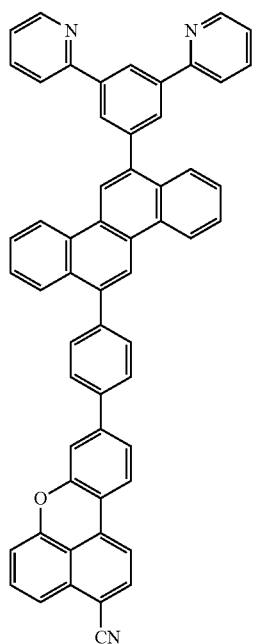
22B
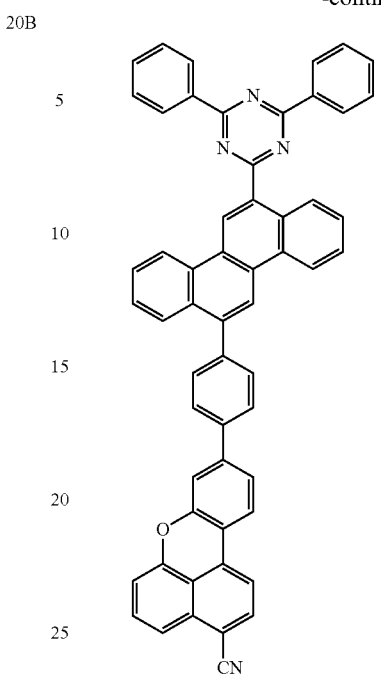
21B
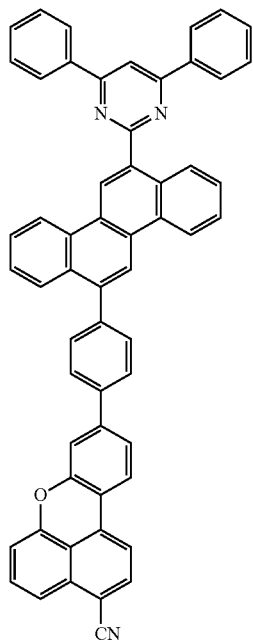
23B
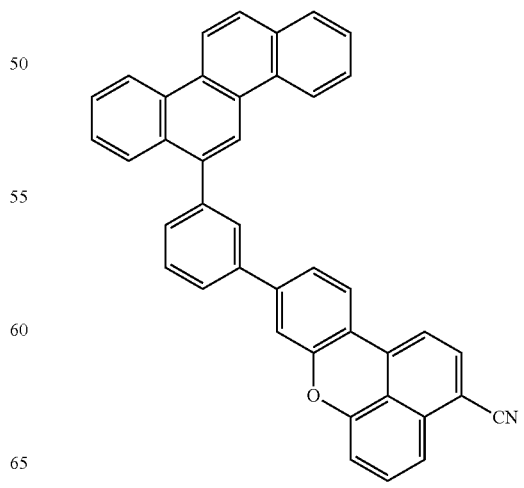

24B
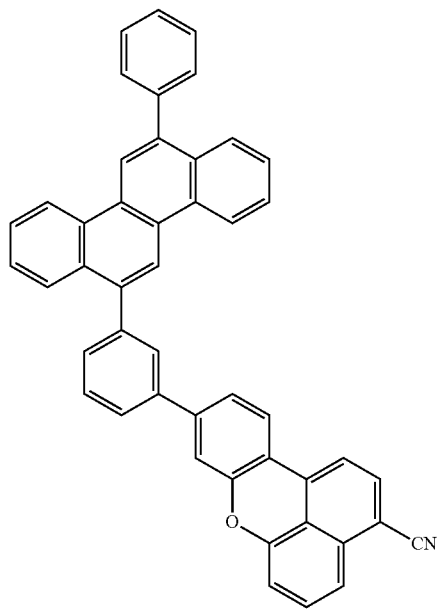
25B
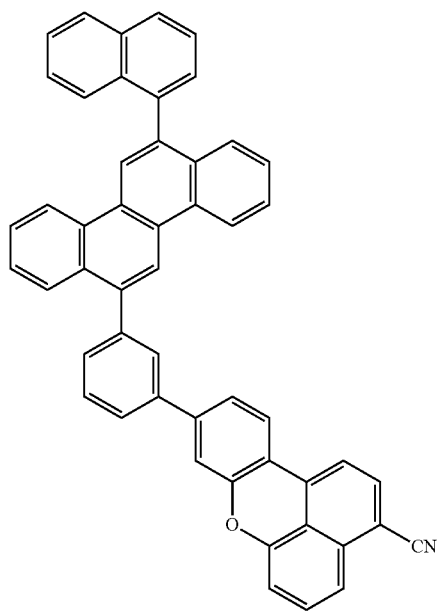
26B
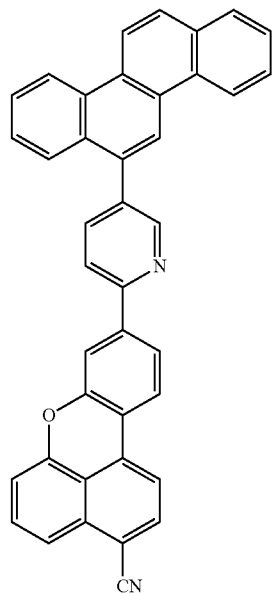
27B
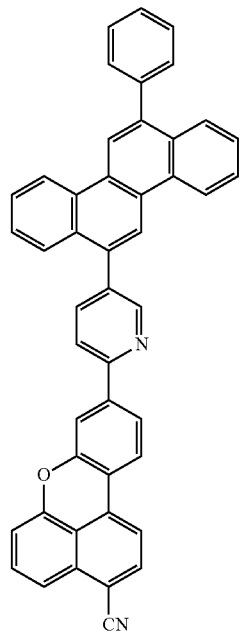

28B
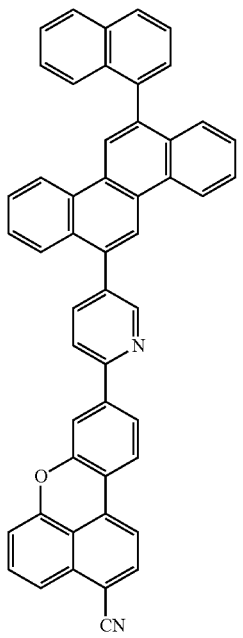
30B
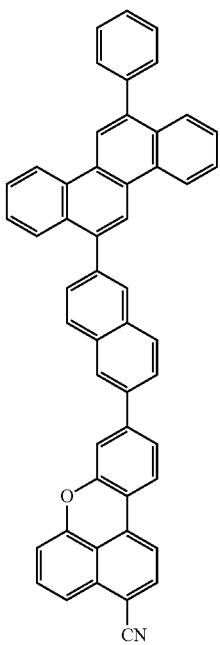
29B
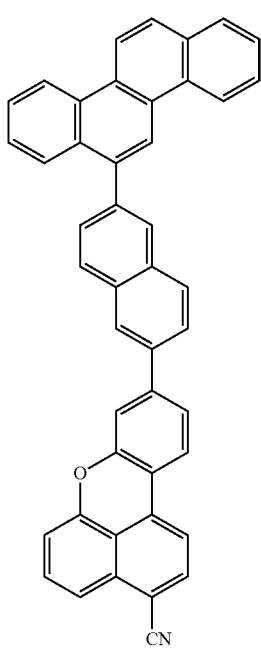
31B
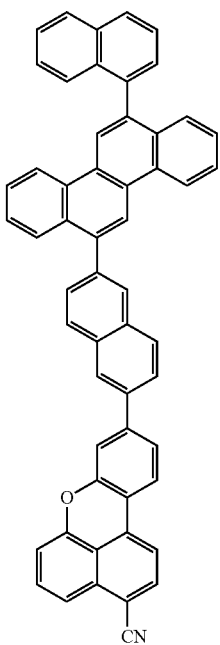

97
-continued
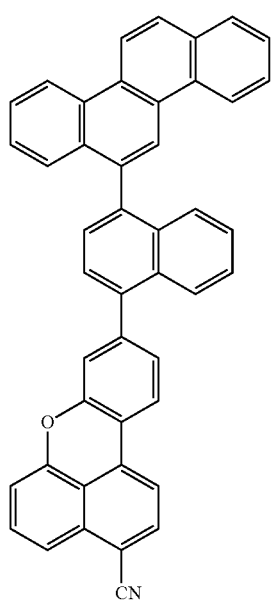
98
-continued
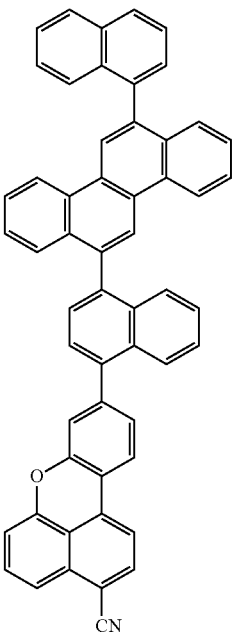
32B
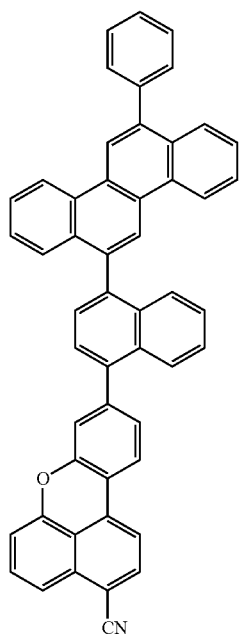
33B
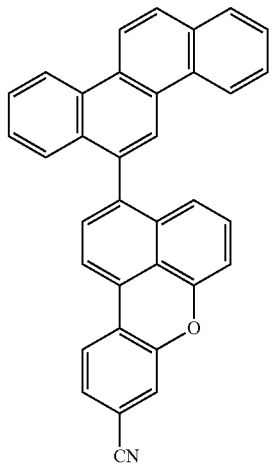
35B 99
-continued
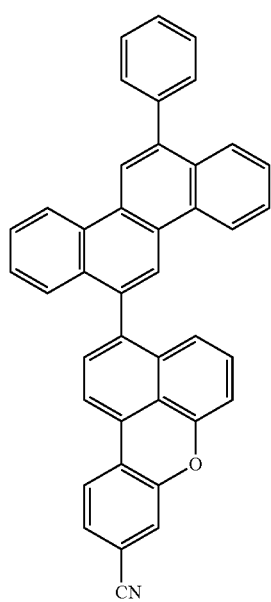
36B
100
-continued
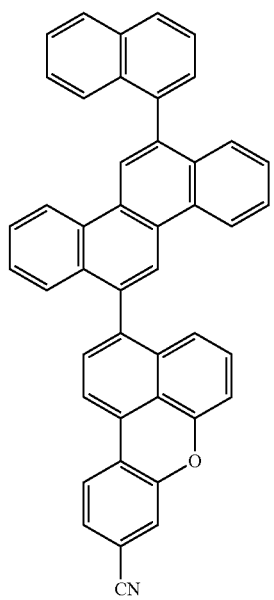
38B
37B
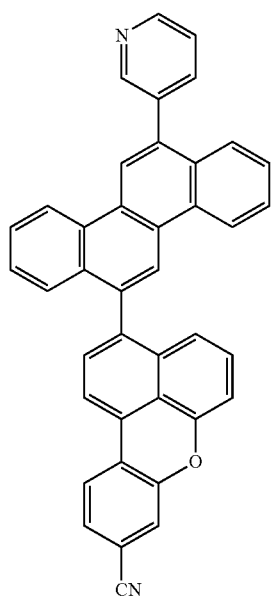
39B
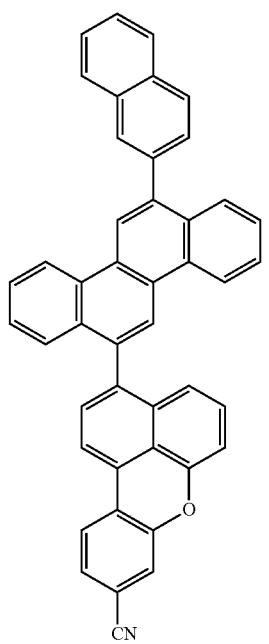

101
-continued
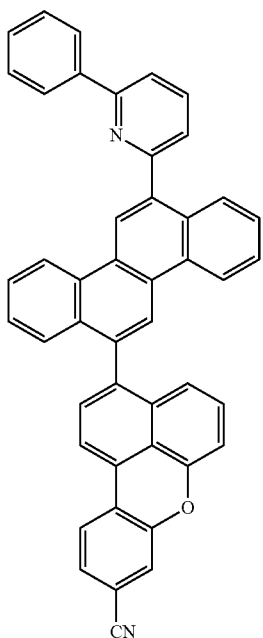
40B
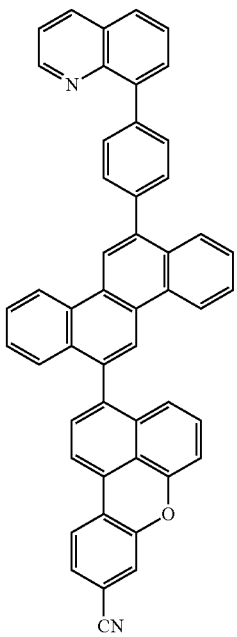
102
-continued
42B
41B
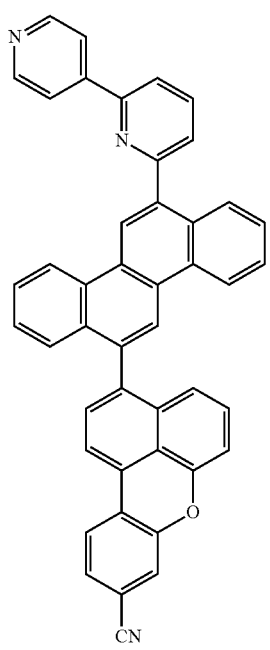
43B
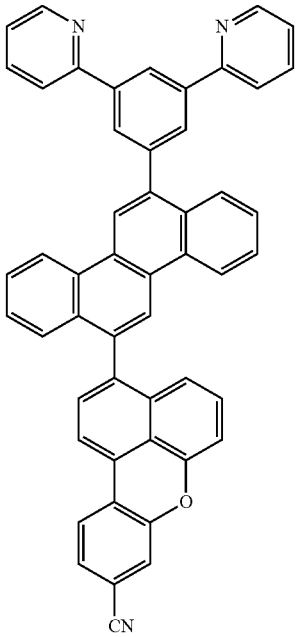

103
-continued
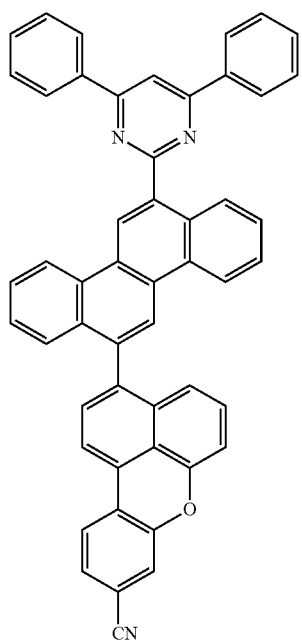
104
-continued
44B
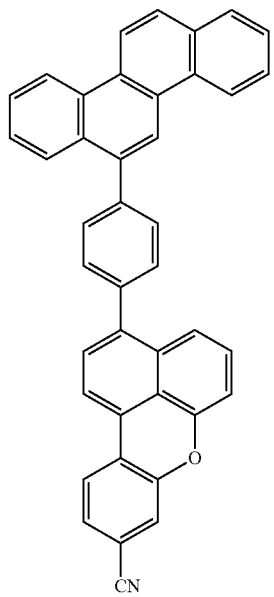
45B
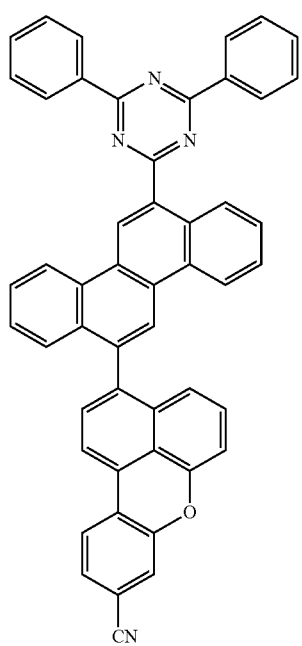
46B
47B
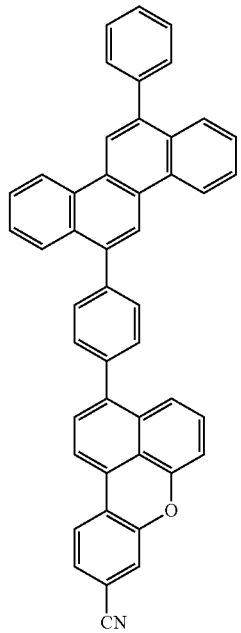

105
-continued
48B
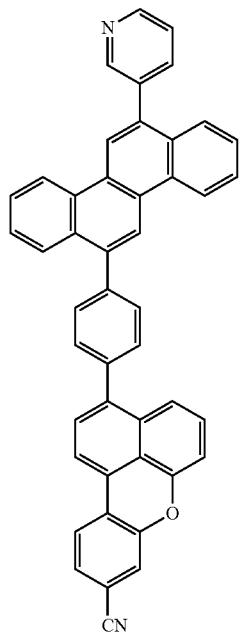
49B
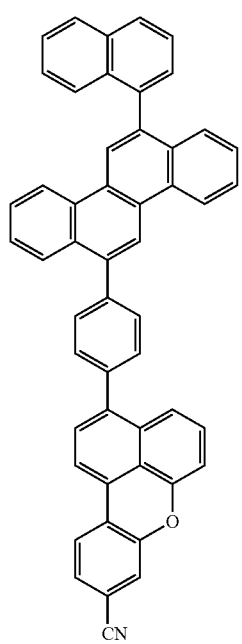
106
-continued
50B
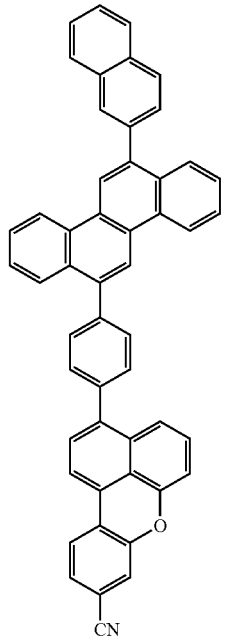
51B
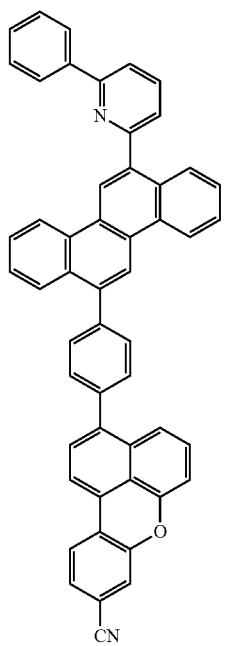

107
-continued
52B
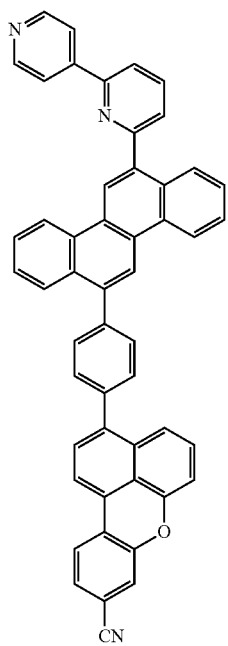
108
-continued
54B
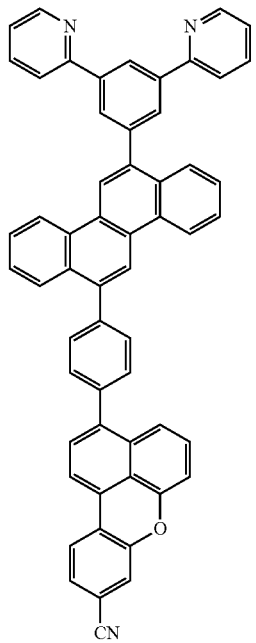
53B
55B
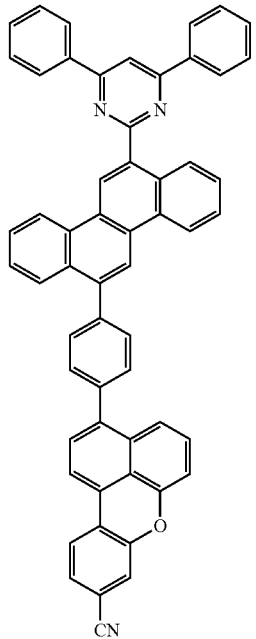

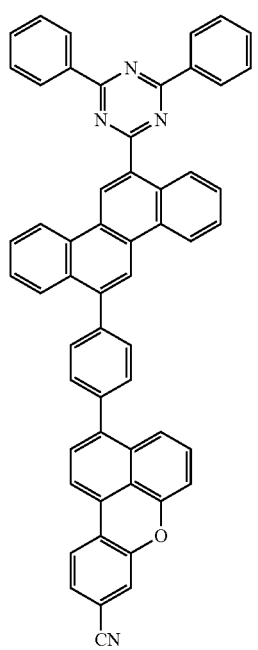
56B
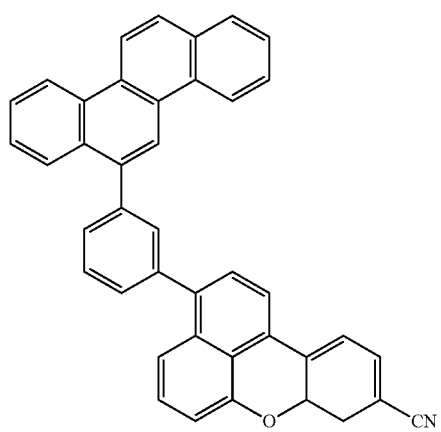
57B
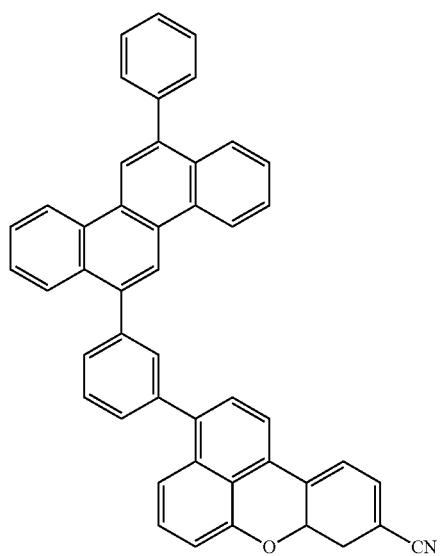
58B
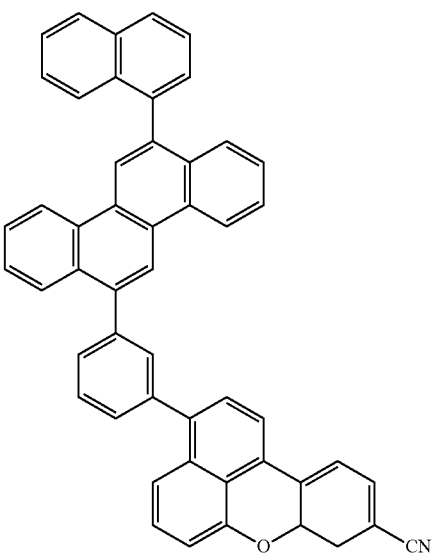
59B
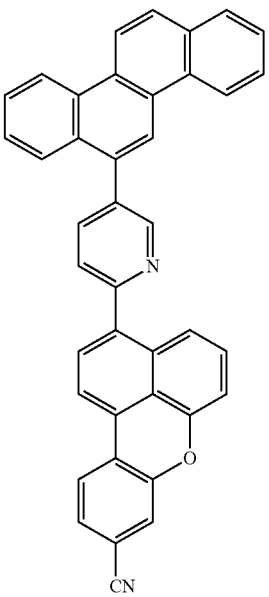
60B

111
-continued
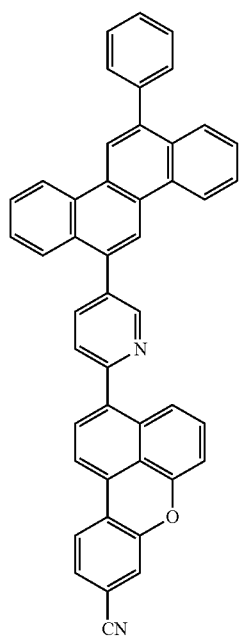
61B
112
-continued
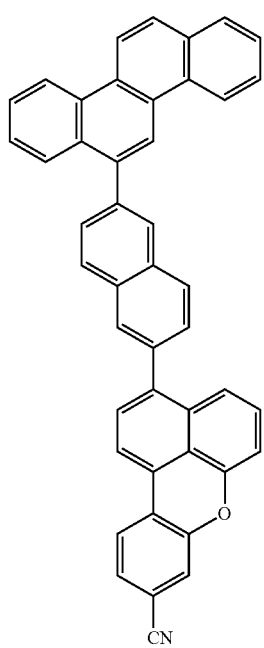
63B
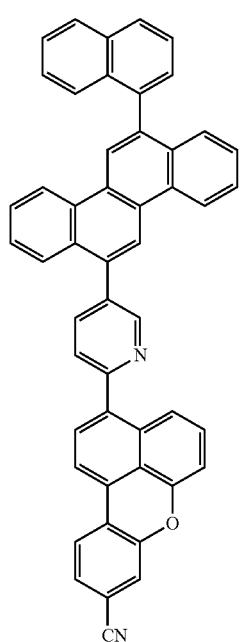
62B
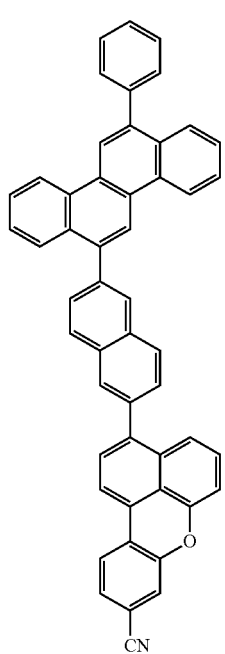
64B 113
-continued
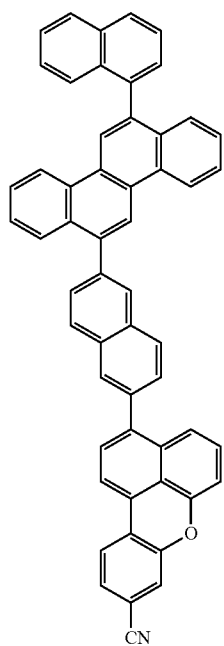
114
-continued
65B
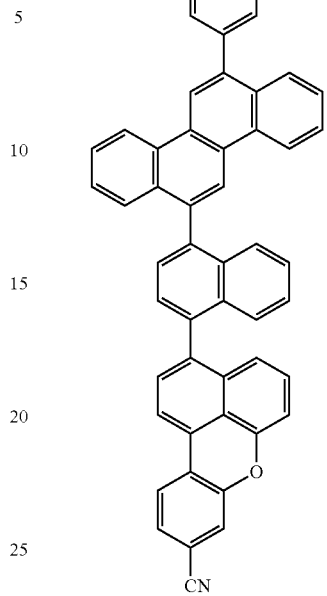
67B
66B
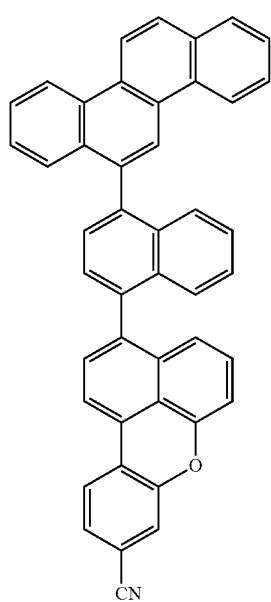
68B
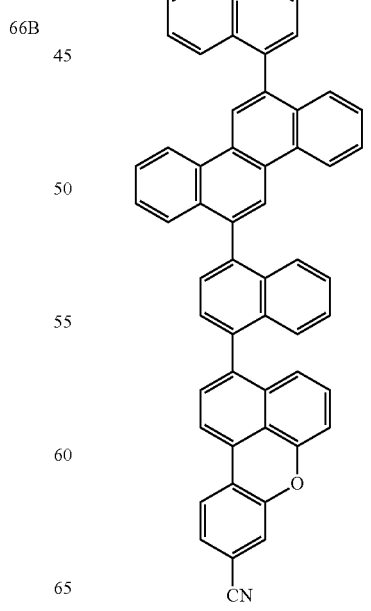

115
-continued
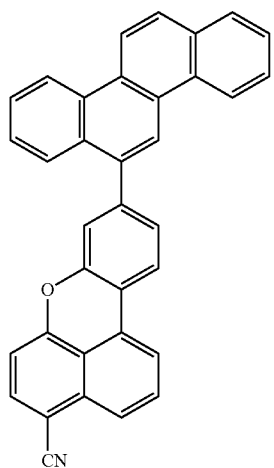
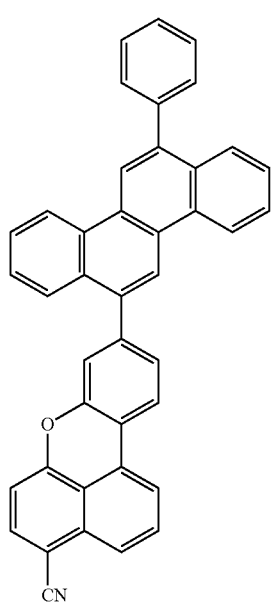
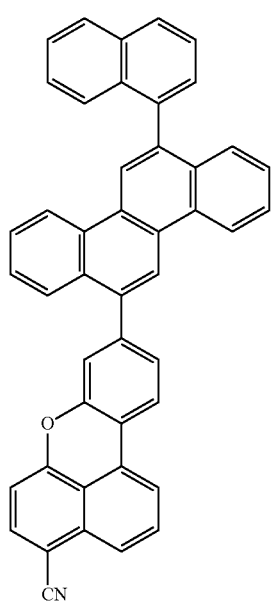
116
-continued
69B
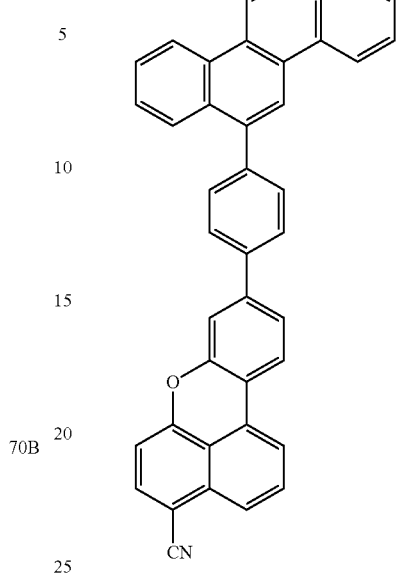
70B
71B
73B
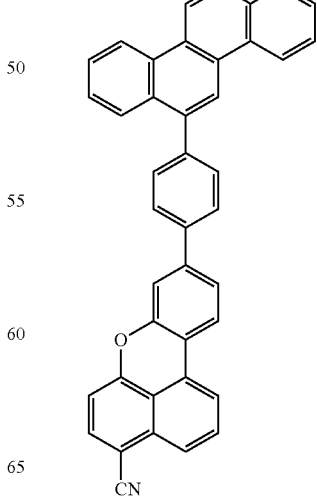
72B 117
-continued
74B
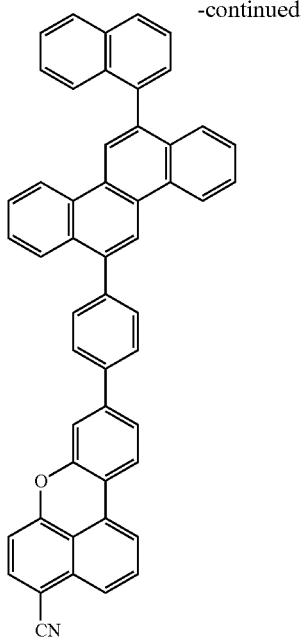
75B
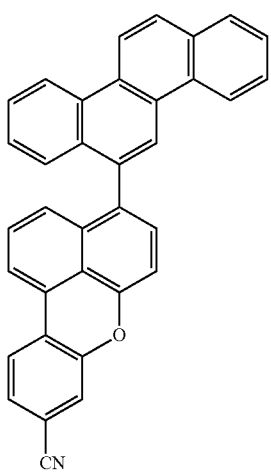
76B
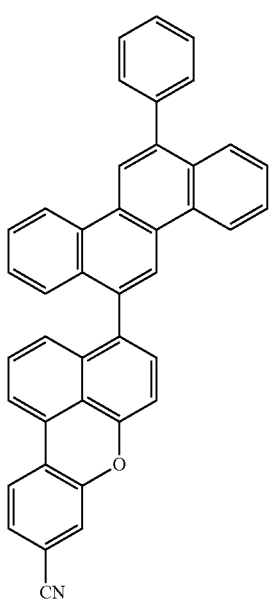
118
-continued
77B
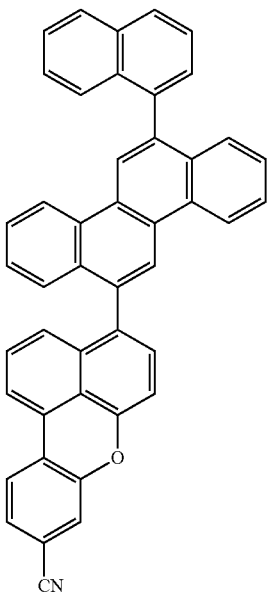
78B
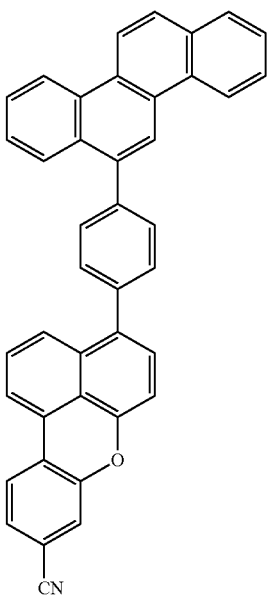

-continued
79B
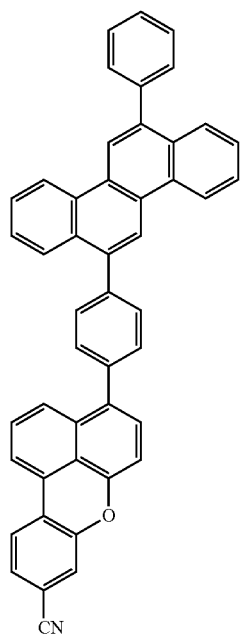
80B
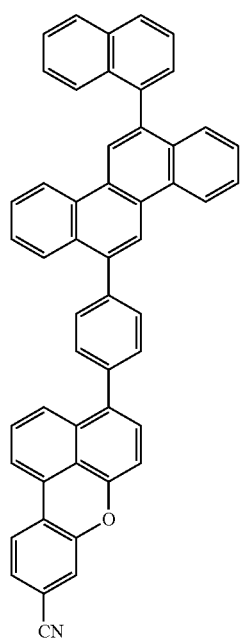
-continued
81B
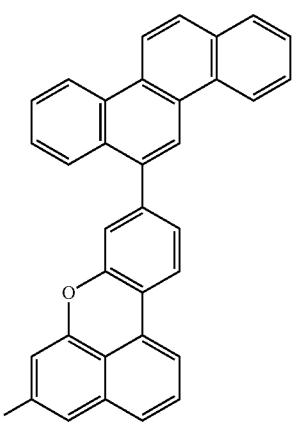
82B
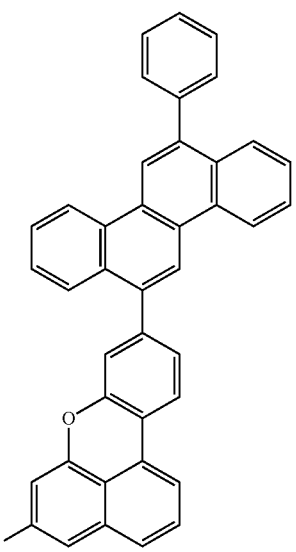
83B
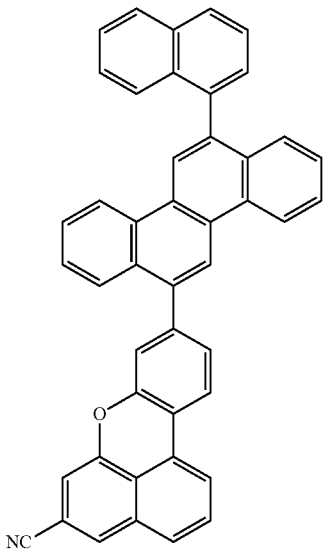

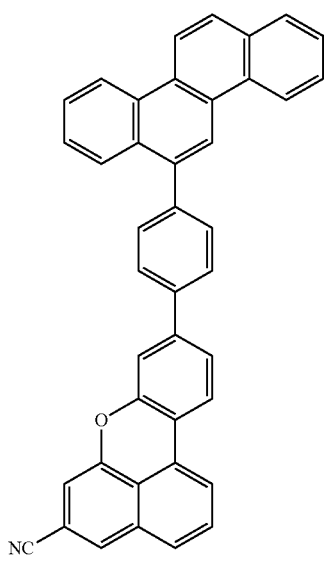
84B
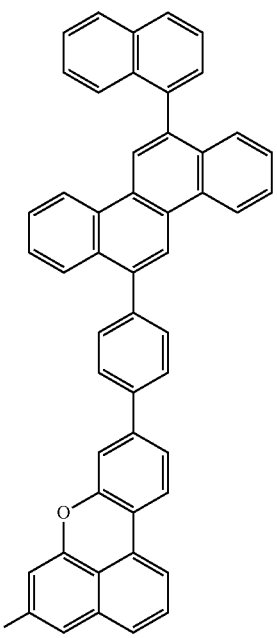
86B
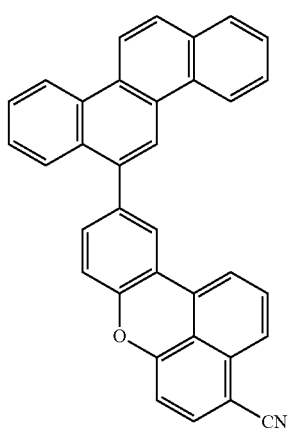
87B
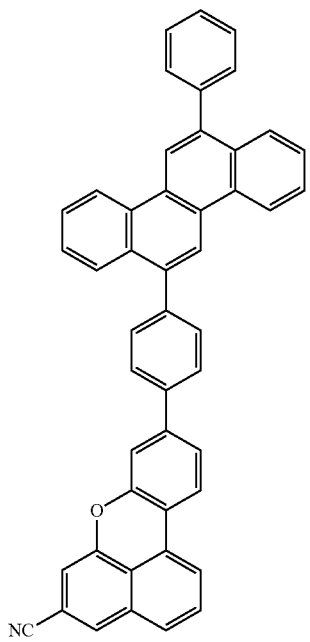
85B
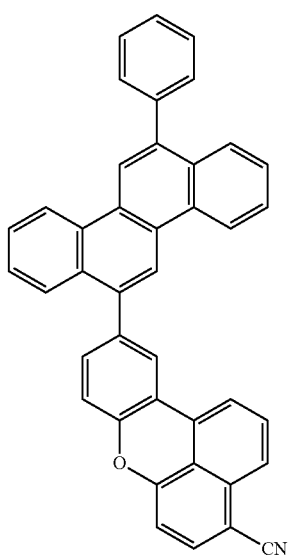
88B

89B 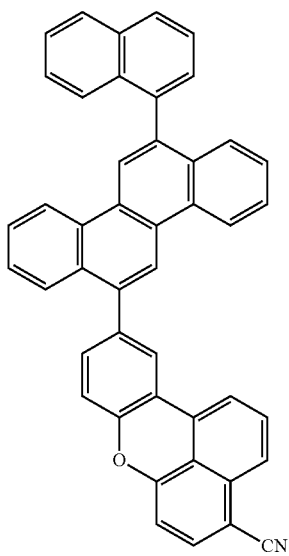

90B 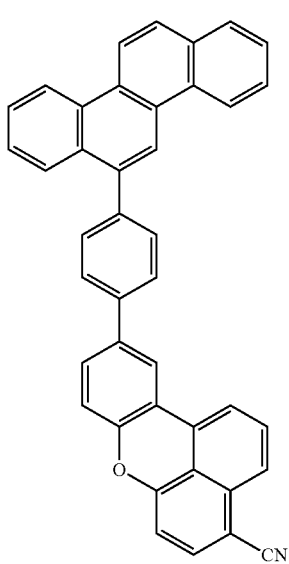

91B 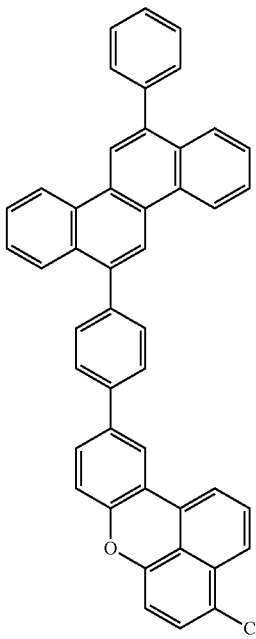

92B 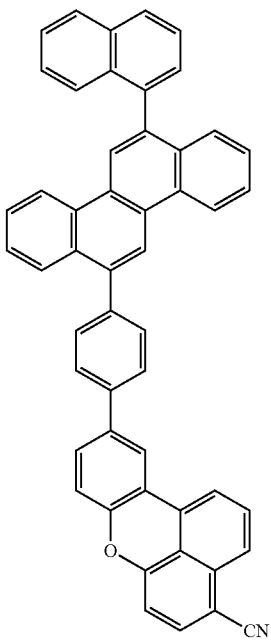

At least one of $R_1$ to $R_{10}$ in Formula 1A may be a group of Formula 2-1 or a group of Formula 2-2, at least one of $R_{11}$ to $R_{22}$ in Formula 1B may be a group of Formula 2-1 or a group of Formula 2-2. Since the groups of Formulae 2-1 and 2-2 have essentially include "—CN (a cyano group)" as a substituent, the condensed cyclic compounds represented by Formulae 1A and 1B may have improved charge transport characteristics, improved emission characteristic, and a high glass transition temperature. Accordingly, an organic light-emitting device including at least one of the condensed cyclic compounds of Formulae 1A and 1B may have enhanced heat resistance against a Joule heat generated between organic layers or between an organic layer and an electrode under high-temperature environments, during storage and/or operation, and thus may have improved lifetime characteristics.

Therefore, an organic light-emitting device including at least one of the condensed cyclic compounds represented by Formulae 1A and 1B above may have a low driving voltage, a high luminance, a high efficiency, and a long lifetime.

The at least one of the condensed cyclic compounds of Formula 1A and 1B may be synthesized using a known organic synthesis method. Methods of synthesizing the condensed cyclic compounds of Formula 1 may be understood by those of ordinary skill in the art based on the examples that will be described below.

The at least one of the condensed cyclic compounds of Formula 1A and 1B may be used between a pair of electrodes of the organic light-emitting device. For example, the at least one of the condensed cyclic compounds of Formula 1A and 1B may be in an electron transport region, for example, in an electron transport layer.

According to another embodiment of the present disclosure, an organic light-emitting device includes a first electrode, a second electrode disposed opposite to the first electrode, and an organic layer disposed between the first electrode and the second electrode and including an emission layer, wherein the organic layer includes at least one of the condensed cyclic compounds of Formula 1A and 1B described above.

As used herein, "(for example, the organic layer) including at least one condensed cyclic compound means that "(the organic layer) including one of the condensed cyclic compounds of Formulae 1A and 1B, or at least two different condensed cyclic compounds of Formula 1A and 1B."

In some embodiments, the organic layer may include only Compound 1A as the condensed cyclic compound. In this regard, Compound 1A may be present in the electron transport layer of the organic light-emitting device. In some embodiments, the organic layer may include Compounds 1A and 2A as the condensed cyclic compounds. In this regard, Compounds 1A and 2A may be present both in the same layer (for example, in the electron transport layer) or may be present in different layers (for example, in the emission layer and the electron transport layer, respectively).

The organic layer may include i) a hole transport region disposed between the first electrode (anode) and the emission layer and including at least one of a hole injection layer, a hole transport layer, a buffer layer, and an electron blocking layer; and ii) an electron transport region disposed between the emission layer and the second electrode (cathode) and including at least one of a hole blocking layer, an electron transport layer, and an electron injection layer. The electron transport region may include at least one of the condensed cyclic compounds of Formulae 1A and 1B. For example, the electron transport region may include the electron transport layer, wherein the electron transport layer may include the at least one of the condensed cyclic compounds of Formulae 1A and 1B.

As used herein, the term "organic layer" refers to a single layer and/or a plurality of layers disposed between the first and second electrodes of the organic light-emitting device. A material in the "organic layer" is not limited to an organic material.

Hereinafter, a structure of an organic light-emitting device according to an embodiment of the present disclosure and a method of manufacturing the same will now be described with reference to the FIGURE.

The FIGURE is a schematic sectional view of an organic light-emitting device 10 according to an embodiment of the present disclosure. Referring to the FIGURE, the organic light-emitting device 10 includes a first electrode 110, an organic layer 150, and a second electrode 190.

A substrate (not shown) may be disposed under the first electrode 110 or on the second electrode 190 in the FIGURE. The substrate may be a glass or transparent plastic substrate with good mechanical strength, thermal stability, transparency, surface smoothness, ease of handling, and water resistance.

For example, the first electrode 110 may be formed by depositing or sputtering a first electrode-forming material on the substrate 11. When the first electrode 110 is an anode, a material having a high work function may be used as the first electrode-forming material to facilitate hole injection. The first electrode 110 may be a reflective electrode, a semi-transmissive electrode, or a transmissive electrode. Transparent and conductive materials such as ITO, IZO, $SnO_2$, and ZnO may be used to form the first electrode. The first electrode 110 as a semi-transmissive electrode or a reflective electrode may comprise at least one material selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a three-layered structure of ITO/Ag/ITO, but is not limited thereto.

The organic layer 150 may be disposed on the first electrode 110. The organic layer 150 may include an emission layer (EML).

The organic layer 150 may include a hole transport region disposed between the first electrode and the EML, and an electron transport region between the EML and the second electrode.

For example, the hole transport region may include at least one of a hole injection layer (HIL), a hole transport layer (HTL), a buffer layer, and an electron blocking layer (EBL). For example, the electron transport layer may include at least one of a hole blocking layer (HBL), an electron transport layer (ETL), and an electron injection layer (EIL). However, embodiments of the present disclosure are not limited thereto.

The hole transport region may have a single-layered structure including a single material, a single-layered structure including a plurality of materials, or a multi-layered structure including a plurality of layers including different materials.

In some embodiments, the electron transport region may have a single-layered structure including a plurality of materials, or a multi-layered structure of HIL/HTL, HIL/HTL/buffer layer, HIL/buffer layer, HTL/buffer layer, or HIL/HTL/EBL, wherein these layers forming a multi-layered structure are sequentially disposed on the first electrode 110 in the order stated above. However, embodiments of the present disclosure are not limited thereto.

When the hole transport region includes a HIL, the HIL may be formed on the first electrode 110 by using any of a variety of methods, for example, by using vacuum deposition, spin coating, casting, Langmuir-Blodgett (LB) deposition, inkjet printing, laser printing, laser induced thermal imaging (LITI), or the like.

When the HIL is formed using vacuum deposition, the deposition conditions may vary depending on the material that is used to form the HIL and the structure of the HIL. For example, the deposition conditions may be selected from the following conditions: a deposition temperature of about 100° C. to about 500° C., a degree of vacuum of about $10^{-8}$ to about $10^{-3}$ torr, and a deposition rate of about 0.01 to 100 Å/sec.

When the HIL is formed using spin coating, the coating conditions may vary depending on the material that is used to form the HIL and the structure of the HIL. For example, the coating conditions may be selected from the following conditions: a coating rate of about 2,000 rpm to about 5,000 5 pm and a heat treatment temperature of about 800° C. to about 200° C.

When the hole transport region includes a HTL, the HTL may be formed on the first electrode 110 or the HIL by using any of a variety of methods, for example, by using vacuum deposition, spin coating, casting, Langmuir-Blodgett (LB) deposition, inkjet printing, laser printing, laser induced thermal imaging (LITI), or the like. When the HTL is formed using vacuum deposition or spin coating, the conditions for deposition and coating may be similar to the above-described deposition and coating conditions for forming the HIL, and accordingly will not be described in detail.

In some embodiments, the hole transport region may include at least one of m-MTDATA, TDATA, 2-TNATA, NPB, β-NPB, TPD, Spiro-TPD, Spiro-NPB, α-NPB, TAPC, HMTPD, 4,4',4''-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201 below, and a compound represented by Formula 202 below.

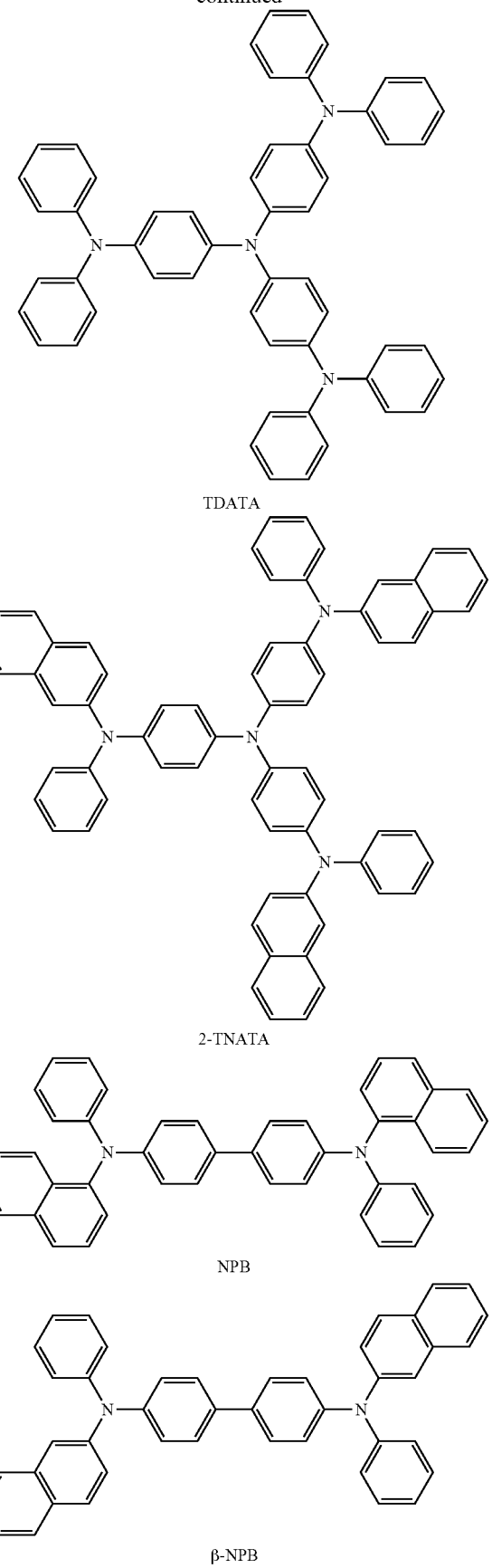

-continued

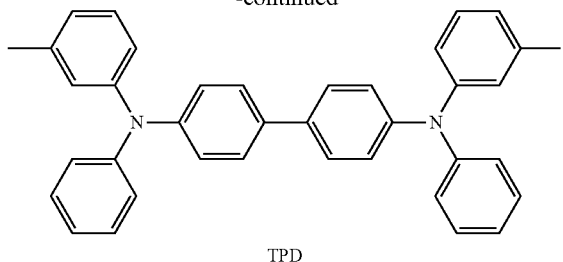
TPD

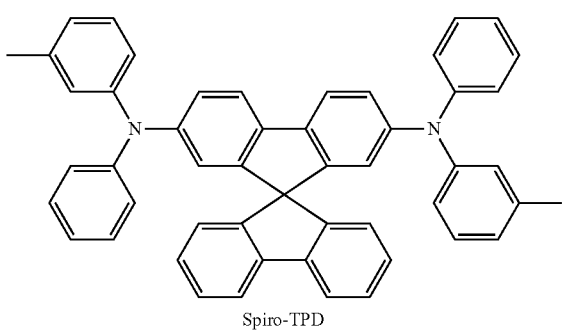
Spiro-TPD

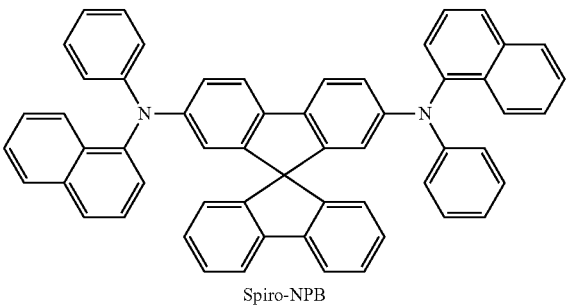
Spiro-NPB

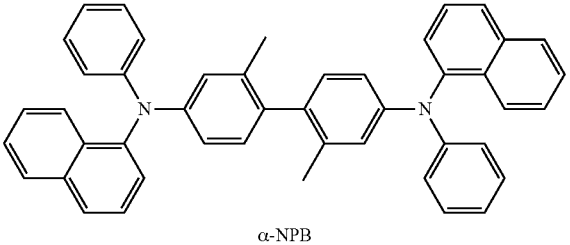
α-NPB

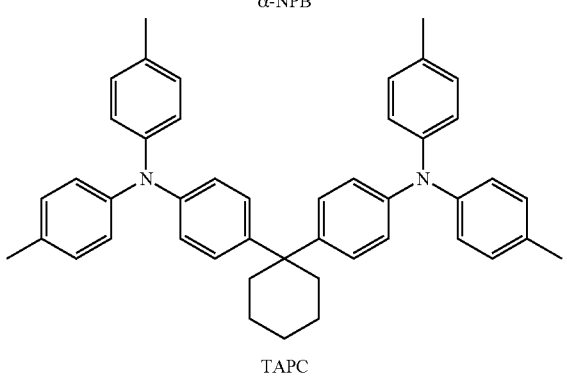
TAPC

-continued

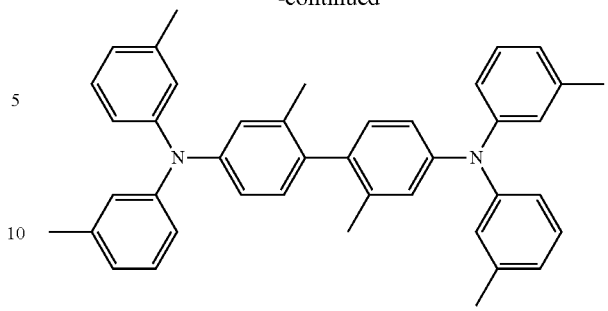
HMTPD

<Formula 201>

$$R_{201}\text{—}(L_{201})_{xa1}\text{—}N\begin{matrix}(L_{202})_{xa2}\text{—}R_{202}\\ \\ (L_{203})_{xa3}\text{—}R_{203}\end{matrix}$$

<Formula 202>

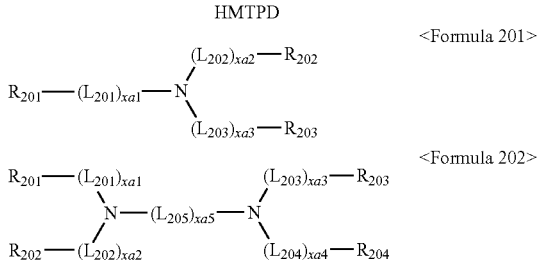

In Formulae 201 and 202, $L_{201}$ to $L_{205}$ may be each independently defined as described above in conjunction with $L_1$ in Formula 1;

xa1 to xa4 are each independently selected from 0, 1, 2, and 3;

xa5 may be selected from 1, 2, 3, 4, and 5;

$R_{201}$ to $R_{204}$ may be each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 201 and 202, $L_{201}$ to $L_{205}$ may be each independently a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene; or a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may be each independently 0, 1, or 2;

xa5 may be 1, 2, or 3;

$R_{201}$ to $R_{204}$ may be each independently, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group. However, embodiments of the present disclosure are not limited thereto.

The compound of Formula 201 may be represented by Formula 201A:

<Formula 201A>

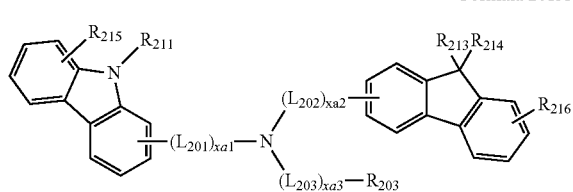

For example, the compound of Formula 201 may be represented by Formula 201A-1, but is not limited thereto:

<Formula 201A-1>

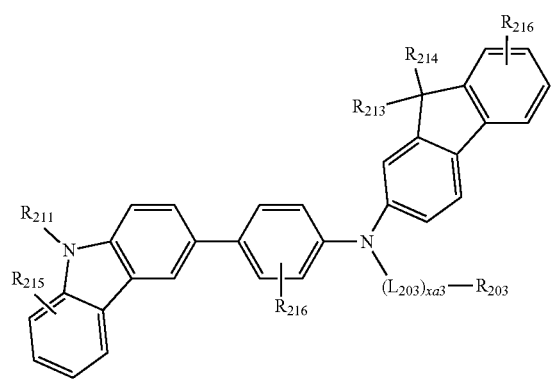

The compound of Formula 202 may be represented by Formula 202A, but is not limited thereto:

<Formula 202A>

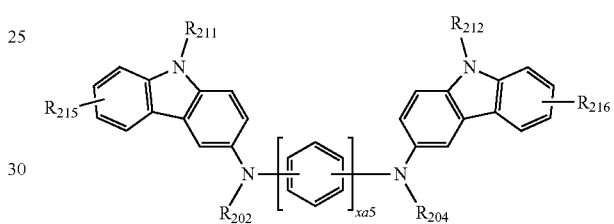

In Formulae 201A, 201A-1, and 202A, $L_{201}$ to $L_{203}$, xa1 to xa3, xa5, and $R_{202}$ to $R_{204}$ may be defined as described in conjunction with Formula 201;

$R_{211}$ may be defined as described in conjunction with $R_{203}$ in Formula 201;

$R_{213}$ to $R_{216}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic hetero-condensed polycyclic group.

In some other embodiments, in Formulae 201A, 201A-1, and 202A, $L_{201}$ to $L_{203}$ may be each independently a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group; or a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xa1 to xa3 may be each independently 0 or 1, $R_{203}$, $R_{211}$, and $R_{212}$ may be each independently a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, $R_{213}$ and $R_{214}$ may be each independently a $C_1$-$C_{20}$ alkyl group or a $C_1$-$C_{20}$ alkoxy group;

a $C_1$-$C_{20}$ alkyl group or a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, $R_{215}$ and $R_{216}$ may be each independently a hydrogen, a deuterium. —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, or a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xa5 may be 1 or 2.

In Formulae 201A and 201A-1, $R_{213}$ and $R_{214}$ may be linked to each other to form a saturated or unsaturated ring.

The compound represented by Formula 201, and the compound represented by Formula 202 may be compounds HT1 to HT20 illustrated below, but are not limited thereto.

HT1

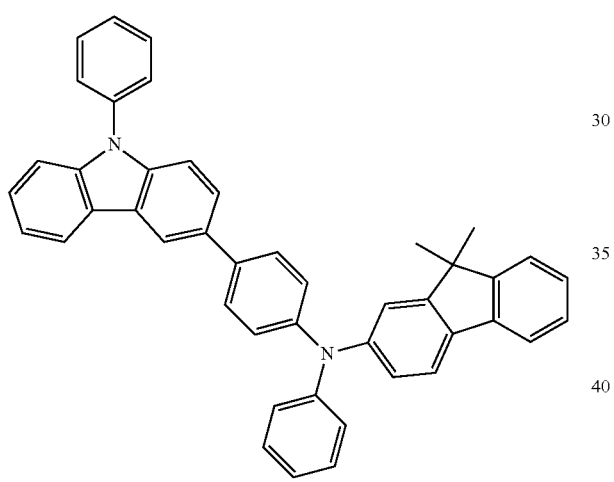

HT2

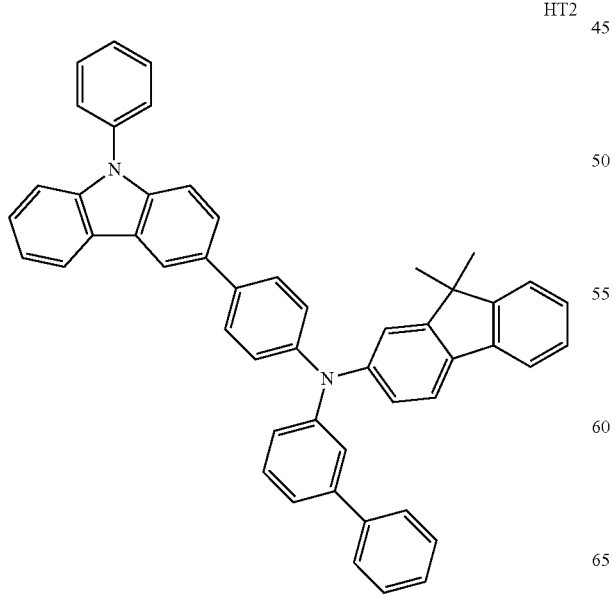

HT3

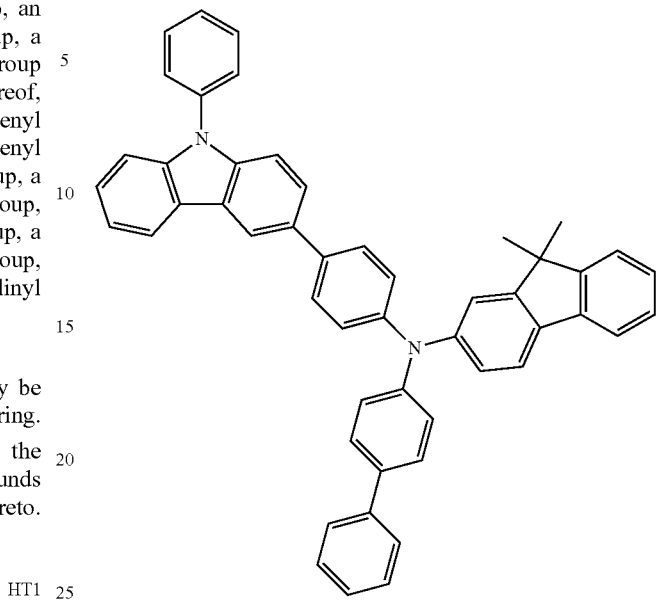

HT4

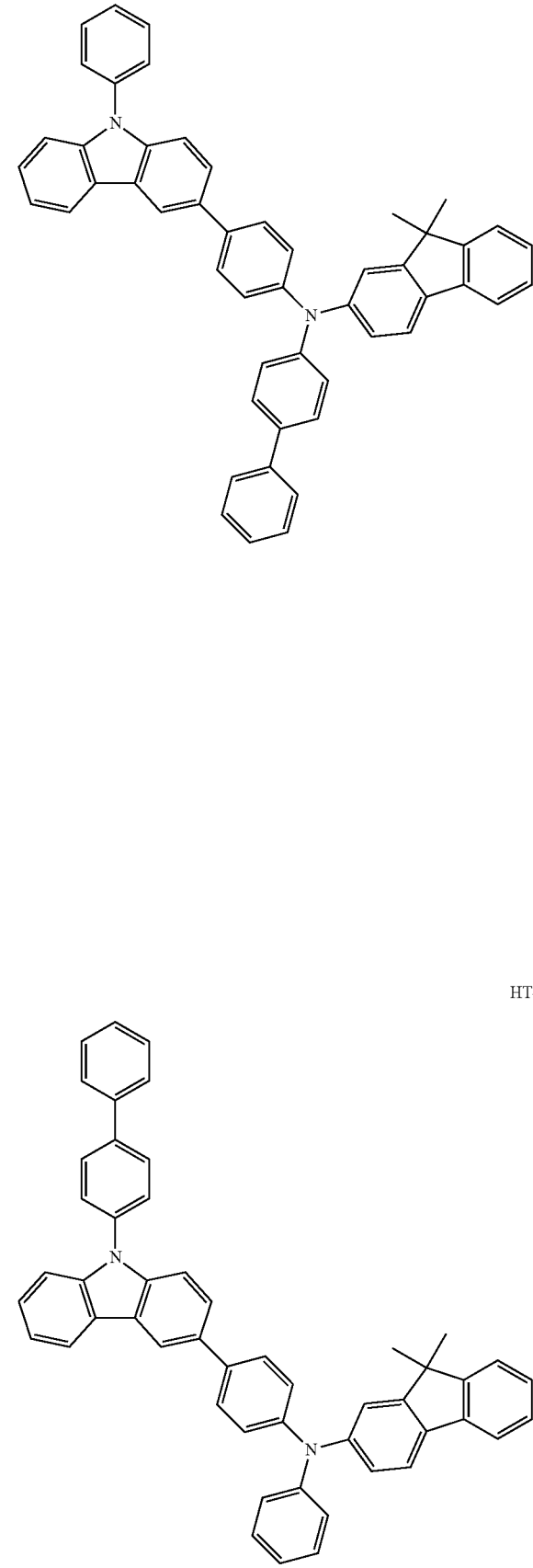

HT5
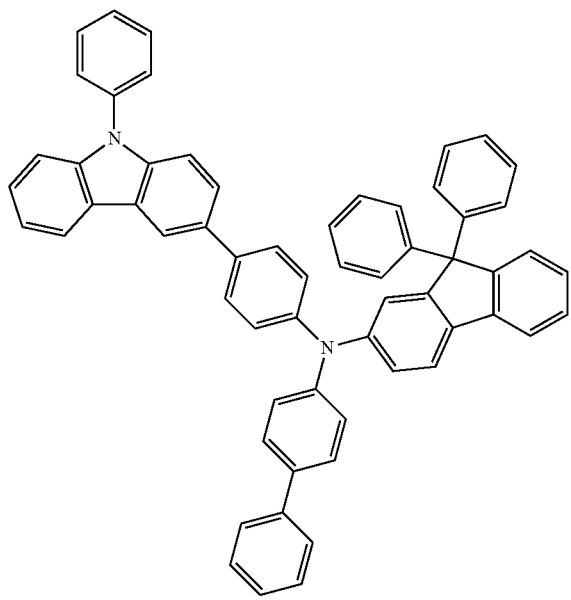
HT7
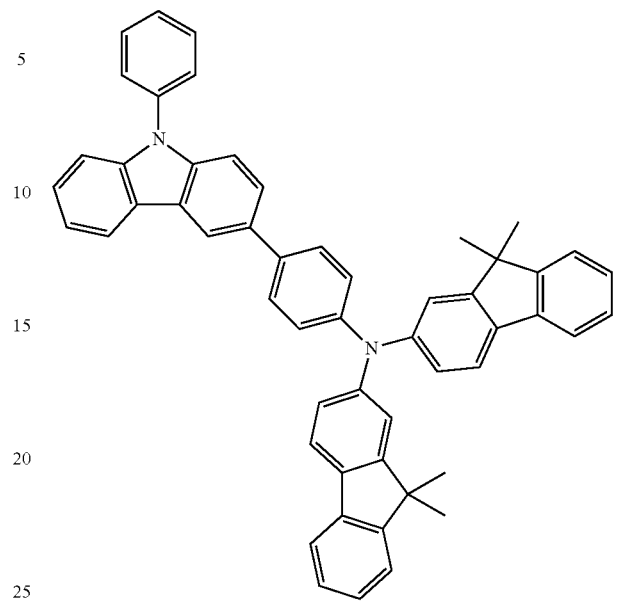
HT6
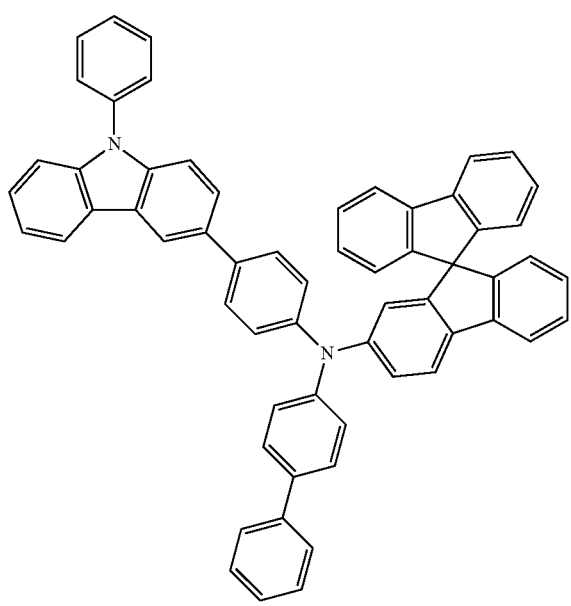
HT8
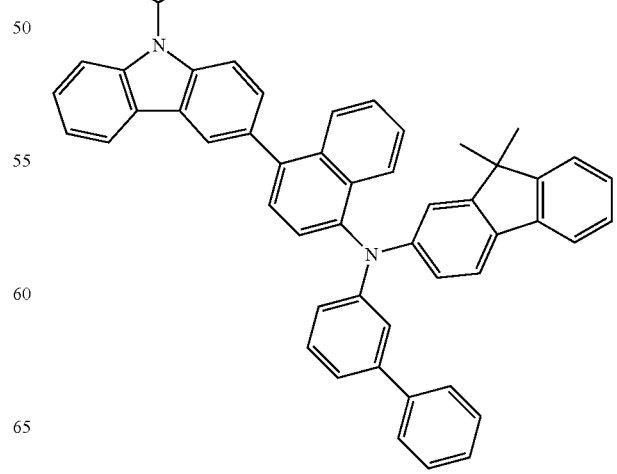

HT9
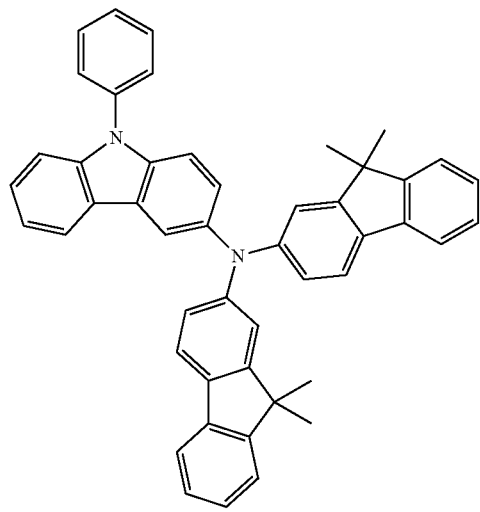
HT11
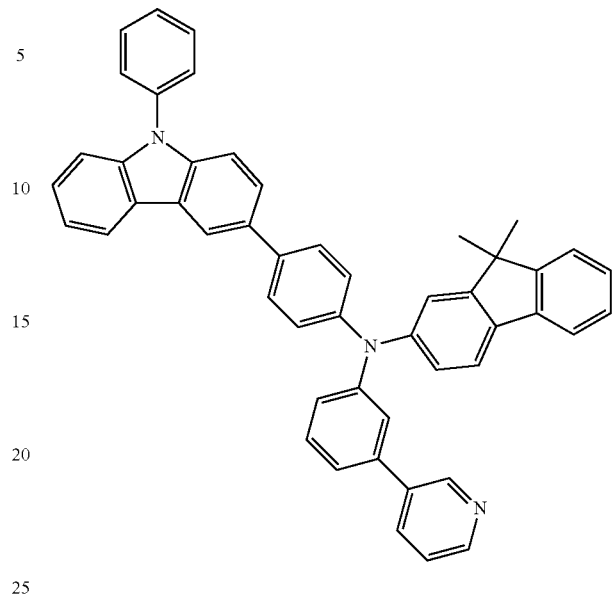
HT12
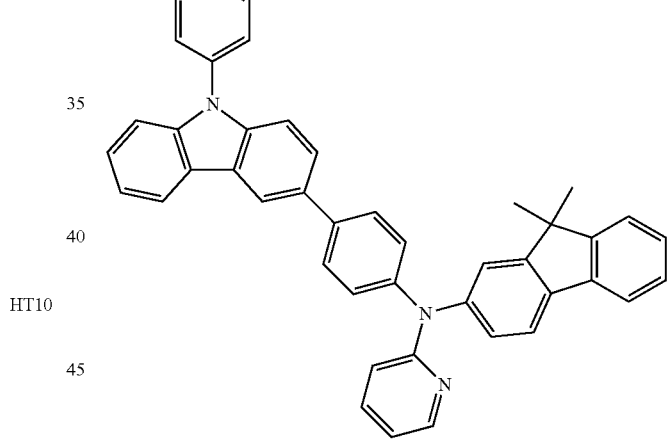
HT10
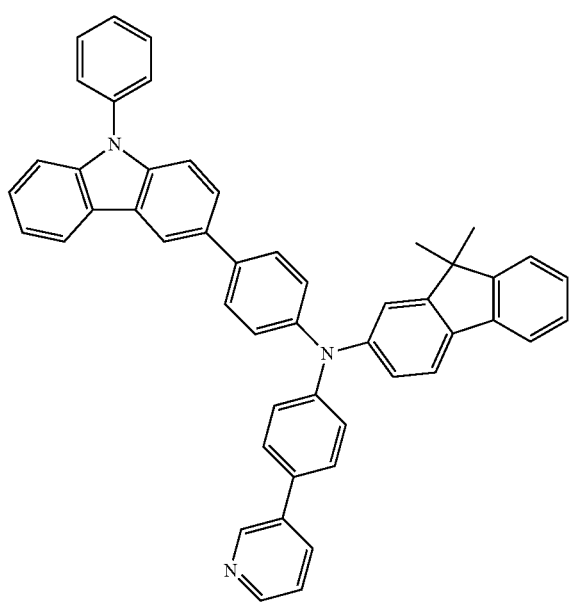
HT13
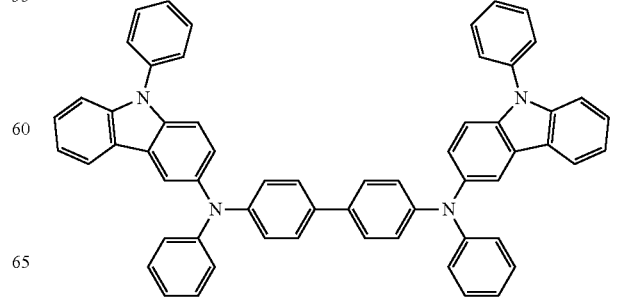

-continued

HT14
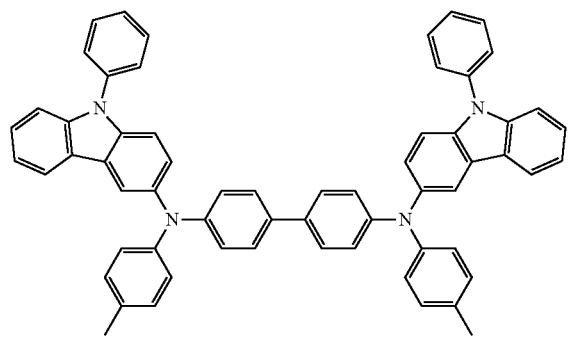

HT15
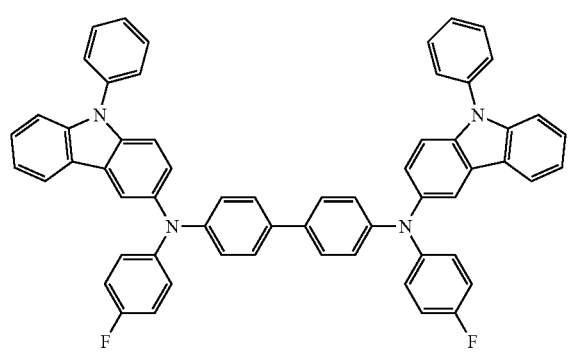

HT16
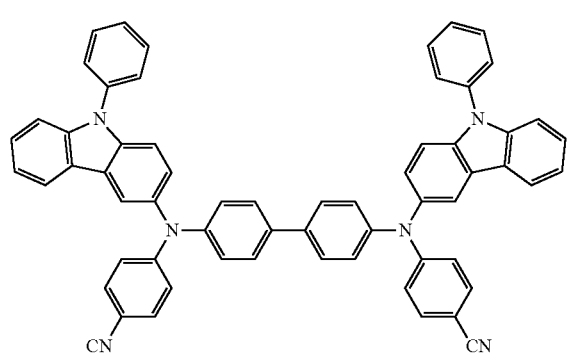

HT17
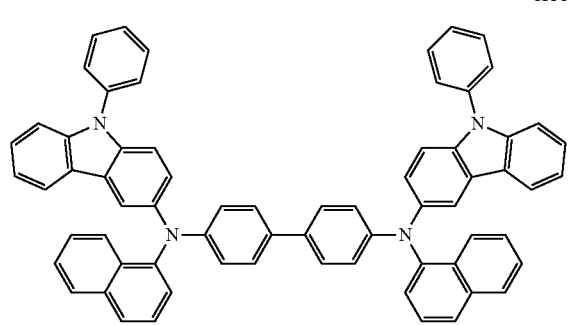

-continued

HT18
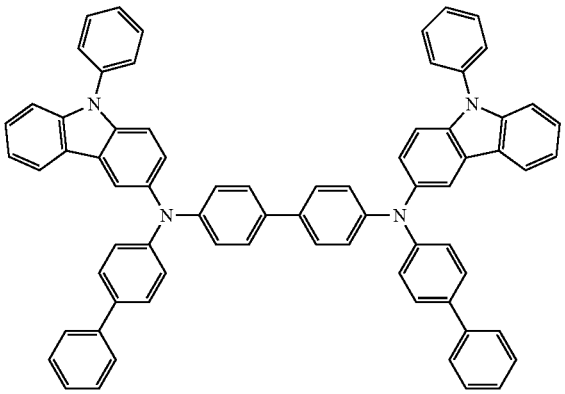

HT19
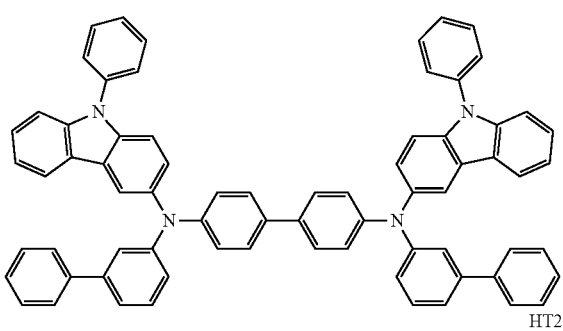

HT20
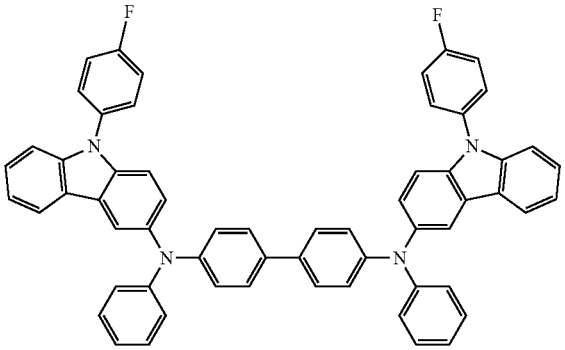

A thickness of the hole transport region may be from about 100 Å to about 10000 Å, and in some embodiments, from about 100 Å to about 1000 Å. When the hole transport region includes a HIL and a HTL, a thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or inhomogeneously dispersed in the hole transport region.

The charge-generating material may be, for example, a p-dopant. The p-dopant may be one of quinine derivatives, metal oxides, and compounds with a cyano group, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like, metal oxides such as tungsten oxide, molybdenum oxide, and the like; and Compound HT-D1 below.

<Compound HT-D1>

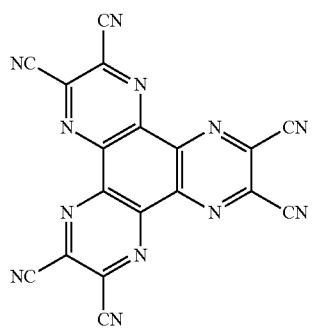

<F4-TCNQ>

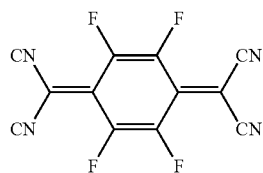

The hole transport region may further include at least one of a buffer layer and an EBL, in addition to the HIL and HTL described above. The buffer layer may compensate for an optical resonance distance of light according to a wavelength of the light emitted from the EML, and thus may improve light-emission efficiency. A material in the buffer layer may be any material used in the hole transport region. The EBL may block migration of electrons from the electron transport region into the EML.

The EML may be formed on the first electrode 110 or the hole transport region by using any of a variety of methods, for example, by using vacuum deposition, spin coating, casting, Langmuir-Blodgett (LB) deposition, inkjet printing, laser printing, laser induced thermal imaging (LITI), or the like. When the EML is formed using vacuum deposition or spin coating, the deposition and coating conditions for forming the EML may be similar to the above-described deposition and coating conditions for forming the HIL, and accordingly will not be described in detail.

When the organic light-emitting device 10 is a full color organic light-emitting device, the EML may be patterned into a red emission layer, a green emission layer, and a blue emission layer to correspond to individual subpixels, respectively. In some embodiments, the EML may have a structure in which a red emission layer, a green emission layer and a blue emission layer are stacked upon one another, or a structure including a mixture of a red light-emitting material, a green light-emitting material, and a blue light-emitting material, and thus may emit white light.

The EML may include a host and a dopant.

For example, the host may include at least one of TPBi, TBADN, ADN (also referred to as "DNA"), CBP, CDBP, and TCP.

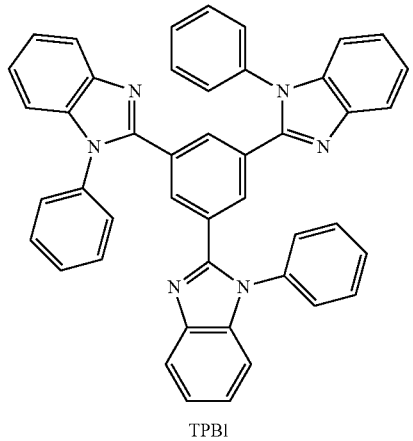

TPBI

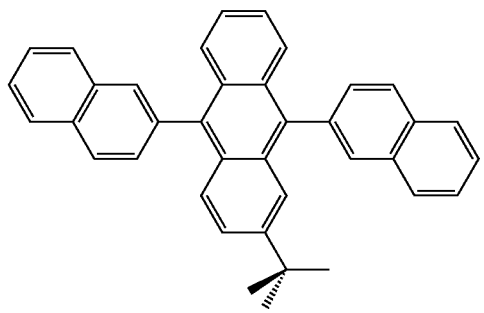

TBADN

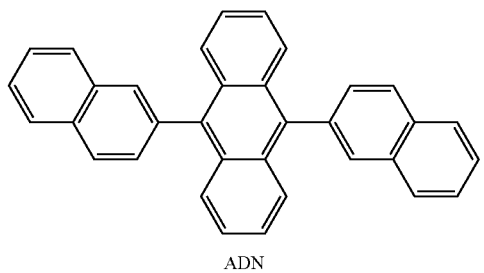

ADN

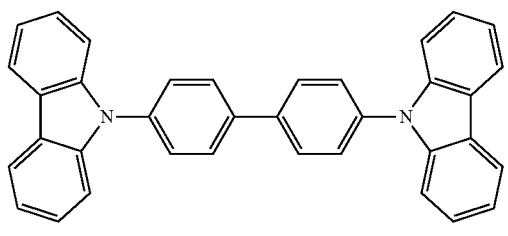

CBP

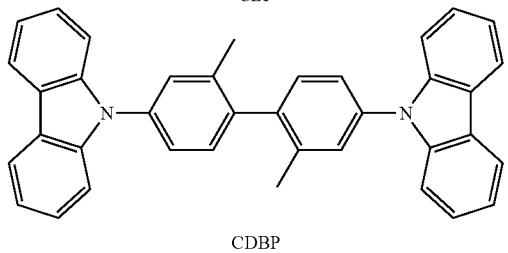

CDBP

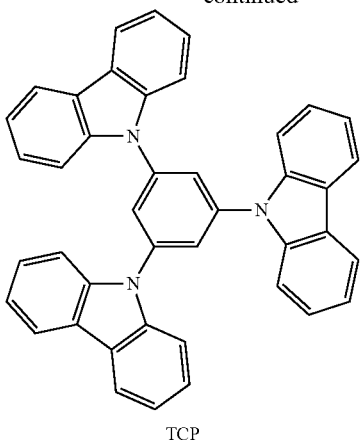

TCP

In some embodiments, the host may include a compound represented by Formula 301.

$$Ar_{301}\text{-}[(L_{301})_{xb1}\text{-}R_{301}]_{xb2} \quad \text{<Formula 301>}$$

In Formula 301, $Ar_{301}$ may be a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, or an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, or an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, and —Si($Q_{301}$)($Q_{302}$)($Q_{303}$) (where $Q_{301}$ to $Q_{303}$ may be each independently, a hydrogen, a $C_1$-$C_{60}$ alkyl group, a $C_2$-$C_{60}$ alkenyl group, a $C_6$-$C_{60}$ aryl group, or a $C_2$-$C_{60}$ heteroaryl group), $L_{301}$ may be defined as described above in conjunction with $L_{201}$ in Formula 201, $R_{301}$ may be a $C_1$-$C_{20}$ alkyl group, or a $C_1$-$C_{20}$ alkoxy group;

a $C_1$-$C_{20}$ alkyl group, or a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, or a triazinyl group, each substituted at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3;

xb2 may be selected from 1, 2, 3, and 4.

For example, in Formula 301, $L_{301}$ may be a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, or a chrysenylene group; or a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, or a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and $R_{301}$ may be a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group. However, embodiments of the present disclosure are not limited thereto.

For example, the host may include a compound represented by Formula 301A:

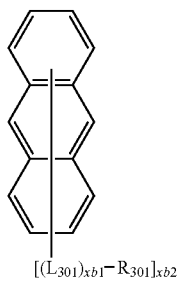

<Formula 301A>

$[(L_{301})_{xb1}-R_{301}]_{xb2}$

Substituents in Formula 301A may be defined as described above in conjunction with other formulas herein.

The compound of Formula 301 may include at least one of Compounds H1 to 42, but is not limited thereto:

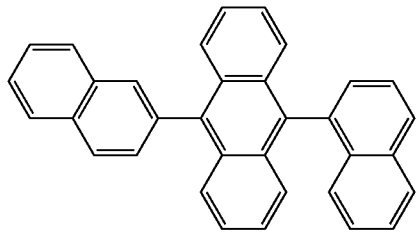

H1

H2

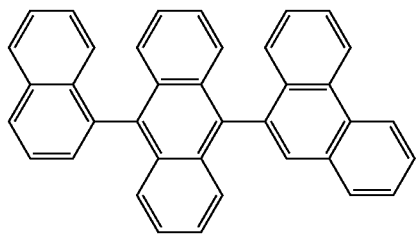

H3

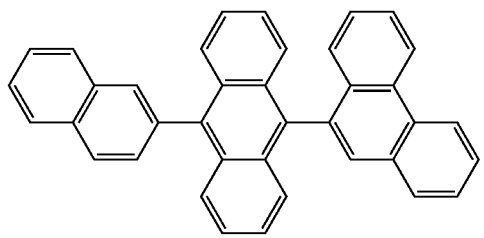

H4

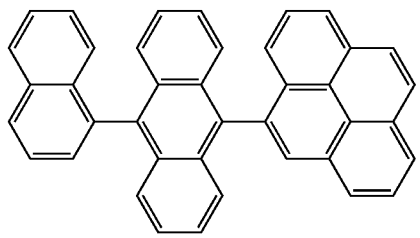

H5

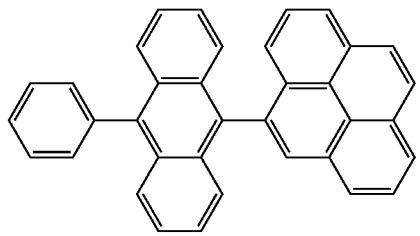

H6

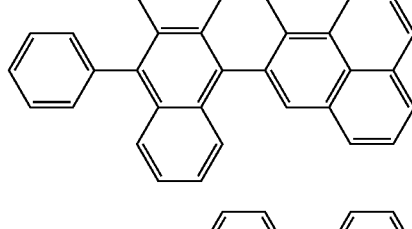

H7

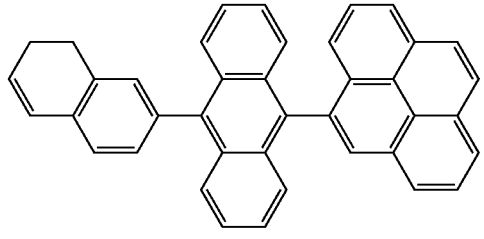

H8

H9
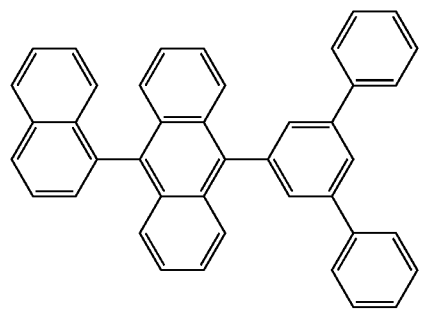
H10
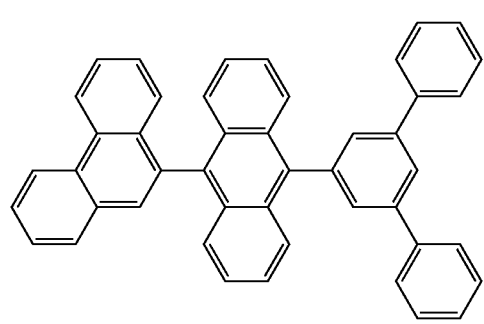
H11
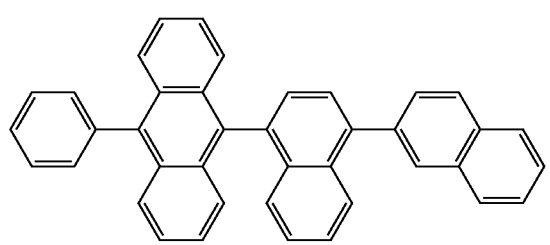
H12
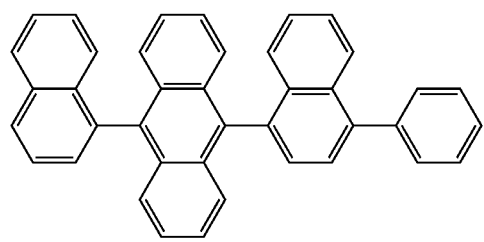
H13
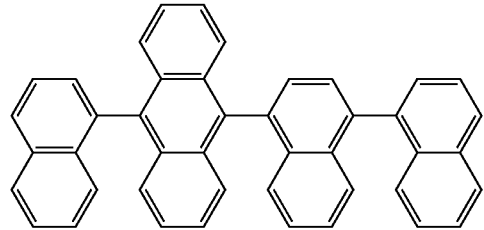
H14
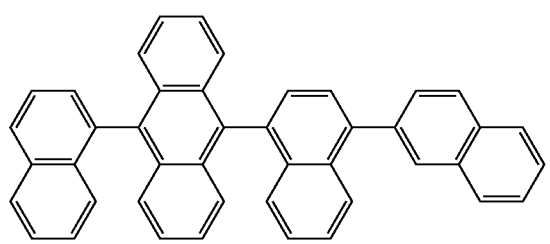
H15
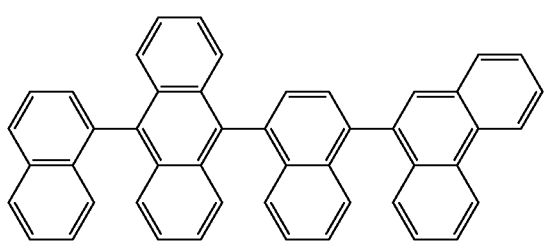
H16
H17
H18
H19
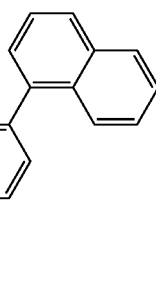

H20
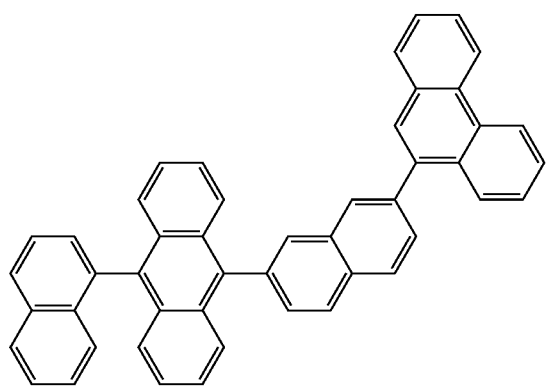
H21
H25
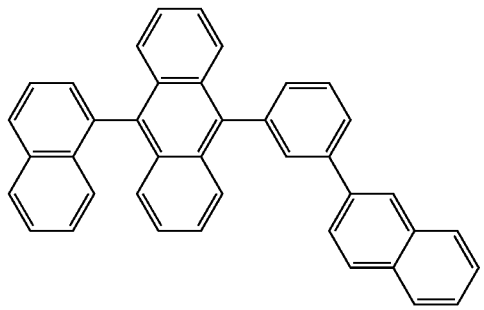
H26
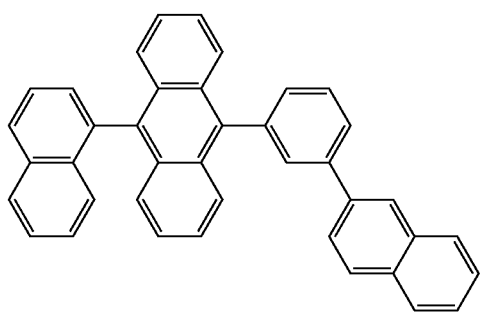
H27
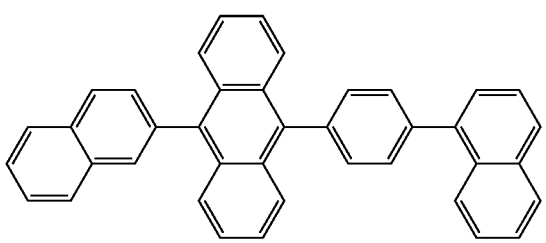
H28
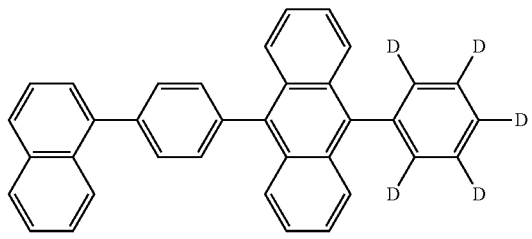
H22
H23
H29
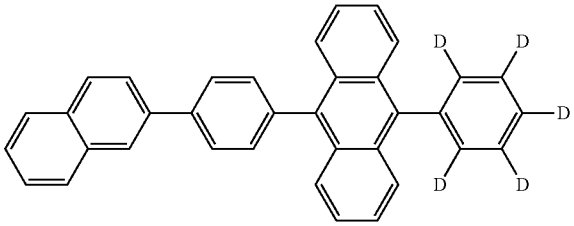
H30
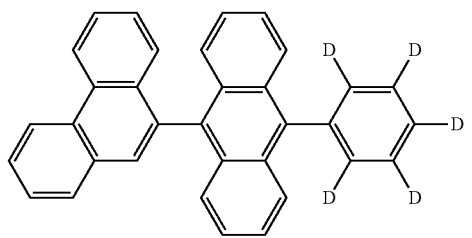
H24

-continued
H31
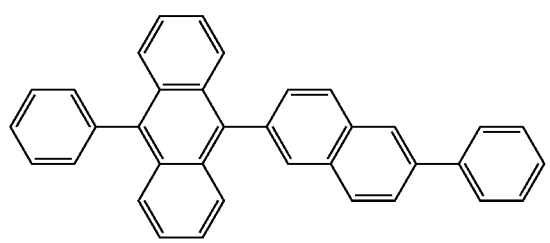
H32
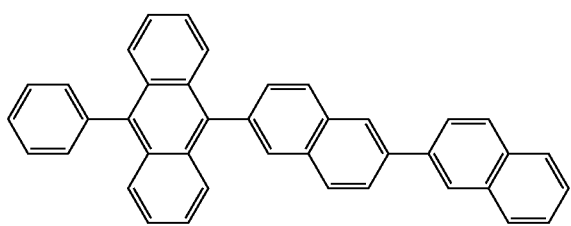
H33
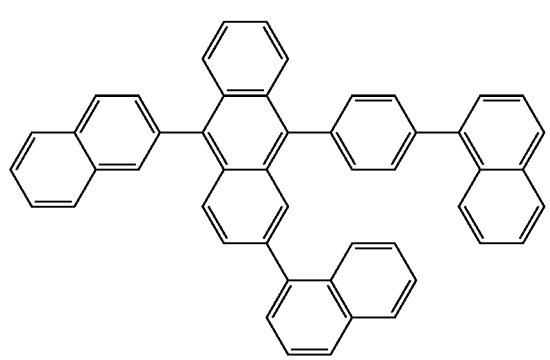
-continued
H35
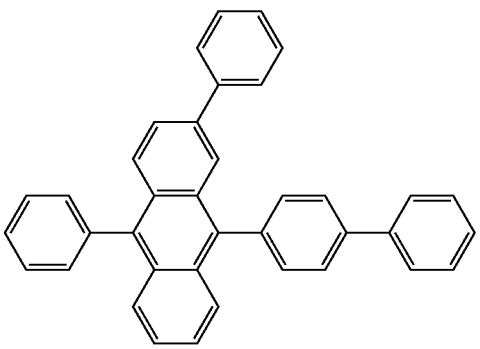
H36
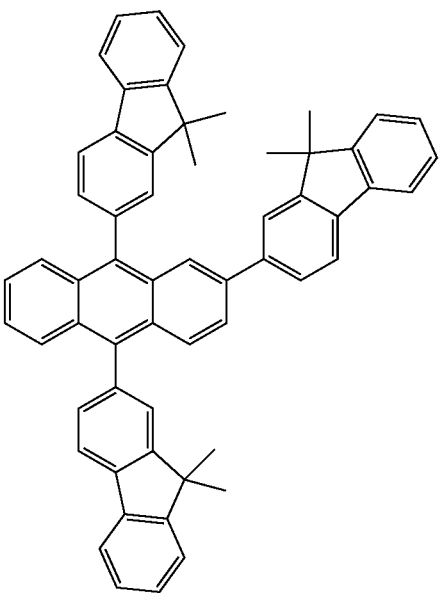
H37
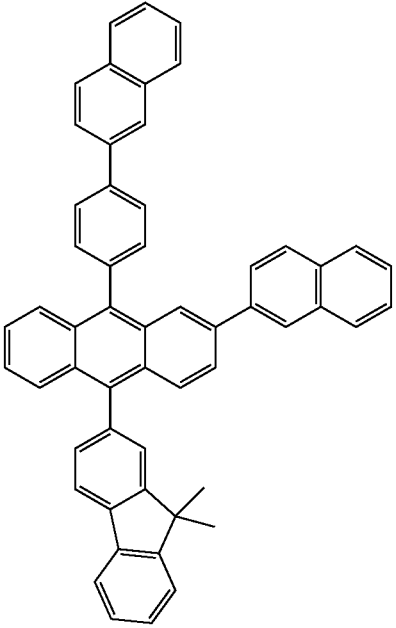
H34

H38
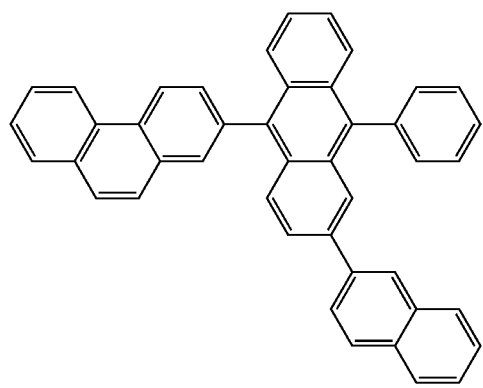
H39
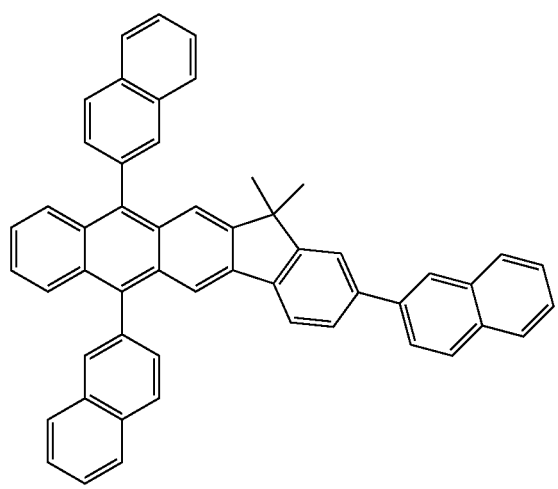
H40
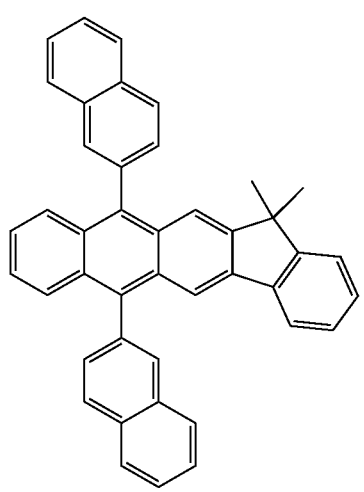
H41
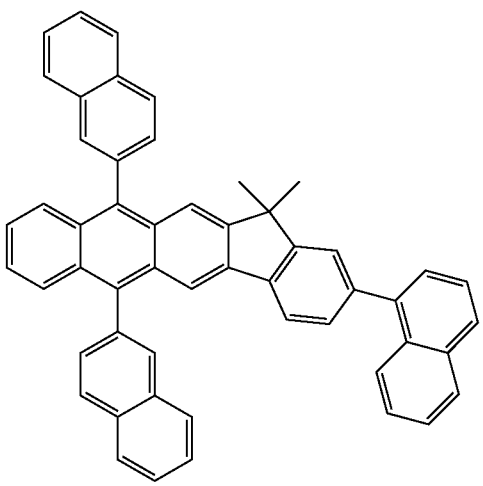
H42
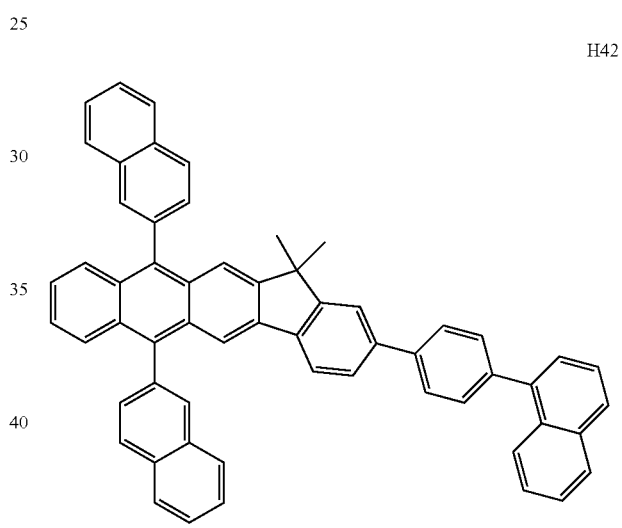
In some other embodiments, the host may include at least one of Compounds H43 to H49, but is not limited thereto:
H43
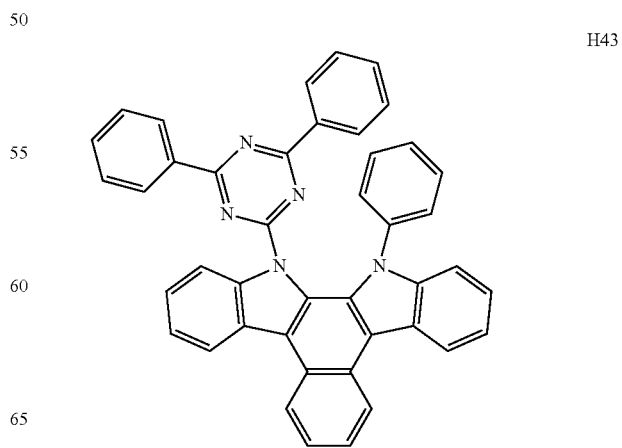

H44
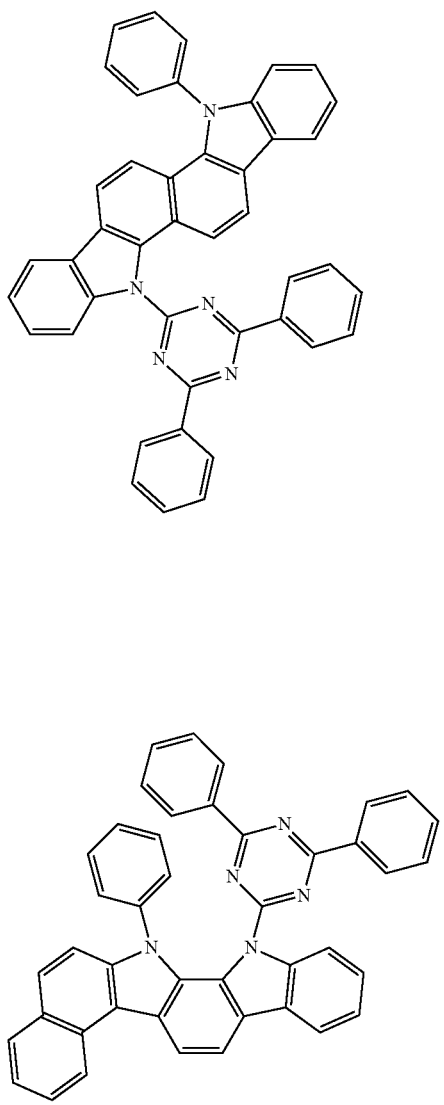
H45
H46
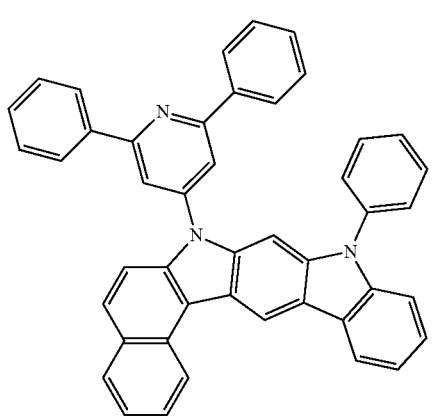
H47
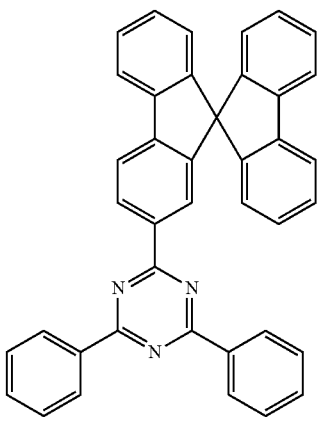
H48
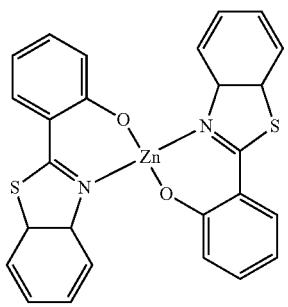
H49
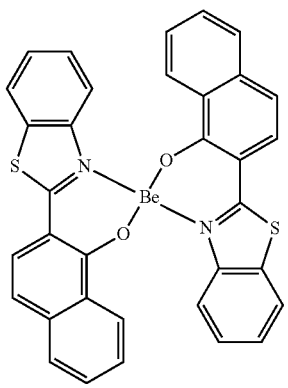
The dopant may include at least one of a fluorescent dopant and a phosphorescent dopant.
The phosphorescent dopant may include an organometallic complex represented by Formula 401:
<Formula 401>
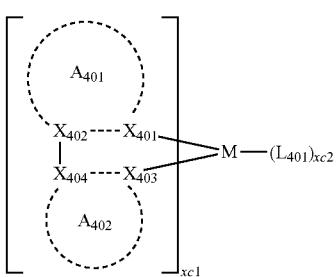

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently a nitrogen or a carbon;

rings $A_{401}$ and $A_{402}$ may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted a dibenzofuran, and a substituted or unsubstituted a dibenzothiophene;

at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxyl group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{401})(Q_{402})$, —$Si(Q_{403})(Q_{404})(Q_{405})$, and —$B(Q_{406})(Q_{407})$, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a monovalent non-aromatic condensed polycyclic group, and a monovalent non-aromatic condensed heteropolycyclic group, a $C_3$-$C_{10}$ cycloalkyl group, a $C_2$-$C_{10}$ heterocycloalkyl group, a $C_3$-$C_{10}$cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{411})(Q_{412})$, —$Si(Q_{413})(Q_{414})(Q_{415})$, and —$B(Q_{416})(Q_{417})$, and —$N(Q_{421})(Q_{422})$, —$Si(Q_{423})(Q_{424})(Q_{425})$, and —$B(Q_{426})(Q_{427})$;

$L_{401}$ may be an organic ligand;

xc1 may be 1, 2, or 3;

xc2 may be 0, 1, 2, or 3.

For example, in Formula 401, $L_{401}$ may be a monovalent, divalent, or trivalent organic ligand. For example, $L_{401}$ in Formula 401 may be selected from a halogen ligand (for example, Cl or F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazolecarboxylate, or benzoate), a carbon monoxide ligand, an isonitrile ligand, a cyano ligand, and a phosphorous ligand (for example, phosphine or phosphite). However, embodiments of the present disclosure are not limited thereto.

When $A_{401}$ in Formula 401 has at least two substituent groups, the at least two substituent groups of $A_{401}$ may be linked to each other to form a saturated or unsaturated ring.

When $A_{402}$ in Formula 401 has at least two substituents groups, the at least two substituent groups of $A_{402}$ 2 may be linked to each other to form a saturated or unsaturated ring.

When xc1 in Formula 401 is 2 or greater, a plurality of ligands

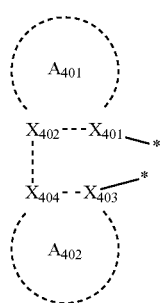

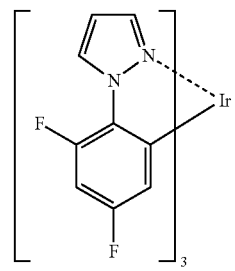
PD4 in Formula 401 may be identical to or different from each other. When xc1 in Formula 1 is 2 or greater, $A_{401}$ and $A_{402}$ may be linked to $A_{401}$ and $A_{402}$ of another adjacent ligand, respectively, directly or via a linking group (for example, a $C_1$-$C_5$ alkylene group, —N(R')— (where R' is a $C_1$-$C_{10}$ alkyl group or a $C_6$-$C_{20}$ aryl group), or C(=O)—).

The fluorescent dopant may include at least one of Compounds PD1 to PD74, but is not limited thereto.

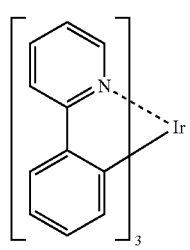
PD1

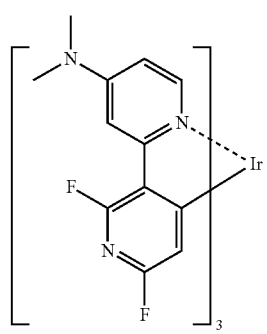
PD5

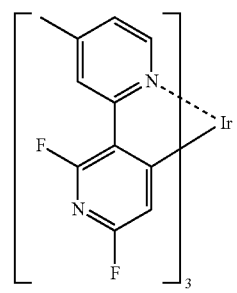
PD6

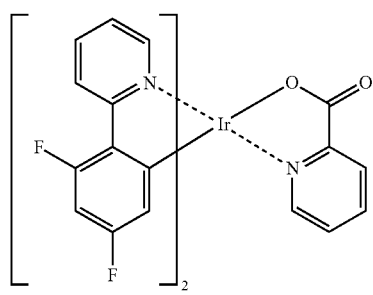
PD2

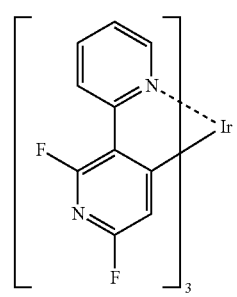
PD7

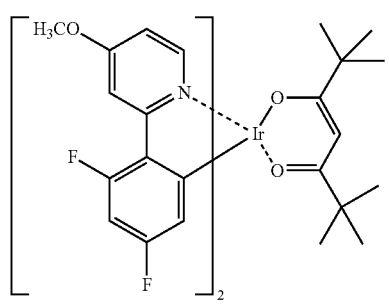
PD3

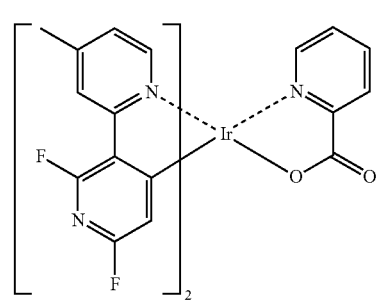
PD8

PD9
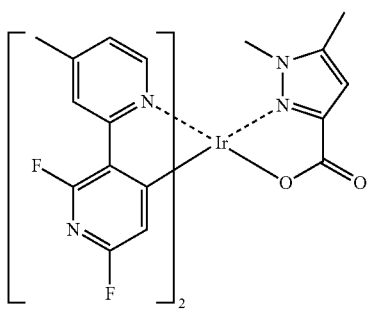
PD10
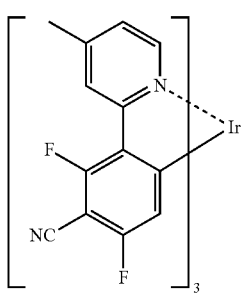
PD11
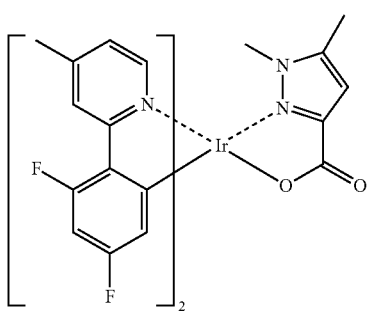
PD12
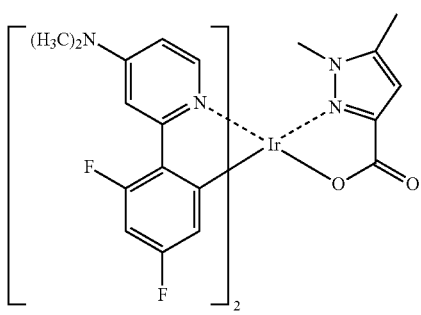
PD13
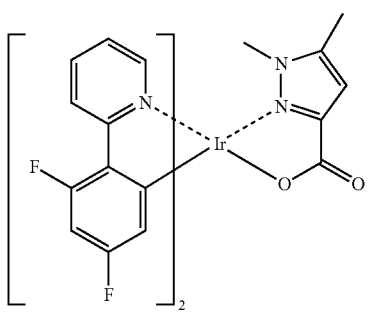
PD14
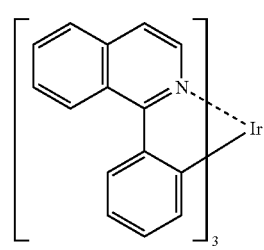
PD15
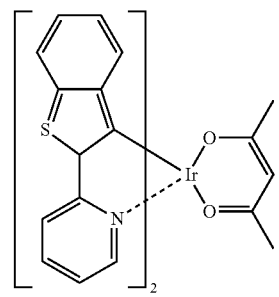
PD16
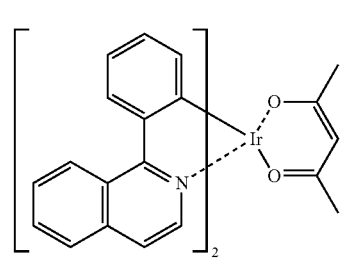
PD17
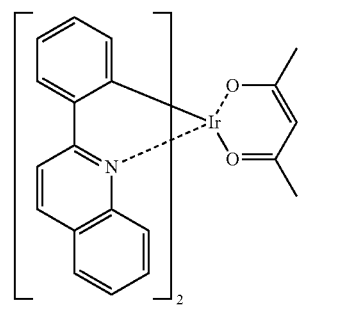
PD18
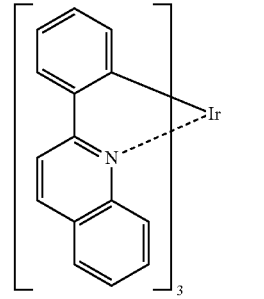

PD19 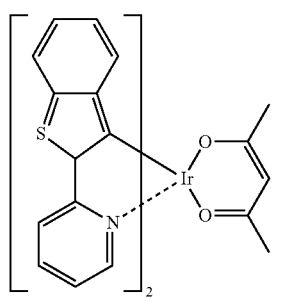
PD20 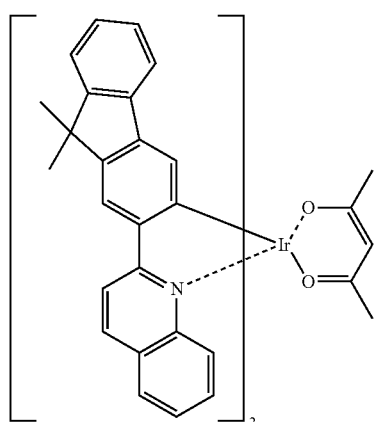
PD21 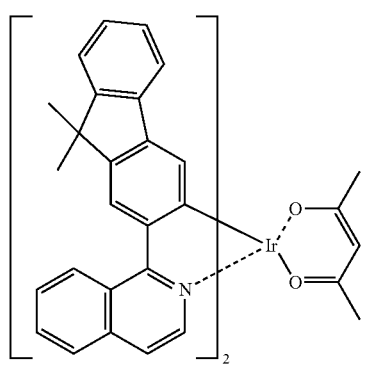
PD22 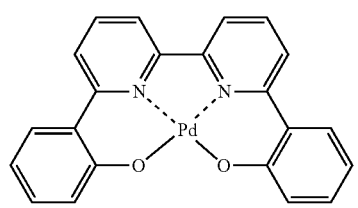
PD23 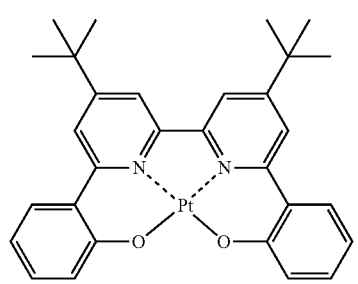
PD24 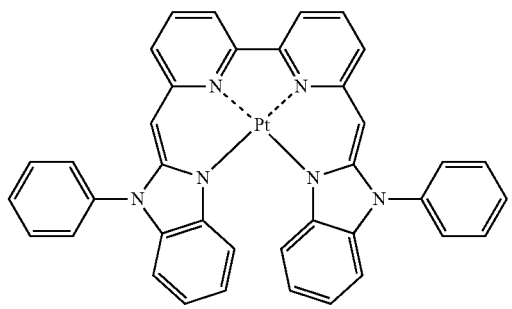
PD25 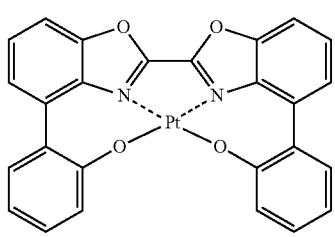
PD26 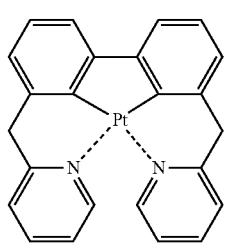
PD27 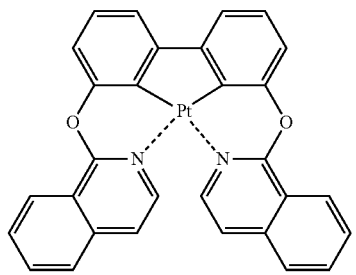
PD28 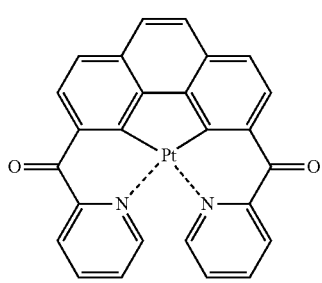
PD29 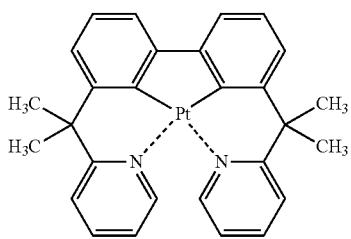

PD30 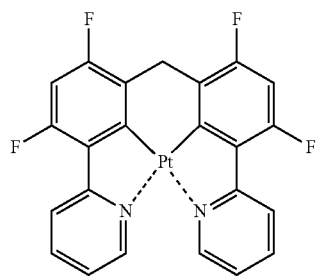
PD31 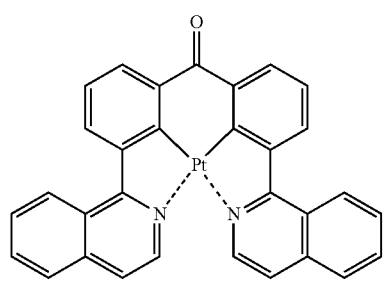
PD32 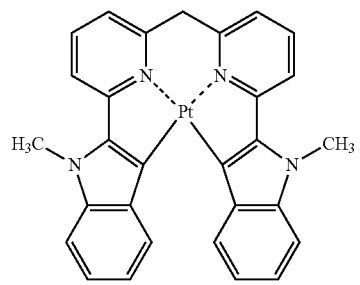
PD33 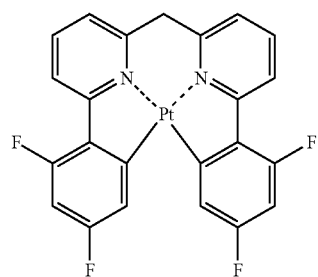
PD34 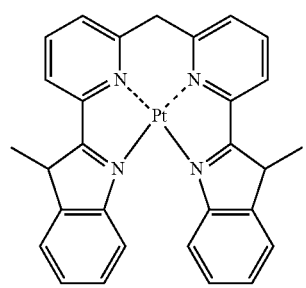
PD35 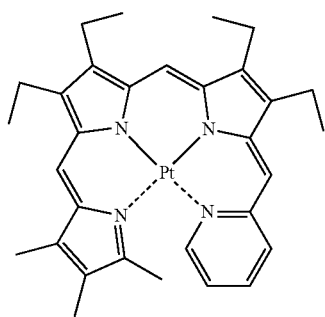
PD36 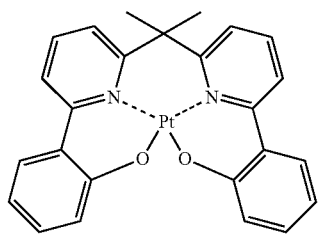
PD37 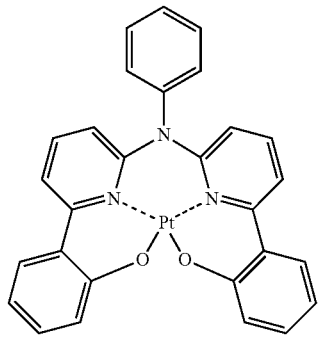
PD38 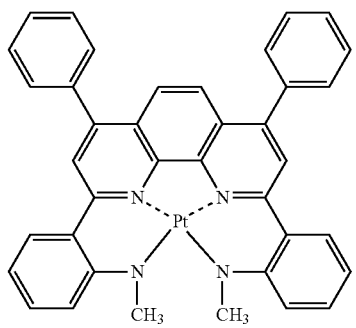
PD39 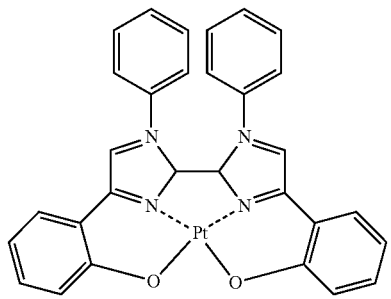

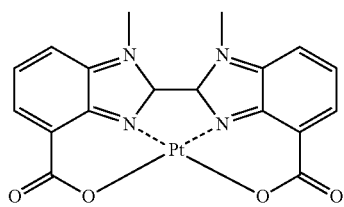
PD40
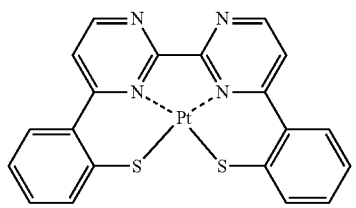
PD41
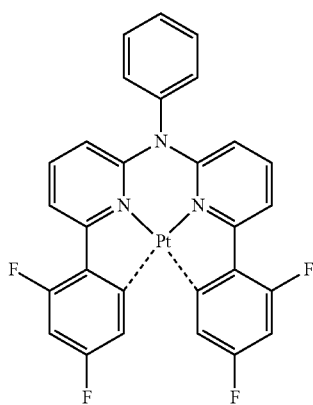
PD42
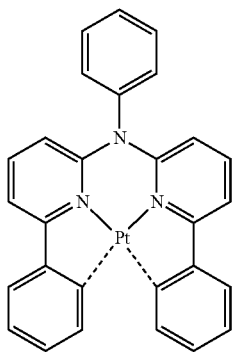
PD43
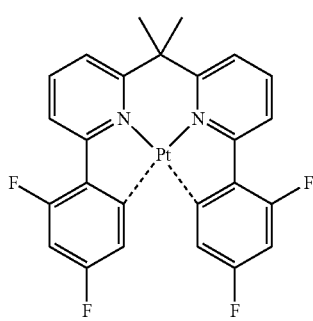
PD44
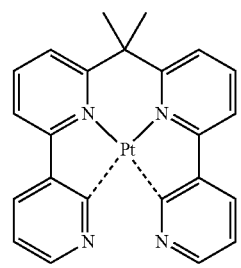
PD45
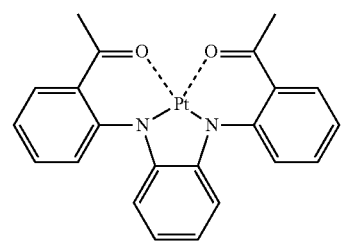
PD46
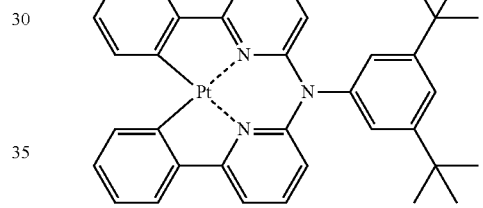
PD47
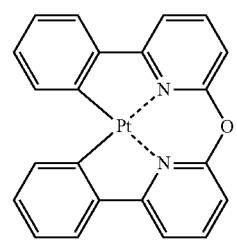
PD48
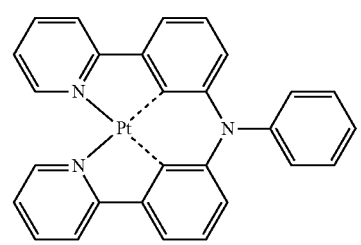
PD49
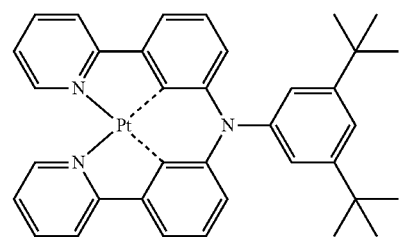
PD50

-continued
PD51
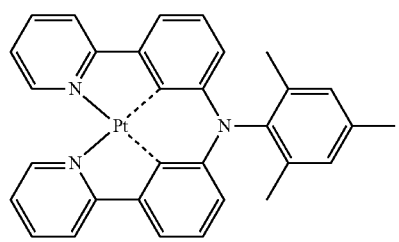
PD52
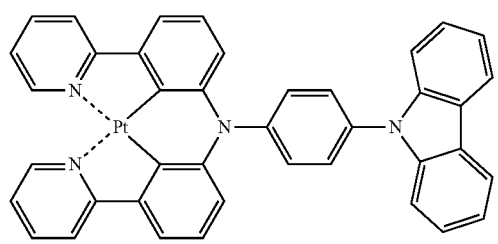
PD53
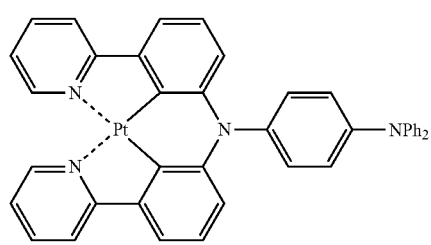
PD54
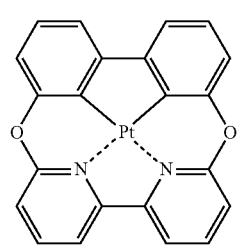
PD55
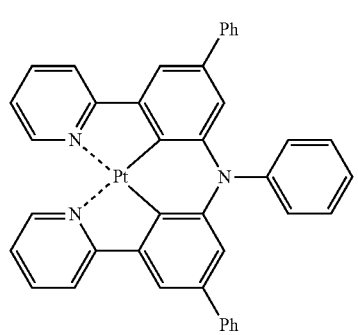
PD56
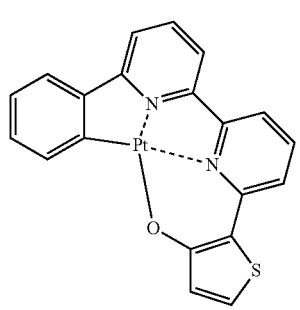
-continued
PD57
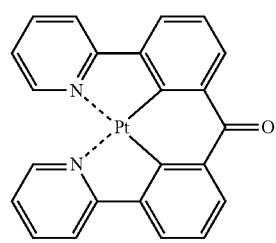
PD58
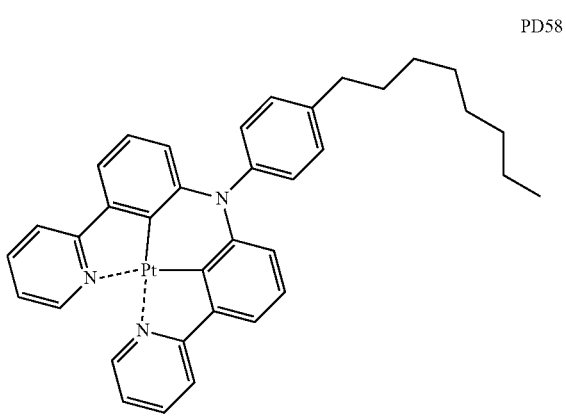
PD59
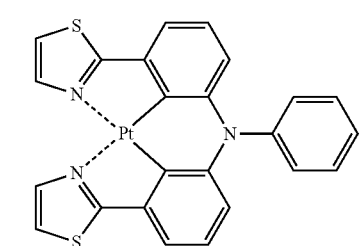
PD60
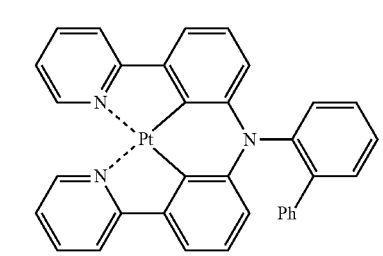
PD61
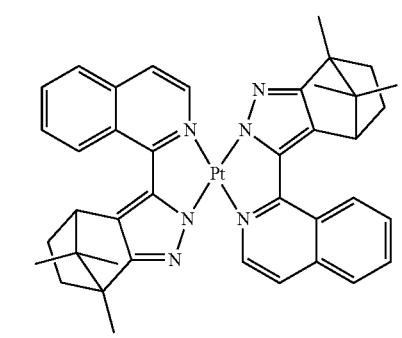

PD62 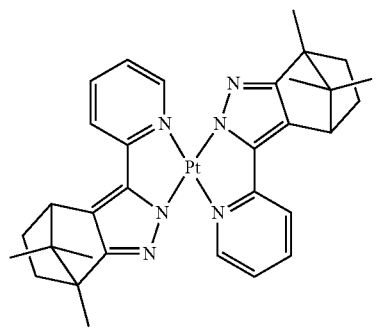
PD63 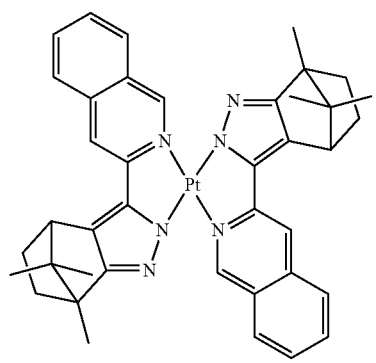
PD64 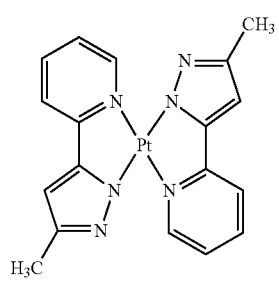
PD65 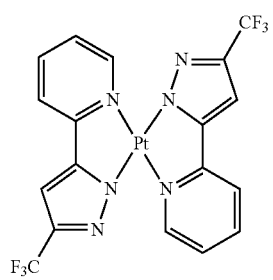
PD66 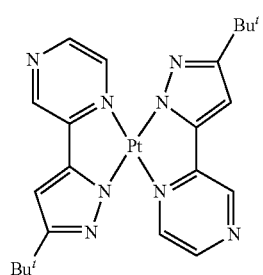
PD67 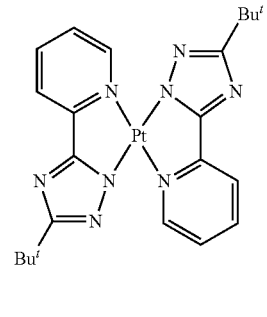
PD68 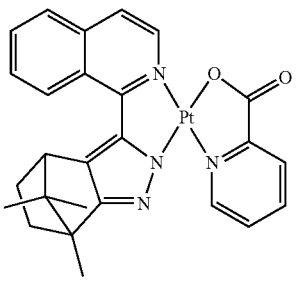
PD69 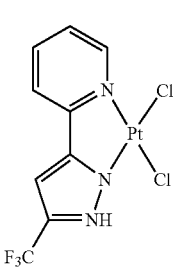
PD70 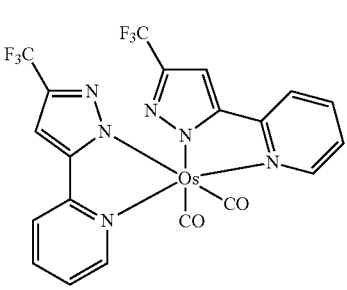
PD71 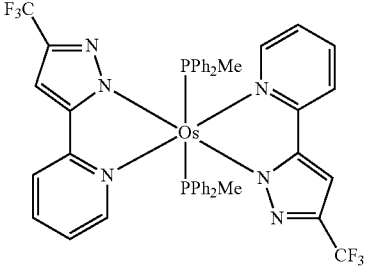

-continued
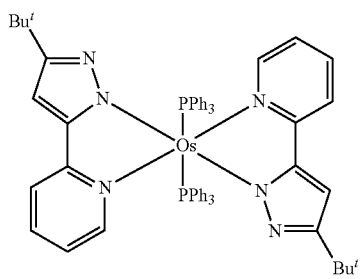
PD72
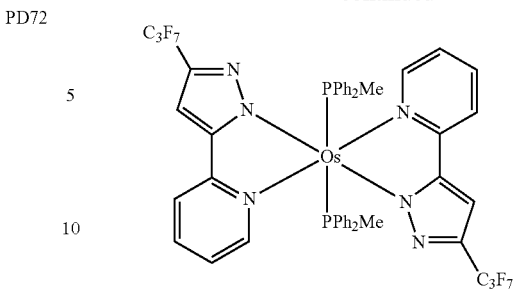
PD74
For example, the phosphorescent dopant may include PtOEP:
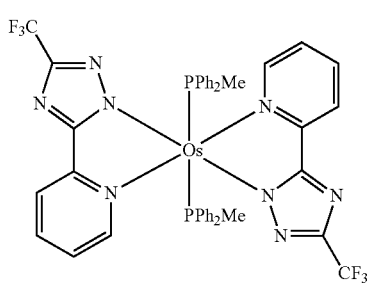
PD73
PtOEP
For example, the fluorescent dopant may further include at least one of DPAVBi, BDAVBi, TBPe, DCM, DCJTB, Coumarin 6, and C545T.
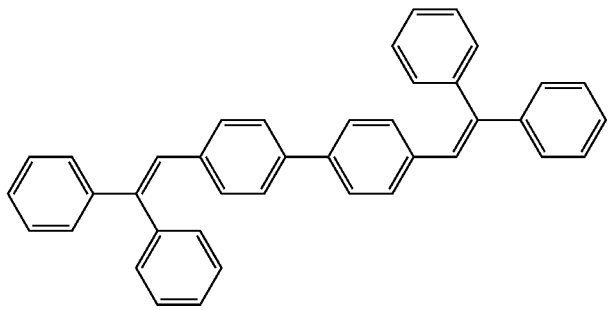
DPVBi
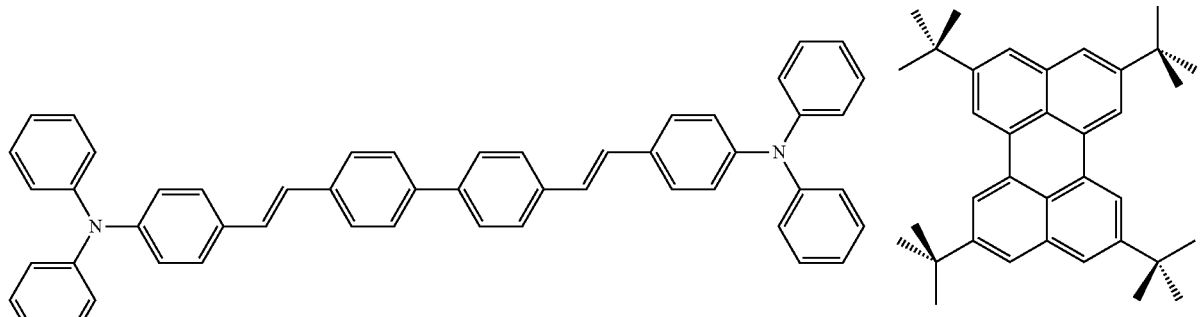
DPAVBi
TBPe

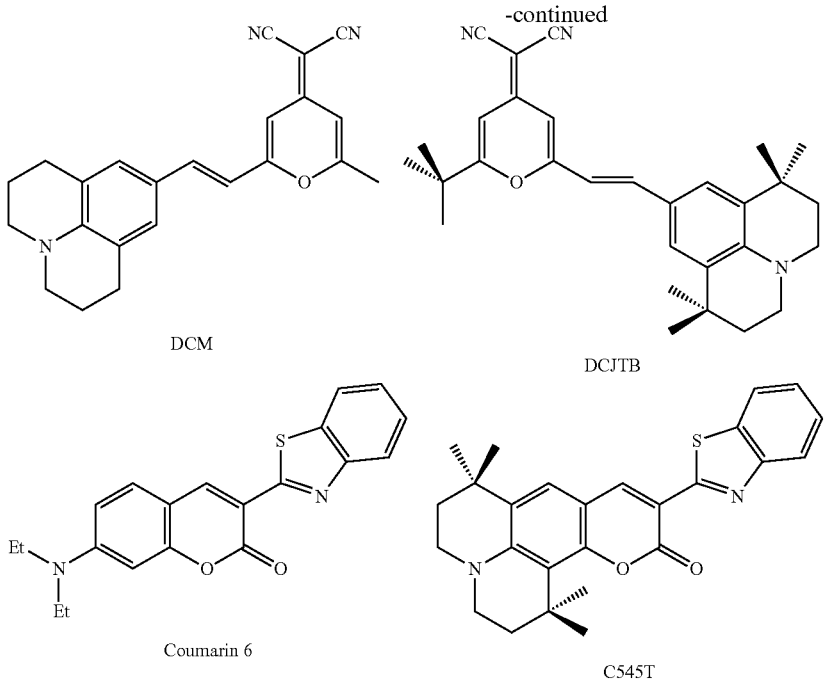

DCM

DCJTB

Coumarin 6

C545T

For example, the fluorescent dopant may include a compound represented by Formula 501:

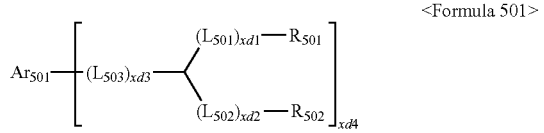

<Formula 501>

In Formula 501, $Ar_{501}$ may be selected from a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene, a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$), wherein $Q_{501}$ to $Q_{503}$ may be each independently selected from a hydrogen, $C_1$-$C_{60}$ alkyl group, a $C_2$-$C_{60}$ alkenyl group, a $C_6$-$C_{60}$ aryl group, and a $C_2$-$C_{60}$ heteroaryl group;

$L_{501}$ to $L_{503}$ may be the same as those for $L_{201}$ defined herein;

$R_{501}$ and $R_{502}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazoly group, a triazinyl group, a dibenzofuranyl group, and a dibenzothio group, and a phenyl group, a naphthyl group, a fluorenyl group, spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothio group, each substituted with at least one selected from a phenyl group, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and a dibenzofuranyl group, and a dibenzothiophenyl group;

xd1 to xd3 may be each independently selected from 0, 1, 2, and 3; and
xb4 may be selected from 1, 2, 3, and 4.
For example, the fluorescent host may include at least one of Compounds FD1 to FD8:
FD1
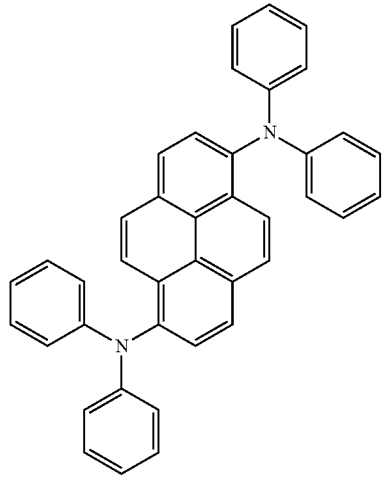
FD2
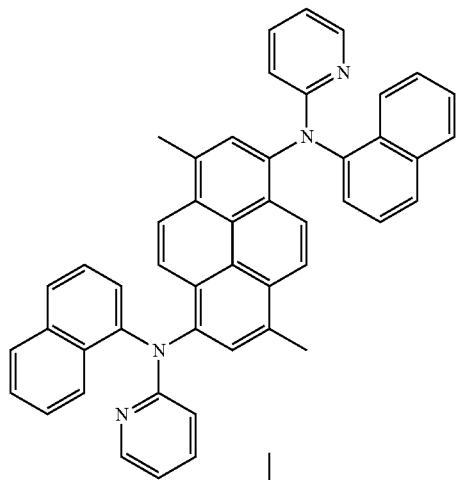
FD3
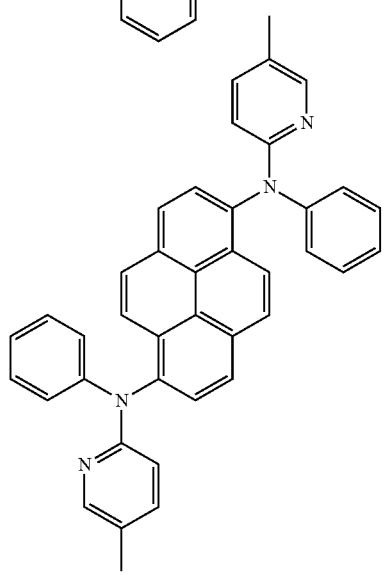
FD4
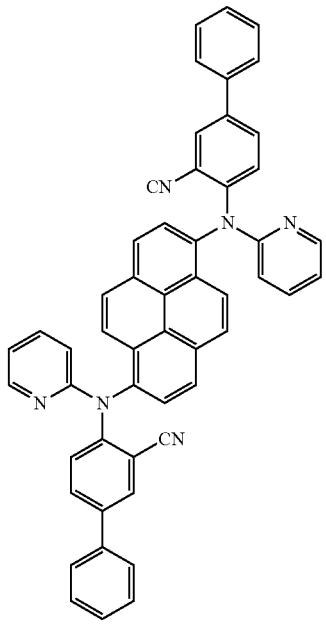
FD5
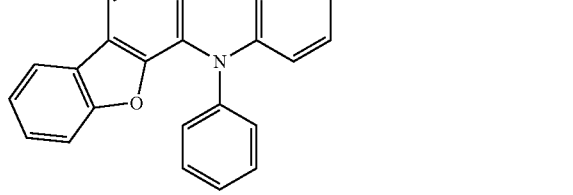
FD6
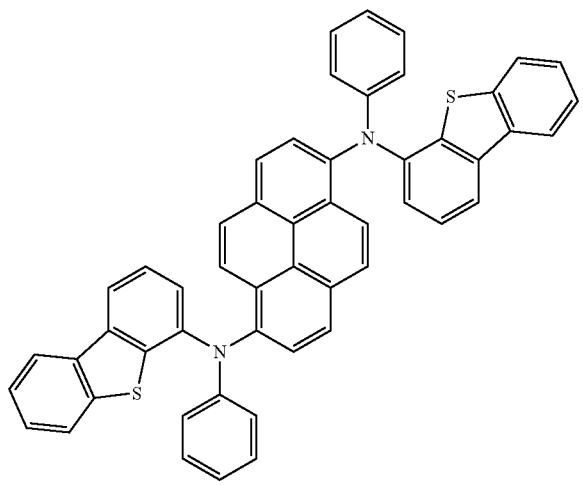

-continued

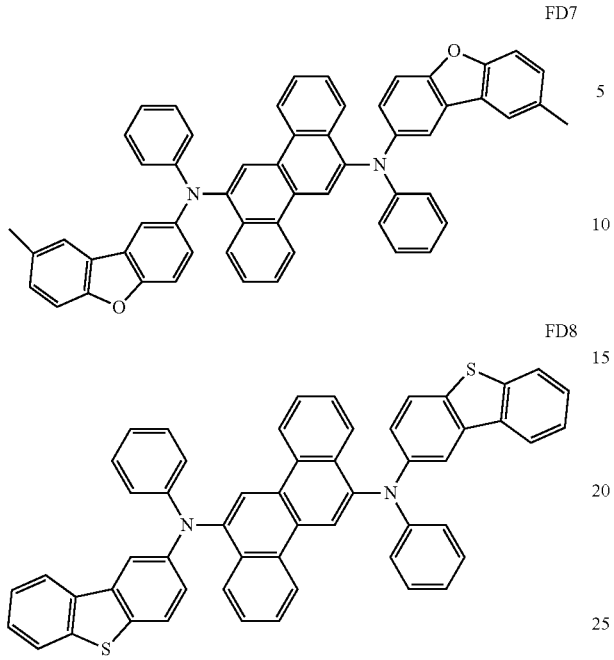

FD7

FD8

An amount of the dopant in the EML may be from about 0.01 parts to about 15 parts by weight based on 100 parts by weight of the host, but is not limited to this range.

The thickness of the EML may be about 100 Å to about 1000 Å, and in some embodiments, may be from about 200 Å to about 600 Å. When the thickness of the EML is within these ranges, the EML may have good light emitting ability without a substantial increase in driving voltage.

Next, the electron transport region may be disposed on the EML.

The electron transport region may include at least one of a HBL, an ETL, and an EIL. However, embodiments of the present disclosure are not limited thereto.

In some embodiments, the electron transport region may have a structure including an ETL/EIL, or a HBL/ETL/EIL, wherein the layers forming a structure of the electron transport region may be sequentially stacked on the EML in the order stated above. However, embodiments of the present disclosure are not limited thereto:

In some embodiments, the organic layer 150 of the organic light-emitting device 10 may include the electron transport region between the EML and the second electrode 190, and at least one of the condensed cyclic compounds of Formulae 1A and 1B may be in the electron transport region.

The electron transport region may include a HBL. When the EML includes a phosphorescent dopant, the HBL may prevent diffusion of triplet exitons or holes into the ETL from the EML.

When the electron transport region includes a HBL, the HBL may be formed on the EML by using any of a variety of methods, for example, by using vacuum deposition, spin coating, casting, Langmuir-Blodgett (LB) deposition, inkjet printing, laser printing, laser induced thermal imaging (LITI), or the like. When the HBL is formed using vacuum deposition or spin coating, the deposition and coating conditions for forming the HBL may be similar to the above-described deposition and coating conditions for forming the HIL, and accordingly will not be described in detail.

For example, the HBL may include at least one of BCP below and Bphen below. However, embodiments of the present disclosure are not limited thereto.

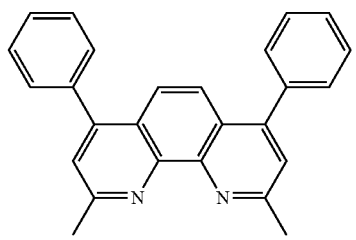

BCP

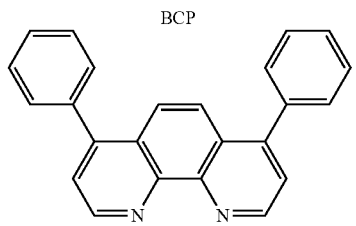

Bphen

A thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The electron transport region may include an ETL. The ETL may be formed on the EML or the HBL by using any of a variety of methods, for example, by using vacuum deposition, spin coating, casting, Langmuir-Blodgett (LB) deposition, inkjet printing, laser printing, laser induced thermal imaging (LITI), or the like. When the ETL is formed using vacuum deposition or spin coating, the deposition and coating conditions for forming the ETL may be similar to the above-described deposition and coating conditions for forming the HIL, and accordingly will not be described in detail.

In some embodiments, the organic layer 150 of the organic light-emitting device may include an electron transport region between the EML and the second electrode 190, wherein the electron transport region may include an ETL, and the ETL may include at least one of the condensed cyclic compounds of Formulae 1A and 1B.

The ETL may further include at least one of BCP, Bphen Alq$_3$, Balq, TAZ, and NTAZ, in addition to the at least one of the condensed cyclic compounds of Formulae 1A and 1B.

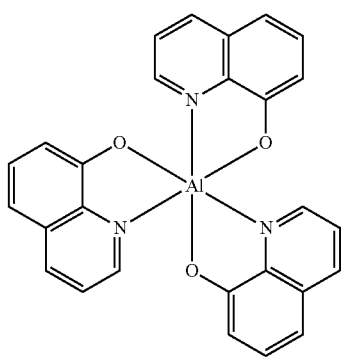

Alq$_3$

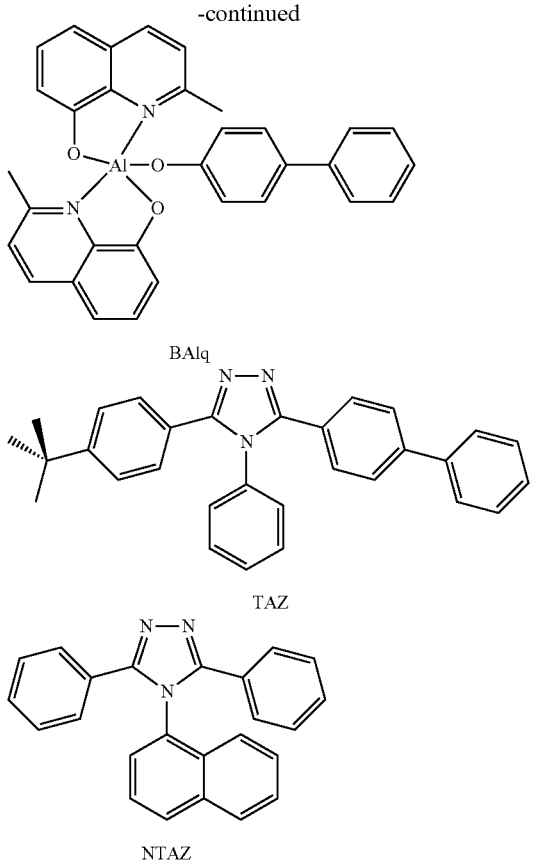

BAlq

TAZ

NTAZ

A thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex are compound ET-D1 below (lithium quinolate (LiQ)), or compound ET-D2.

ET-D1

ET-D2

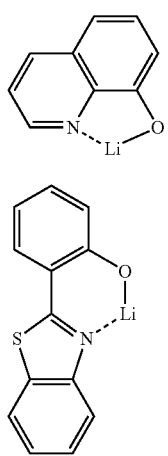

The electron transport region may include an EIL that may facilitate injection of electrons from the second electrode 190.

The EIL may be formed on the ETL by using any of a variety of methods, for example, by using vacuum deposition, spin coating, casting, Langmuir-Blodgett (LB) deposition, inkjet printing, laser printing, laser induced thermal imaging (LITI), or the like. When the EIL is formed using vacuum deposition or spin coating, the deposition and coating conditions for forming the EIL may be similar to the above-described deposition and coating conditions for forming the HIL, and accordingly will not be described in detail.

The EIL may include at least one selected from LiF, NaCl, CsF, $Li_2O$, BaO, and LiQ.

A thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

The second electrode 190 may be disposed on the organic layer 150, as described above. The second electrode 190 may be a cathode as an electron injecting electrode. A material for forming the second electrode 190 may be a metal, an alloy, an electrically conductive compound, which have a low-work function, or a mixture thereof. Non-limiting examples of materials for forming the second electrode 190 are lithium (Li), magnesium (Mg), aluminum (Al), aluminum-lithium (Al—Li), calcium (Ca), magnesium-indium (Mg—In), and magnesium-silver (Mg—Ag). In some embodiments, a material for forming the second electrode 190 may be ITO or IZO. The second electrode 190 may be a reflective electrode, a semi-transmissive electrode, or a transmissive electrode.

Although the organic light-emitting device of the FIGURE is described above, embodiments of the present disclosure are not limited thereto.

As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group a methyl group, a ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$ alkyl group as described above. Non-limiting examples of the $C_1$-$C_{60}$ alkoxy group are a methoxy group, an ethoxy group, and an isopropyloxy group.

As used herein, a $C_2$-$C_{60}$ alkenyl group refers to a hydrocarbon group including at least one carbon double bond in the middle or terminal of the $C_2$-$C_{60}$ alkyl group. Non-limiting examples of the $C_2$-$C_{60}$ alkenyl group are an ethenyl group, a prophenyl group, and a butenyl group. A $C_2$-$C_{60}$ alkylene group refers to a divalent group having the same structure as the $C_2$-$C_{60}$ alkenyl group.

As used herein, a $C_2$-$C_{60}$ alkynyl group refers to a hydrocarbon group including at least one carbon triple bond in the middle or terminal of the $C_2$-$C_{60}$ alkyl group. Non-limiting examples of the $C_2$-$C_{60}$ alkynyl group are an ethynyl group and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_2$-$C_{10}$ heterocycloalkyl group refers to a monovalent monocyclic group having 2 to 10 carbon atoms in which at least one hetero atom selected from N, O, P, and S is included as a ring-forming atom. Non-limiting examples of the $C_2$-$C_{10}$ heterocycloalkyl group are a tetrahydrofuranyl group and a tetrahydrothiophenyl group. A $C_2$-$C_{10}$ heterocycloalkylene group refers to a divalent group having the same structure as the $C_2$-$C_{10}$ heterocycloalkyl group.

As used herein, a $C_3$-$C_{10}$ cycloalkenyl group refers to a monovalent monocyclic group having 3 to 10 carbon atoms that includes at least one double bond in the ring but does not have aromacity. Non-limiting examples of the $C_3$-$C_{10}$ cycloalkenyl group are a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_2$-$C_{10}$ heterocycloalkenyl group used herein refers to a monovalent monocyclic group having 2 to 10 carbon atoms that includes at least one double bond in the ring and in which at least one hetero atom selected from N, O, P, and S is included as a ring-forming atom. Non-limiting examples of the $C_2$-$C_{10}$ heterocycloalkenyl group are a 2,3-hydrofuranyl group and a 2,3-hydrothiophenyl group. A $C_2$-$C_{10}$ heterocycloalkenylene group used herein refers to a divalent group having the same structure as the $C_3$-$C_{10}$ heterocycloalkenyl group.

As used herein, a $C_6$-$C_{60}$ aryl group refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include at least two rings, the rings may be fused to each other.

As used herein, a $C_2$-$C_{60}$ heteroaryl group refers to a monovalent, aromatic carbocyclic aromatic group having 2 to 60 carbon atoms in which at least one hetero atom selected from N, O, P, and S is included as a ring-forming atom, and 2 to 60 carbon atoms. A $C_2$-$C_{60}$ heteroarylene group refers to a divalent, aromatic carbocyclic group having 2 to 60 carbon atoms in which at least one hetero atom selected from N, O, P, and S is included as a ring-forming atom. Non-limiting examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl and the $C_2$-$C_{60}$ heteroarylene include at least two rings, the rings may be fused to each other.

As used herein, a $C_6$-$C_{60}$ aryloxy group indicates —$OA_{102}$ (where $A_{102}$ is a $C_6$-$C_{60}$ aryl group as described above), and a $C_6$-$C_{60}$ arylthio group indicates —$SA_{103}$ (where $A_{103}$ is a $C_6$-$C_{60}$ aryl group as described above).

As used herein, a monovalent non-aromatic condensed polycyclic group refers to a monovalent group having at least two rings condensed to each other, in which only carbon atoms (for example, 8 to 60 carbon atoms) are exclusively included as ring-forming atoms and the entire molecule has non-aromacity. A non-limiting example of the monovalent non-aromatic condensed polycyclic group is a fluorenyl group. A divalent non-aromatic condensed polycyclic group refers to a divalent group having the same structure as the monovalent non-aromatic condensed polycyclic group.

As used herein, a monovalent non-aromatic condensed heteropolycyclic group refers to a monovalent group having at least two rings condensed to each other, in which carbon atoms (for example, 2 to 60 carbon atoms) and a hetero atom selected from N, O, P, and S are as ring-forming atoms and the entire molecule has non-aromacity. A non-limiting example of the monovalent non-aromatic condensed heteropolycyclic group is a carbazolyl group. A divalent non-aromatic condensed heteropolycyclic group refers to a divalent group having the same structure as the monovalent non-aromatic condensed heteropolycyclic group.

As used herein, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed cyclic group, the substituted divalent non-aromatic hetero-condensed cyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic hetero-condensed polycyclic group, may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxyl group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one of a deuterium. —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

For example, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ heteroarylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an sobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$), a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an sobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an sobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexcenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an sobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, —N($Q_{21}$)($Q_{22}$), —Si($Q_{23}$)($Q_{24}$)($Q_{25}$), and —B($Q_{26}$)($Q_{27}$), and
—N($Q_{31}$)($Q_{32}$), —Si($Q_{33}$)($Q_{34}$)($Q_{35}$), and —B($Q_{36}$)($Q_{37}$),
wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexcenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an sobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The acronym "Ph" used herein refers to phenyl, the acronym "Me" used herein refers to methyl, the acronym "Et" used herein refers to ethyl, and the acronym "ter-Bu" or "Bu'" used herein refers to tert-butyl.

One or more embodiments of the present disclosure, which include condensed cyclic compounds, and organic light-emitting devices including the same, will now be described in detail with reference to the following examples. However, these examples are only for illustrative purposes and are not intended to limit the scope of the one or more embodiments of the present disclosure. In the following synthesis example, the expression that "'B' instead of 'A' was used" means that the amounts of 'B' and 'A' were the same in equivalent amounts.

EXAMPLES

Synthesis Example 1: Synthesis of Compound 1A

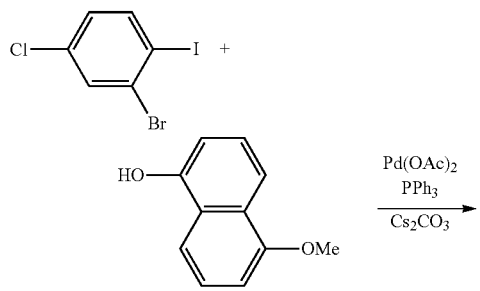

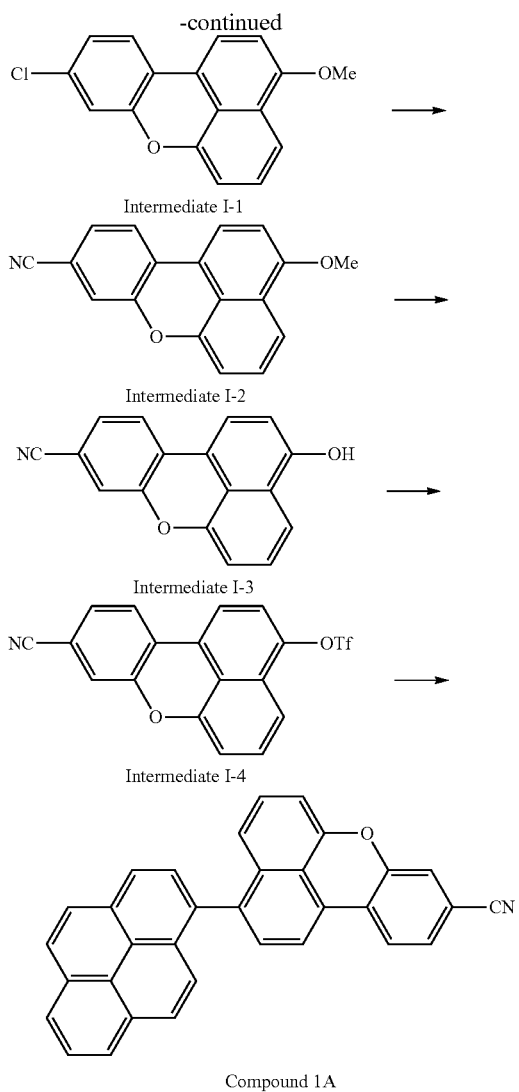

Intermediate I-1

Intermediate I-2

Intermediate I-3

Intermediate I-4

Compound 1A

Synthesis of Intermediate I-1

3.17 g (10 mmol) of 2-bromo-4-chloro-1-iodobenzene, 1.92 g (11 mmol) of 5-methoxy-1-naphthol, 0.112 g (0.5 mmol) of palladium acetate, 0.651 g (2.0 mmol) of triphenylphosphine, and 13 g (40 mmol) of cesium carbonate were dissolved in 60 mL of dimethylformamide (DMF), and then stirred at about 140° C. for about 24 hours. The resulting mixture was cooled down to room temperature, and 60 mL of water was added thereto, followed by extraction three times with ethylether. An organic layer was collected and was dried using magnesium sulfate to evaporate the solvent. The residue was separated and purified using silica gel column chromatography to obtain 1.70 g of Intermediate I-1 (Yield: 60%). This compound was identified using liquid chromatography-mass spectroscopy (LC-MS).

$C_{17}H_{11}ClO_2$: M+ 282.0

Synthesis of Intermediate I-2

1.70 g (4.2 mmol) of Intermediate I-1, 19 mg (0.084 mmol) of palladium acetate, 60 mg (0.13 mmol) of Xphos (dicyclohexyl(2',4',6'-triisopropyl-2-biphenylyl)phosphine), 0.44 g (1.05 mmol) of $K_4[Fe(CN)_6]\cdot 3\,H_2O$, and 0.58 g (4.2 mmol) of potassium carbonate were dissolved in 20 mL of a mixture of $H_2O$ and 1,4-dioxane (1:1 by volume), and then stirred at about 120° C. for about 10 hours. The resulting mixture was cooled down to room temperature, followed by extraction three times with 30 mL of water and 30 mL of diethyl ether. An organic layer was collected and was dried using magnesium sulfate to evaporate the solvent. The residue was separated and purified using silica gel column chromatography to obtain 0.99 g of Intermediate I-2 (Yield: 86%). This compound was identified using LC-MS.

$C_{18}H_{11}NO_2$: M+ 273.1

Synthesis of Intermediate I-3

0.99 g (3.6 mmol) of Intermediate I-2 was dissolved in 20 mL of methylene chloride (MC), and 0.51 mL (5.4 mmol) of $BBr_3$ was slowly dropwise added thereto at about −78° C. The temperature of the resulting mixture was raised to room temperature and stirred at room temperature for about 24 hours. After termination of the reaction, 10 mL of MeOH and 20 mL of $H_2O$ were added thereto, followed by extraction three times with 20 mL of MC. An organic layer was collected and was dried using magnesium sulfate to evaporate the solvent. The residue was separated and purified using silica gel column chromatography to obtain 0.87 g of Intermediate I-3 (Yield: 93%). This compound was identified using LC-MS.

$C_{17}H_9NO_2$: M+ 259.1

Synthesis of Intermediate I-4

0.87 g (3.3 mmol) of Intermediate I-3 was dissolved in 10 mL of toluene and 10 mL of a 30% potassium phosphate mixture, and 1.09 g (3.9 mmol) of trifluoromethane sulfonic anhydride was slowly dropwise added thereto at about 0° C. The reaction temperature was raised to room temperature, and the resulting mixture was stirred for about 3 hours. 20 mL of water was added thereto, followed by extraction three times with 20 mL of ethylether. An organic layer was collected and was dried using magnesium sulfate to evaporate the solvent. The residue was separated and purified using silica gel column chromatography to obtain 1.06 g of Intermediate I-4 (Yield: 82%). This compound was identified using LC-MS.

$C_{18}H_8F_3NO_4S$: M+ 391.0

Synthesis of Compound 1A 1.06 g (2.71 mmol) of Intermediate I-4, 0.67 g (2.71 mmol) of pyrene boronic acid, 0.17 g (0.14 mmol) of $Pd(PPh_3)_4$, and 1.12 g (8.13 mmol) of $K_2CO_3$ were dissolved in 40 mL of a mixed solution of THF and $H_2O$ (2:1 by volume), and then stirred at about 80° C. for about 12 hours. The resulting mixture was cooled down to room temperature, followed by extraction three times with 30 mL of water and 30 mL of ethylacetate. An organic layer was collected and was dried using magnesium sulfate to evaporate the solvent. The residue was separated and purified using silica gel column chromatography to obtain 0.99 g of Compound 1A (Yield: 83%). This compound was identified using mass spectroscopy/fast atom bombardment (MS/FAB) and $^1H$ NMR.

$C_{33}H_{17}NO$ cal. 443.13, found 443.14.

Synthesis Example 2: Synthesis of Compound 3A

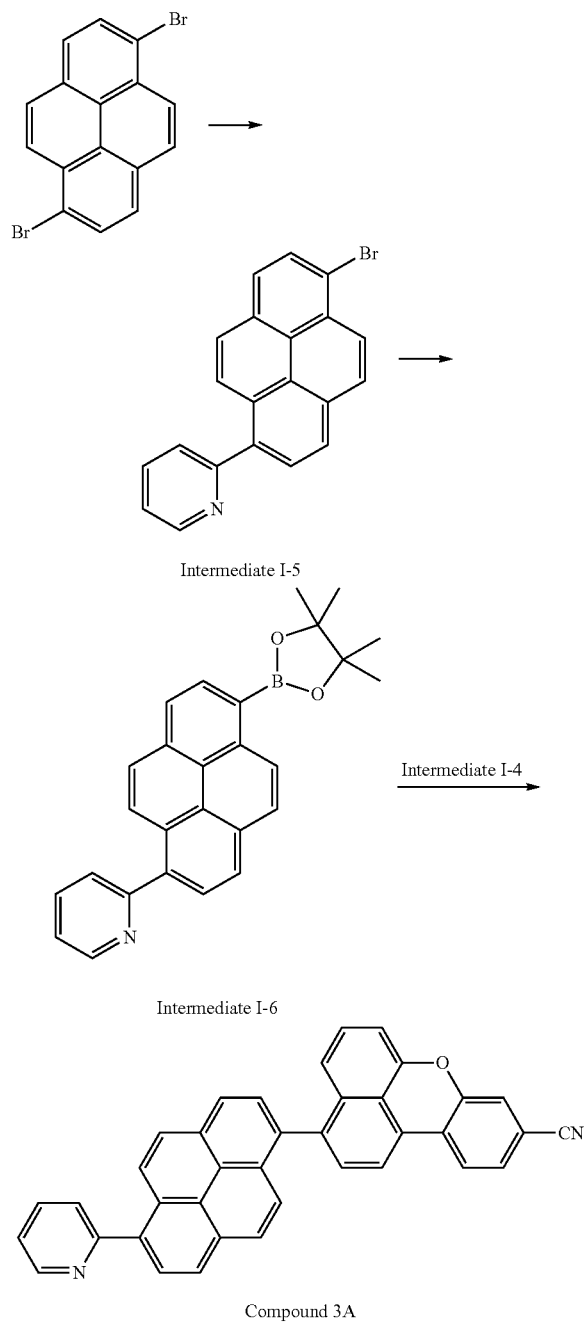

Intermediate I-5

Intermediate I-6

Compound 3A

Synthesis of Intermediate I-5

5.40 g (15 mmol) of 1,6-dibromopyrene, 1.90 g (10 mmol) of 2-pyridine boronic acid, 0.58 g (0.5 mmol) of tetrakis(triphenylphosphine)palladium (Pd(PPh$_3$)$_4$), and 4.15 g (30 mmol) of K$_2$CO$_3$ were dissolved in 60 mL of a mixed solution of THF and H$_2$O (2:1 by volume), and then stirred at about 70° C. for about 5 hours. The resulting mixture was cooled down to room temperature, followed by extraction three times with 50 mL of water and 50 mL of ethylether. An organic layer was collected and was dried using magnesium sulfate to evaporate the solvent. The residue was separated and purified using silica gel column chromatography to obtain 2.26 g of Intermediate I-5 (Yield: 63%). This compound was identified using LC-MS.

C$_{21}$H$_{12}$BrN: M$^+$ 357.0

Synthesis of Intermediate I-6

2.26 g (6.30 mmol) of Intermediate I-5 was dissolved in 50 mL of THF, and 3.0 mL (6.94 mmol, 2.5M in hexane) of n-BuLi was slowly dropwise added thereto, and stirred at the same temperature for about 1 hour. Then, 1.7 mL (8.23 mmol) of 2-isoproxy-4,4,5,5-tetramethyl-1,3,2-dioxaborolane was dropwise added thereto and stirred at room temperature for about 24 hours. After termination of the reaction, 40 mL of water was added thereto, followed by extraction three times with 40 mL of diethyl ether. An organic layer was collected and was dried using magnesium sulfate to evaporate the solvent. The residue was separated and purified using silica gel column chromatography to obtain 1.97 g of Intermediate I-6 (Yield: 77%). This compound was identified using LC-MS.

C$_{27}$H$_{24}$BNO$_2$: M$^+$ 405.2

Synthesis of Compound 3A 1.97 g (4.86 mmol) of Intermediate I-6, 1.90 g (4.86 mmol) of Intermediate I-4, 0.28 g (0.24 mmol) of Pd(PPh$_3$)$_4$, and 2.01 g (14.6 mmol) of K$_2$CO$_3$ were dissolved in 50 mL of a mixed solution of THF and H$_2$O (2:1 by volume), and then stirred at about 80° C. for about 12 hours. The resulting mixture was cooled down to room temperature, followed by extraction three times with 40 mL of water and 40 mL of ethylacetate. An organic layer was collected and was dried using magnesium sulfate to evaporate the solvent. The residue was separated and purified using silica gel column chromatography to obtain 1.90 g of Compound 3A (Yield: 75%). This compound was identified using mass spectroscopy/fast atom bombardment (MS/FAB) and $^1$H NMR.

C$_{38}$H$_{20}$N$_2$O cal. 520.16, found 520.15.

Synthesis Example 3: Synthesis of Compound 16A

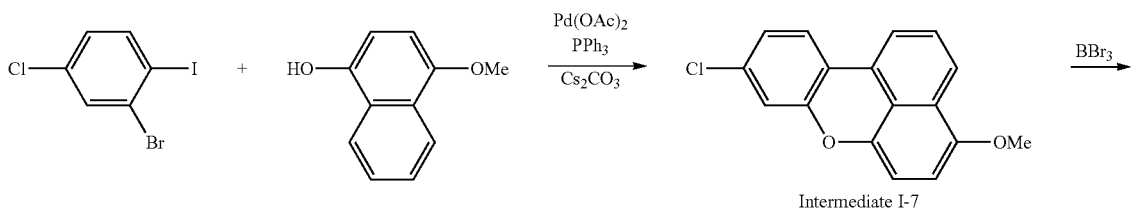

Intermediate I-7

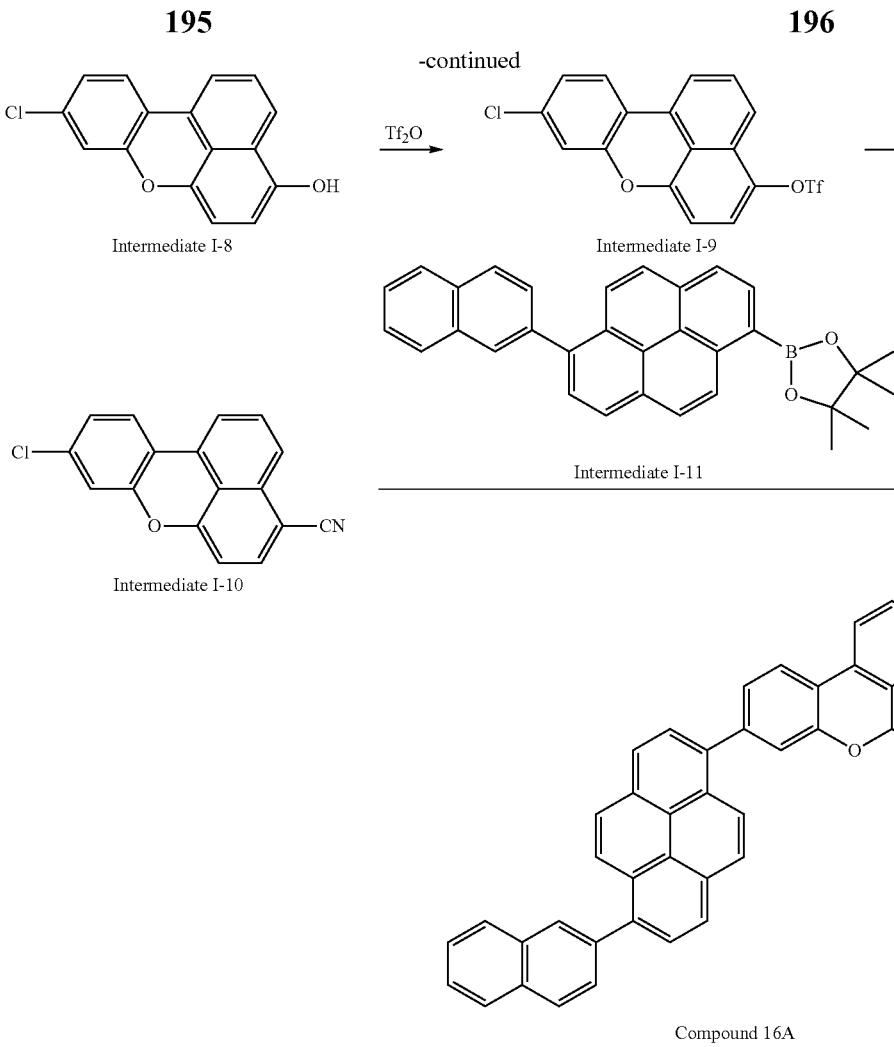

Compound 16A

Synthesis of Intermediate I-7

3.17 g (10 mmol) of 2-bromo-4-chloro-1-iodobenzene, 1.92 g (11 mmol) of 4-methoxy-1-naphthol, 0.112 g (0.5 mmol) of palladium acetate, 0.651 g (2.0 mmol) of triphenylphosphine, and 13 g (40 mmol) of cesium carbonate were dissolved in 60 mL of dimethylformamide (DMF), and then stirred at about 140° C. for about 24 hours. The resulting mixture was cooled down to room temperature, and 60 mL of water was added thereto, followed by extraction three times with ethylether. An organic layer was collected and was dried using magnesium sulfate to evaporate the solvent. The residue was separated and purified using silica gel column chromatography to obtain 1.64 g of Intermediate I-7 (Yield: 58%). This compound was identified using LC-MS.

$C_{17}H_{11}ClO_2$: $M^+$ 282.0

Synthesis of Intermediate I-8

1.64 g (5.8 mmol) of Intermediate I-7 was dissolved in 60 mL of MC, and 0.82 mL (8.7 mmol) of $BBr_3$ was slowly dropwise added thereto at about −78° C. The reaction temperature was raised to room temperature, and the resulting mixture was stirred at room temperature for about 24 hours. After termination of the reaction, 15 mL of MeOH and 30 mL of $H_2O$ were added thereto, followed by extraction three times with 30 mL of MC. An organic layer was collected and was dried using magnesium sulfate to evaporate the solvent. The residue was separated and purified using silica gel column chromatography to obtain 1.43 g of Intermediate I-8 (Yield: 92%). This compound was identified using LC-MS.

$C_{16}H_9ClO_2$: $M^+$ 268.0

Synthesis of Intermediate I-9

1.43 g (5.3 mmol) of Intermediate I-8 was dissolved in 20 mL of toluene and 20 mL of a 30% potassium phosphate mixture, and 1.79 g (6.4 mmol) of trifluoromethane sulfonic anhydride was slowly dropwise added thereto at about 0° C. The reaction temperature was raised to room temperature, and the resulting mixture was stirred for about 3 hours. 30 mL of water was added thereto, followed by extraction three times with 30 mL of ethylether. An organic layer was collected and was dried using magnesium sulfate to evaporate the solvent. The residue was separated and purified using silica gel column chromatography to obtain 1.70 g of Intermediate I-9 (Yield: 80%). This compound was identified using LC-MS.

$C_{17}H_8ClF_3O_4S$: $M^+$ 400.0

Synthesis of Intermediate I-10

1.70 g (4.2 mmol) of Intermediate I-9, 4.7 mg (0.021 mmol) of palladium acetate, 0.39 g (0.92 mmol) of $K_4[Fe(CN)_6] \cdot 3 H_2O$, and 0.58 g (4.2 mmol) of potassium carbonate were dissolved in 20 mL of a mixed solution of $H_2O$ and 1,4-dioxane (1:1 by volume), and then stirred at about 140° C. for about 10 hours. The resulting mixture was cooled down to room temperature, followed by extraction three times with 30 mL of water and 30 mL of diethyl ether. An organic layer was collected and was dried using magnesium sulfate to evaporate the solvent. The residue was separated and purified using silica gel column chromatography to obtain 0.96 g of Intermediate I-10 (Yield: 82%). This compound was identified using LC-MS.

$C_{17}H_8ClNO$: $M^+$ 277.0

Synthesis of Intermediate I-11

Intermediate I-11 (2.26 g, Yield: 79%) was obtained in the same manner as the synthesis of Intermediate I-5, except that 2-naphthylboronic acid, instead of 2-pyridine boronic acid, was used to synthesize Intermediate I-5 of Synthesis Example 2. This compound was identified using LC-MS.

$C_{32}H_{27}BO_2$: $M^+$ 454.2

Synthesis of Compound 16A 0.96 g (3.4 mmol) of Intermediate I-10, 1.54 g (3.4 mmol) of Intermediate I-11, 0.046 g (0.05 mmol) of $Pd_2(dba)_3$, 0.02 g (0.1 mmol) of $PtBu_3$, and 1.66 g (5.1 mmol) of cesium carbonate were dissolved in 30 mL of a 1,4-dioxane solution, and then stirred at about 90° C. for about 20 hours. The resulting mixture was cooled down to room temperature, and 40 mL of water was added thereto, followed by extraction three times with ethylether. An organic layer was collected and was dried using magnesium sulfate to evaporate the solvent. The residue was separated and purified using silica gel column chromatography to obtain 1.41 g of Compound 16A (Yield: 73%). This compound was identified using MS/FAB.

$C_{43}H_{23}NO$: calc. 569.18, found 569.20.

Synthesis Example 4: Synthesis of Compound 24A

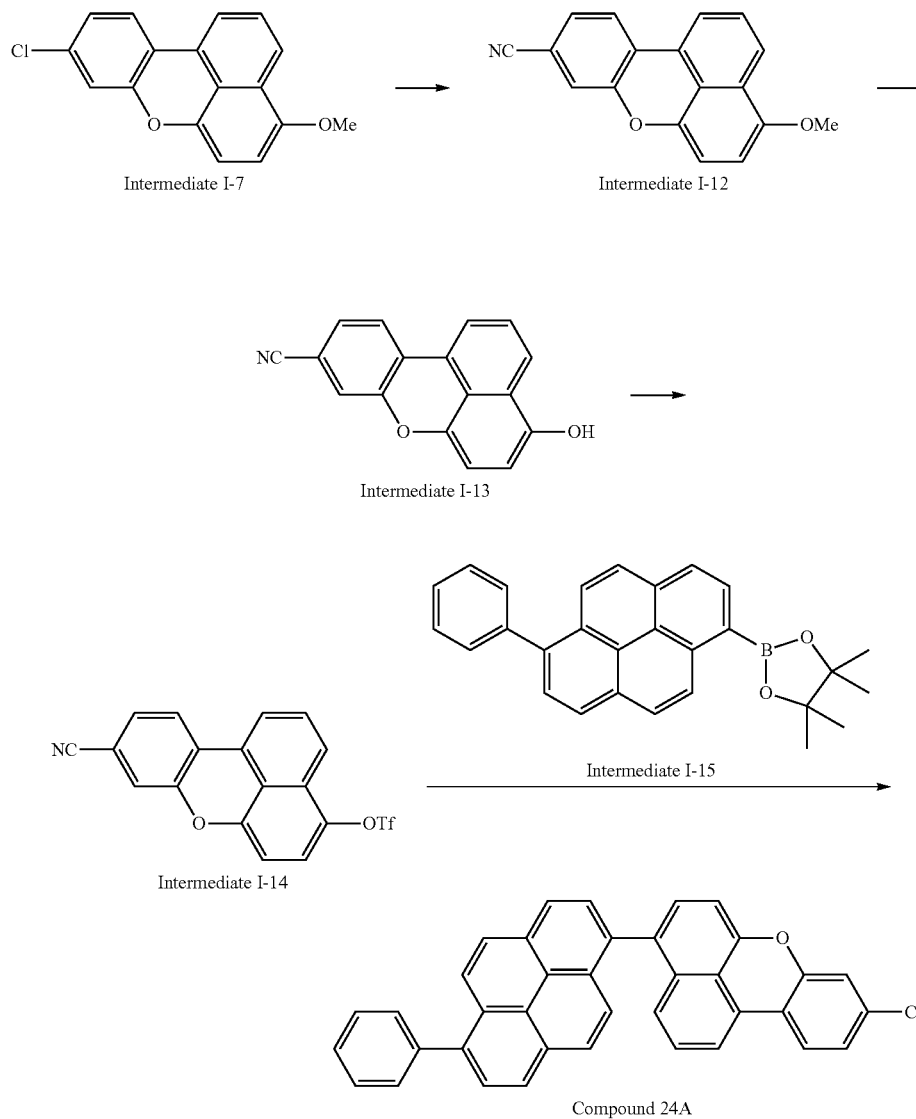

Synthesis of Intermediate I-12

Intermediate I-9 (0.99 g, Yield: 86%) was obtained in the same manner as in the synthesis of Intermediate I-2 of Synthesis Example 1, except that Intermediate I-7 instead of Intermediate I-1 was used. This compound was identified using LC-MS.

$C_{18}H_{11}NO_2$: M$^+$ 273.1

Synthesis of Intermediate I-13

Intermediate I-13 (0.87 g, Yield: 93%) was obtained in the same manner as in the synthesis of Intermediate I-3 of Synthesis Example 1, except that intermediate I-12 instead of Intermediate I-2 was used. This compound was identified using LC-MS.

$C_{17}H_9NO_2$: M$^+$ 259.1

Synthesis of Intermediate I-14

Intermediate I-14 (1.06 g, Yield: 82%) was obtained in the same manner as in the synthesis of Intermediate I-4 of Synthesis Example 1, except that intermediate I-13 instead of Intermediate I-3 was used. This compound was identified using LC-MS.

$C_{18}H_8F_3NO_4S$: M$^+$ 391.0

Synthesis of Compound 24A

Compound 24A (1.20 g, Yield: 85%) was obtained in the same manner as in the synthesis of Compound 1A of Synthesis Example 1, except that Intermediate I-14 and Intermediate I-15, instead of Intermediate I-4 and 1-pyrene boronic acid, respectively, were used. This compound was identified using MS/FAB and $^1$H NMR.

$C_{39}H_{21}NO$ cal. 519.16, found 519.17.

Synthesis Example 5: Synthesis of Compound 72A

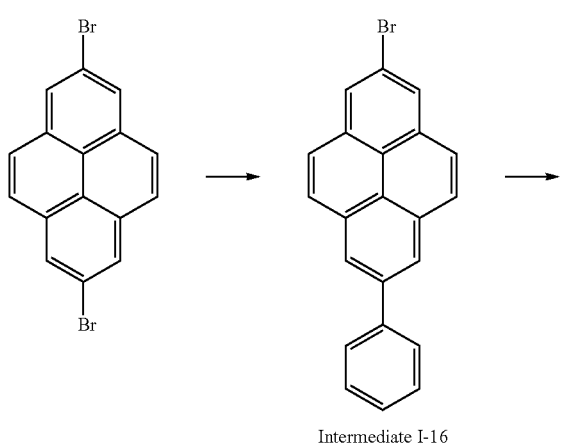

Intermediate I-16

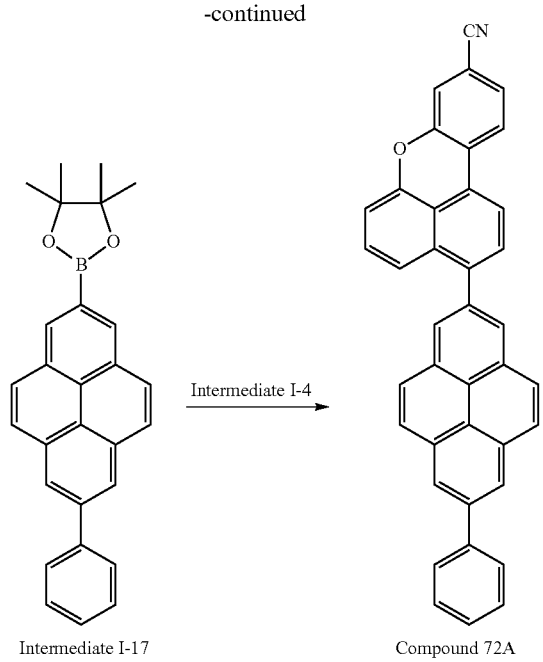

Synthesis of Intermediate I-16

Intermediate I-16 (2.39 g, Yield: 67%) was obtained in the same manner as the synthesis of Intermediate I-5 of Synthesis Example 2, except that 2,7-dibromopyrene and phenyl boronic acid, instead of 1,6-dibromopyrene and 2-pyridine boronic acid, respectively, were used. This compound was identified using LC-MS.

$C_{22}H_{13}Br$: M$^+$ 356.0

Synthesis of Intermediate I-17

Intermediate I-17 (2.11 g, Yield: 78%) was obtained in the same manner as in the synthesis of Intermediate I-6 of Synthesis Example 2, except that intermediate I-16 instead of Intermediate I-5 was used. This compound was identified using LC-MS.

$C_{28}H_{25}BO_2$: M$^+$ 404.2

Synthesis of Compound 72A

Compound 72A (2.14 g, Yield: 79%) was obtained in the same manner as in the synthesis of Compound 1A of Synthesis Example 1, except that Intermediate I-17, instead of 1-pyrene boronic acid, was used. This compound was identified using MS/FAB and $^1$H NMR.

$C_{39}H_{21}NO$ cal. 519.16, found 519.15.

Synthesis Example 6: Synthesis of Compound 20A

Compound 20A (1.20 g, Yield: 85%) was obtained in the same manner as in the synthesis of Compound 1A of Synthesis Example 1, except that Intermediate I-20 and Intermediate I-20A, instead of Intermediate I-4 and 1-pyrene boronic acid, respectively, were used. The synthesis of Intermediate I-20 is follows.

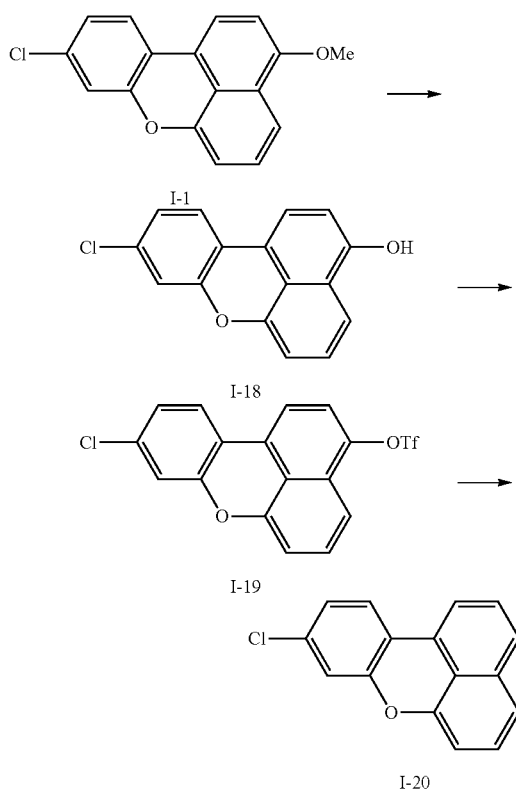

Synthesis of Intermediate I-18

Intermediate I-18 (0.87 g, Yield: 93%) was obtained in the same manner as in the synthesis of Intermediate I-8 of Synthesis Example 3, except that intermediate I-1 instead of Intermediate I-7 was used to. This compound was identified using LC-MS.

$C_{16}H_9ClO_2$: M$^+$ 268.0

Synthesis of Intermediate I-19

Intermediate I-19 (1.06 g, Yield: 82%) was obtained in the same manner as in the synthesis of Intermediate I-9 of Synthesis Example 3, except that intermediate I-18 instead of Intermediate I-8 was used. This compound was identified using LC-MS.

$C_{17}H_8ClF_3O_4S$: M$^+$ 400.0

Synthesis of Intermediate I-20

Intermediate I-20 (1.06 g, Yield: 82%) was obtained in the same manner as in the synthesis of Intermediate I-10 of Synthesis Example 3, except that intermediate I-9 instead of Intermediate I-19 was used to synthesize Intermediate I-10 of Synthesis Example 3. This compound was identified using LC-MS.

$C_{17}H_8ClNO$: M$^+$ 277.0

Synthesis Example 7: Synthesis of Compound 32A

Compound 32A was synthesized in the same manner as in the synthesis of Compound 1A of Synthesis Example 1, except that Intermediate I-32A instead of 1-pyrene boronic acid was used.

Synthesis Example 8: Synthesis of Compound 39A

Compound 39A was synthesized in the same manner as in the synthesis of Compound 1A of Synthesis Example 1, except that Intermediate I-29 and Intermediate I-39A, instead of Intermediate I-4 and 1-pyrene boronic acid, respectively, were used. Intermediate I-29 was synthesized in the same manner as in the synthesis of Intermediate I-7, Intermediate I-8, Intermediate I-9, and Intermediate I-10 of Synthesis Example 2, except that 2-bromo-5-chloro-1-iodobenzene, instead of 2-bromo-4-chloro-1-iodobenzene, was used.

Synthesis Example 9: Synthesis of Compound 46A

Compound 46A was synthesized in the same manner as in the synthesis of Compound 1A of Synthesis Example 1, except that Intermediate I-20 and Intermediate I-46A, instead of Intermediate I-4 and 1-pyrene boronic acid, respectively, were used.

Synthesis Example 10: Synthesis of Compound 51A

Compound 51A was synthesized in the same manner as in the synthesis of Compound 1A of Synthesis Example 1, except that Intermediate I-13 and Intermediate I-15A, instead of Intermediate I-4 and 1-pyrene boronic acid, respectively, were used.

Synthesis Example 11: Synthesis of Compound 55A

Compound 55A was synthesized in the same manner as in the synthesis of Compound 1A of Synthesis Example 1, except that Intermediate I-55A instead of 1-pyrene boronic acid was used.

Synthesis Example 12: Synthesis of Compound 62A

Compound 62A was synthesized in the same manner as in the synthesis of Compound 1A of Synthesis Example 1, except that Intermediate I-10 and Intermediate I-62A, instead of Intermediate I-4 and 1-pyrene boronic acid, respectively, were used.

Synthesis Example 13: Synthesis of Compound 66A

Compound 66A was synthesized in the same manner as in the synthesis of Compound 1A of Synthesis Example 1, except that Intermediate I-10 and Intermediate I-66A, instead of Intermediate I-4 and 1-pyrene boronic acid, respectively, were used.

Synthesis Example 14: Synthesis of Compound 76A

Compound 76A was synthesized in the same manner as in the synthesis of Compound 1A of Synthesis Example 1, except that Intermediate I-76A instead of 1-pyrene boronic acid was used.

Synthesis Example 15: Synthesis of Compound 81A

Compound 81A was synthesized in the same manner as in the synthesis of Compound 1A of Synthesis Example 1, except that Intermediate I-13 and Intermediate I-81A, instead of Intermediate I-4 and 1-pyrene boronic acid, respectively, were used.

Synthesis Example 16: Synthesis of Compound 85A

Compound 85A was synthesized in the same manner as in the synthesis of Compound 1A of Synthesis Example 1, except that Intermediate I-29 and Intermediate I-85A, instead of Intermediate I-4 and 1-pyrene boronic acid, respectively, were used.

Synthesis Example 17: Synthesis of Compound 94A

Compound 94A was synthesized in the same manner as in the synthesis of Compound 1A of Synthesis Example 1, except that Intermediate I-10 and Intermediate I-94A, instead of Intermediate I-4 and 1-pyrene boronic acid, respectively, were used.

Synthesis Example 18: Synthesis of Compound 109A

Compound 109A was synthesized in the same manner as in the synthesis of Compound 1A of Synthesis Example 1, except that Intermediate I-20 and Intermediate I-109A, instead of Intermediate I-4 and 1-pyrene boronic acid, respectively, were used.

Synthesis Example 19: Synthesis of Compound 13A

Compound 113A was synthesized in the same manner as in the synthesis of Compound 1A of Synthesis Example 1, except that Intermediate I-20 and Intermediate I-113A, instead of Intermediate I-4 and 1-pyrene boronic acid, respectively, were used.

Synthesis Example 20: Synthesis of Compound 119A

Compound 119A was synthesized in the same manner as in the synthesis of Compound 1A of Synthesis Example 1, except that Intermediate I-119A instead of 1-pyrene boronic acid was used.

Synthesis Example 21: Synthesis of Compound 123A

Compound 112A was synthesized in the same manner as in the synthesis of Compound 1A of Synthesis Example 1, except that Intermediate I-20 and Intermediate I-122A, instead of Intermediate I-4 and 1-pyrene boronic acid, respectively, were used.

Synthesis Example 22: Synthesis of Compound 128A

Compound 128A was synthesized in the same manner as in the synthesis of Compound 1A of Synthesis Example 1, except that Intermediate I-20 and Intermediate I-128A, instead of Intermediate I-4 and 1-pyrene boronic acid, respectively, were used.

Synthesis Example 23: Synthesis of Compound 131A

Compound 131A was synthesized in the same manner as in the synthesis of Compound 1A of Synthesis Example 1, except that Intermediate I-29 and Intermediate I-119A, instead of Intermediate I-4 and 1-pyrene boronic acid, respectively, were used to synthesize Compound 1A of Synthesis Example 1.

Synthesis Example 24: Synthesis of Compound 3B

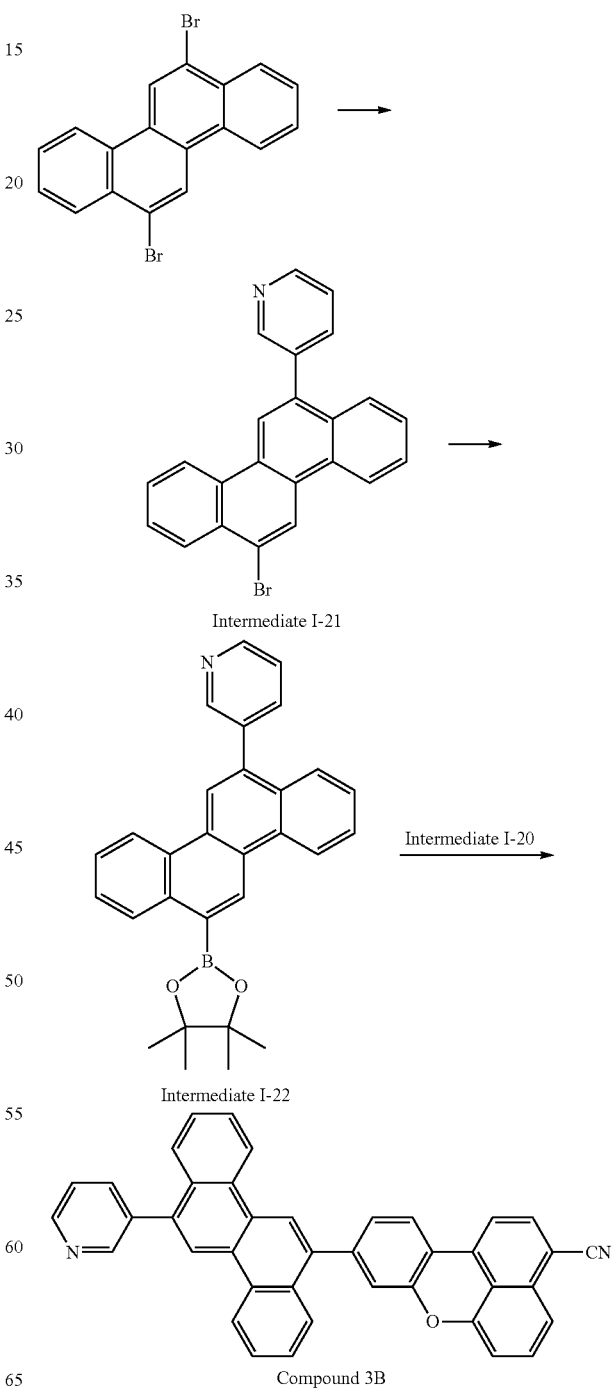

Compound 3B

Synthesis of Intermediate I-21

Intermediate I-21 (2.57 g, Yield: 67%) was obtained in the same manner as the synthesis of Intermediate I-5 of Synthesis Example 2, except that 6,12-dibromochrysene and 3-pyridine boronic acid, instead of 1,6-dibromopyrene and 2-pyridine boronic acid, respectively, were used. This compound was identified using LC-MS.

$C_{23}H_{14}BrN$: $M^+$ 383.0

Synthesis of Intermediate I-22

Intermediate I-22 (2.08 g, Yield: 72%) was obtained in the same manner as in the synthesis of Intermediate I-6 of Synthesis Example 2, except that intermediate I-21 instead of Intermediate I-5 was used. This compound was identified using LC-MS.

$C_{29}H_{26}BNO_2$: $M^+$ 431.2

Synthesis of Compound 3B

Compound 3B (1.60 g, Yield: 77%) was obtained in the same manner as in the synthesis of Compound 16An of Synthesis Example 3, except that Intermediate I-20 and Intermediate I-22, instead of Intermediate I-10 and Intermediate I-11, respectively, were used. This compound was identified using MS/FAB and $^1$H NMR.

$C_{40}H_{22}N_2O$ cal. 546.17, found 546.16.

Synthesis Example 25: Synthesis of Compound 13B

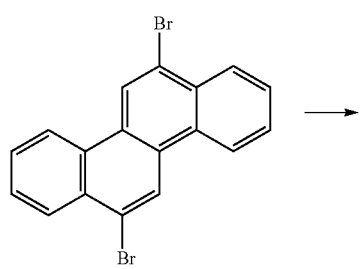

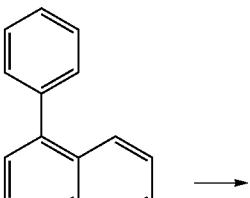

Intermediate I-23

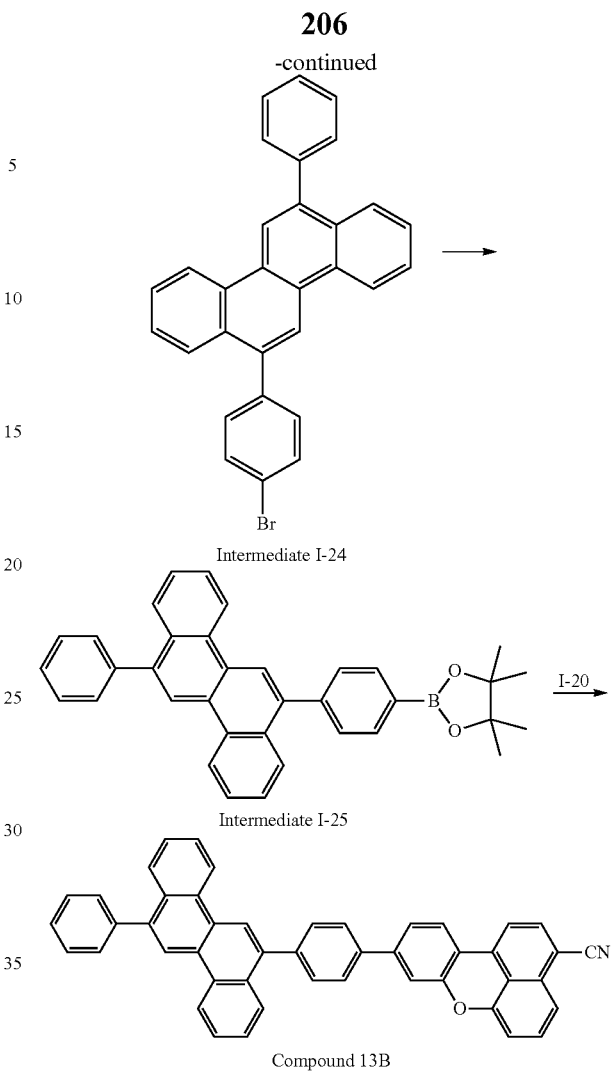

Intermediate I-24

Intermediate I-25

Compound 13B

Synthesis of Intermediate I-23

Intermediate I-23 (2.64 g, Yield: 69%) was obtained in the same manner as in the synthesis of Intermediate I-21 of Synthesis Example 24, except that phenyl boronic acid instead of 3-pyridine boronic acid was used. This compound was identified using LC-MS.

$C_{24}H_{15}Br$: $M^+$ 382.0

Synthesis of Intermediate I-24

Intermediate I-23 (2.06 g, Yield: 65%) was obtained in the same manner as the synthesis of Intermediate I-21 of Synthesis Example 24, except that Intermediate I-23 and 4-bromophenyl boronic acid, instead of 6,12-dibromochrysene and 3-pyridine boronic acid, respectively, were used. This compound was identified using LC-MS.

$C_{30}H_{19}Br$: $M^+$ 458.1

Synthesis of Intermediate I-25

Intermediate I-25 (1.61 g, Yield: 71%) was obtained in the same manner as in the synthesis of Intermediate I-23, except that intermediate I-24 instead of Intermediate I-21 was used. This compound was identified using LC-MS.

$C_{36}H_{31}BO_2$: $M^+$ 506.2

Synthesis of Compound 13B

Compound 13B (1.87 g, Yield: 79%) was obtained in the same manner as in the synthesis of Compound 16An of Synthesis Example 3, except that Intermediate I-20 and Intermediate I-25, instead of Intermediate I-10 and Intermediate I-11, respectively, were used. This compound was identified using MS/FAB and $^1$H NMR.

$C_{47}H_{27}NO$ cal. 621.21, found 621.20.

Synthesis Example 26: Synthesis of Compound 38B

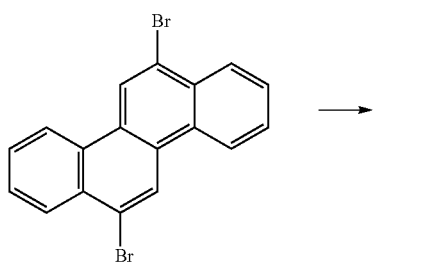

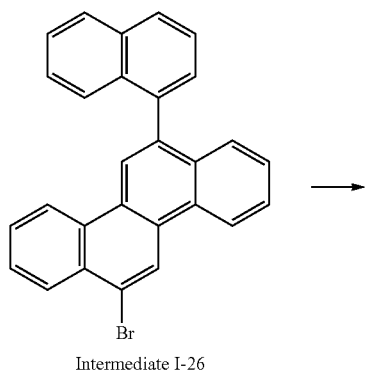
Intermediate I-26

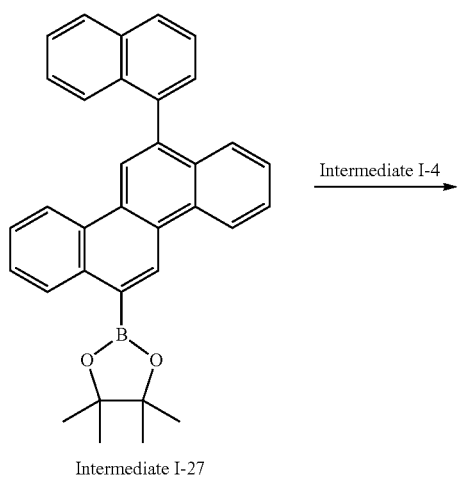
Intermediate I-27

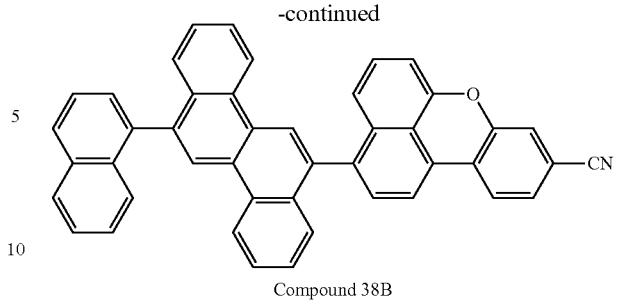
Compound 38B

Synthesis of Intermediate I-26

Intermediate I-26 (2.77 g, Yield: 64%) was obtained in the same manner as in the synthesis of Intermediate I-21 of Synthesis Example 24, except that 1-naphthylboronic acid instead of 3-pyridine boronic acid was used This compound was identified using LC-MS.

$C_{28}H_{17}Br$: M$^+$ 432.0

Synthesis of Intermediate I-27

Intermediate I-27 (2.30 g, Yield: 75%) was obtained in the same manner as in the synthesis of Intermediate I-22 of Synthesis Example 24, except that intermediate I-26 instead of Intermediate I-21 was used. This compound was identified using LC-MS.

$C_{34}H_{29}BO_2$: M$^+$ 480.2

Synthesis of Compound 38B

Compound 38B (2.17 g, Yield: 76%) was obtained in the same manner as in the synthesis of Compound 1A of Synthesis Example 1, except that Intermediate I-27, instead of 1-pyrene boronic acid, was used. This compound was identified using MS/FAB and $^1$H NMR.

$C_{45}H_{25}NO$ cal. 595.19, found 595.20.

Synthesis Example 27: Synthesis of Compound 22B

Compound 22B was synthesized in the same manner as in the synthesis of Compound 1A of Synthesis Example 1, except that Intermediate I-20 and Intermediate I-22B, instead of Intermediate I-4 and 1-pyrene boronic acid, respectively, were used.

Synthesis Example 28: Synthesis of Compound 32B

Compound 32B was synthesized in the same manner as in the synthesis of Compound 1A of Synthesis Example 1, except that Intermediate I-20 and Intermediate I-32B, instead of Intermediate I-4 and 1-pyrene boronic acid, respectively, were used.

Synthesis Example 29: Synthesis of Compound 42B

Compound 42B was synthesized in the same manner as in the synthesis of Compound 1A of Synthesis Example 1, except that Intermediate I-42B instead of 1-pyrene boronic acid was used.

Synthesis Example 30: Synthesis of Compound 54B

Compound 54B was synthesized in the same manner as in the synthesis of Compound 1A of Synthesis Example 1, except that Intermediate I-54B instead of 1-pyrene boronic acid was used.

Synthesis Example 31: Synthesis of Compound 64B

Compound 64B was synthesized in the same manner as in the synthesis of Compound 1A of Synthesis Example 1, except that Intermediate I-64B instead of 1-pyrene boronic acid was used.

Synthesis Example 32: Synthesis of Compound 79B

Compound 79B was synthesized in the same manner as in the synthesis of Compound 1A of Synthesis Example 1, except that Intermediate I-13 and Intermediate I-79B, instead of Intermediate I-4 and 1-pyrene boronic acid, respectively, were used.

Synthesis Example 33: Synthesis of Compound 85B

Compound 85A was synthesized in the same manner as in the synthesis of Compound 1A of Synthesis Example 1, except that Intermediate I-10 and Intermediate I-79B, instead of Intermediate I-4 and 1-pyrene boronic acid, respectively, were used.

Synthesis Example 34: Synthesis of Compound 91B

Compound 91B was synthesized in the same manner as in the synthesis of Compound 1A of Synthesis Example 1, except that Intermediate I-29 and Intermediate I-79B, instead of Intermediate I-4 and 1-pyrene boronic acid, respectively, were used.

Intermediate I-4

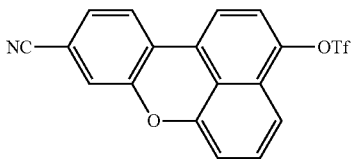

Intermediate I-10

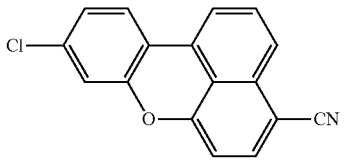

Intermediate I-13

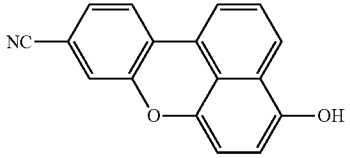

Intermediate I-20

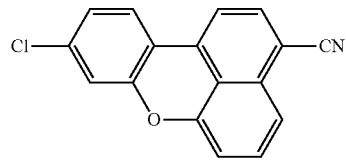

Intermediate I-29

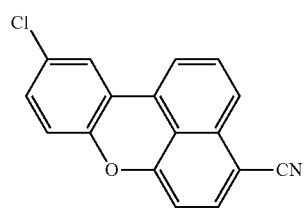

Intermediate I-20A

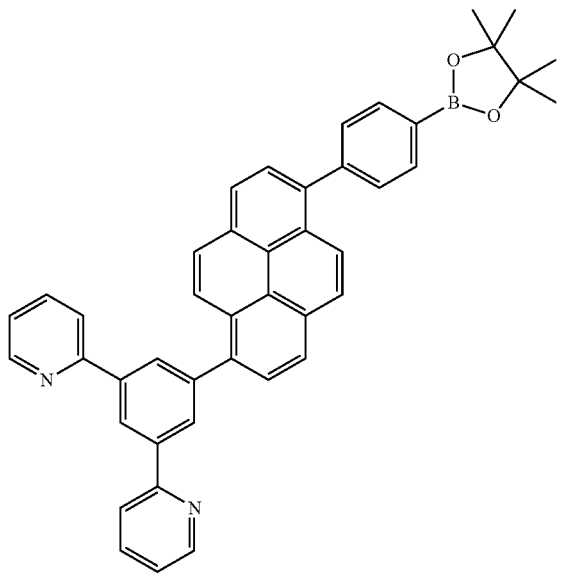

Intermediate I-32A

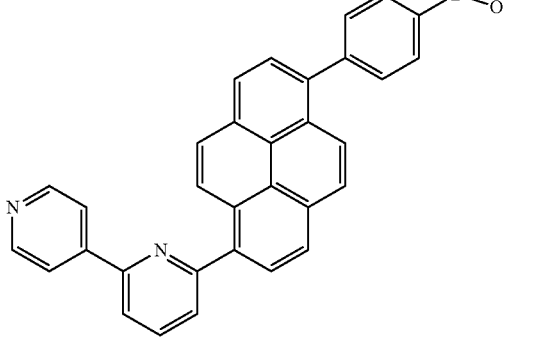

Intermediate I-39A
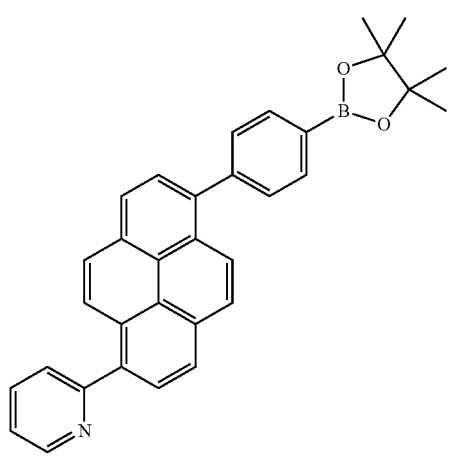
Intermediate I-55A
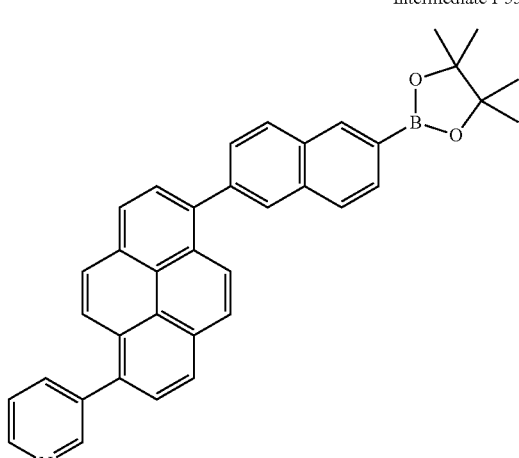
Intermediate I-46A
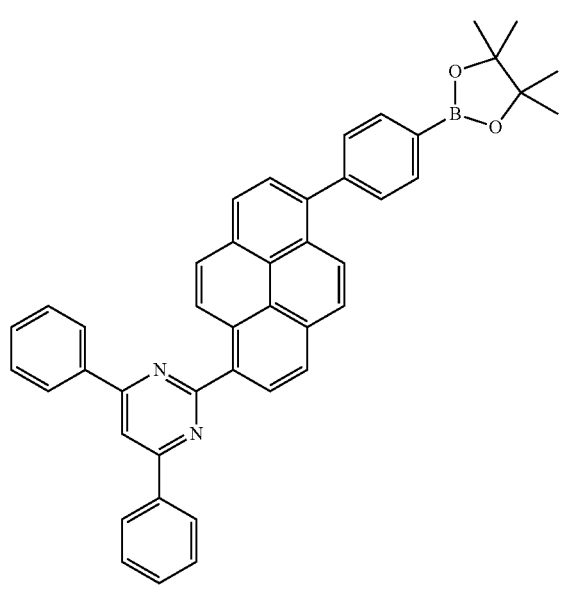
Intermediate I-62A
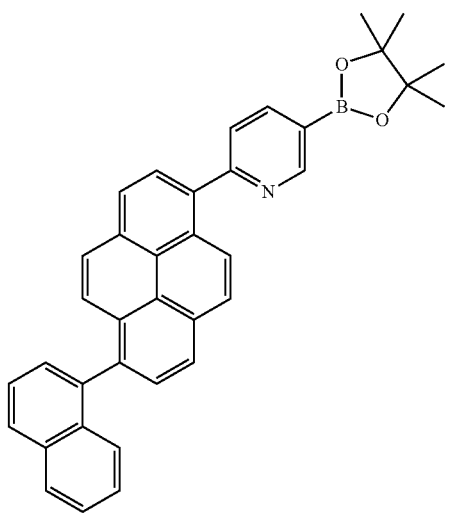
Intermediate I-51A
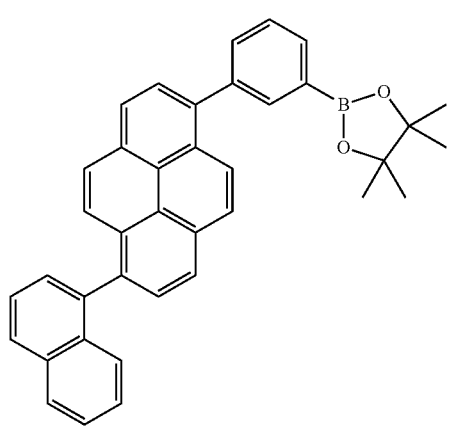
Intermediate I-66A
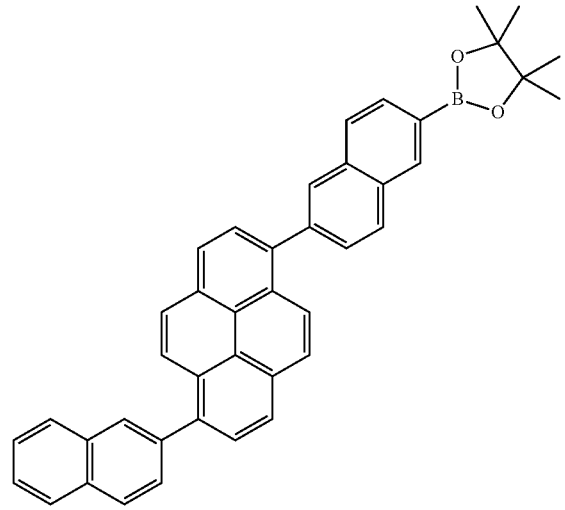

Intermediate I-76A
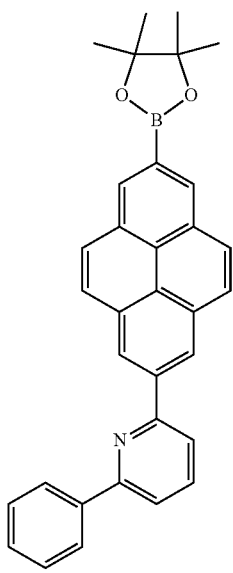
Intermediate I-94A
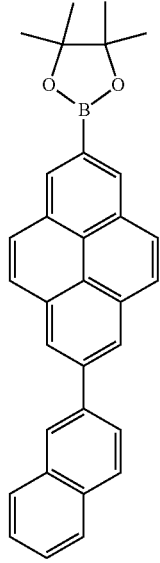
Intermediate I-81A
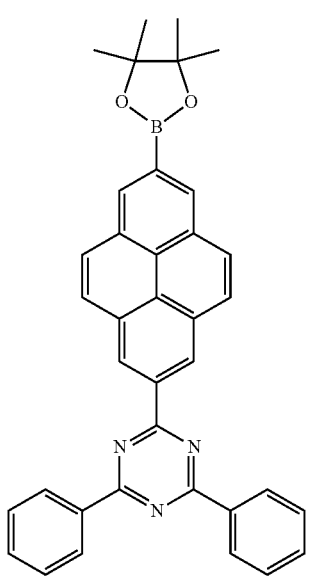
Intermediate I-85A
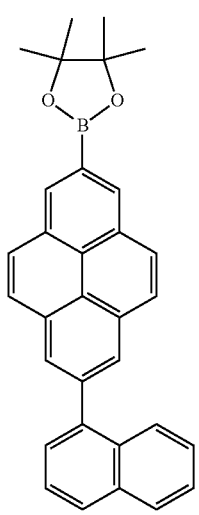
Intermediate I-109A
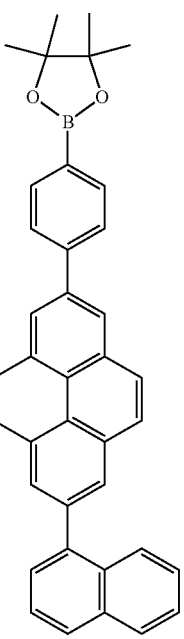

Intermediate I-113A
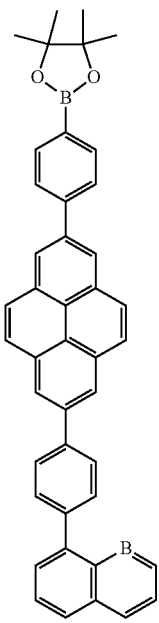
Intermediate I-123A
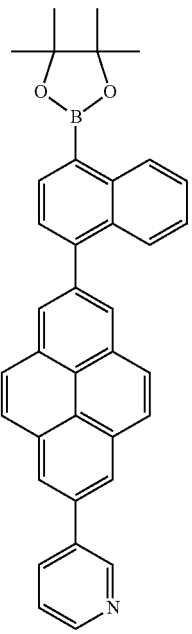
Intermediate I-119A
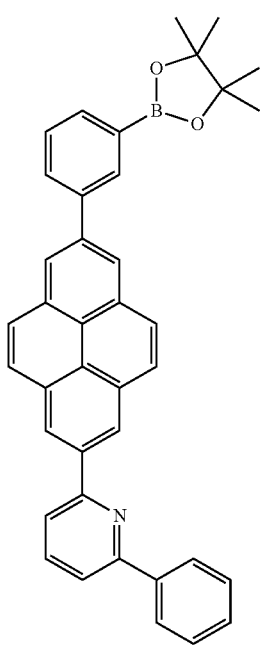
Intermediate I-128A
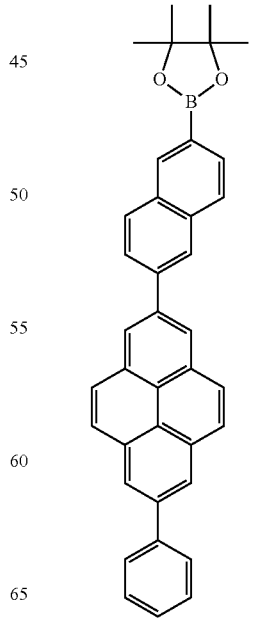

-continued
Intermediate I-119A
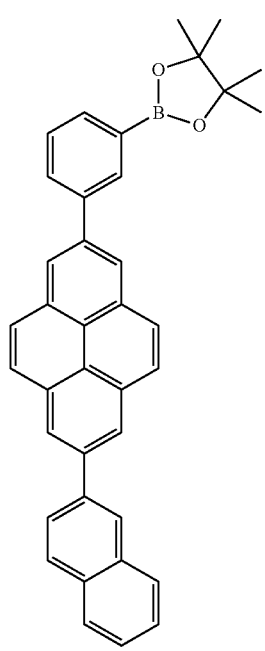
Intermediate I-22B
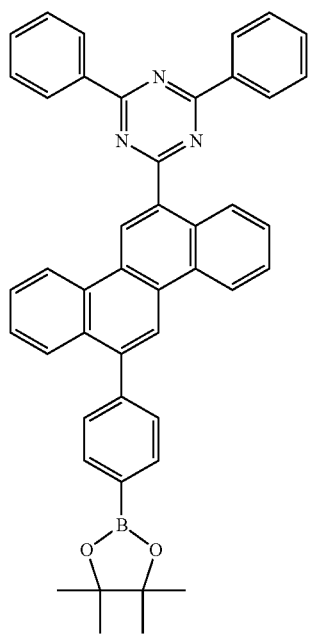
-continued
Intermediate I-32B
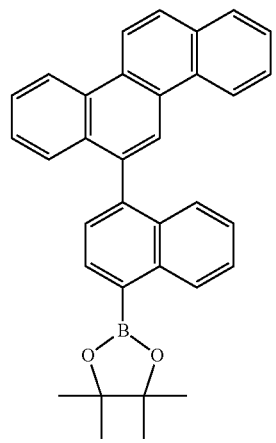
Intermediate I-42B
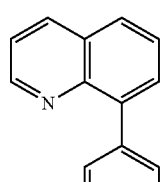
Intermediate I-54B
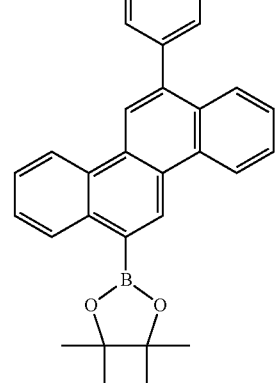

-continued

Intermediate I-64B

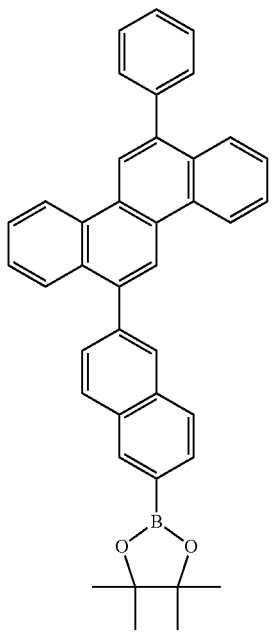

-continued

Intermediate I-79B

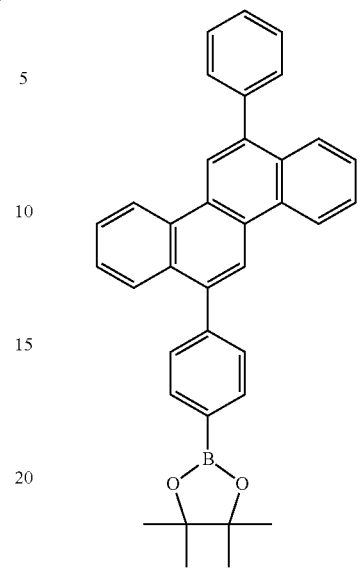

$^1$H NMR and MS/FAB data of the synthesized compounds are shown in Table 1.

TABLE 1

| Compound | $^1$H NMR (CDCl$_3$, 400 MHz) | MS/FAB found | MS/FAB calc. |
|---|---|---|---|
| 1A | δ = 8.42-8.40 (m, 1H), 8.26-8.25 (m, 1H), 8.24-8.23 (m, 1H), 8.21-8.20 (m, 2H), 8.18-8.16 (m, 2H), 8.09-8.07 (m, 1H), 8.04-8.02 (m, 1H), 7.91-7.88 (m, 2H), 7.69-7.67 (m, 1H), 7.65-7.62 (m, 2H), 7.58-7.54 (m, 1H), 7.50-7.48 (m, 1H), 7.22-7.20 (m, 1H) | 443.14 | 443.13 |
| 3A | δ = 8.63-8.59 (m, 2H), 8.46-8.44 (m, 1H), 8.31-8.26 (m, 4H), 8.19-8.17 (m, 1H), 8.05-8.02 (m, 2H), 7.95-7.93 (m, 1H), 7.90-7.88 (m, 1H), 7.84-7.79 (m, 1H), 7.71-7.68 (m, 1H), 7.66-7.63 (m, 2H), 7.58-7.54 (m, 1H), 7.50-7.48 (m, 1H), 7.36-7.33 (m, 1H), 7.21-7.19 (m, 1H) | 520.15 | 520.16 |
| 16A | δ = 8.48-8.46 (m, 1H), 8.33-8.31 (m, 1H), 8.28-8.25 (m, 2H), 8.23-8.22 (m, 1H), 8.21-8.20 (m, 1H), 8.16-8.11 (m, 4H), 8.08-8.05 (m, 2H), 7.97-7.94 (m, 1H), 7.91-7.87 (m, 3H), 7.84-7.79 (m, 2H), 7.64-7.51 (m, 3H), 7.32-7.31 (dd, 1H), 7.26-7.24 (m, 1H) | 569.20 | 569.18 |
| 20A | δ = 8.60-8.59 (dd, 2H), 8.56 (d, 2H), 8.49-8.47 (m, 1H), 8.45-8.40 (m, 2H), 8.24-8.23 (m, 1H), 8.22-8.21 (m, 1H), 8.16-8.14 (m, 1H), 8.12-8.10 (m, 3H), 8.08-8.05 (m, 2H), 7.98-7.94 (m, 2H), 7.76-7.71 (m, 2H), 7.66-7.57 (m, 4H), 7.32-7.28 (m, 3H), 7.24-7.22 (dd, 1H) | 673.21 | 673.22 |
| 24A | δ = 8.33-8.30 (m, 1H), 8.29-8.27 (m, 1H), 8.26-8.23 (m, 2H), 8.21-8.17 (m, 4H), 8.12-8.10 (m, 1H), 8.05-8.02 (m, 3H), 7.66-7.65 (m, 1H), 7.63-7.61 (m, 2H), 7.51-7.46 (m, 3H), 7.38-7.31 (m, 2H), 7.27-7.25 (m, 1H) | 519.17 | 519.16 |
| 32A | δ = 8.69 (d, 1H), 8.54-8.53 (m, 2H), 8.30-8.27 (m, 2H), 8.25-8.24 (m, 1H), 8.18-8.12 (m, 2H), 8.05-8.02 (m, 4H), 7.98-7.96 (m, 1H), 7.92-7.88 (m, 2H), 7.80-7.70 (m, 5H), 7.65-7.62 (m, 4H), 7.55-7.50 (m, 2H), 7.22-7.20 (dd, 1H) | 673.23 | 673.22 |
| 39A | δ = 8.63-8.59 (m, 2H), 8.55-8.52 (dd, 1H), 8.31-8.28 (m, 2H), 8.26-8.25 (m, 1H), 8.16-8.08 (m, 4H), 8.03 (d, 1H), 7.95-7.93 (m, 1H), 7.84-7.79 (m, 4H), 7.75-7.62 (m, 4H), 7.46-7.43 (dd, 1H), 7.32-7.26 (m, 2H), 7.20-7.18 (m, 1H) | 596.21 | 596.19 |
| 46A | δ = 8.69 (d, 1H), 8.39-8.37 (m, 1H), 8.33-8.26 (m, 6H), 8.18-8.11 (m, 3H), 8.08-8.06 (m, 1H), 8.01-7.95 (m, 5H), 7.87-7.83 (m, 2H), 7.76-7.71 (m, 2H), 7.65-7.61 (m, 2H), 7.53-7.48 (m, 4H), 7.44-7.43 (m, 1H), 7.31-7.27 (m, 2H), 7.24-7.22 (dd, 1H) | 749.24 | 749.25 |

TABLE 1-continued

| Compound | $^1$H NMR (CDCl$_3$, 400 MHz) | MS/FAB found | calc. |
|---|---|---|---|
| 51A | δ = 8.33-8.27 (m, 2H), 8.25-8.19 (m, 5H), 8.14-8.11 (m, 2H), 8.04-8.02 (m, 1H), 7.88 (t, 1H), 7.84-7.80 (m, 2H), 7.68-7.61 (m, 7H), 7.59-7.57 (m, 1H), 7.55-7.51 (m, 2H), 7.34-7.27 (m, 2H), 7.22-7.20 (m, 1H), 7.12-7.09 (m, 1H) | 645.23 | 645.21 |
| 55A | δ = 8.79-8.77 (m, 1H), 8.54-8.52 (m, 1H), 8.41-8.36 (m, 2H), 8.32-8.31 (m, 1H), 8.29-8.21 (m, 6H), 8.12 (d, 1H), 8.07-8.01 (m, 4H), 7.93-7.82 (m, 4H), 7.66-7.63 (m, 2H), 7.60-7.53 (m, 2H), 7.48-7.45 (m, 1H), 7.20-7.18 (m, 1H) | 646.19 | 646.20 |
| 62A | δ = 8.82 (d, 1H), 8.68 (d, 1H), 8.50-8.48 (dd, 1H), 8.31-8.22 (m, 4H), 8.14-8.11 (m, 1H), 8.08-8.04 (m, 2H), 8.01-7.92 (m, 3H), 7.84-7.80 (m, 2H), 7.69-7.59 (m, 7H), 7.52-7.51 (m, 1H), 7.31-7.24 (m, 2H), 7.11-7.08 (m, 1H) | 646.21 | 646.20 |
| 66A | δ = 8.51-8.49 (m, 1H), 8.34-8.33 (m, 2H), 8.31-8.30 (m, 1H), 8.29-8.28 (m, 1H), 8.26-8.25 (m, 2H), 8.23-8.21 (m, 2H), 8.13-8.12 (m, 1H), 8.11-8.10 (m, 2H), 8.08-7.99 (m, 3H), 7.96-7.94 (m, 1H), 7.91-7.88 (m, 3H), 7.84-7.83 (m, 1H), 7.82-7.79 (m, 2H), 7.64-7.54 (m, 5H), 7.44-7.43 (dd, 1H), 7.26-7.24 (m, 1H) | 695.23 | 695.22 |
| 72A | δ = 8.42-8.41 (m, 2H), 8.33-8.32 (m, 2H), 8.04-8.02 (m, 1H), 8.00-7.99 (m, 4H), 7.93-7.91 (m, 1H), 7.88-7.86 (m, 1H), 7.72-7.69 (m, 2H), 7.65-7.63 (m, 2H), 7.60-7.54 (m, 2H), 7.45-7.40 (m, 3H), 7.22-7.20 (m, 1H) | 519.15 | 519.16 |
| 76A | δ = 8.53-8.52 (m, 2H), 8.32-8.31 (m, 2H), 8.24-8.22 (m, 2H), 8.17-8.11 (m, 4H), 8.04-8.02 (m, 1H), 7.93-7.86 (m, 2H), 7.74-7.69 (m, 3H), 7.66-7.63 (m, 2H), 7.60-7.54 (m, 2H), 7.51-7.47 (m, 2H), 7.42-7.38 (m, 1H), 7.21-7.19 (m, 1H) | 596.18 | 596.19 |
| 81A | δ = 8.98-8.97 (m, 1H), 8.68-8.66 (m, 4H), 8.45-8.41 (m 4H), 8.33 (s, 2H), 8.21-8.19 (dd, 1H), 8.04-8.02 (dd, 1H), 7.66-7.61 (m, 3H), 7.55-7.51 (m, 5H), 7.45-7.37 (m, 3H), 7.21 (d, 1H) | 674.22 | 674.21 |
| 85A | δ = 8.55-8.52 (m, 1H), 8.40-8.39 (m, 2H), 8.36-8.35 (m, 2H), 8.21-8.20 (dd, 1H), 8.11-8.08 (m, 1H), 8.03-8.00 (m, 4H), 7.92-7.90 (m, 1H), 7.83-7.77 (m, 2H), 7.69-7.61 (m, 3H), 7.57-7.48 (m, 2H), 7.30-7.19 (m, 3H), 7.10-7.09 (dd, 1H) | 569.20 | 569.18 |
| 94A | δ = 8.50-8.49 (m, 2H), 8.47-8.45 (dd, 1H), 8.40-8.39 (m, 2H), 8.23-8.22 (m, 1H), 8.08-8.05 (m, 1H), 8.03-8.01 (dd, 1H), 7.99-7.98 (m, 4H), 7.96-7.93 (m, 3H), 7.87-7.82 (m, 2H), 7.66-7.56 (m, 3H), 7.52-7.48 (m, 1H), 7.42-7.41 (m, 1H), 7.26-7.24 (m, 1H) | 569.19 | 569.18 |
| 109A | δ = 8.44-8.42 (m, 4H), 8.08-8.06 (m, 1H), 8.01-7.96 (m, 7H), 7.92-7.86 (m, 3H), 7.79-7.67 (m, 6H), 7.57-7.48 (m, 2H), 7.43-7.42 (m, 1H), 7.28-7.19 (m, 3H) | 645.23 | 645.21 |
| 113A | δ = 8.89-8.87 (dd, 1H), 8.43-8.42 (m, 4H), 8.38-8.36 (dd, 1H), 8.20-8.18 (dd, 1H), 8.12-8.10 (dd, 1H), 8.08-8.06 (m, 1H), 8.01-7.98 (m, 7H), 7.90-7.81 (m, 4H), 7.77-7.71 (m, 6H), 7.60-7.56 (m, 1H), 7.47-7.43 (m, 2H), 7.24-7.22 (m, 1H) | 722.25 | 722.24 |
| 119A | δ = 8.57-8.56 (m, 2H), 8.49-8.48 (m, 2H), 8.24-8.23 (m, 1H), 8.21-8.20 (m, 1H), 8.14-8.08 (m, 4H), 8.04-8.02 (m, 1H), 7.91-7.84 (m, 4H), 7.76-7.69 (m, 4H), 7.66-7.63 (m, 2H), 7.60-7.56 (m, 1H), 7.53-7.47 (m, 4H), 7.42-7.38 (m, 1H), 7.21-7.19 (m, 1H) | 672.21 | 672.22 |
| 123A | δ = 8.99-8.98 (m, 1H), 8.61-8.59 (m, 1H), 8.50 (d, 1H), 8.43-8.42 (m, 2H), 8.40-8.39 (m, 2H), 8.10-8.08 (m, 2H), 8.05-7.99 (m, 4H), 7.86 (d, 1H), 7.77-7.75 (m, 1H), 7.72-7.63 (m, 5H), 7.58-7.54 (m, 1H), 7.50-7.48 (m, 1H), 7.44-7.41 (m, 1H), 7.25-7.23 (dd, 1H), 7.19-7.12 (m, 2H) | 646.19 | 646.20 |
| 128A | δ = 8.50-8.49 (m, 2H), 8.42-8.41 (m, 2H), 8.26-8.25 (m, 1H), 8.09-8.08 (m, 1H), 8.06-8.05 (m, 1H), 8.02-7.94 (m, 9H), 7.76-7.70 (m, 4H), 7.60-7.57 (m, 2H), 7.44-7.40 (m, 4H), 7.25-7.23 (m, 1H) | 645.22 | 645.21 |
| 131A | δ = 8.56-8.54 (dd, 1H), 8.45-8.44 (m, 4H), 8.24-8.23 (m, 1H), 8.15-8.14 (dd, 1H), 8.12-8.08 (m, 2H), 8.00-7.99 (m, 4H), 7.96-7.93 (m, 3H), 7.87-7.80 (m, 3H), 7.73-7.69 (m, 2H), 7.66-7.64 (m, 1H), 7.60-7.56 (m, 1H), 7.52-7.48 (m, 1H), 7.42-7.40 (dd, 1H), 7.28-7.26 (dd, 1H), 7.15-7.13 (dd, 1H) | 645.23 | 645.21 |

TABLE 1-continued

| Compound | ¹H NMR (CDCl₃, 400 MHz) | MS/FAB found | MS/FAB calc. |
|---|---|---|---|
| 3B | δ = 8.88-8.87 (m, 1H), 8.75-8.73 (m, 1H), 8.71-8.69 (m, 1H), 8.64-8.63 (m, 1H), 8.50-8.47 (m, 2H), 8.09-8.02 (m, 3H), 7.98-7.94 (m, 2H), 7.89-7.86 (m, 1H), 7.76-7.65 (m, 5H), 7.50-7.41 (m, 3H), 7.26-7.22 (m, 2H) | 546.16 | 546.17 |
| 13B | δ= 8.72-8.71 (m, 1H), 8.70-8.69 (m, 1H), 8.62-8.61 (m, 1H), 8.52-8.51 (m, 1H), 8.08-8.04 (m, 3H), 7.99-7.95 (m, 3H), 7.90-7.87 (m, 2H), 7.83-7.81 (dd, 1H), 7.76-7.65 (m, 5H), 7.62-7.59 (m, 2H), 7.49-7.36 (m, 6H), 7.26-7.24 (dd, 1H) | 621.20 | 621.21 |
| 22B | δ = 9.23-9.22 (m, 1H), 9.06-9.05 (m, 1H), 8.95-8.90 (m, 2H), 8.70-8.68 (m, 4H), 8.55-8.53 (m, 1H), 8.08-8.05 (dd, 1H), 7.98-7.95 (m, 3H), 7.90-7.86 (m, 2H), 7.83-7.65 (m, 6H), 7.62-7.60 (m, 2H), 7.55-7.51 (m, 4H), 7.45-7.38 (m, 4H), 7.25-7.23 (dd, 1H) | 776.28 | 776.26 |
| 32B | δ = 9.11-9.10 (m, 1H), 8.82-8.80 (m, 1H), 8.68-8.66 (m, 1H), 8.33-8.31 (m, 1H), 8.08-8.06 (dd, 1H), 8.04-8.02 (m, 1H), 7.98-7.91 (m, 5H), 7.76-7.71 (m, 2H), 7.68-7.59 (m, 6H), 7.51-7.49 (m, 1H), 7.40-7.38 (m, 1H), 7.31-7.30 (m, 1H), 7.26-7.24 (dd, 1H), 7.11-7.06 (m, 2H) | 595.21 | 595.19 |
| 38B | δ = 9.18-9.17 (m, 1H), 9.04-9.03 (m, 1H), 8.81-8.79 (m, 2H), 8.07-8.04 (m, 1H), 7.98-7.96 (m, 1H), 7.86-7.76 (m, 3H), 7.72-7.48 (m, 11H), 7.43-7.40 (m, 2H), 7.32-7.28 (m, 1H), 7.17 (d, 1H), 7.11-7.08 (m, 1H) | 595.20 | 595.19 |
| 42B | δ = 9.20-9.19 (m, 1H), 8.89-8.87 (m, 1H), 8.76-8.72 (m, 3H), 8.38-8.36 (dd, 1H), 8.20-8.18 (dd, 1H), 8.12-8.10 (dd, 1H), 8.05-7.99 (m, 3H), 7.95-7.93 (m, 1H), 7.83-7.56 (m, 11H), 7.50-7.38 (m, 4H), 7.19-7.17 (m, 1H) | 672.21 | 672.22 |
| 54B | δ = 9.10-9.09 (m, 1H), 8.88-8.86 (m, 1H), 8.83-8.81 (m, 1H), 8.77-8.76 (m, 1H), 8.68 (d, 2H), 8.66-8.65 (m, 2H), 8.44 (t, 1H), 8.19-8.16 (dd, 1H), 8.05-8.02 (m, 1H), 7.98-7.96 (m, 1H), 7.92-7.90 (m, 1H), 7.83-7.81 (m, 1H), 7.70-7.52 (m, 14H), 7.47-7.38 (m, 2H), 7.32-7.29 (m, 2H), 7.15-7.13 (dd, 1H) | 775.24 | 775.26 |
| 64B | δ = 8.86-8.80 (m, 2H), 8.68-8.67 (m, 1H), 8.64-8.63 (m, 1H), 8.33-8.32 (m, 1H), 8.25-8.24 (m, 1H), 8.05-8.00 (m, 5H), 7.95-7.93 (m, 1H), 7.91-7.86 (m, 4H), 7.75-7.73 (m, 1H), 7.69-7.63 (m, 4H), 7.60-7.56 (m, 1H), 7.53-7.36 (m, 6H), 7.14-7.12 (dd, 1H) | 671.21 | 671.22 |
| 79B | δ = 8.99-8.98 (m, 1H), 8.83-8.79 (m, 3H), 8.05-8.02 (m, 1H), 7.98-7.96 (m, 1H), 7.92-7.90 (m, 1H), 7.86-7.81 (m, 2H), 7.72-7.61 (m, 11H), 7.57-7.50 (m, 4H), 7.43-7.38 (m, 2H), 7.31-7.27 (m, 1H), 7.14-7.08 (m, 2H) | 671.23 | 671.22 |
| 85B | δ = 8.81-8.80 (m, 1H), 8.79-8.78 (m, 1H), 8.72-8.70 (m, 1H), 8.65-8.64 (m, 1H), 8.17-8.16 (m, 1H), 8.05-8.03 (m, 2H), 7.98-7.94 (m, 3H), 7.90-7.87 (m, 2H), 7.84-7.82 (m, 1H), 7.75-7.73 (m, 1H), 7.69-7.60 (m, 6H), 7.57-7.53 (m, 2H), 7.49-7.44 (m, 2H), 7.42-7.38 (m, 3H) | 621.19 | 621.21 |
| 91B | δ = 8.82-8.81 (m, 1H), 8.80-8.79 (m, 1H), 8.74-8.73 (m, 1H), 8.66-8.65 (m, 1H), 8.63-8.61 (dd, 1H), 8.14-8.13 dd, 1H), 8.11-8.08 (m, 1H), 8.06-8.03 (m, 2H), 7.85-7.80 (m, 4H), 7.75-7.64 (m, 6H), 7.48-7.36 (m, 6H), 7.28-7.26 (m, 1H), 7.19-7.17 (m, 1H) | 621.20 | 621.21 |

Example 1

A corning 15 Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting ITO glass substrate was mounted into a vacuum deposition device.

After 2-TNATA was vacuum-deposited on the ITO anode of the ITO glass substrate to form an HIL having a thickness of 600 Å, NPB was deposited on the HIL to form a HTL having a thickness of about 300 Å, and then DNA (host) and DPAVBi (dopant) were co-deposited in a weight ratio of 98:2 on the HTL to form an EML having a thickness of about 300 Å.

Then, Compound 1A was deposited on the EML to form an ETL having a thickness of about 300 Å, and then LiF was deposited on the ETL to form an EIL having a thickness of about 10 Å. Then, Al was deposited on the EIL to form a cathode having a thickness of about 3000 Å, thereby completing the manufacture of an organic light-emitting device.

Example 2

An organic light-emitting device was manufactured in the same manner as in Example 1, except that Compound 3A instead of Compound 1A was used to form the ETL.

Example 3

An organic light-emitting device was manufactured in the same manner as in Example 1, except that Compound 16A instead of Compound 1A was used to form the ETL.

Example 4

An organic light-emitting device was manufactured in the same manner as in Example 1, except that Compound 24A instead of Compound 1A was used to form the ETL.

Example 5

An organic light-emitting device was manufactured in the same manner as in Example 1, except that Compound 39A instead of Compound 1A was used to form the ETL.

Example 6

An organic light-emitting device was manufactured in the same manner as in Example 1, except that Compound 51A instead of Compound 1A was used to form the ETL.

Example 7

An organic light-emitting device was manufactured in the same manner as in Example 1, except that Compound 62A instead of Compound 1A was used to form the ETL.

Example 8

An organic light-emitting device was manufactured in the same manner as in Example 1, except that Compound 72A instead of Compound 1A was used to form the ETL.

Example 9

An organic light-emitting device was manufactured in the same manner as in Example 1, except that Compound 81A instead of Compound 1A was used to form the ETL.

Example 10

An organic light-emitting device was manufactured in the same manner as in Example 1, except that Compound 113A instead of Compound 1A was used to form the ETL.

Example 11

An organic light-emitting device was manufactured in the same manner as in Example 1, except that Compound 3B instead of Compound 1A was used to form the ETL.

Example 12

An organic light-emitting device was manufactured in the same manner as in Example 1, except that Compound 13B instead of Compound 1A was used to form the ETL.

Example 13

An organic light-emitting device was manufactured in the same manner as in Example 1, except that Compound 38B instead of Compound 1A was used to form the ETL.

Example 14

An organic light-emitting device was manufactured in the same manner as in Example 1, except that Compound 79B instead of Compound 1A was used to form the ETL.

Comparative Example 1

An organic light-emitting device was manufactured in the same manner as in Example 1, except that Alq$_3$ instead of Compound 1A was used to form the ETL.

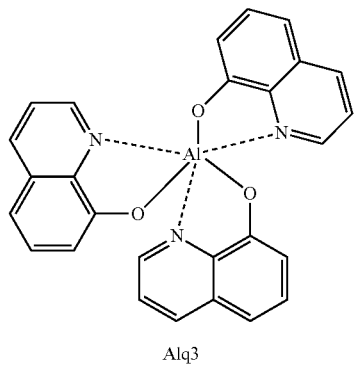

Alq3

Comparative Example 2

An organic light-emitting device was manufactured in the same manner as in Example 1, except that Compound A instead of Compound 1 was used to form the ETL.

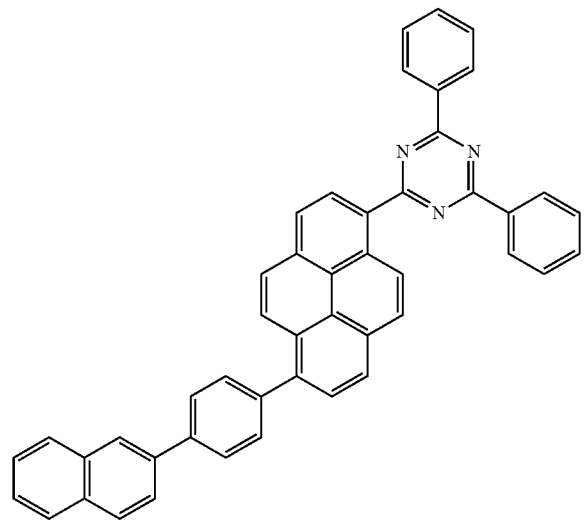

<Compound A>

Evaluation Example 1

Driving voltages, current densities, luminances, efficiencies, and half-lifetimes of the organic light-emitting devices of Examples 1 to 14 and Comparative Examples 1 and 2 were evaluated using a Kethley Source-Measure Unit (SMU 236) and a PR650 (Spectroscan) Source Measurement Unit. (available from Photo Research, Inc.). The results are shown in Table 2 below. A half-lifetime was measured as the time taken until a measured initial luminance (assumed as 100%) is reduced to 50%.)

TABLE 2

| Example | ETL | Driving voltage (V) | Current density (mA/cm²) | Luminance (cd/m²) | Efficiency (cd/A) | Emission color | Half-lifetime (hr @100 mA/cm²) |
|---|---|---|---|---|---|---|---|
| Example 1 | Compound 1A | 5.48 | 50 | 3215 | 6.43 | Blue | 421 |
| Example 2 | Compound 3A | 5.15 | 50 | 3290 | 6.58 | Blue | 437 |
| Example 3 | Compound 16A | 5.31 | 50 | 3235 | 6.47 | Blue | 466 |
| Example 4 | Compound 24A | 5.33 | 50 | 3200 | 6.40 | Blue | 433 |
| Example 5 | Compound 39A | 5.25 | 50 | 3275 | 6.55 | Blue | 417 |
| Example 6 | Compound 51A | 5.42 | 50 | 3105 | 6.21 | Blue | 395 |
| Example 7 | Compound 62A | 5.26 | 50 | 3230 | 6.46 | Blue | 438 |
| Example 8 | Compound 72A | 5.19 | 50 | 3090 | 6.18 | Blue | 441 |
| Example 9 | Compound 81A | 5.24 | 50 | 3255 | 6.51 | Blue | 425 |
| Example 10 | Compound 113A | 5.38 | 50 | 3130 | 6.26 | Blue | 412 |
| Example 11 | Compound 3B | 4.97 | 50 | 3285 | 6.57 | Blue | 462 |
| Example 12 | Compound 13B | 5.26 | 50 | 3195 | 6.39 | Blue | 507 |
| Example 13 | Compound 38B | 5.13 | 50 | 3470 | 6.94 | Blue | 516 |
| Example 14 | Compound 79B | 5.58 | 50 | 3085 | 6.17 | Blue | 481 |
| Comparative Example 1 | Alq₃ | 7.35 | 50 | 2065 | 4.13 | Blue | 145 |
| Comparative Example 2 | Compound A | 5.67 | 50 | 2975 | 5.95 | Blue | 293 |

Referring to Table 1, the organic light-emitting devices of Examples 1 to 14 were found to have lower driving voltages, improved current densities, improved luminances, improved efficiencies, and improved half-lifetimes, compared to those of the organic light-emitting devices of Comparative Examples 1 and 2.

As described above, according to the one or more of the above embodiments of the present disclosure, an organic light-emitting device including a condensed cyclic compound of Formula 1 above may have a low driving voltage, a high efficiency, a high luminance, and a long lifetime.

It should be understood that the example embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the FIGURES, it will be understood by those of ordinary skill in the art that various changes in form and details may be made therein without departing from the spirit and scope of the present disclosure as defined by the following claims.

What is claimed is:

1. A compound represented by Formula 1A or 1B:

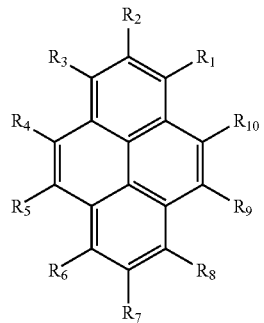

<Formula 1A>

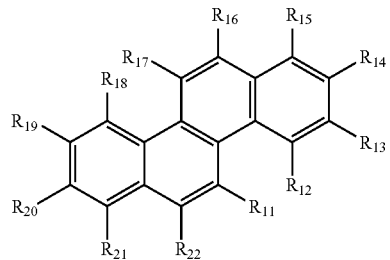

<Formula 1B> wherein, in Formulae 1A and 1B, $R_1$ to $R_{22}$ are each independently selected from a group represented by Formula 2-1, a group represented by Formula 2-2, a hydrogen, a deuterium, —F, —Cl, —Br, —I, a hydroxyl group, a cyano group, a nitro group, an amino group, an amidino group, a hydrazine group, a hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, a substituted or unsubstituted monovalent nonaromatic condensed heteropolycyclic group, —N($Q_1$)($Q_2$), —Si($Q_3$)($Q_4$)($Q_5$), and —B($Q_6$)($Q_7$);

at least one of $R_1$ to $R_{10}$ is a group represented by Formula 2-1 or 2-2, and at least one of $R_{11}$ to $R_{22}$ is a group represented by Formula 2-1 or 2-2;

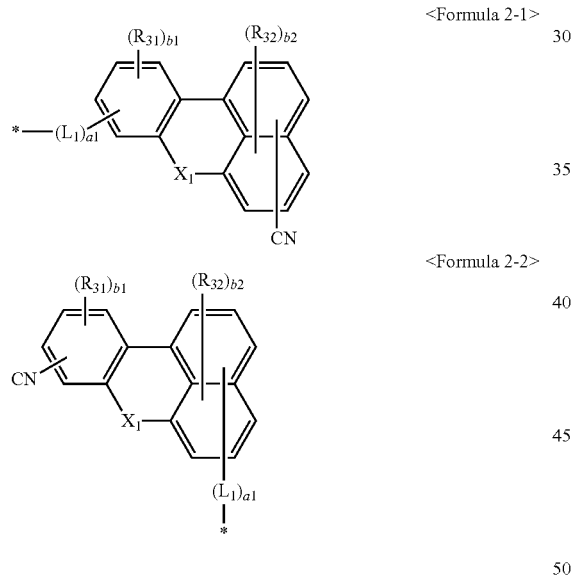

<Formula 2-1>

<Formula 2-2>

$X_1$ is O or S;

$L_1$ is selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent nonaromatic condensed polycyclic group, and a substituted or unsubstituted divalent nonaromatic condensed heteropolycyclic group;

a1 is selected from 0, 1, 2, and 3;
b1 is an integer selected from 1 to 3;
b2 is an integer selected from 1 to 5; and
* in Formulae 2-1 and 2-2 is a binding site with a core represented by Formula 1A or Formula 1B;

wherein at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocyclolalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent nonaromatic condensed polycyclic group, and the substituted monovalent nonaromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, each substituted with at least one of a deuterium atom, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{21}$)($Q_{22}$), —Si($Q_{23}$)($Q_{24}$)($Q_{25}$), and —B($Q_{26}$)($Q_{27}$), —N($Q_{31}$)($Q_{32}$), —Si($Q_{33}$)($Q_{34}$)($Q_{35}$), and —B($Q_{36}$)($Q_{37}$), wherein $R_{31}$, $R_{32}$, $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent nonaromatic condensed polycyclic group, and a monovalent aromatic condensed heteropolycyclic group.

2. The compound of claim 1, wherein, in Formulae 2-1 and 2-2, $L_1$ is selected from a phenylene group, a pentalenylene group, an indeylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolyene group, an imidazopyridinylene group, an imidazopyrimidinylene group, a phenylene group, a pentalenylene group, an indeylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolyene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, an a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The compound of claim 1, wherein $L_1$ in Formulae 2-1 and 2-2 is represented by one of Formulae 3-1 to 3-32:

Formula 3-1
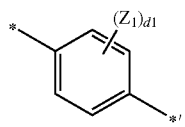

Formula 3-2
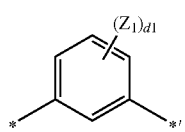

Formula 3-3
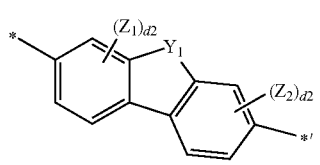

Formula 3-4
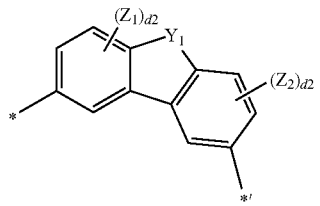

Formula 3-5
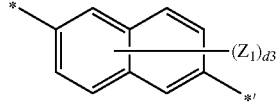

Formula 3-6
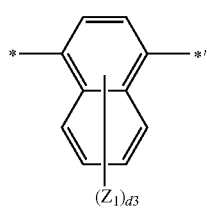

Formula 3-7
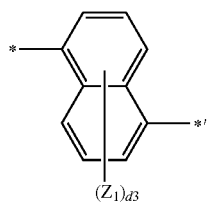

Formula 3-8
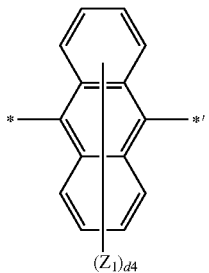

Formula 3-9
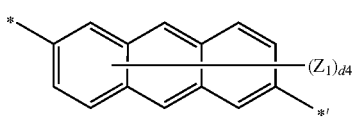

Formula 3-10
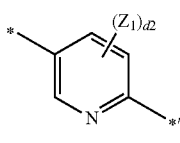

Formula 3-11
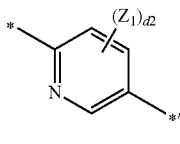

Formula 3-12
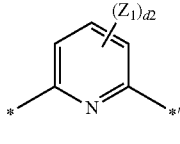

Formula 3-13
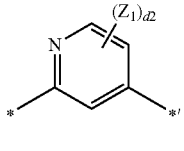

Formula 3-14
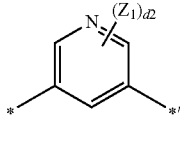

Formula 3-15
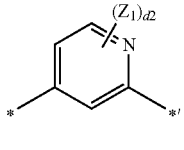

Formula 3-16
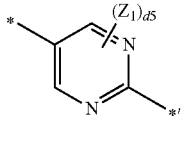

Formula 3-17
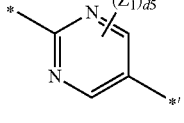

-continued

Formula 3-18 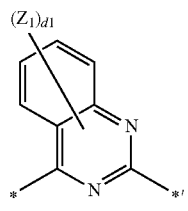

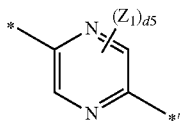

Formula 3-19 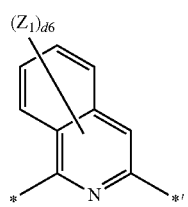

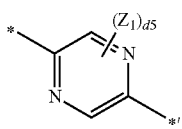

Formula 3-20

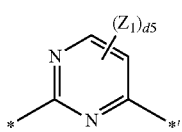

Formula 3-21 

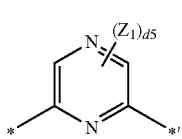

Formula 3-22 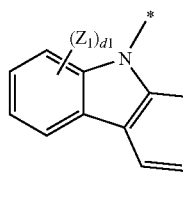

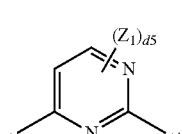

Formula 3-23

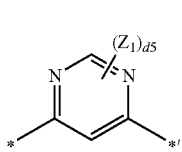

Formula 3-24

Formula 3-25 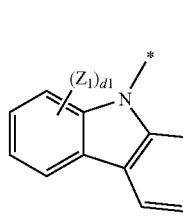

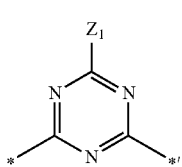

Formula 3-26

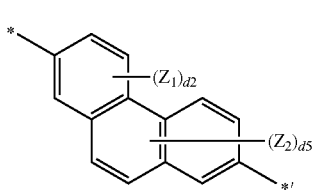

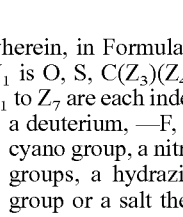

Formula 3-27

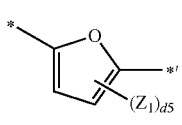

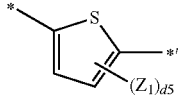

Formula 3-28

Formula 3-29

Formula 3-30

Formula 3-31 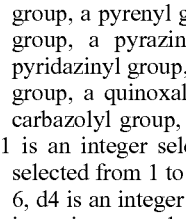

Formula 3-32 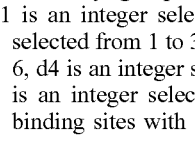

wherein, in Formulae 3-1 to 3-32,
$Y_1$ is O, S, C($Z_3$)($Z_4$), N($Z_5$), or Si($Z_6$)($Z_7$);
$Z_1$ to $Z_7$ are each independently selected from a hydrogen, a deuterium, —F, —Cl, —Br, —I, a hydroxyl group, a cyano group, a nitro group, an amino group, an amidino groups, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;
d1 is an integer selected from 1 to 4, d2 is an integer selected from 1 to 3, d3 is an integer selected from 1 to 6, d4 is an integer selected from 1 to 8, d5 is 1 or 2, d6 is an integer selected from 1 to 5, and * and *' are binding sites with adjacent atoms.

4. The compound of claim 1, wherein $L_1$ in Formulae 2-1 and 2-2 is represented by one of Formulae 4-1 to 4-23:
Formula 4-1
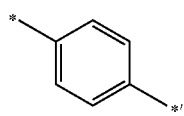
Formula 4-2
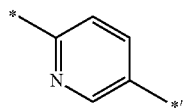
Formula 4-3
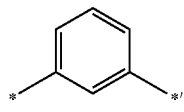
Formula 4-4
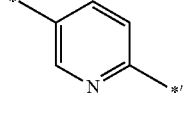
Formula 4-5
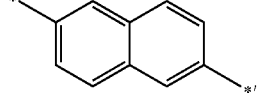
Formula 4-6
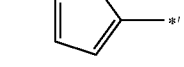
Formula 4-7
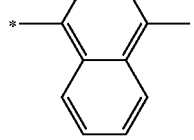
Formula 4-8
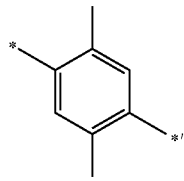
Formula 4-9
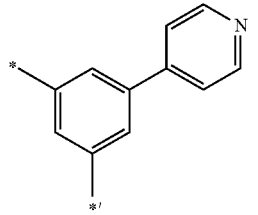
-continued
Formula 4-10
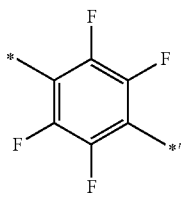
Formula 4-11
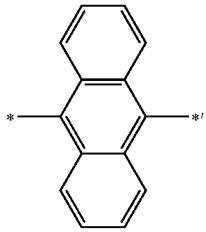
Formula 4-12
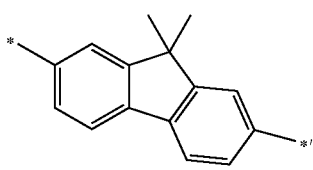
Formula 4-13
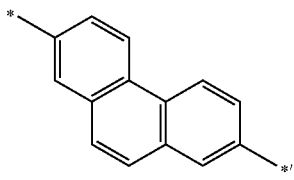
Formula 4-14
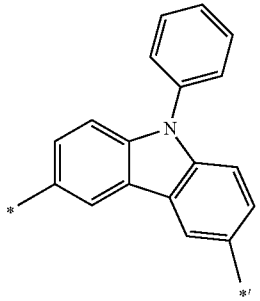
Formula 4-15
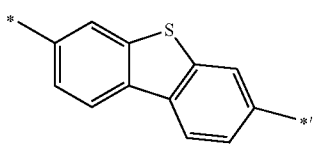
Formula 4-16
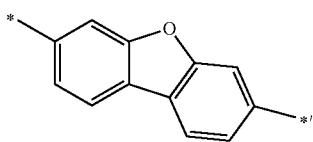
Formula 4-17
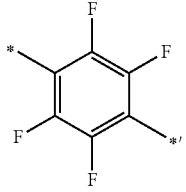

-continued

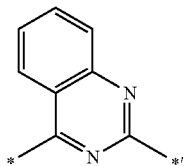
Formula 4-18

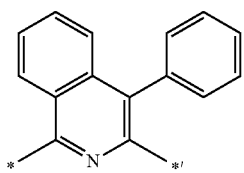
Formula 4-19

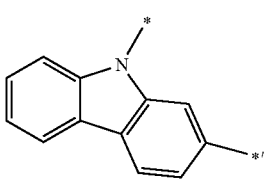
Formula 4-20

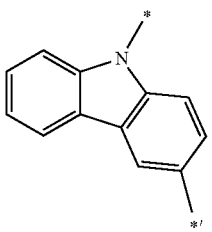
Formula 4-21

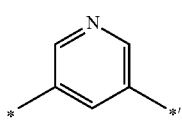
Formula 4-22

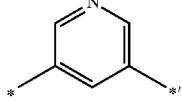
Formula 4-23 wherein, in Formulae 4-1 to 4-23, * and *' are binding sites with adjacent atoms.

5. The compound of claim 1, wherein a1 in Formulae 2-1 and 2-2 is 0 or 1.

6. The compound of claim 1, wherein $X_1$ in Formulae 2-1 and 2-2 is O.

7. The compound of claim 1, wherein at least one substituent of $R_1$ to $R_{10}$ in Formula 1A, except for the groups represented by Formulae 2-1 and Formula 2-2, and at least one substituent of $R_{11}$ to $R_{22}$ in Formula 1B, except for the groups represented by Formulae 2-1 and Formula 2-2, are each independently selected from a substituted or unsubstituted $C_2$-$C_{20}$ heteroaryl group, and a substituted or unsubstituted monovalent non-aromatic condensed heteropolycyclic group.

8. The compound of claim 1, wherein $R_1$ to $R_{22}$ are each independently selected from a group represented by Formula 2-1, a group represented by Formula 2-2, a hydrogen, a deuterium, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, and $Si(Q_3)(Q_4)(Q_5)$, wherein $Q_3$ to $Q_5$ are each independently selected from a $C_1$-$C_{20}$ alkyl group, a $C_1$-$C_{20}$ alkoxy group, a phenyl group, and a nahtyl group; and at least one of $R_1$ to $R_{10}$ is a group represented by Formula 2-1 or Formula 2-2, and at least one of $R_{11}$ to $R_{22}$ is a group represented by Formula 2-1 or Formula 2-2.

9. The compound of claim 1, wherein $R_1$ to $R_{22}$ are each independently selected from a group represented by Formula 2-1, a group represented by Formulae 2-2, hydrogen, a deuterium, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and $Si(Q_3)(Q_4)(Q_5)$, wherein $Q_3$ to $Q_5$ are each independently selected from a $C_1$-$C_{20}$ alkyl group, a $C_1$-$C_{20}$ alkoxy group, a phenyl group, and a nahtyl group; and at least one of $R_1$ to $R_{10}$ is a group represented by Formula 2-1 or Formula 2-2, and at least one of $R_{11}$ to $R_{22}$ is a group represented by Formula 2-1 or Formula 2-2.

10. The compound of claim 1, wherein $R_1$ or $R_2$ in Formula 1A is a group represented by Formula 2-1 or Formula 2-2, and $R_{22}$ in Formula 1B is a group represented by Formula 2-1 or Formula 2-2.

11. The compound of claim 1, wherein one of $R_1$ to $R_{10}$ in Formula 1A is a group represented by Formula 2-1 or Formula 2-2.

12. The compound of claim 1, wherein $R_1$ to $R_{22}$ are each independently selected from a group represented by Formula 2-1, a group represented by Formula 2-2, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, $Si(Q_3)(Q_4)(Q_5)$ (where $Q_3$ to $Q_5$ are each independently selected from a $C_1$-$C_{20}$ alkyl group, a $C_1$-$C_{20}$ alkoxy group, a phenyl group, and a naphthyl group), and groups represented by Formulae 5-1 to 5-35; and at least one of $R_1$ to $R_{10}$ is a group represented by Formula 2-1 or Formula 2-2, and at least one of $R_{11}$ to $R_{22}$ is a group represented by Formula 2-1 or Formula 2-2:

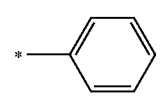

Formula 5-1

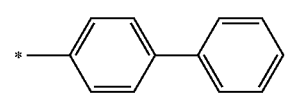

Formula 5-2

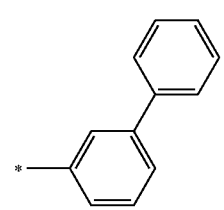

Formula 5-3

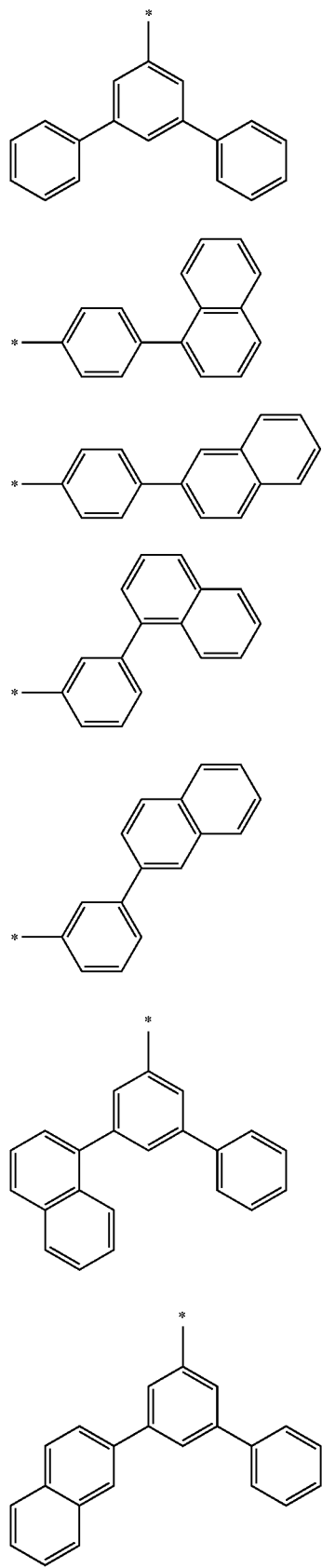
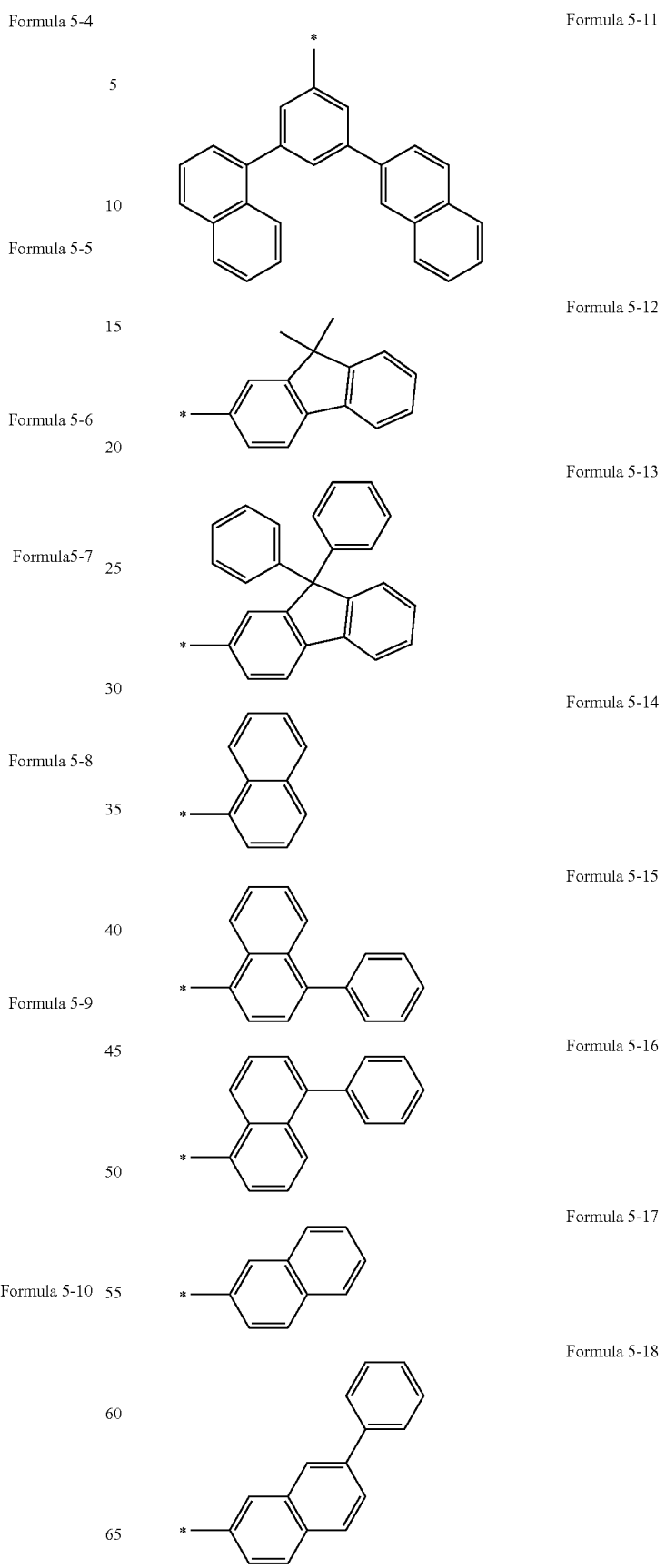
Formula 5-4
Formula 5-5
Formula 5-6
Formula5-7
Formula 5-8
Formula 5-9
Formula 5-10
Formula 5-11
Formula 5-12
Formula 5-13
Formula 5-14
Formula 5-15
Formula 5-16
Formula 5-17
Formula 5-18

-continued
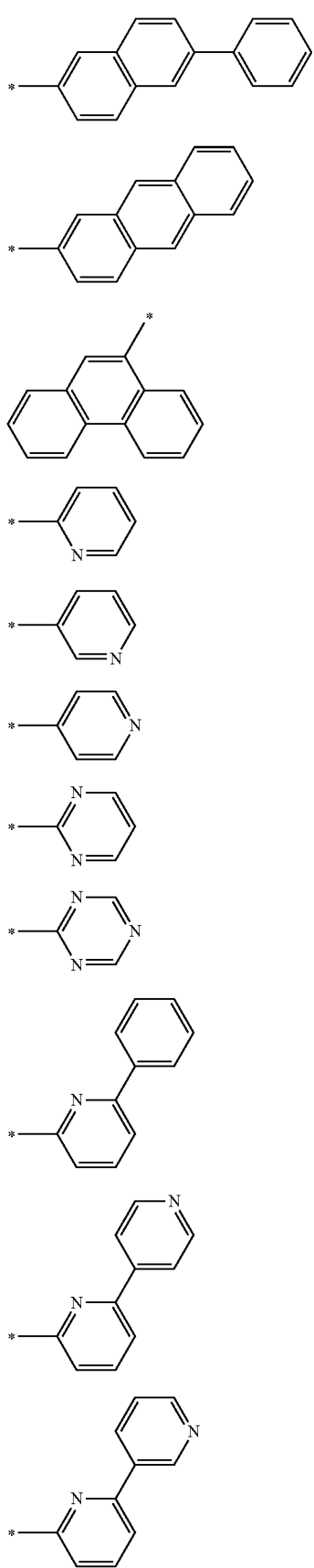
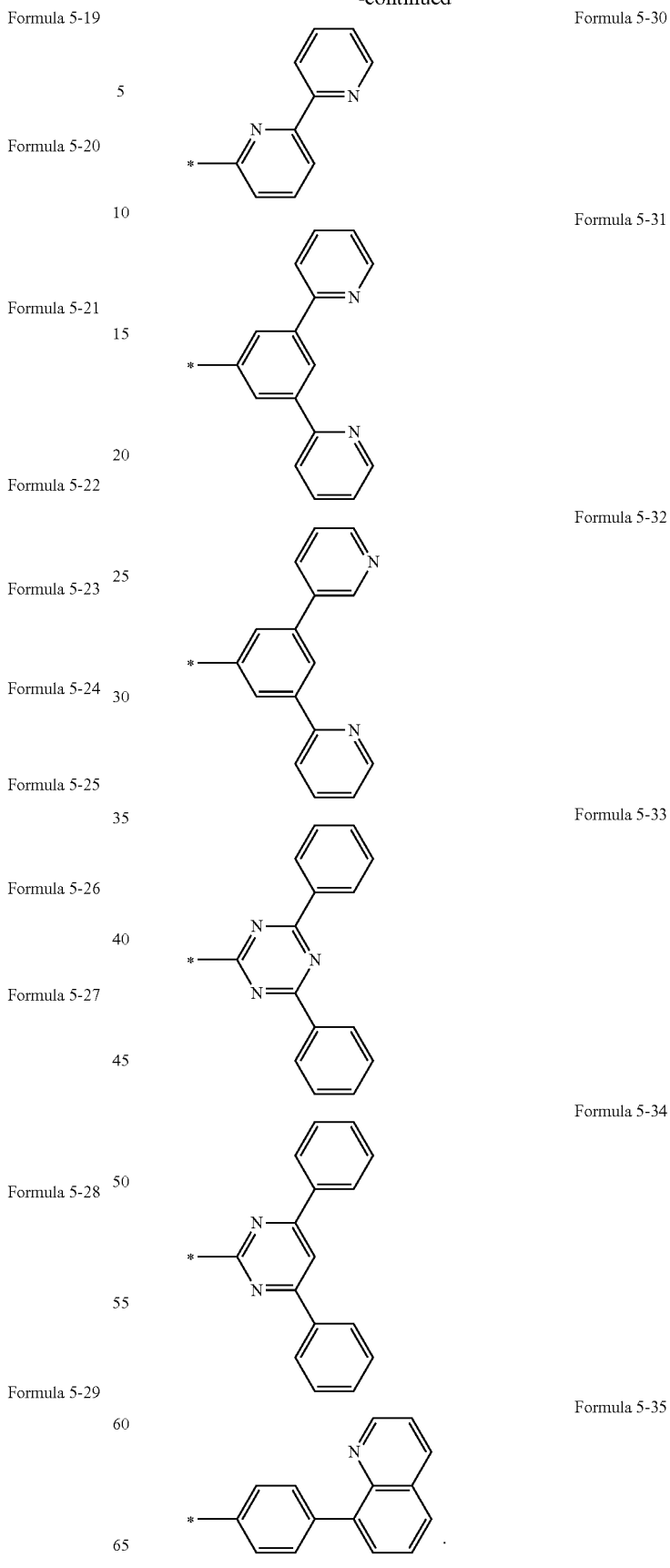
Formula 5-19
Formula 5-20
Formula 5-21
Formula 5-22
Formula 5-23
Formula 5-24
Formula 5-25
Formula 5-26
Formula 5-27
Formula 5-28
Formula 5-29
Formula 5-30
Formula 5-31
Formula 5-32
Formula 5-33
Formula 5-34
Formula 5-35

13. The compound of claim 1, wherein $R_{31}$ and $R_{32}$ are each independently selected from a hydrogen, a deuterium, —F, —Cl, —Br, —I, a hydroxyl group, a cyano group, a nitro group, an amino group, an amidino groups, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

14. The compound of claim 1, wherein the compound of Formula 1A or 1B is represented by one of Formulae 1A-1 to 1A-4, 1B-1, and 1B-2:

<Formula 1A-1>

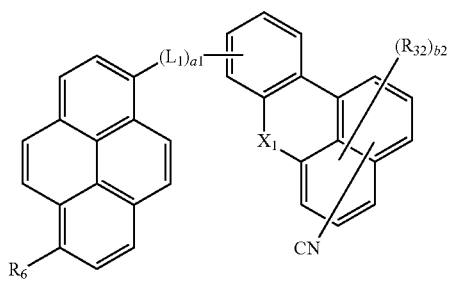

<Formula 1A-2>

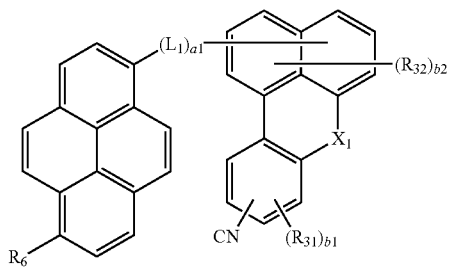

<Formula 1A-3>

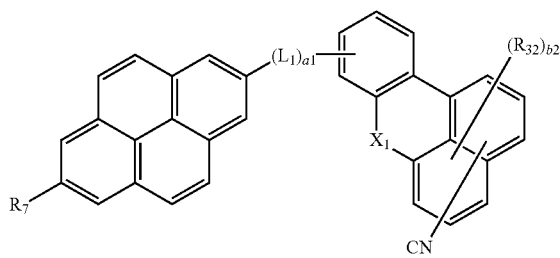

<Formula 1A-4>

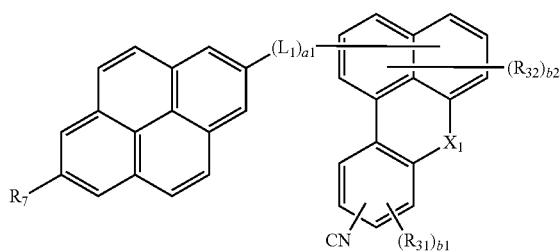

<Formula 1B-1>

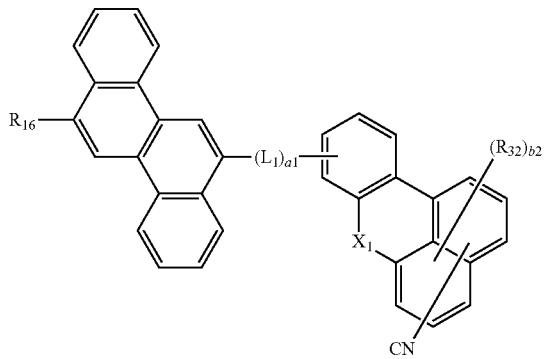

<Formula 1B-2>

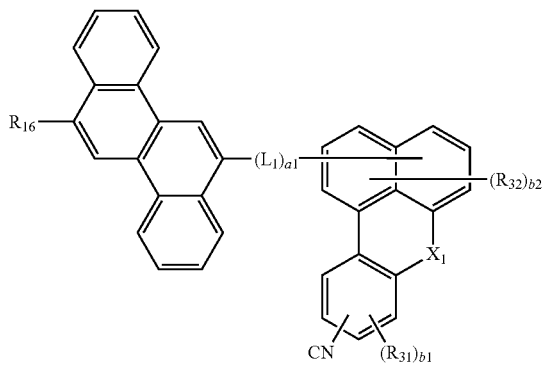

wherein, in Formulae 1A-1 to 1A-4, 1B-1, and 1B-2, $X_1$, $L_1$, a1, $R_6$, $R_7$, $R_{16}$, $R_{31}$, $R_{32}$, b1, and b2 are the same as those defined in claim 1.

15. The compound of claim 1, wherein the compound of Formula 1A or 1B is represented by one of Formulae 1A-1(1), 1A-1(2), 1A-2(1), 1A-2(2), 1A-3(1), 1A-3(2), 1A-3(3), 1A-4(1), 1A-4(2), 1B-1(1), 1B-1(2), 1B-1(3), 1B-2(1), and 1B-2(2):

<Formula 1A-1(1)>

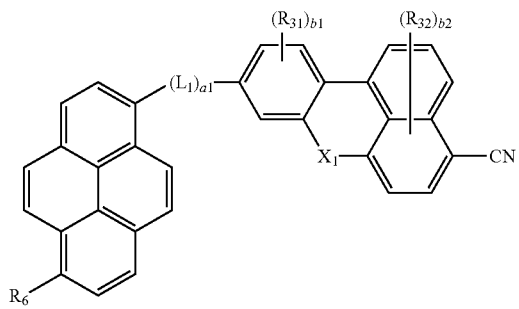

<Formula 1A-1(2)>
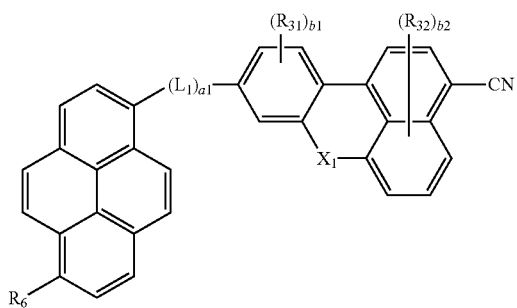
<Formula 1A-2(1)>
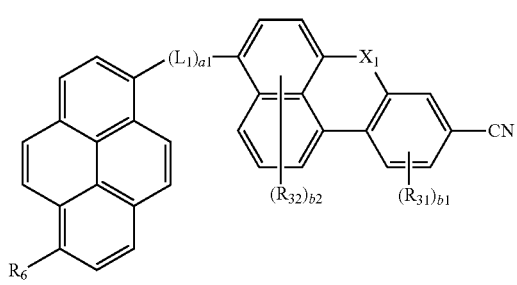
<Formula 1A-2(2)>
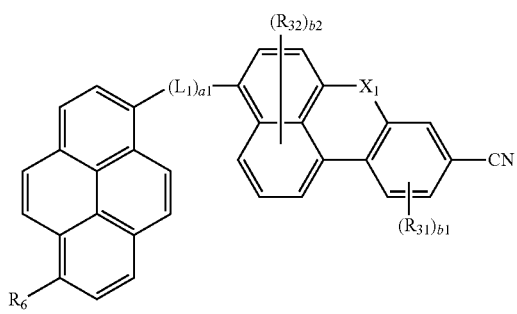
<Formula 1A-3(1)>
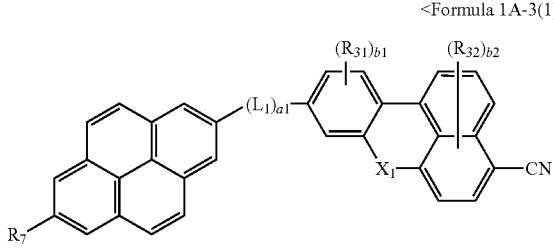
<Formula 1A-3(2)>
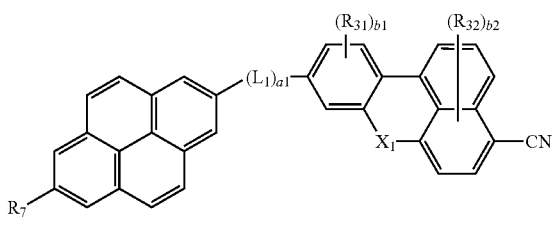
<Formula 1A-3(3)>
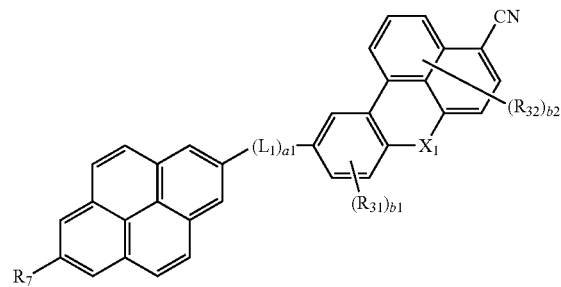
<Formula 1A-4(1)>
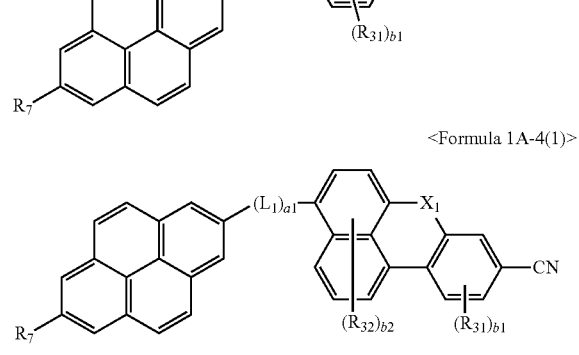
<Formula 1A-4(2)>
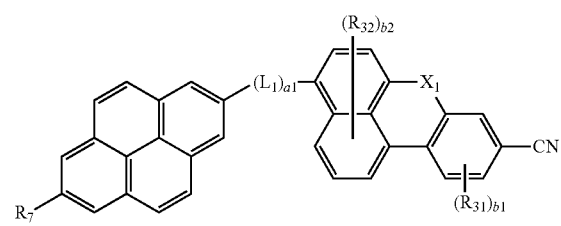
<Formula 1B-1(1)>
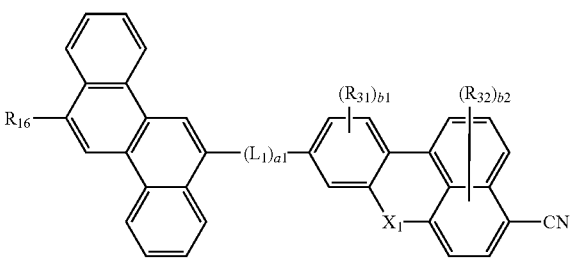
<Formula 1B-1(2)>
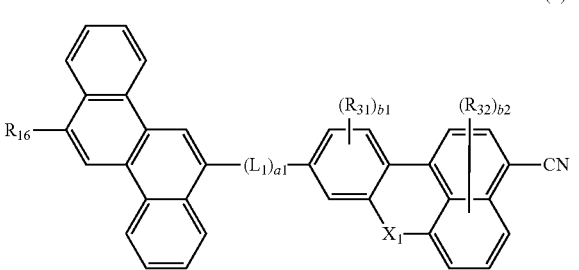
<Formula 1B-1(3)>
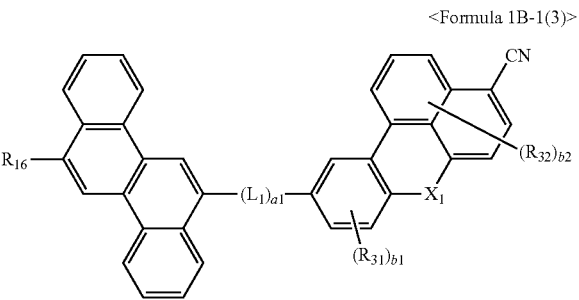

<Formula 1B-2(1)>
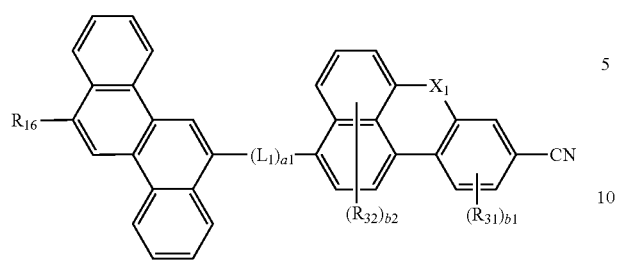
<Formula 1B-2(2)>
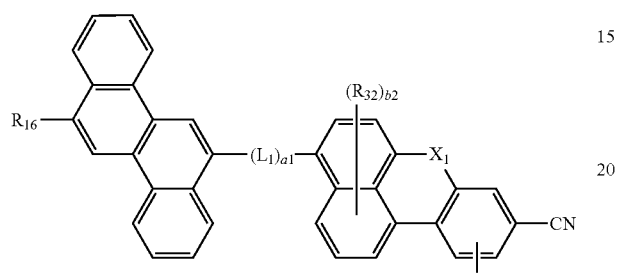
wherein, in Formulae 1A-1(1), 1A-1(2), 1A-2(1), 1A-2(2), 1A-3(1), 1A-3(2), 1A-3(3), 1A-4(1), 1A-4(2), 1B-1(1), 1B-1(2), 1B-1(3), 1B-2(1), and 1B(2), $X_1$, $L_1$, a1, $R_6$, $R_7$, $R_{31}$, $R_{32}$, b1, and b2 are the same as those defined in claim 1.
16. The compound of claim 1, wherein the compound of Formula 1A or 1B is one of Compounds 1A to 133A, and Compounds 1B to 92B:
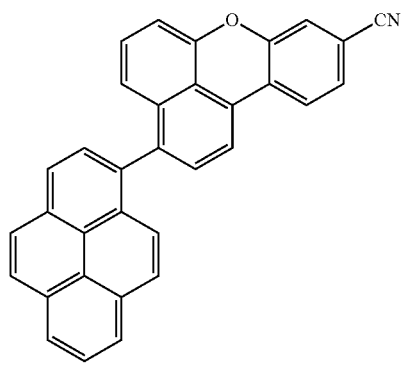
1A
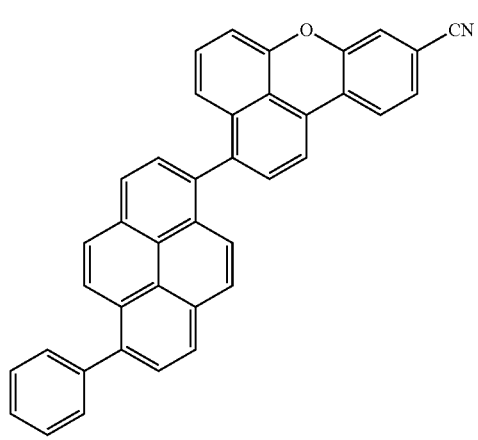
2A
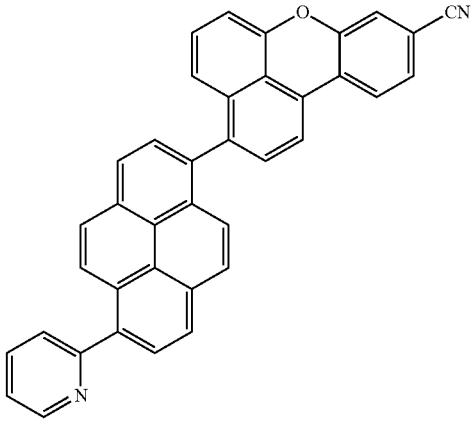
3A
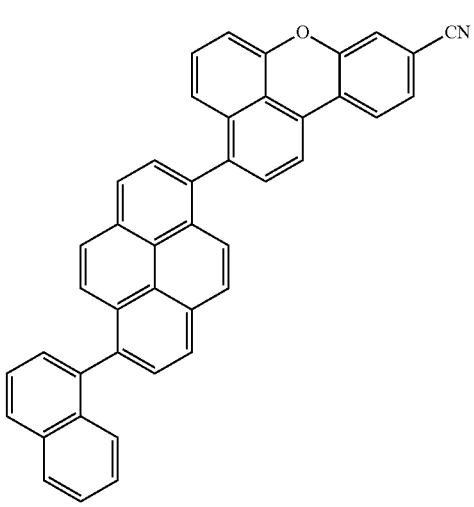
4A
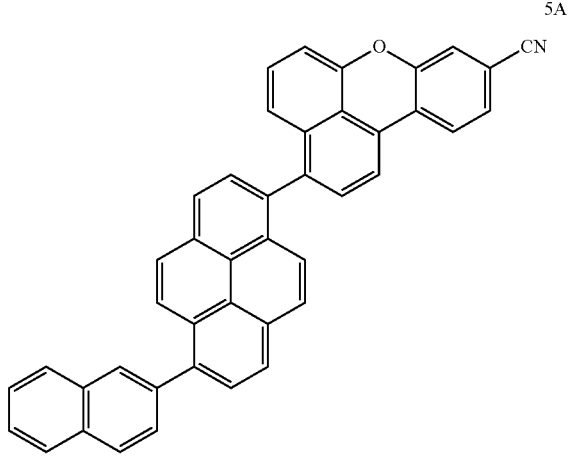
5A

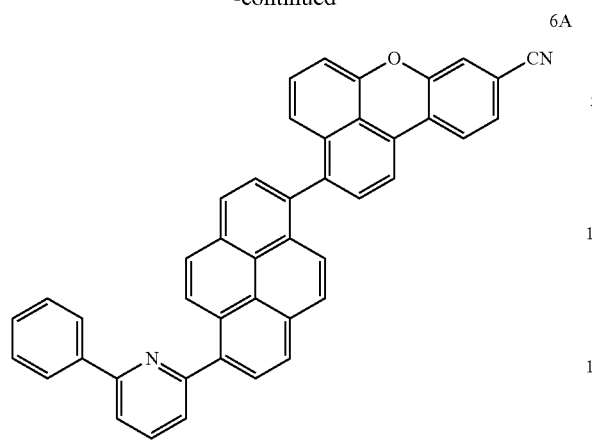
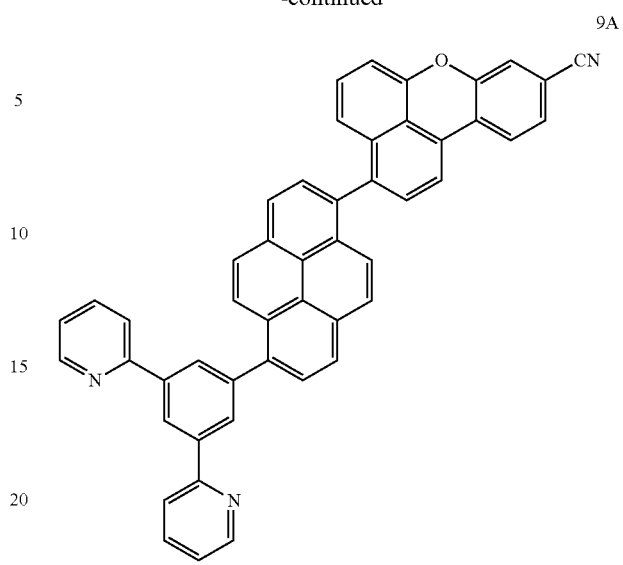
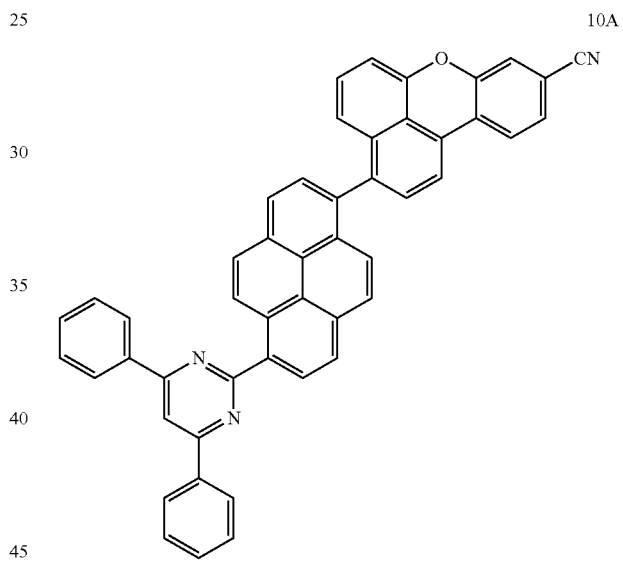
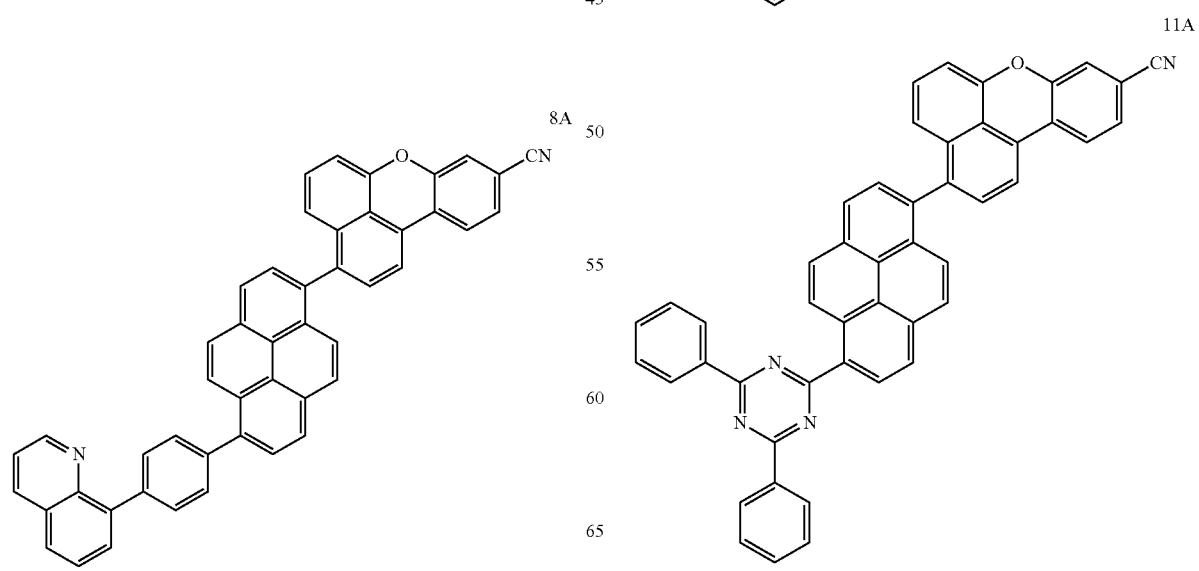

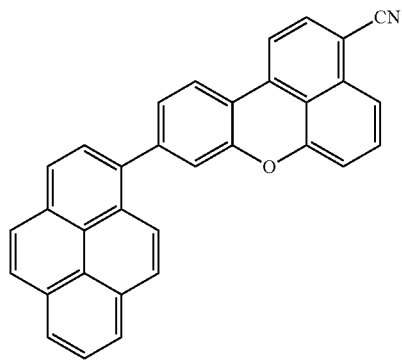
12A
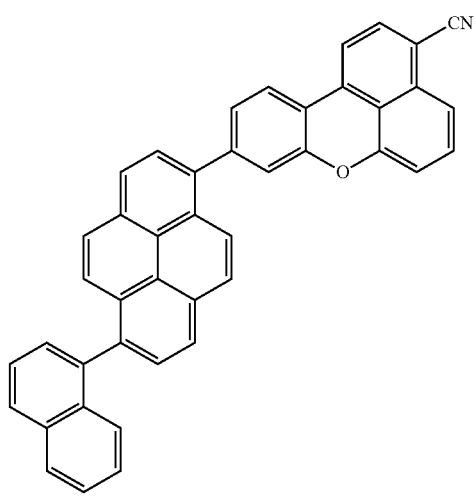
15A
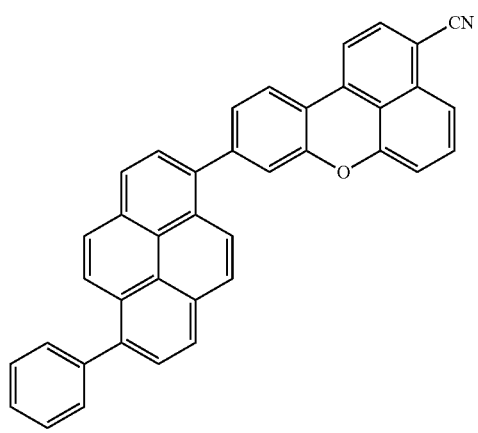
13A
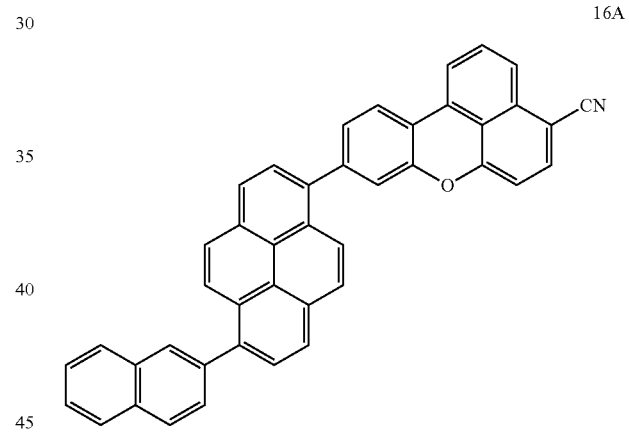
16A
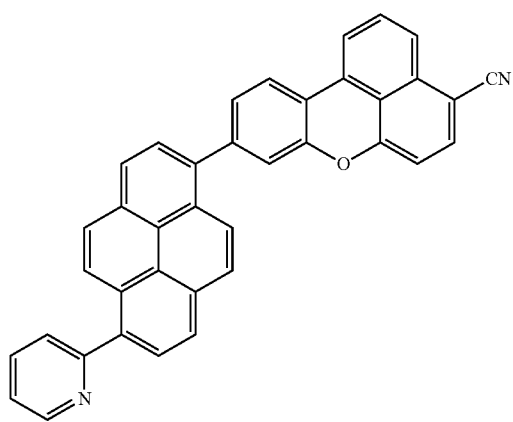
14A
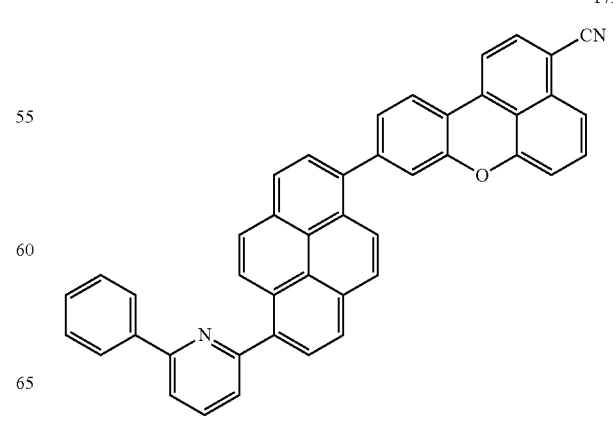
17A 257
-continued
18A
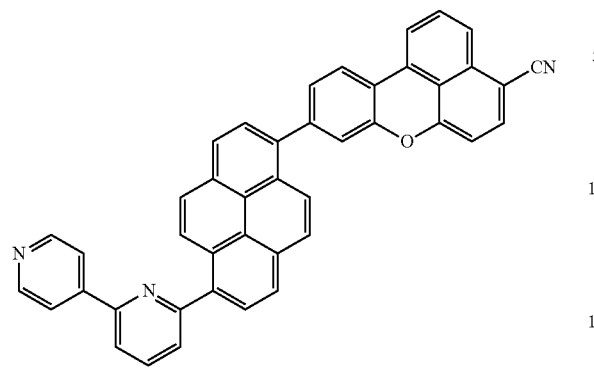
19A
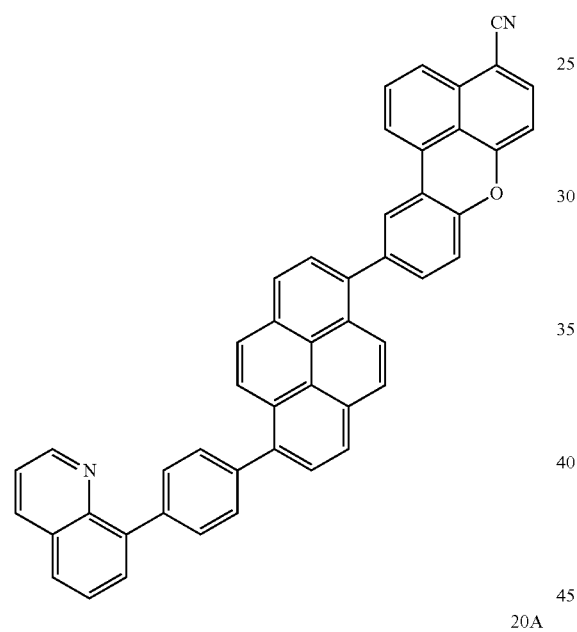
20A
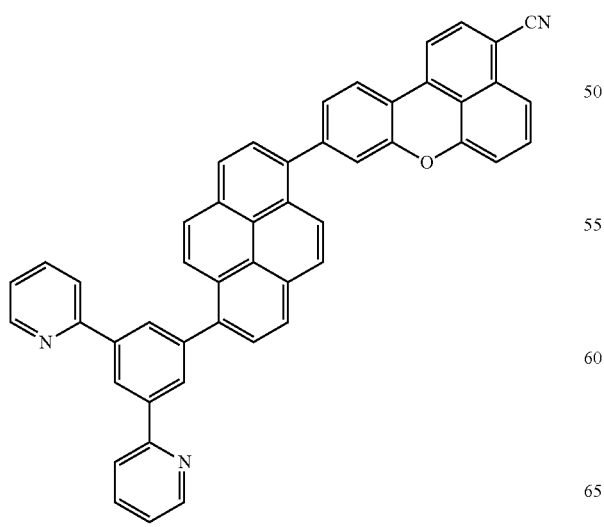
258
-continued
21A
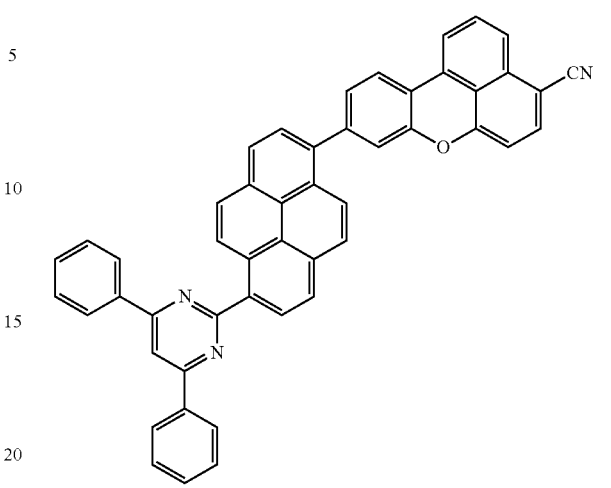
22A
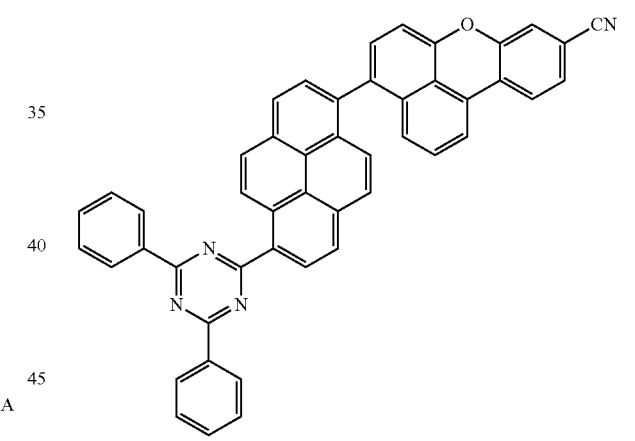
23A
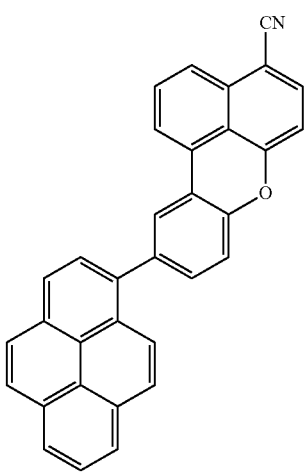

-continued
24A
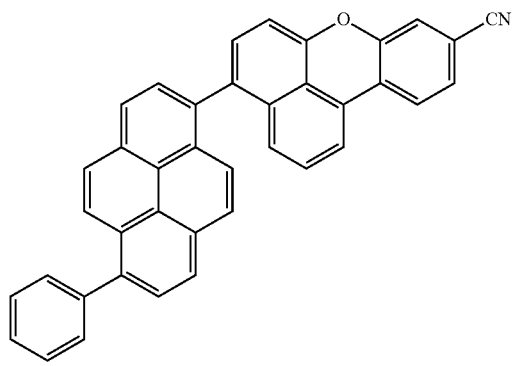
25A
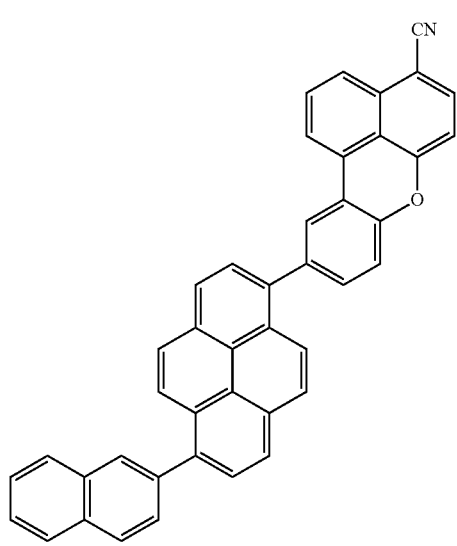
26A
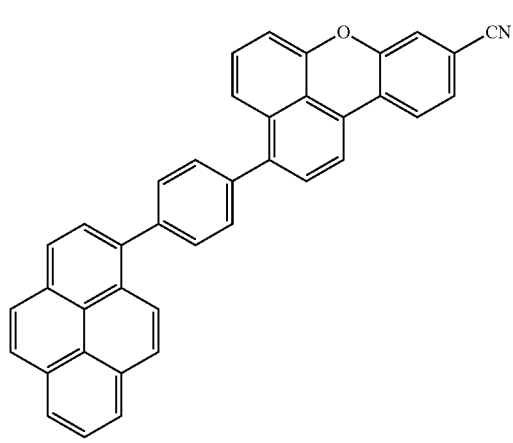
-continued
27A
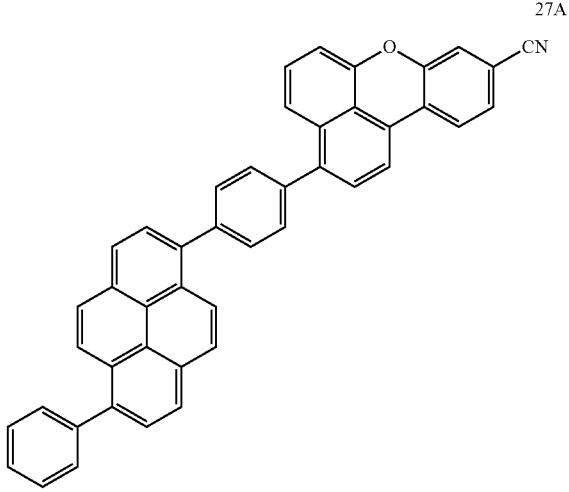
28A
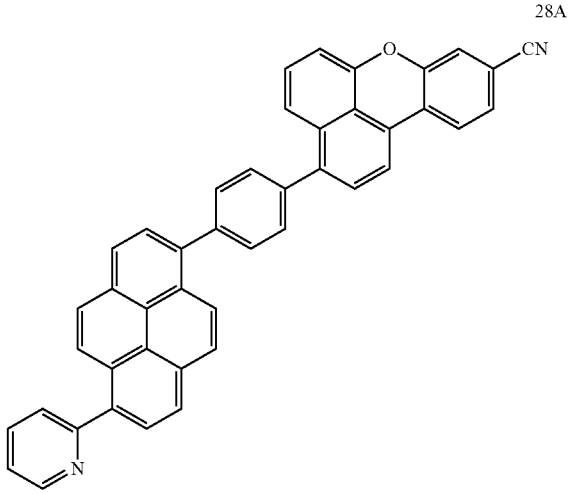
29A
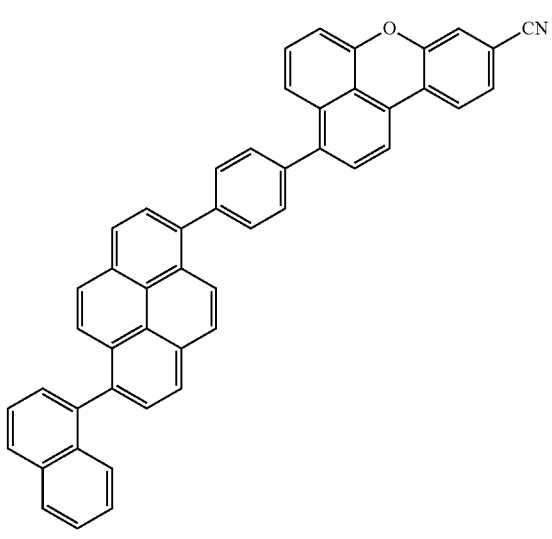

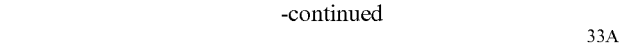
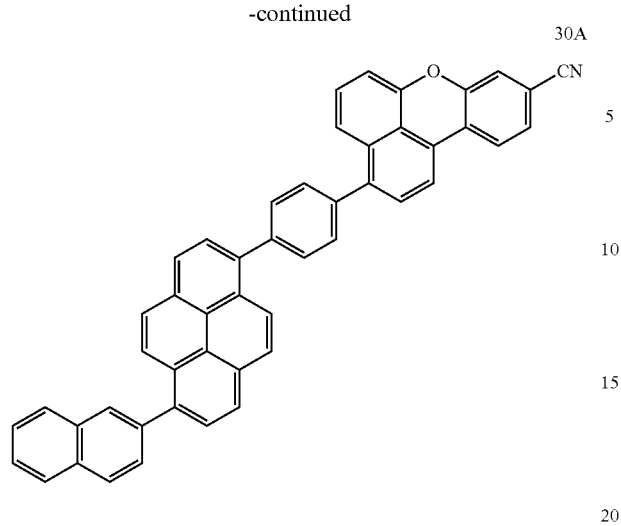
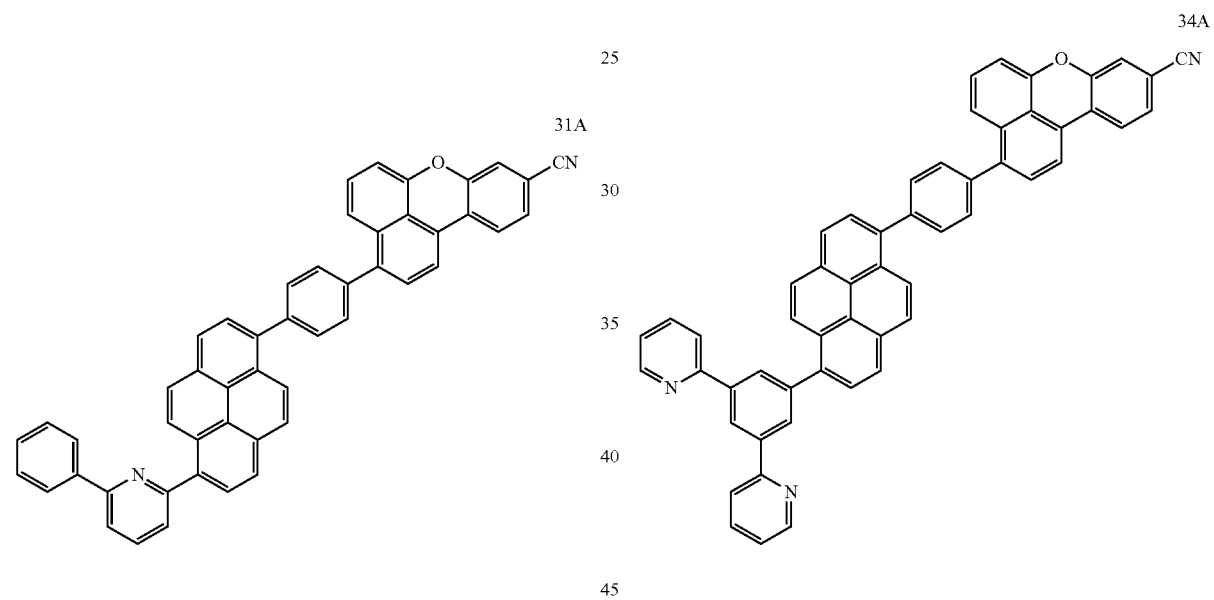
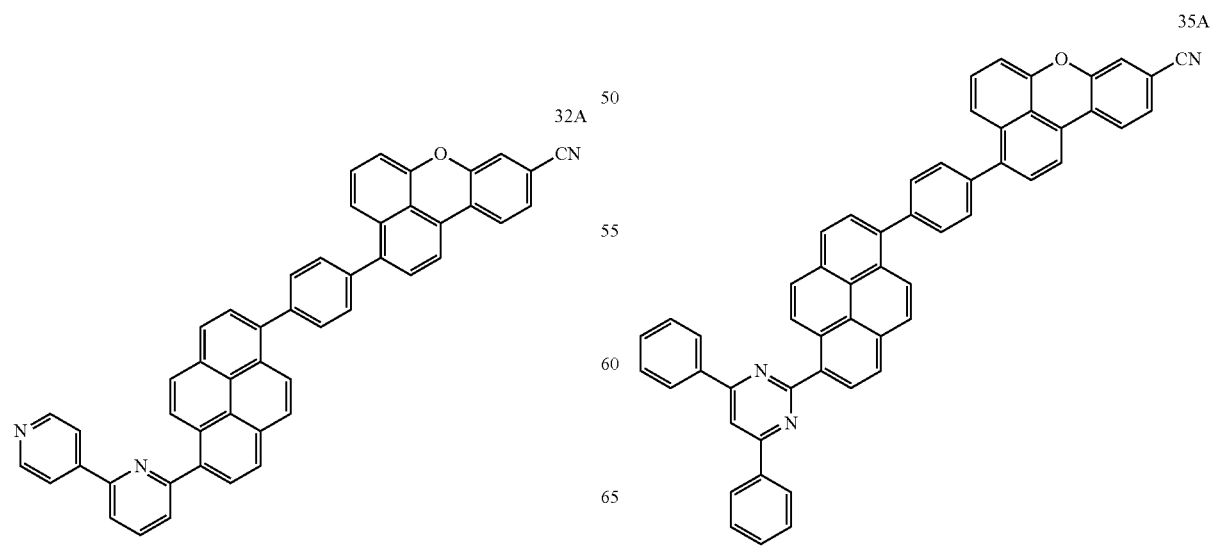

-continued
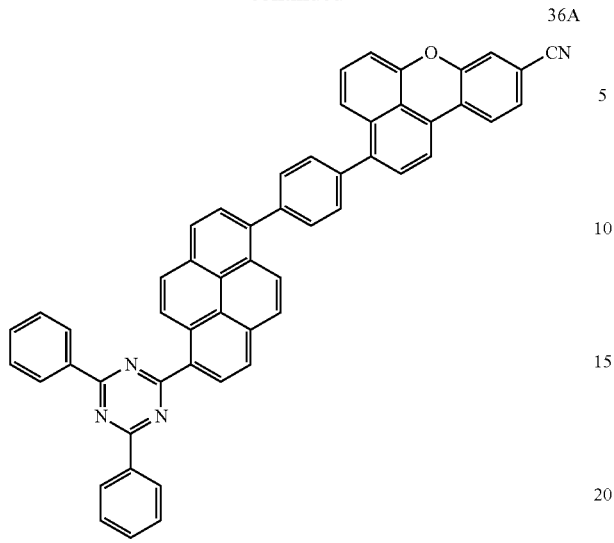
36A
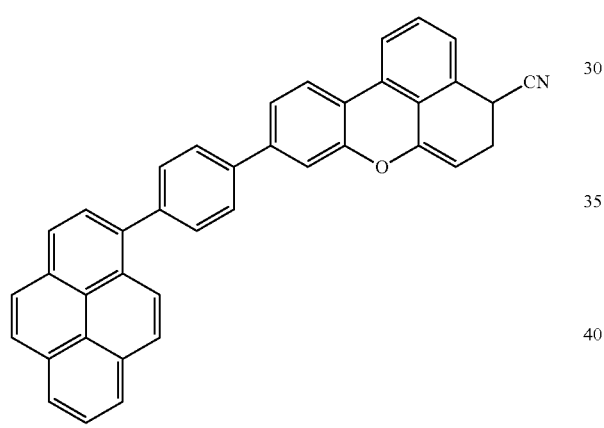
37A
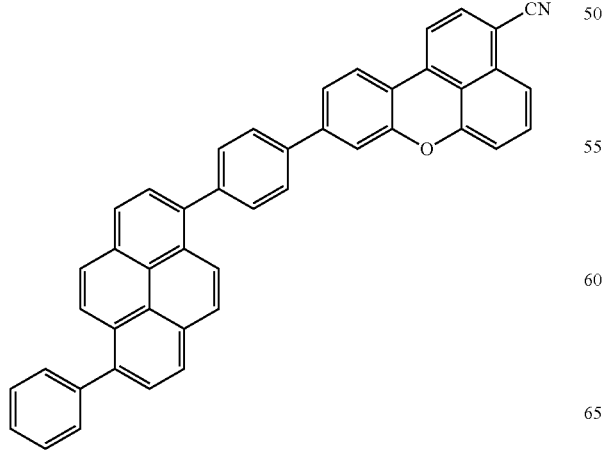
38A
-continued
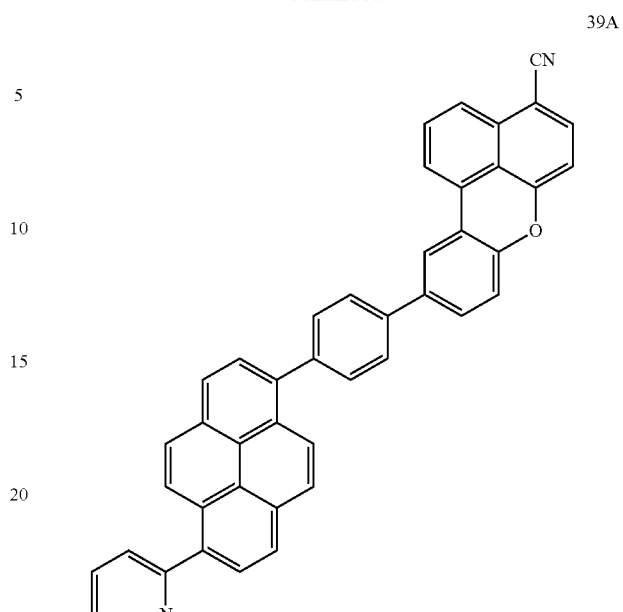
39A
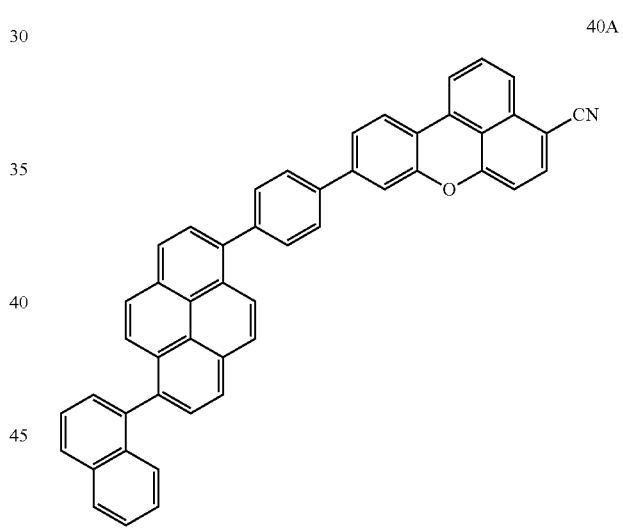
40A
41A -continued
42A
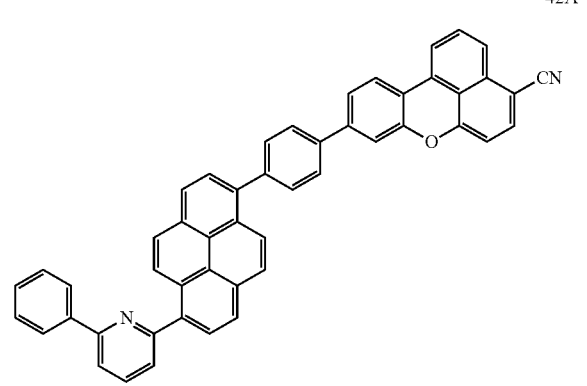
43A
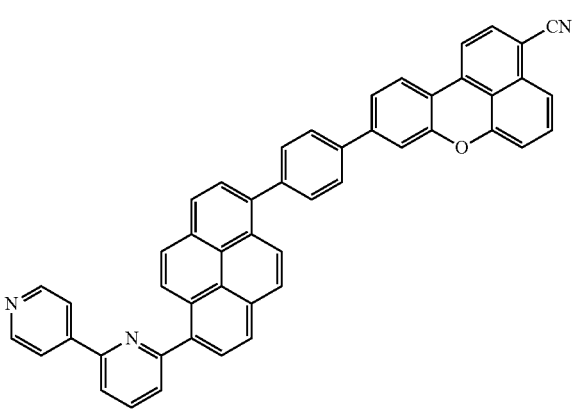
44A
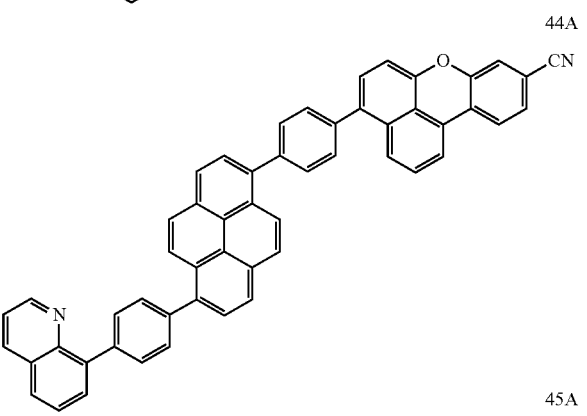
45A
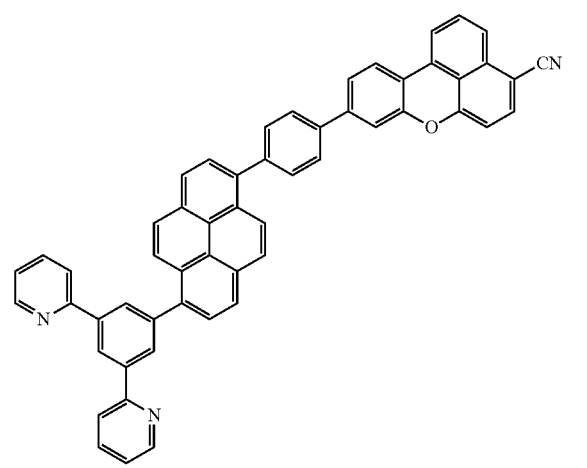
-continued
46A
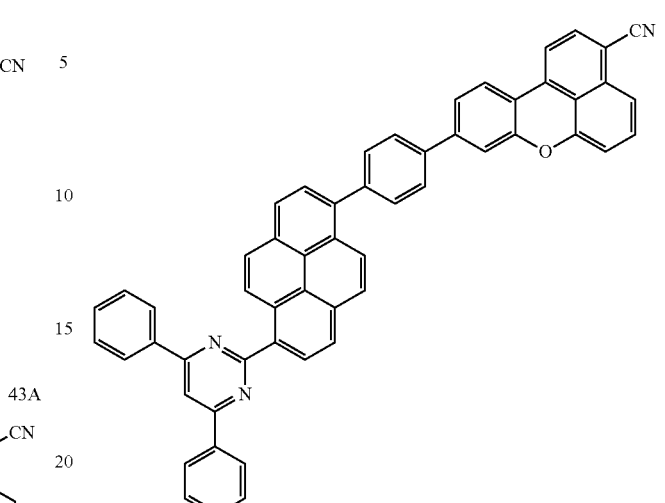
47A
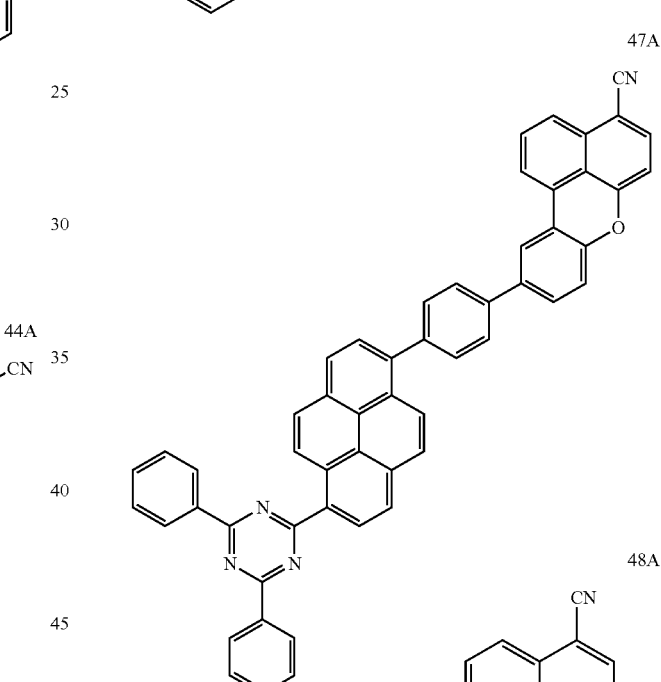
48A
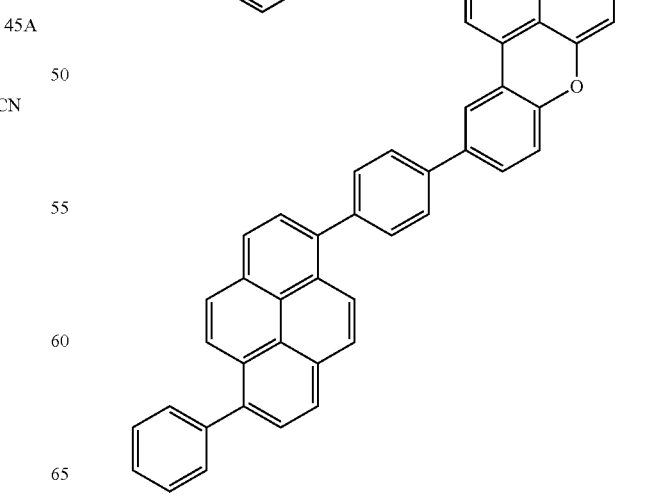

-continued
49A
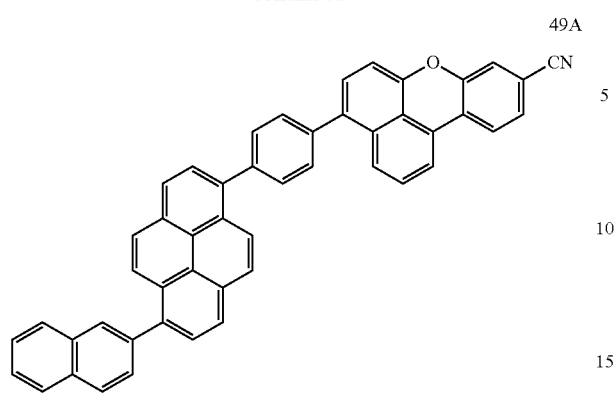
50A
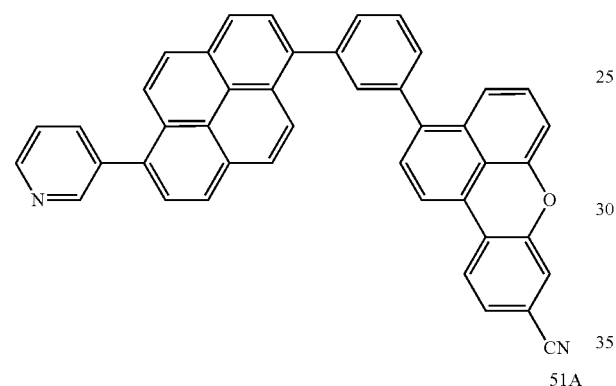
51A
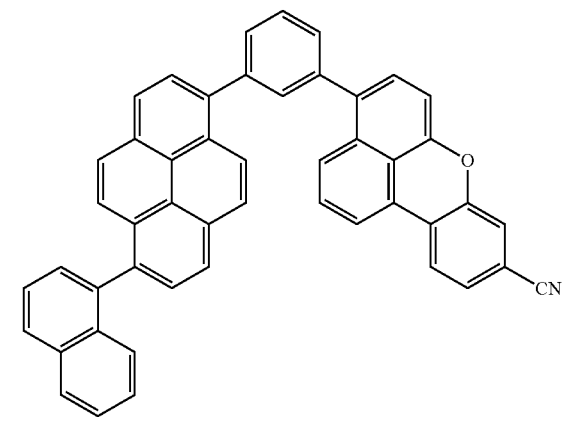
52A
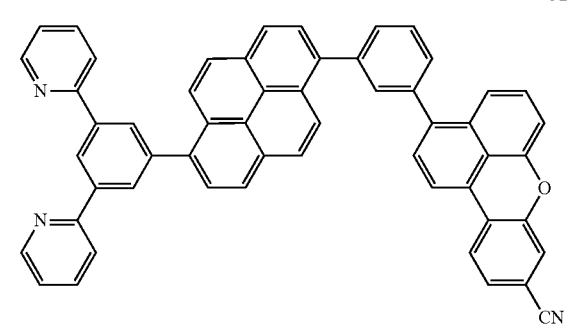
-continued
53A
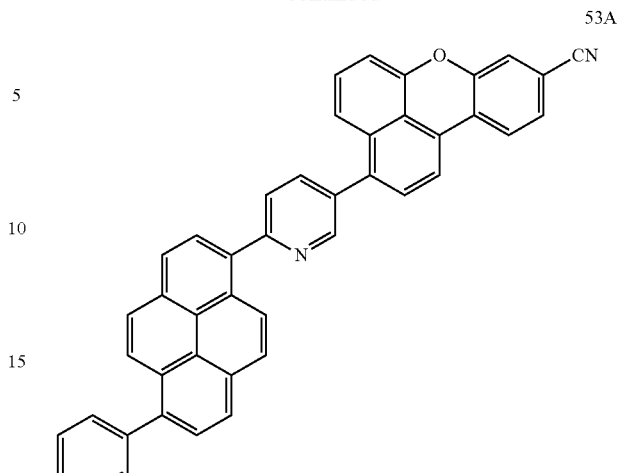
54A
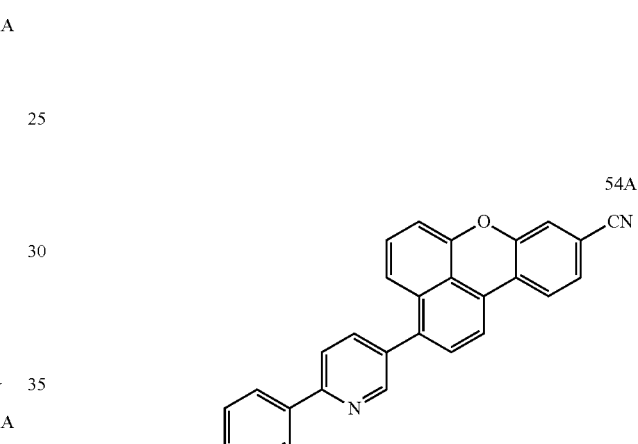
55A
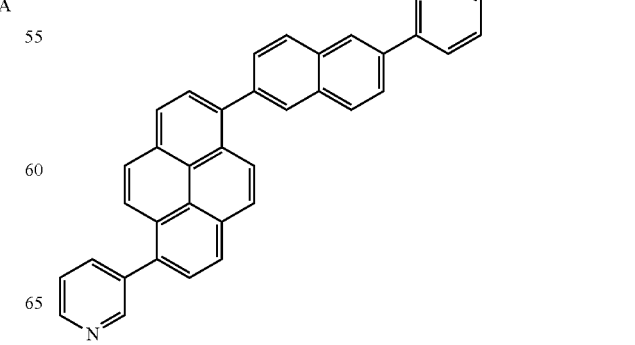

-continued
56A
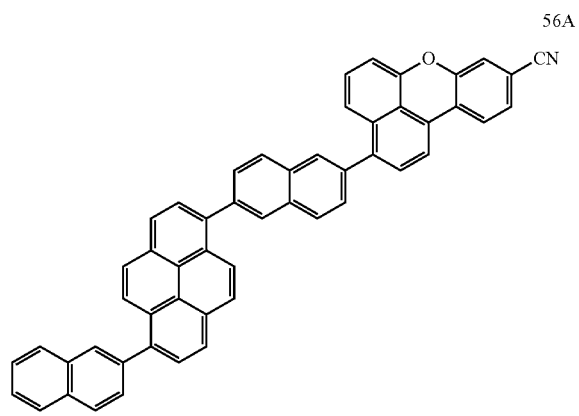
57A
58A
59A
-continued
60A
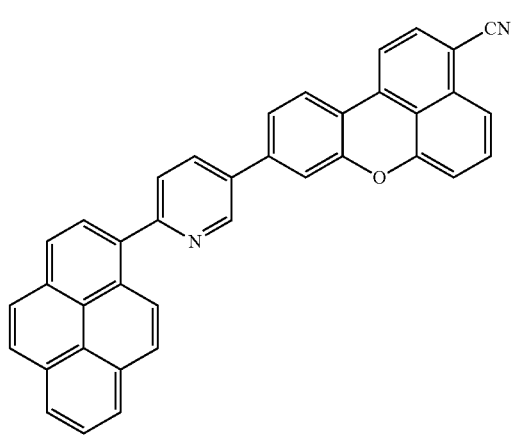
61A
62A
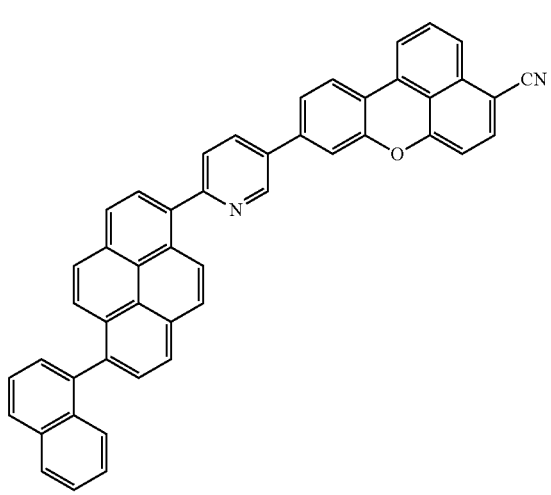

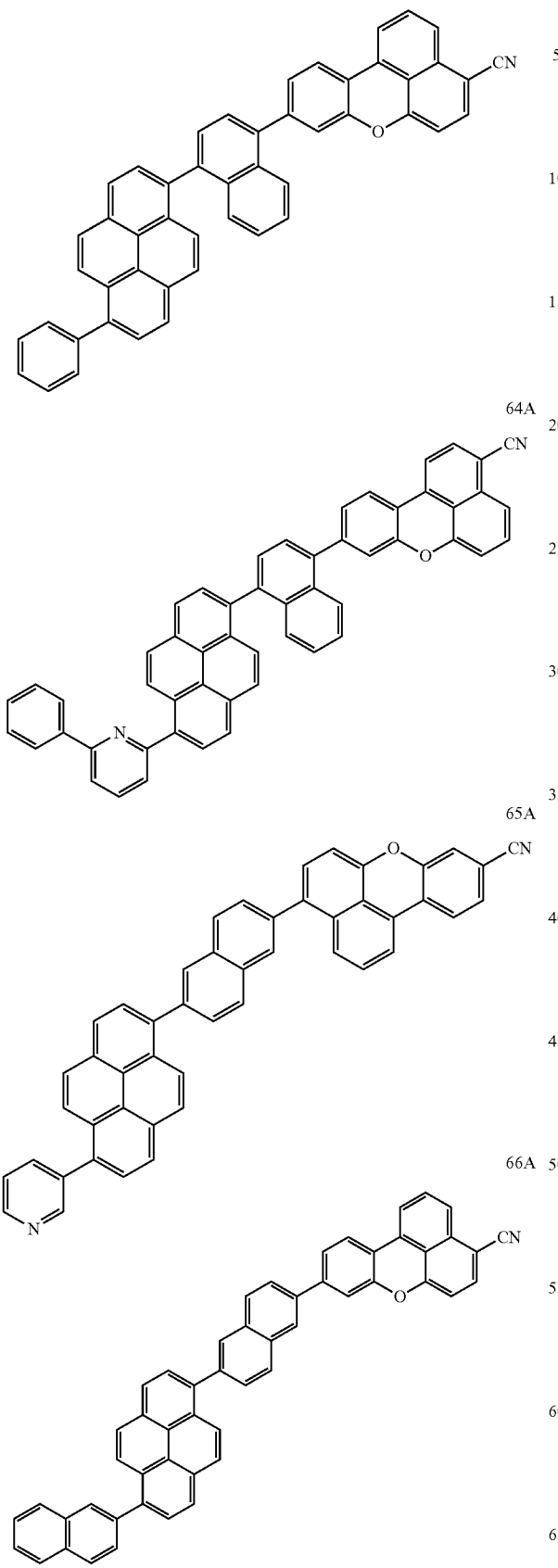
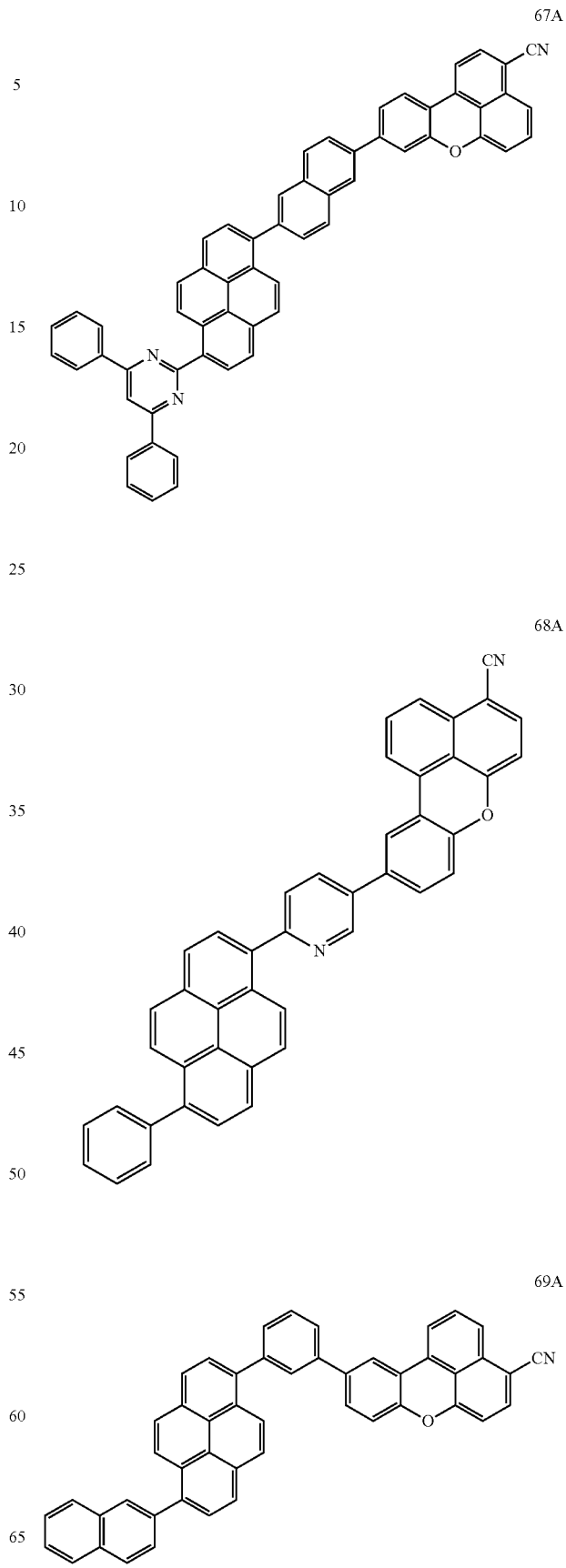

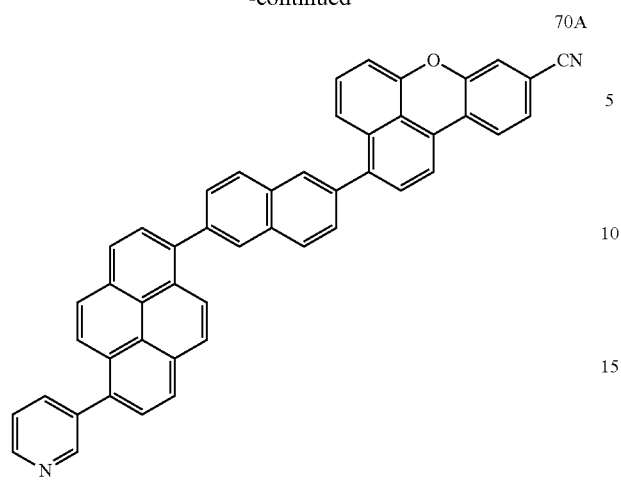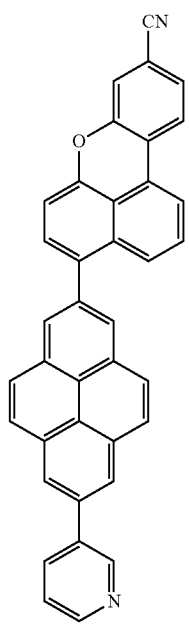

275
-continued
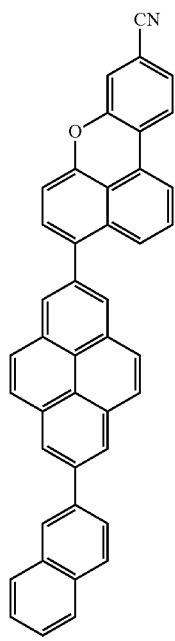
276
-continued
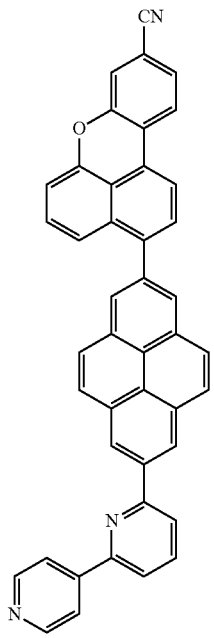
75A
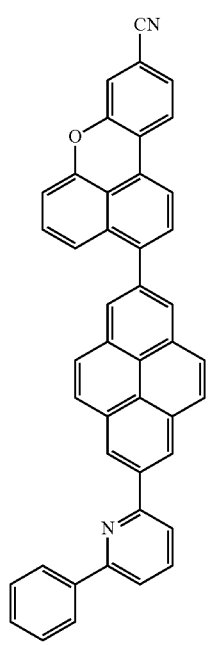
76A
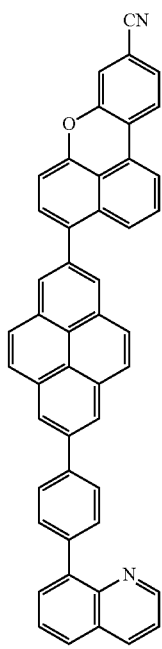
77A
78A 277
-continued
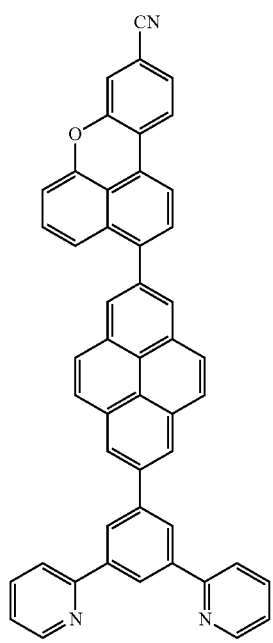
79A
278
-continued
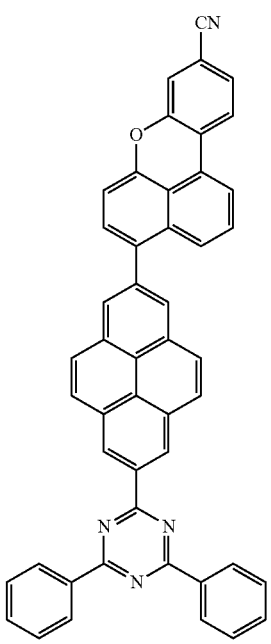
81A
80A
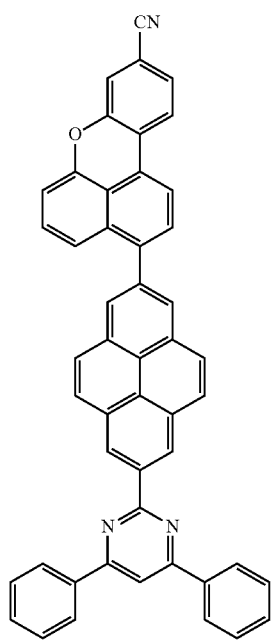
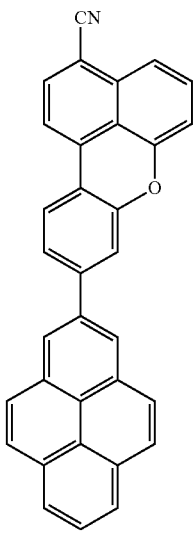
82A 83A
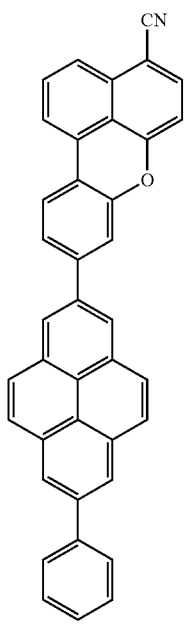
85A
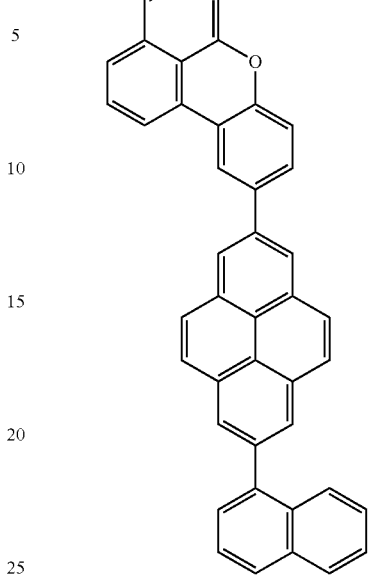
84A
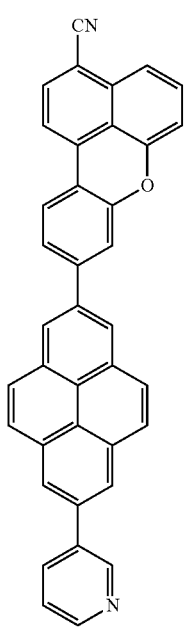
86A
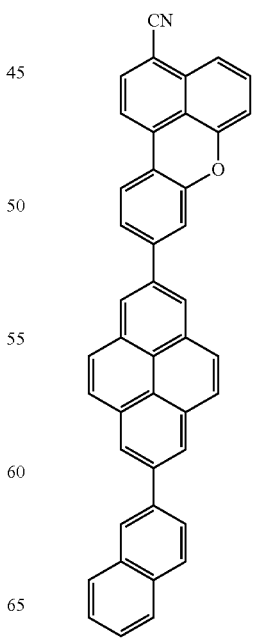

281    282
-continued    -continued
87A
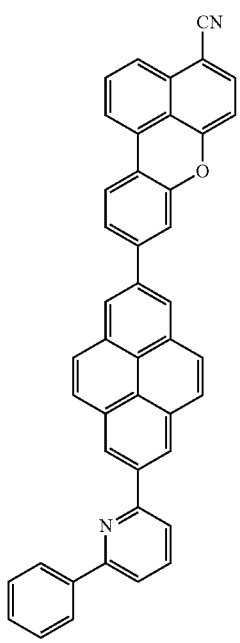
89A
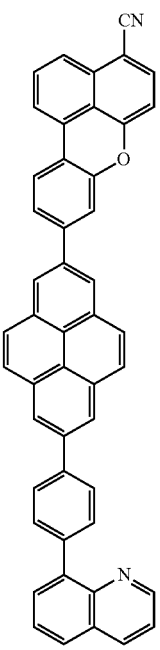
88A
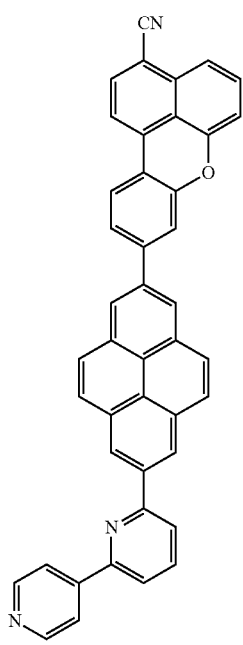
90A
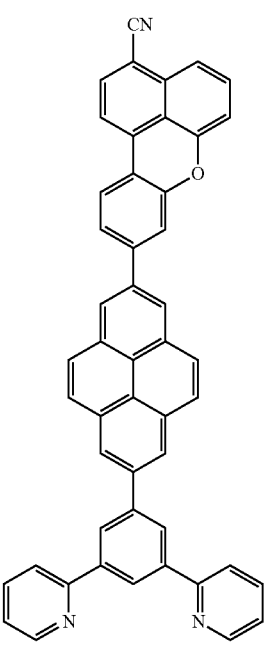

283
-continued
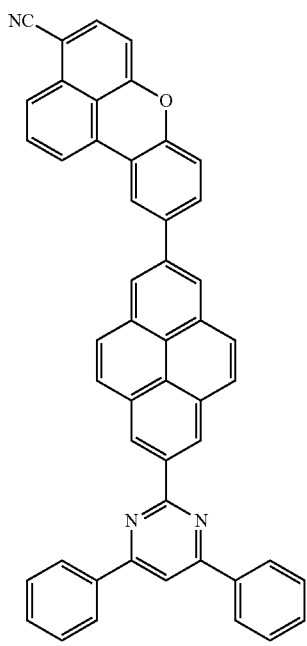
284
-continued
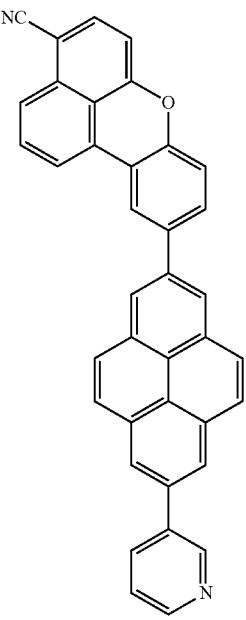
91A
92A
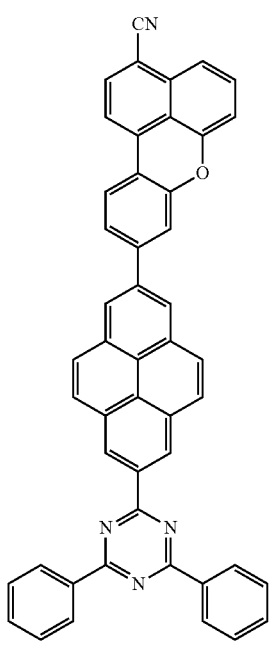
93A
94A 285
-continued
286
-continued
95A
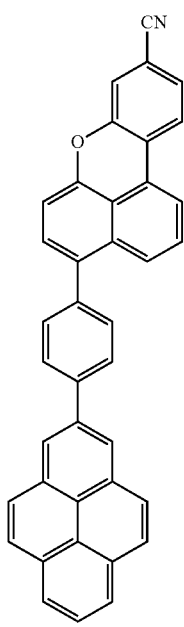
97A
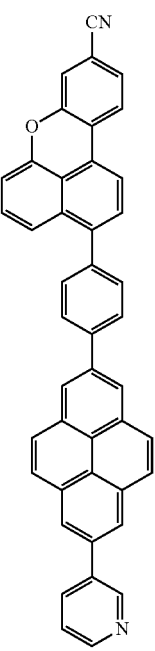
96A
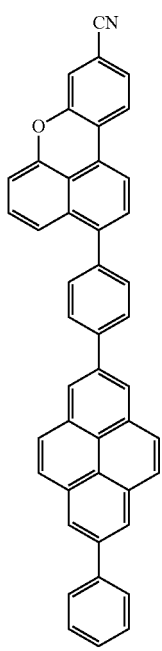
98A
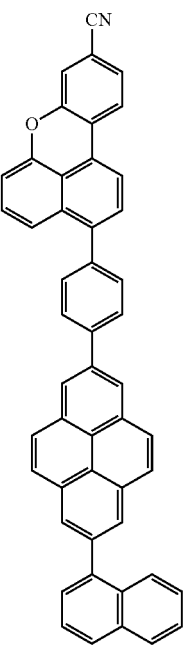

287
-continued
288
-continued
99A
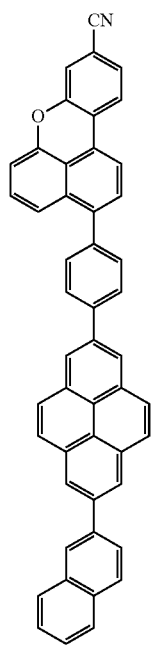
101A
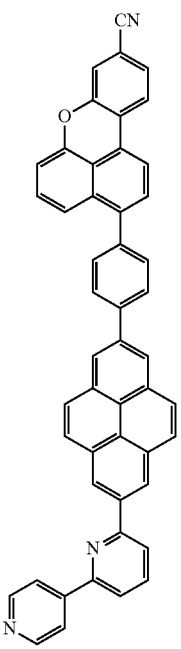
100A
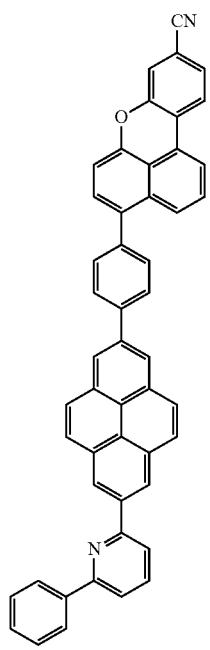
102A
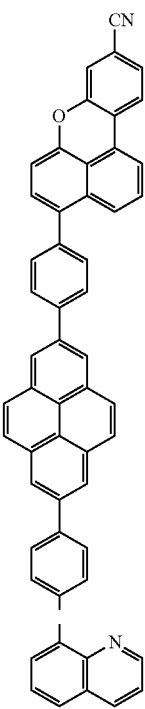

289
-continued
103A
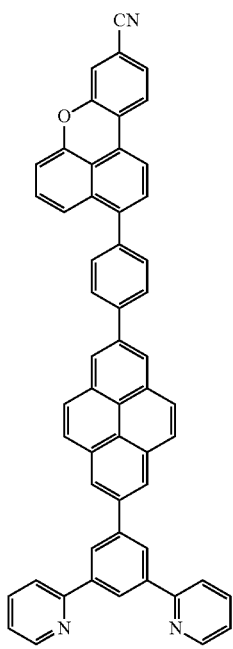
104A
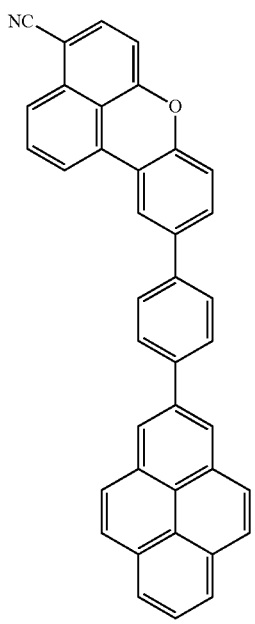
290
-continued
105A
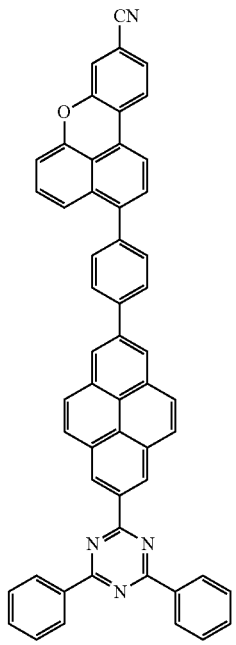
106A 291
-continued
107A
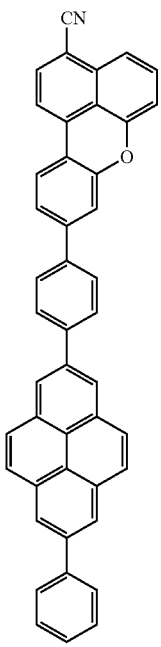
108A
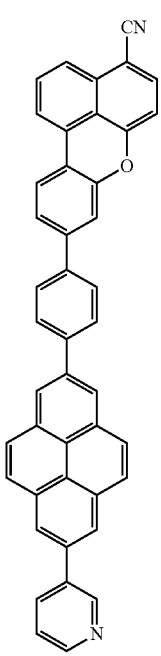
292
-continued
109A
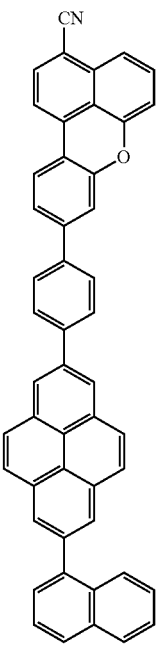
110A
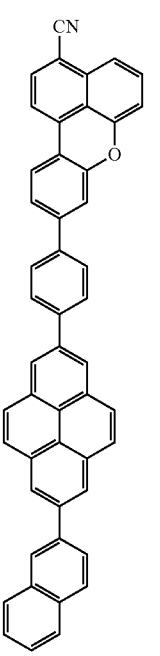

293
-continued
294
-continued
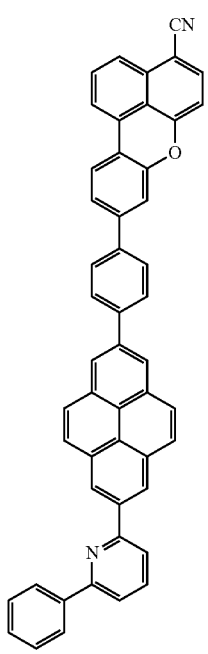
111A
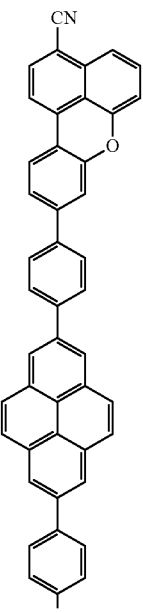
113A
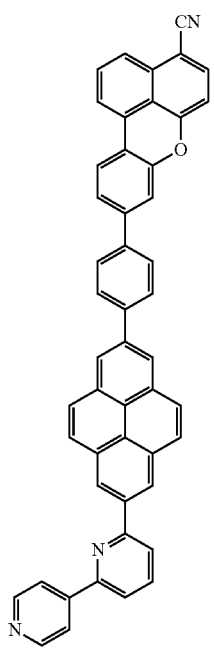
112A
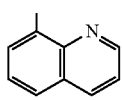
114A 295
-continued
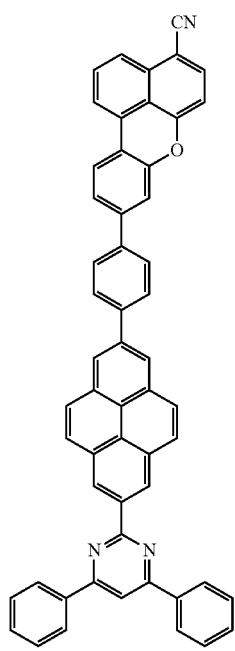
115A
116A
296
-continued
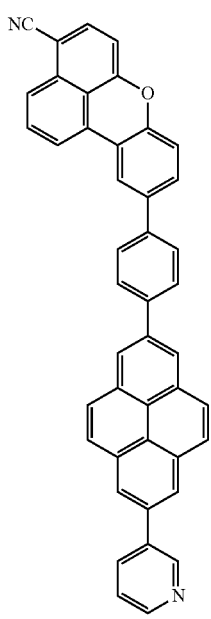
117A
118A 297
-continued
298
-continued
119A
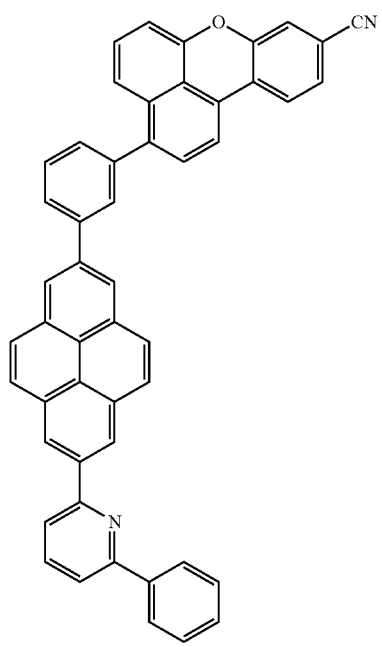
121A
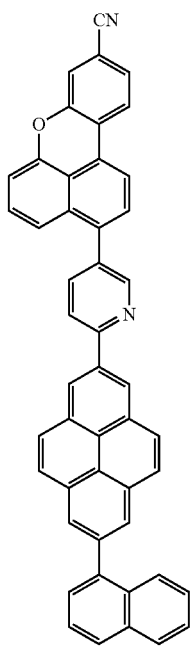
120A
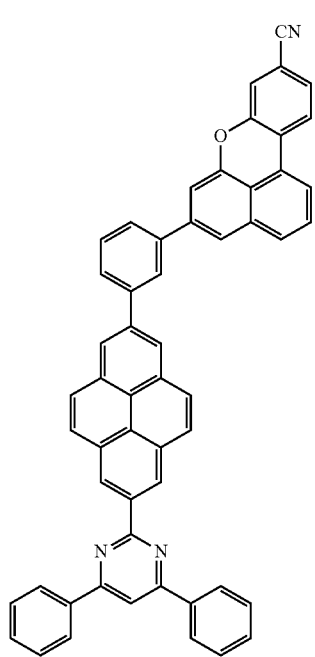
122A
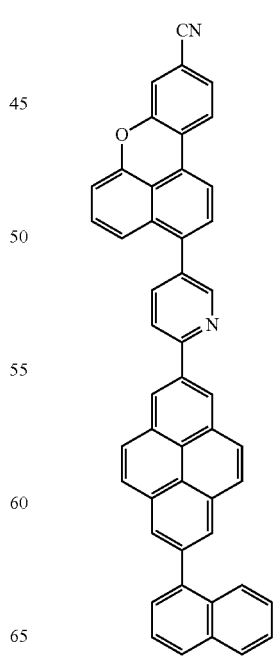

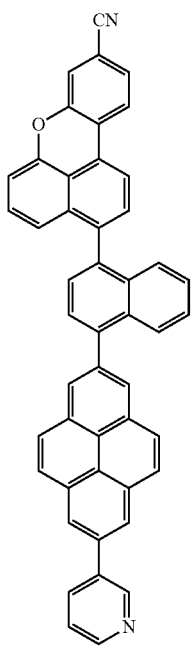
123A
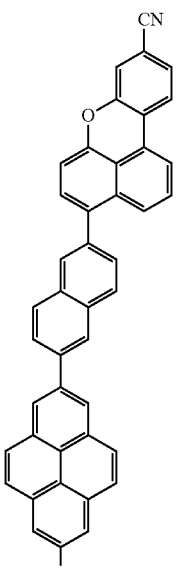
125A
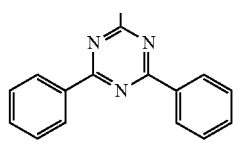
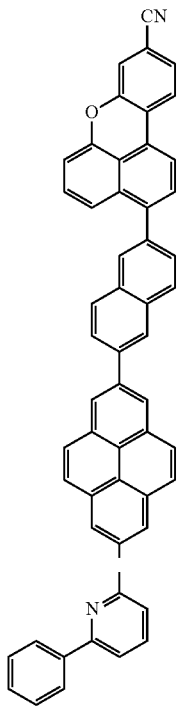
124A
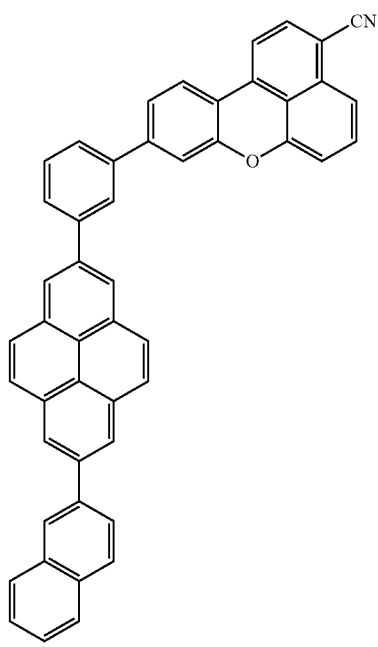
126A

301
-continued
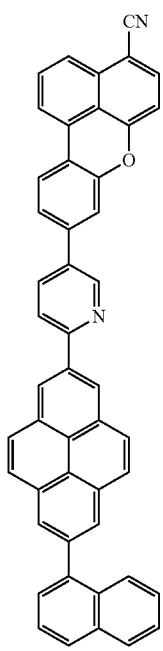
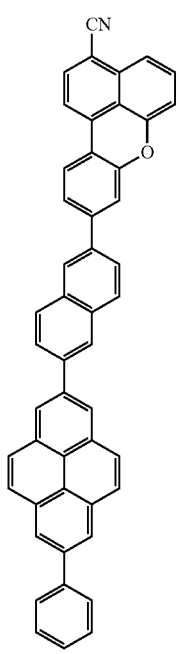
302
-continued
127A
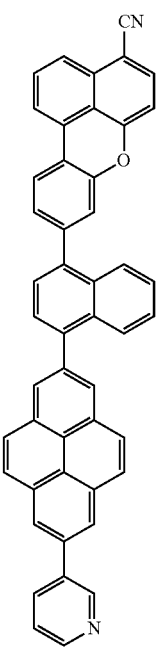
128A
129A
130A
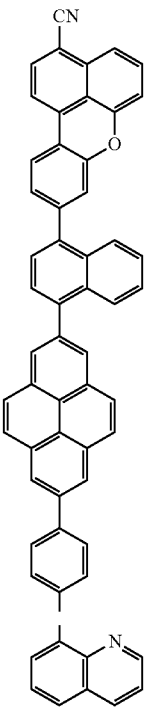

303
-continued
131A
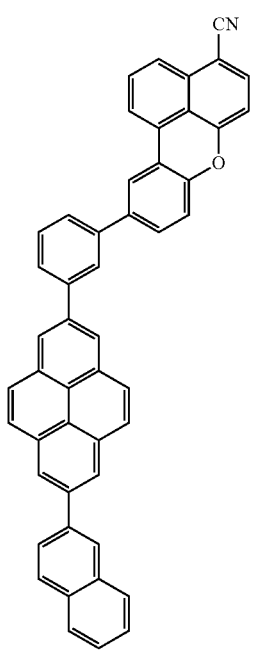
132A
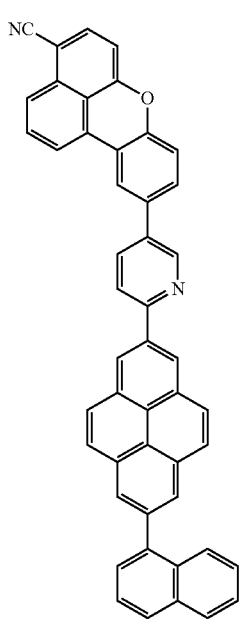
304
-continued
133A
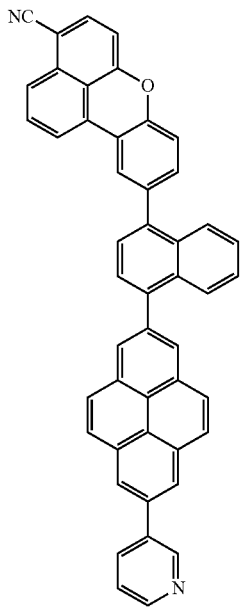
1B
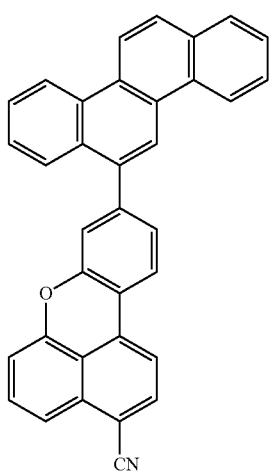
2B 305
-continued
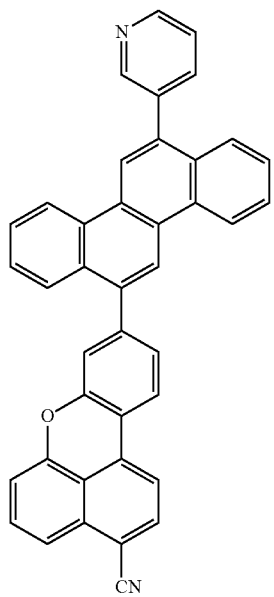
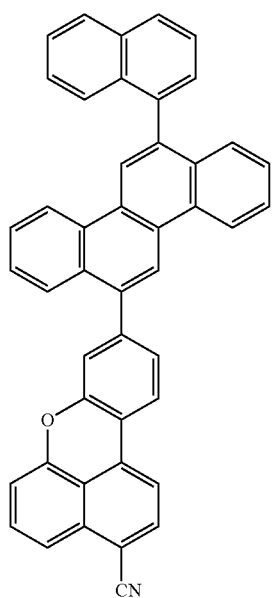
306
-continued
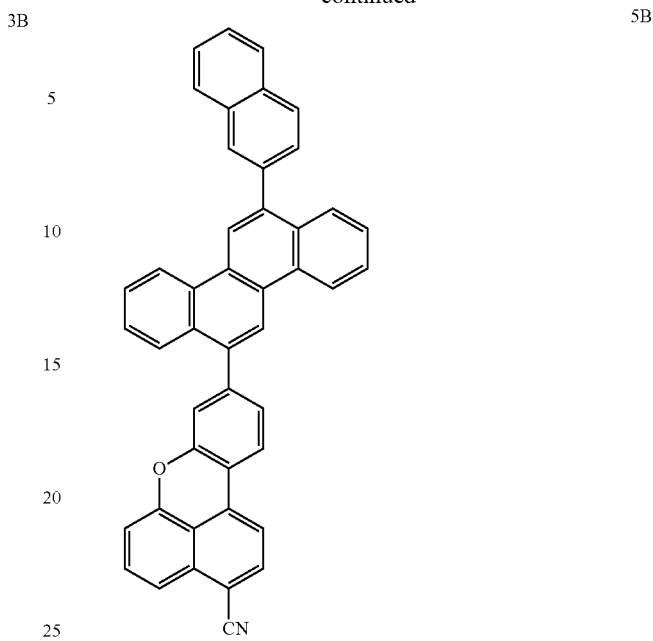
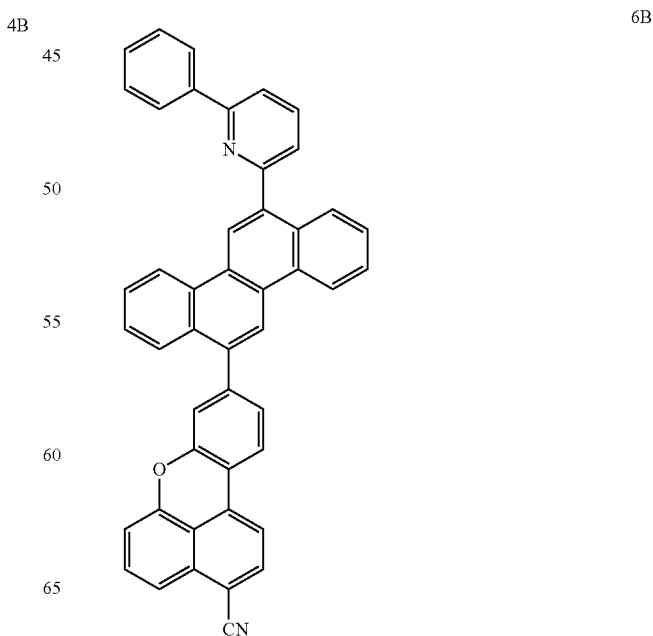

307
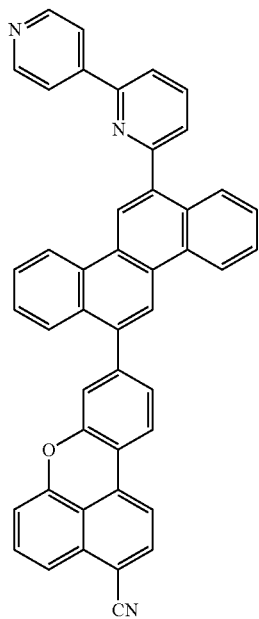
308
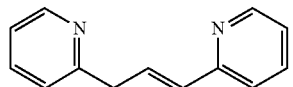
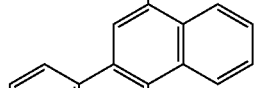
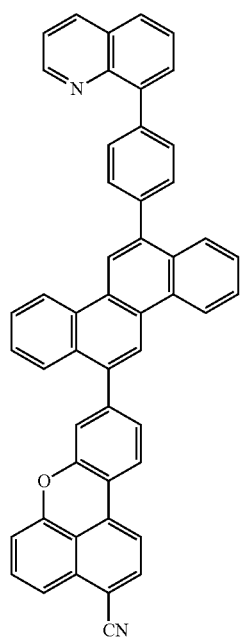
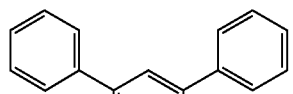
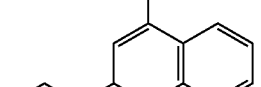
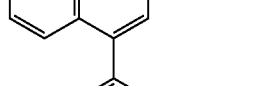

309
-continued
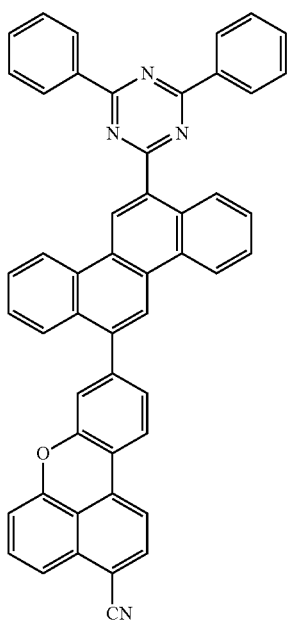
310
-continued
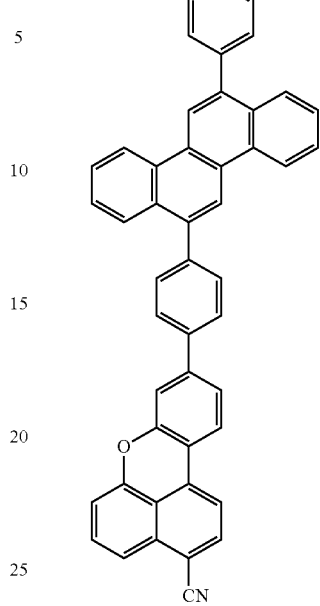
11B
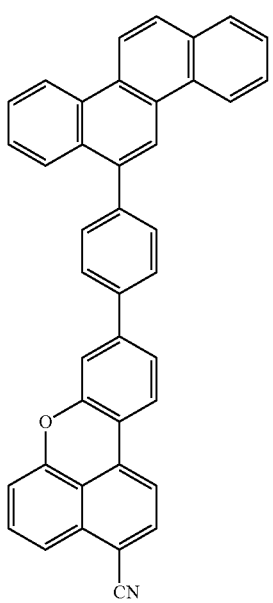
12B
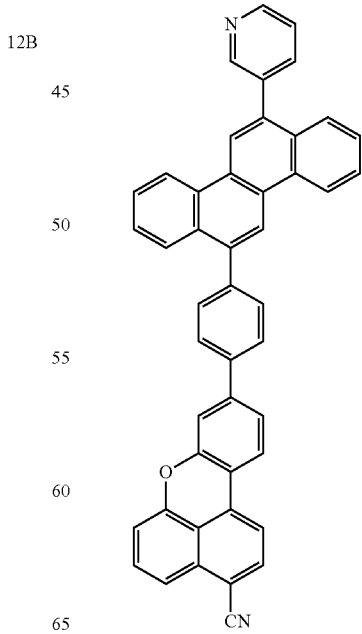
13B
14B 311
-continued
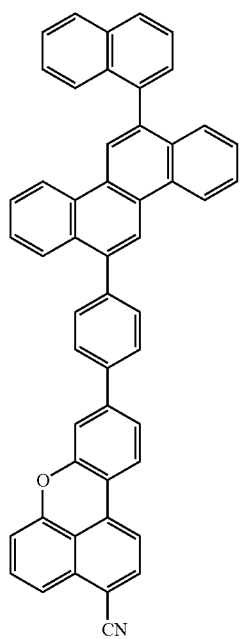
312
-continued
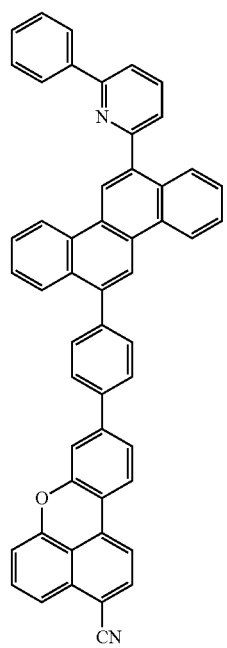
15B
17B
16B
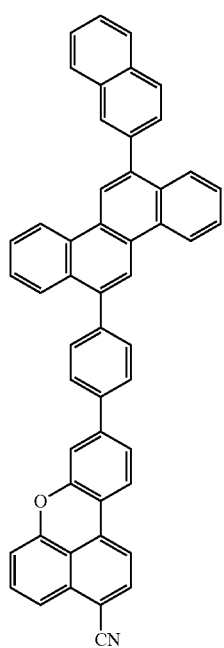
18B
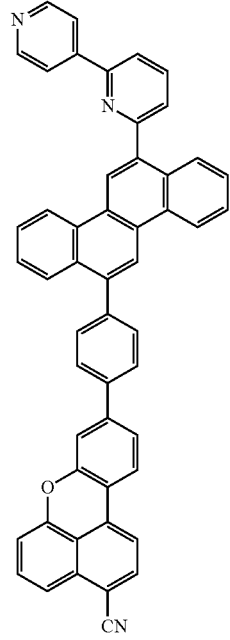

313
-continued
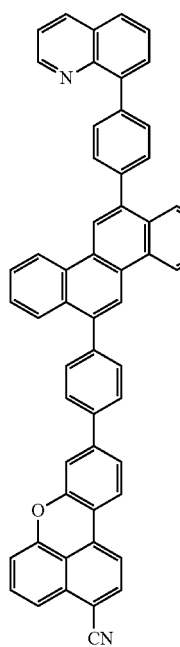
19B
314
-continued
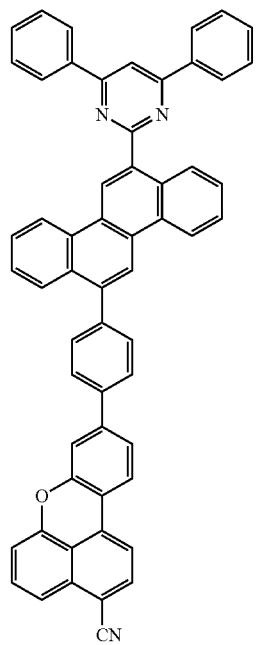
21B
20B
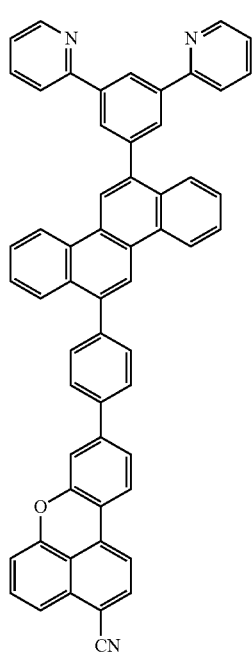
22B
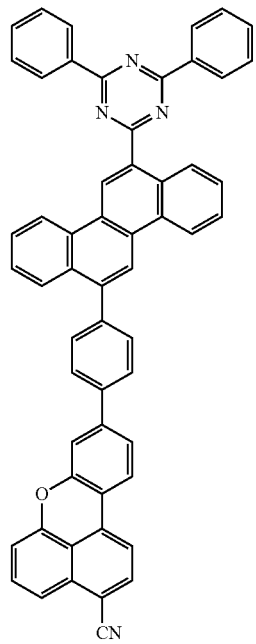

315
-continued
316
-continued
23B
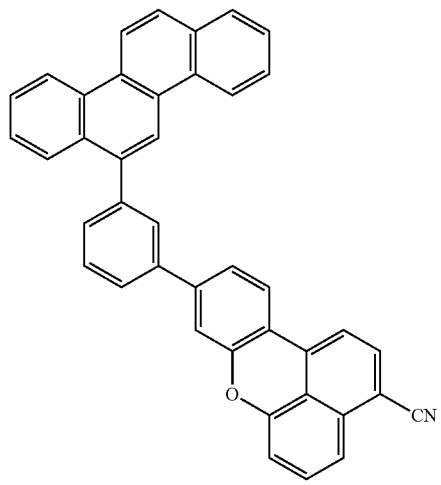
25B
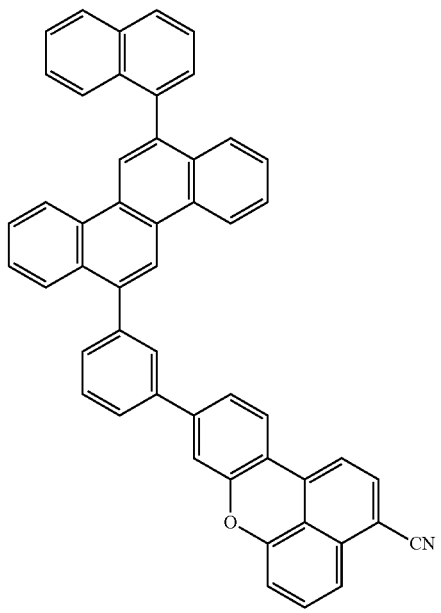
24B
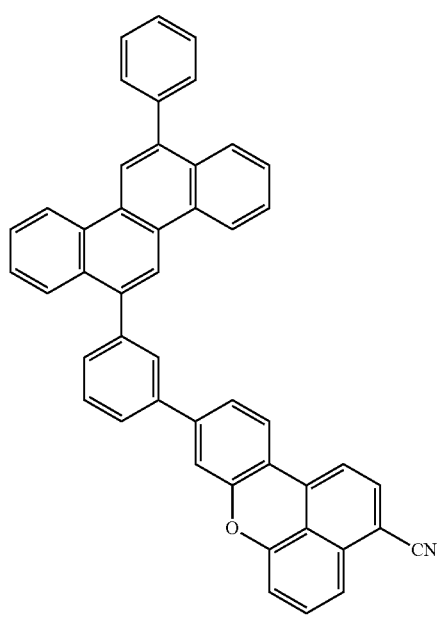
26B
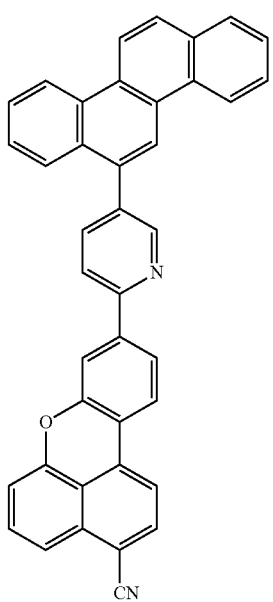

317
-continued
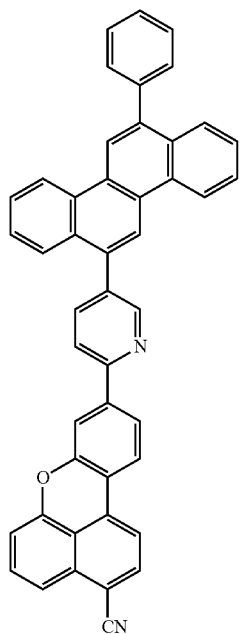
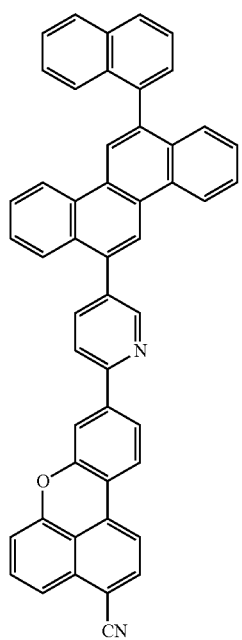
318
-continued
27B
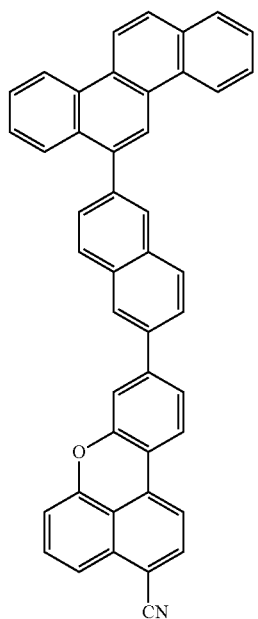
28B
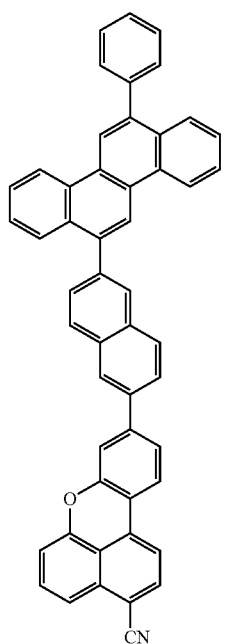
29B
30B 319
-continued
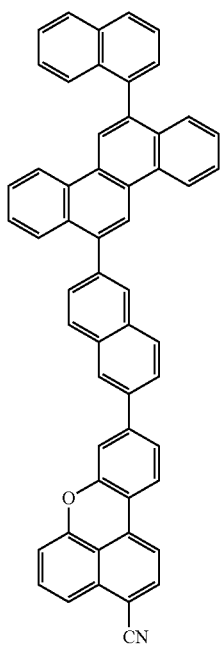
320
-continued
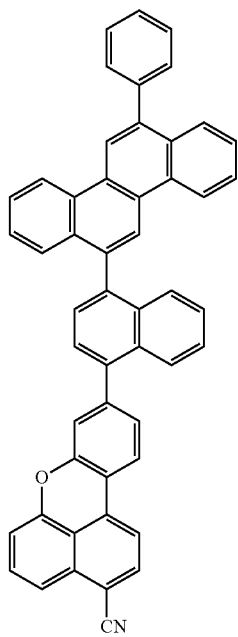
31B
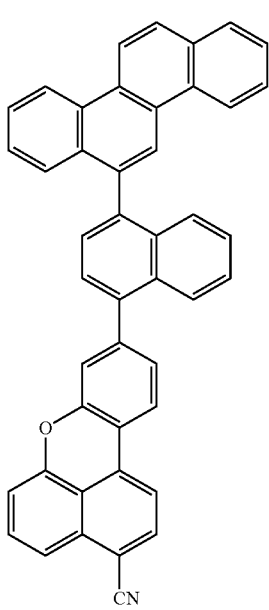
32B
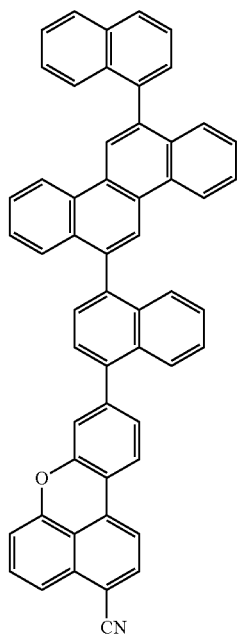
33B
34B

321
-continued
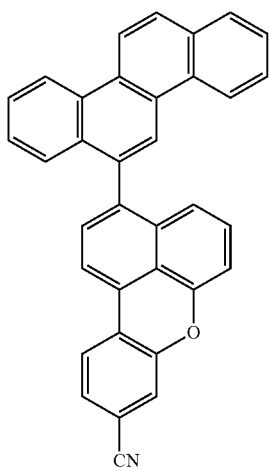
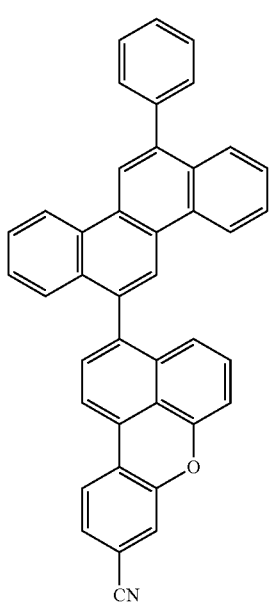
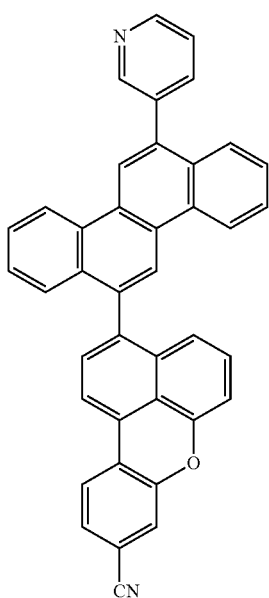
322
-continued
35B
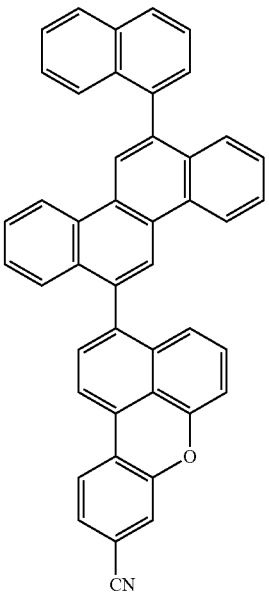
36B
37B
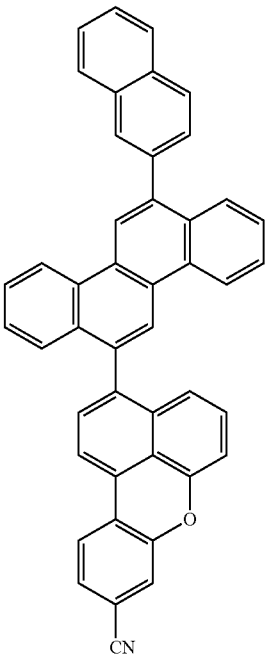
38B
39B 323
-continued
324
-continued
40B
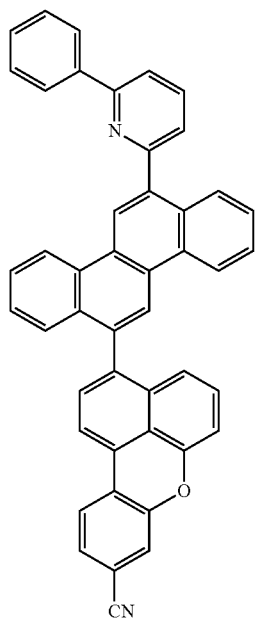
42B
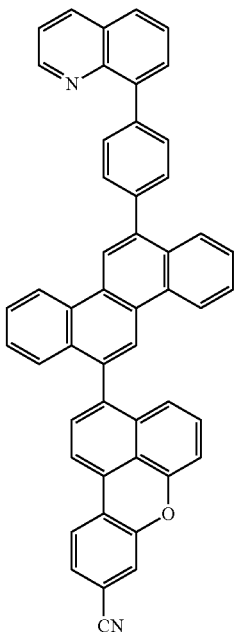
41B
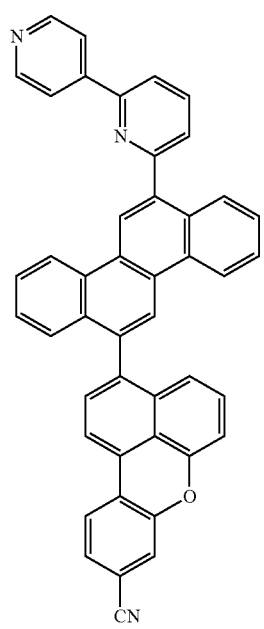
43B
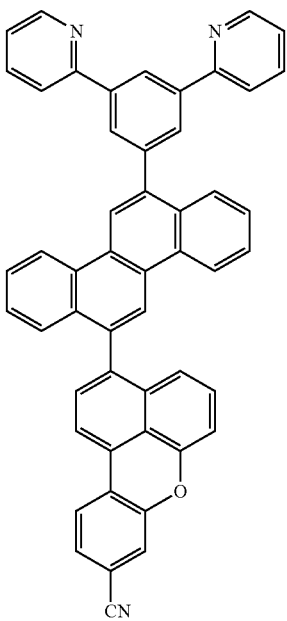

325
-continued
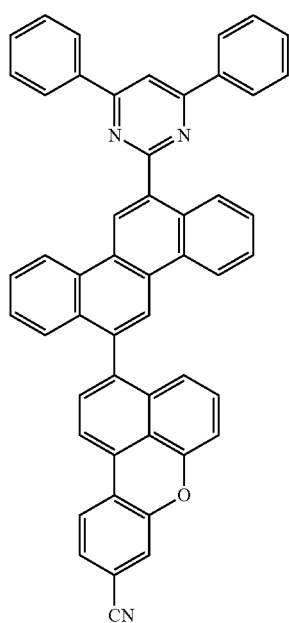
326
-continued
44B
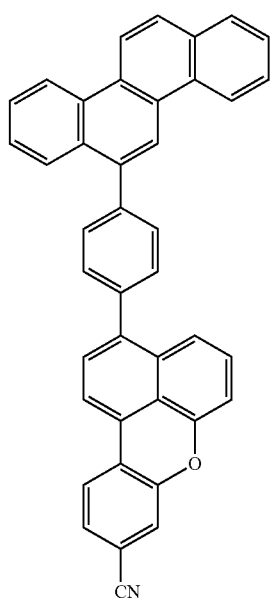
45B
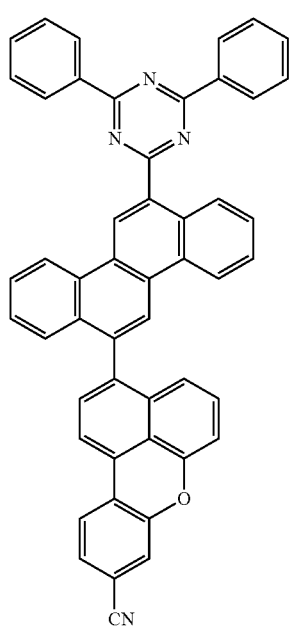
46B
47B
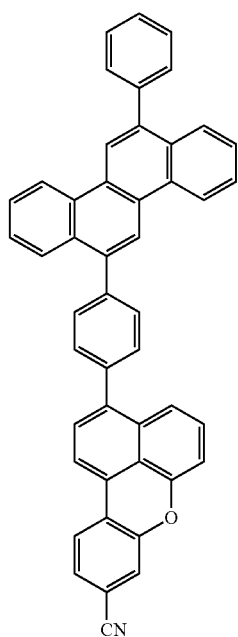

327
-continued
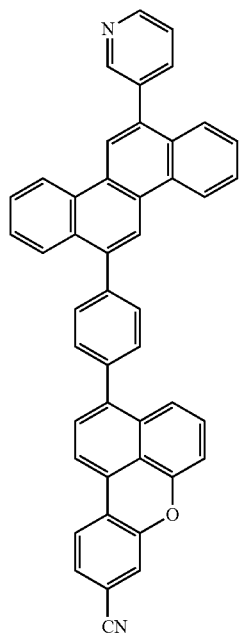
328
-continued
48B
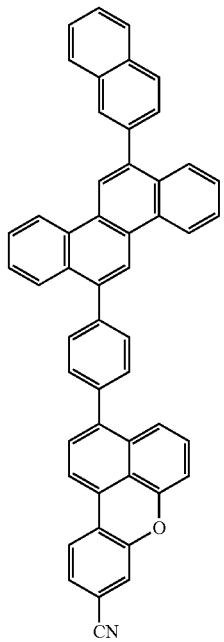
50B
49B
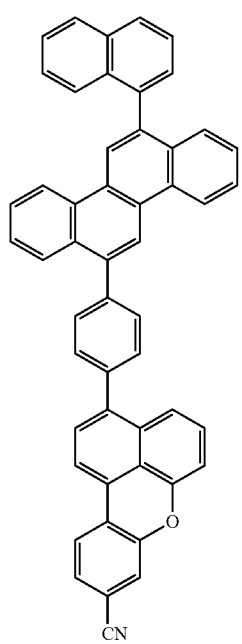
51B
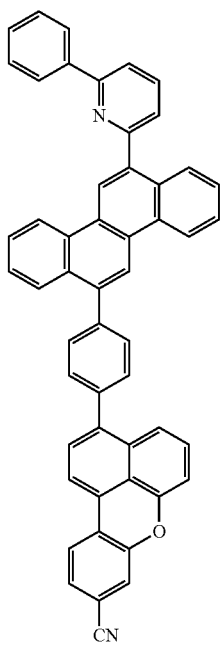

329
-continued
330
-continued
52B
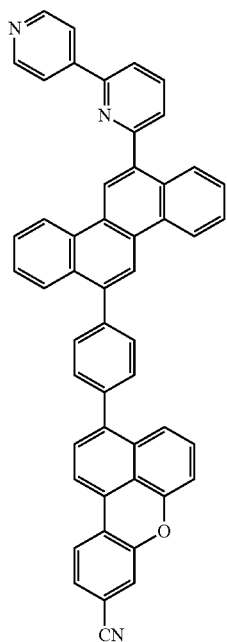
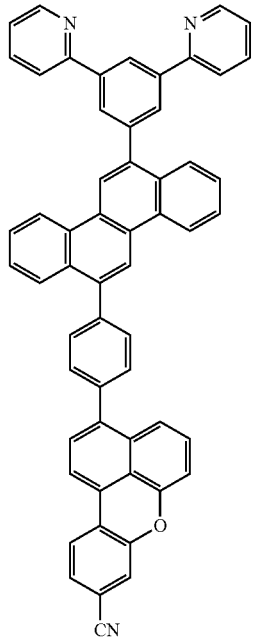
53B
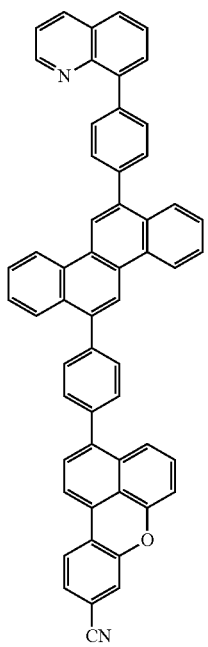
54B
55B
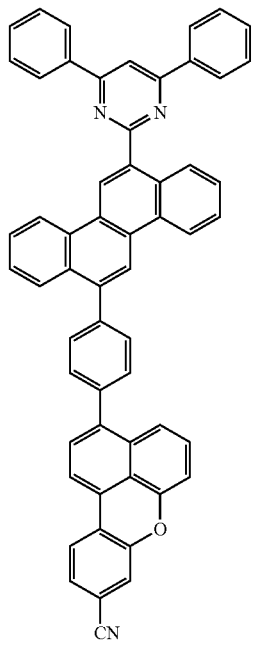

331
-continued
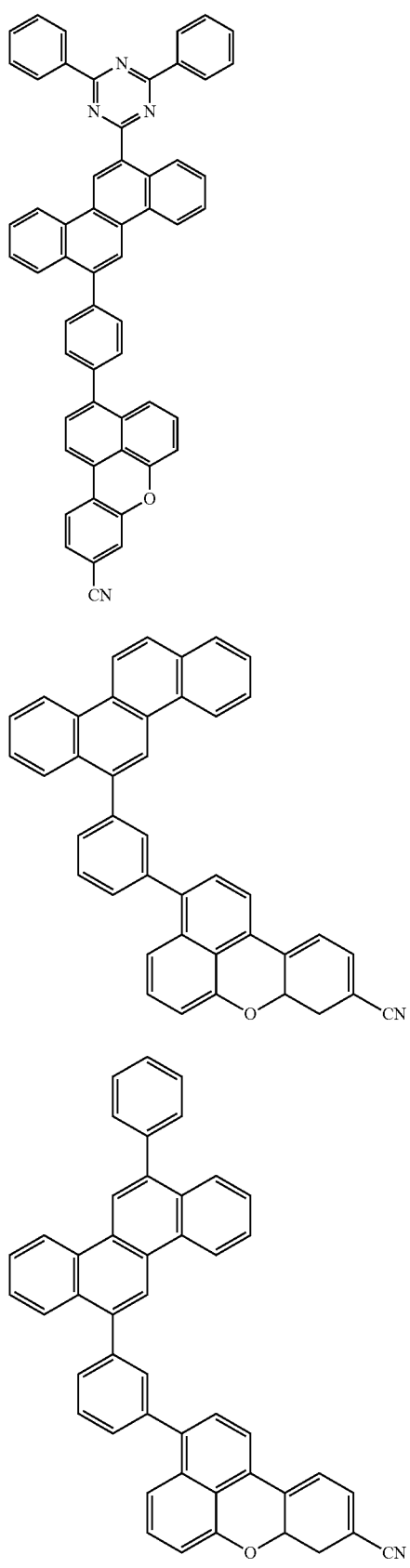
56B
57B
58B
332
-continued
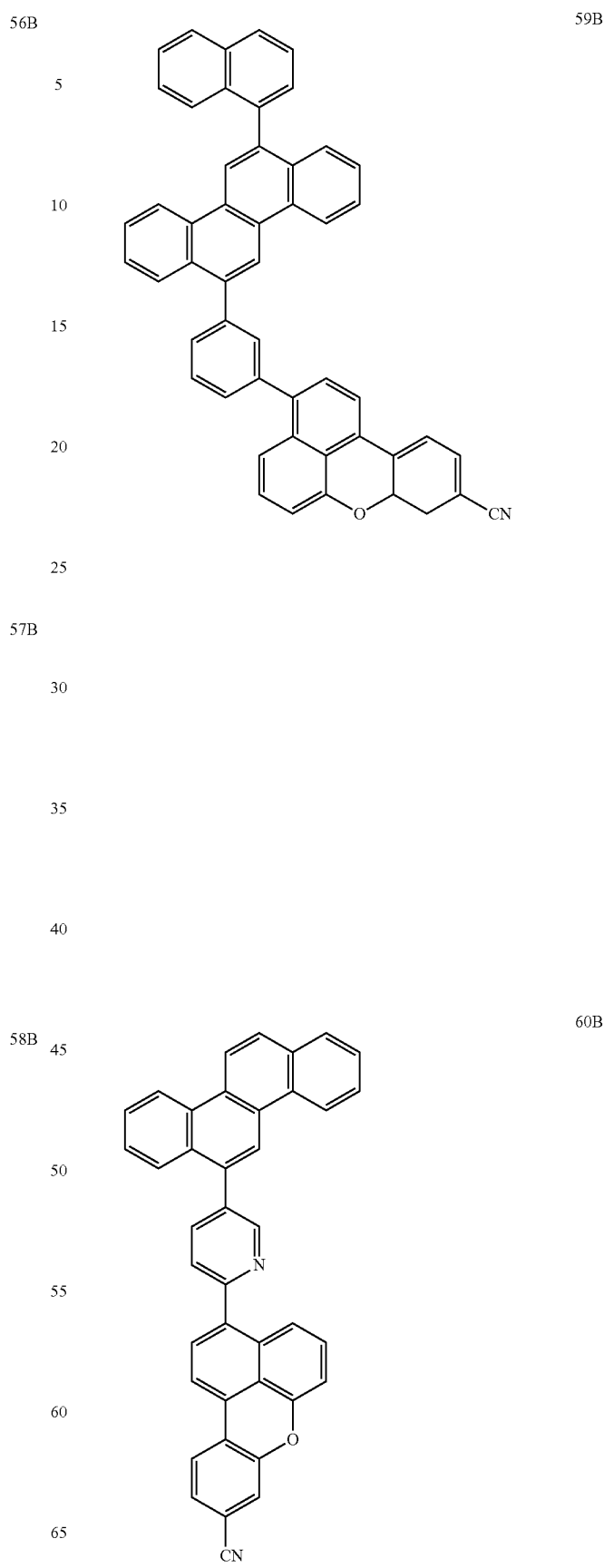
59B
60B 333
-continued
| 61B | 334 -continued | 63B |
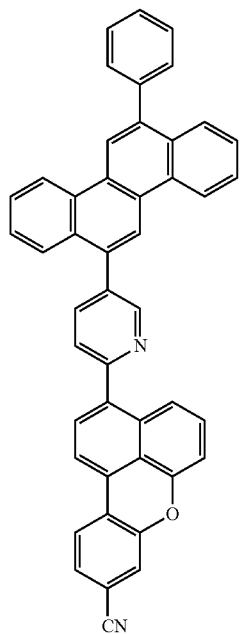
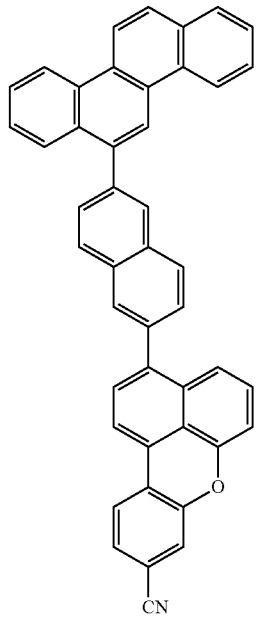
| 62B | | 64B |
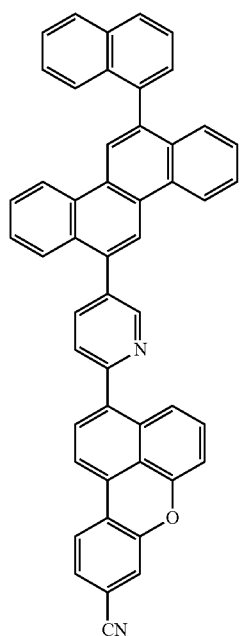
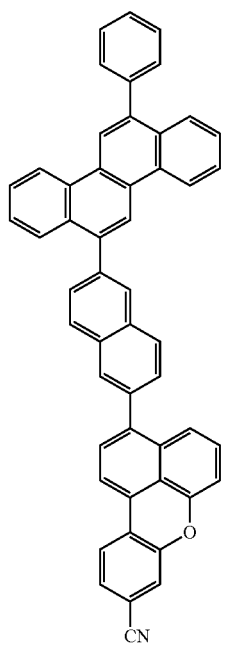

335
-continued
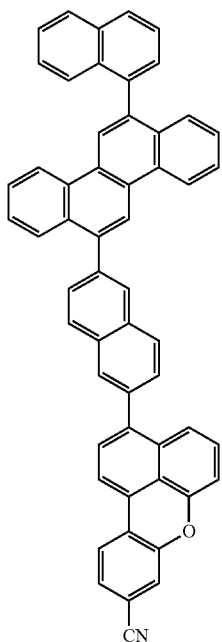
336
-continued
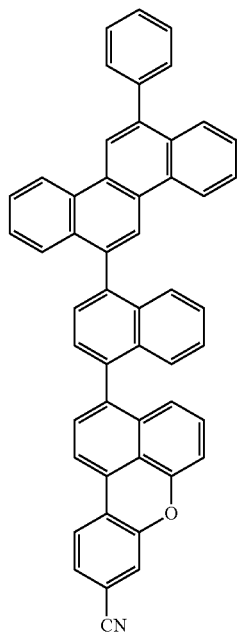
65B
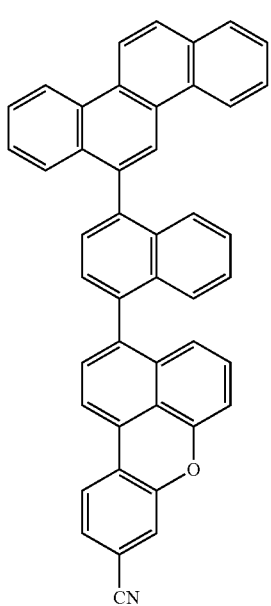
66B
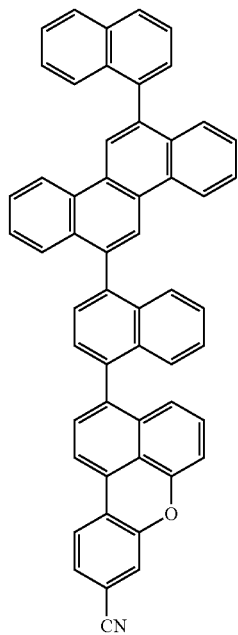
67B
68B

337
-continued
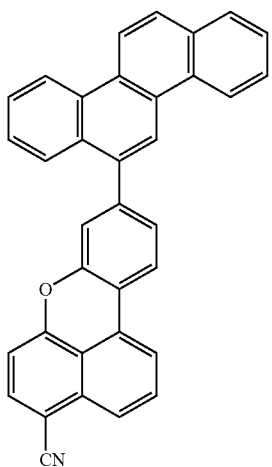
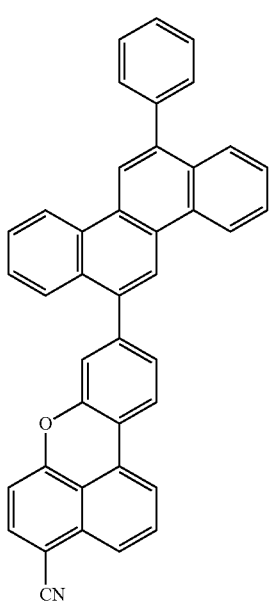
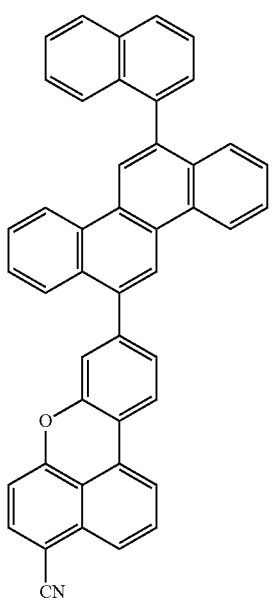
338
-continued
69B
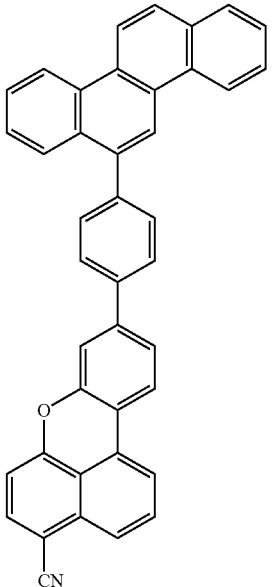
71B
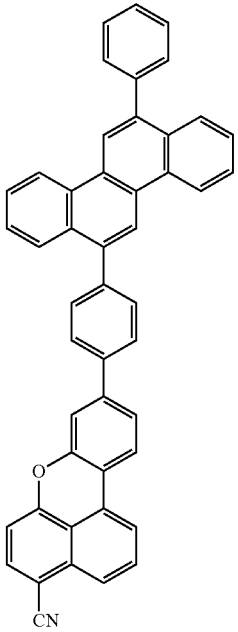
72B
73B 339
-continued
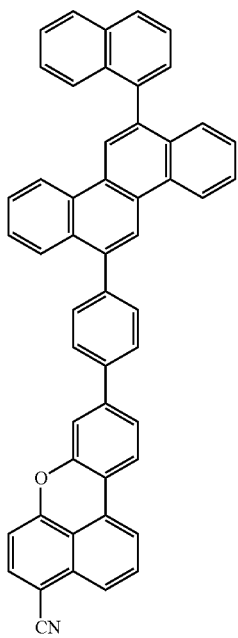
340
-continued
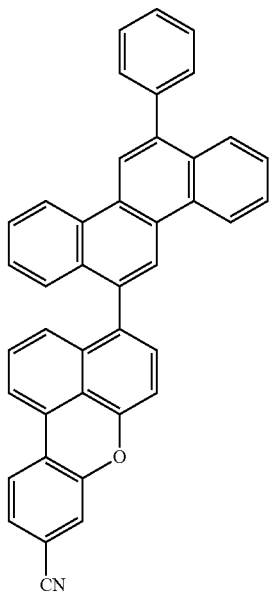
74B
75B
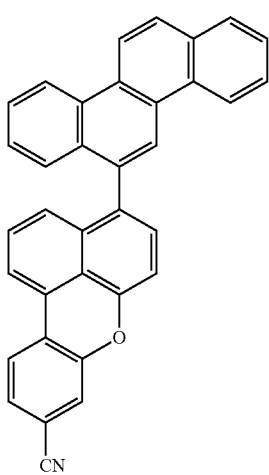
76B
77B
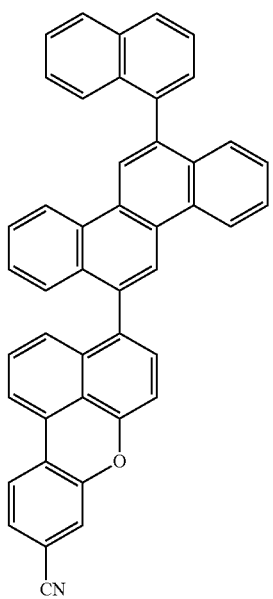

341
-continued
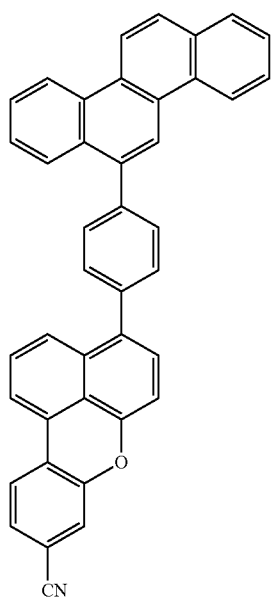
342
-continued
78B
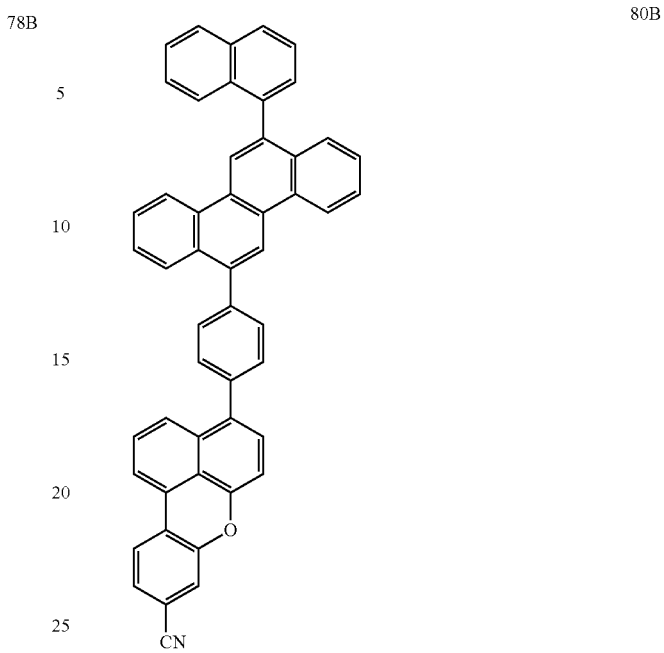
79B
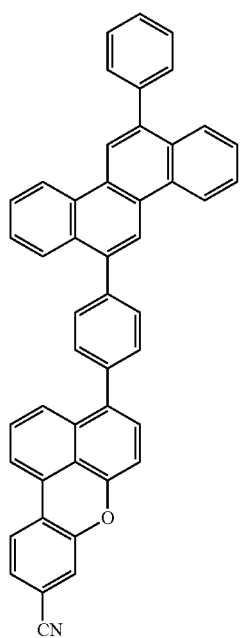
80B
81B
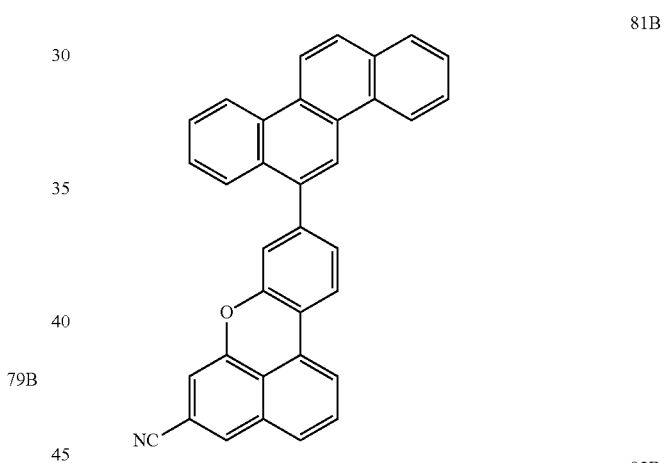
82B
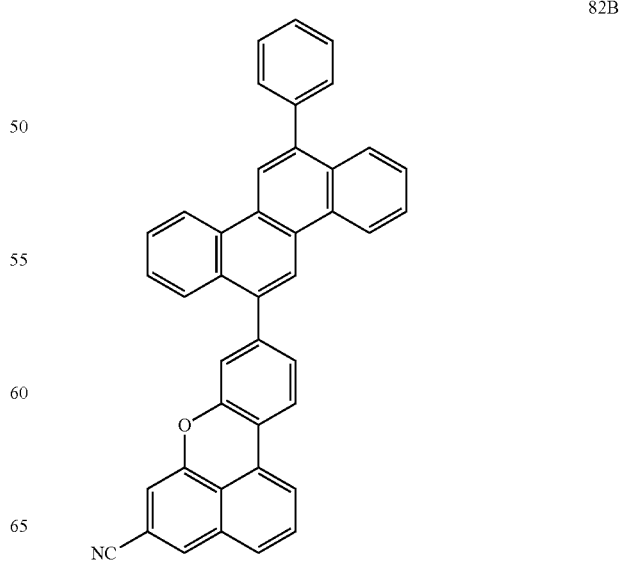

343
-continued
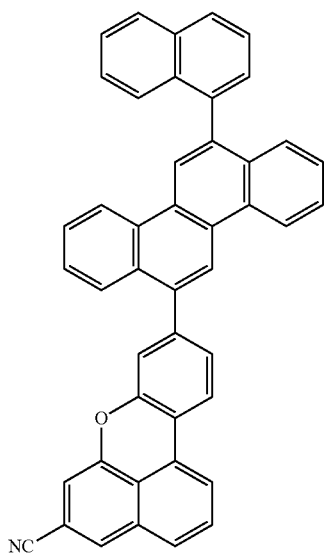
83B
344
-continued
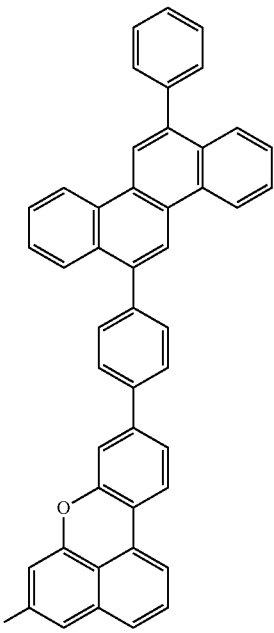
85B
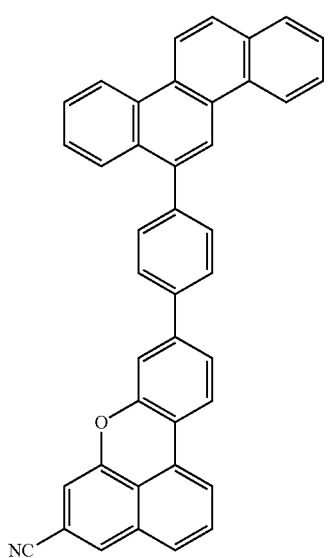
84B
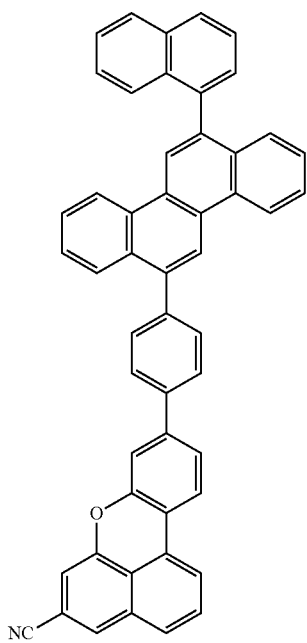
86B 345
-continued
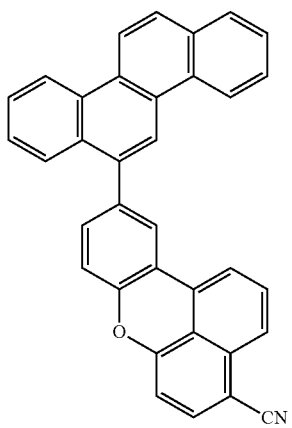
87B
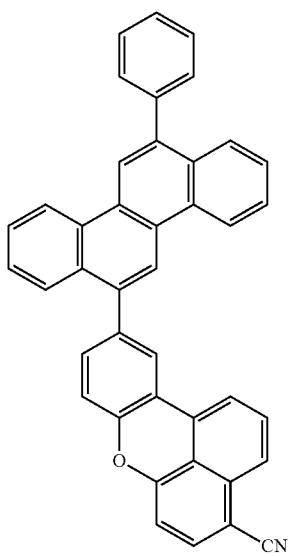
88B
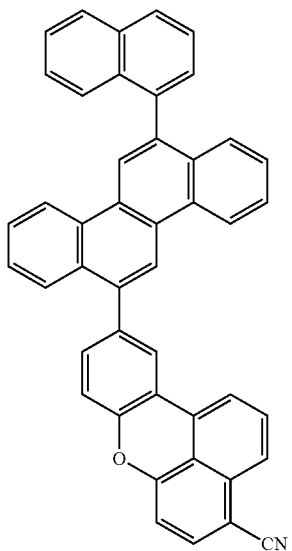
89B
346
-continued
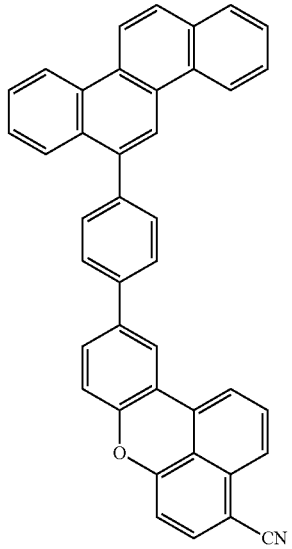
90B
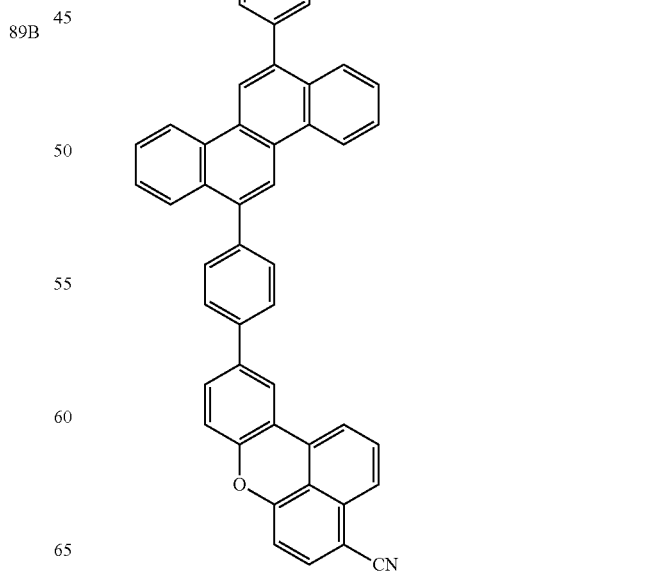
91B

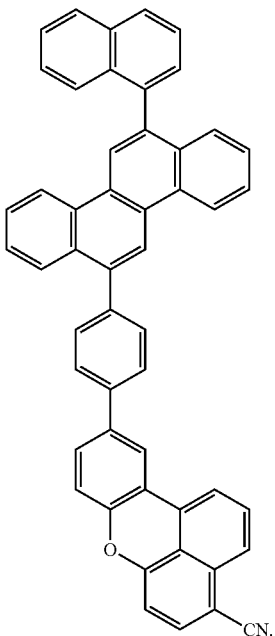

92B

17. An organic light-emitting device comprising: a first electrode; a second electrode disposed opposite to the first electrode; and an organic layer disposed between the first electrode and the second electrode and comprising an emission layer, wherein the organic layer comprises at least one of the compounds of claim 1.

18. The organic light-emitting device of claim 17, wherein
the first electrode is an anode,
the second electrode is a cathode,
the organic layer comprises i) a hole transport region disposed between the first electrode and the emission layer and comprising at least one of a hole injection layer, a hole transport layer, a buffer layer, and an electron blocking layer, and ii) an electron transport region disposed between the emission layer and the second electrode and comprising at least one of a hole blocking layer, an electron transport layer, and an electron injection layer.

19. The organic light-emitting device of claim 18, wherein the electron transport region comprises the at least one of the compounds of claim 1.

20. The organic light-emitting device of claim 18, wherein the hole transport region comprises at least one of a compound represented by Formula 201A and a compound represented by Formula 202A:

<Formula 201A>

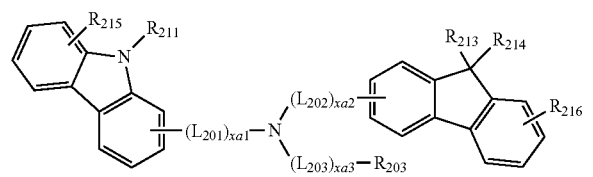

<Formula 202A>

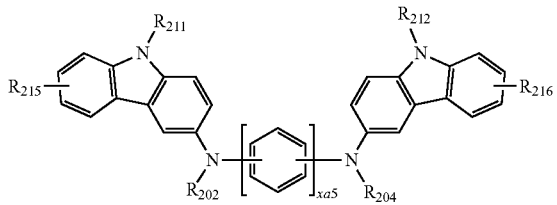

wherein, in Formulae 201A and 202A,
$L_{201}$ and $L_{203}$ are each independently selected from
a phenylene group, a naphthylene group, a fluorenylene group, a spiro-fluorenylene group, a benzofluorenylene group, a dibenzofluorenylene group, a phenanthrenyl group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, and
a phenylene group, a naphthylene group, a fluorenylene group, a spiro-fluorenylene group, a benzofluorenylene group, a dibenzofluorenylene group, a phenanthrenyl group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;
xa1 to xa3 are each independently 0 or 1;
$R_{203}$, $R_{211}$, and $R_{212}$ are each independently selected from
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ are each independently selected from a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ are each independently selected from a hydrogen, a deuterium, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 is 1 or 2.

* * * * *